United States Patent
Su et al.

(10) Patent No.: US 9,701,680 B2
(45) Date of Patent: Jul. 11, 2017

(54) PYRIMIDINE AND PYRIDINE COMPOUNDS AND THEIR USAGE

(71) Applicant: HUTCHISON MEDIPHARMA LIMITED, Shanghai (CN)

(72) Inventors: Wei-Guo Su, Shanghai (CN); Weihan Zhang, Shanghai (CN); Jinshui Li, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

(21) Appl. No.: 14/775,653

(22) PCT Filed: Mar. 14, 2014

(86) PCT No.: PCT/CN2014/073444
§ 371 (c)(1),
(2) Date: Sep. 11, 2015

(87) PCT Pub. No.: WO2014/139465
PCT Pub. Date: Sep. 18, 2014

(65) Prior Publication Data
US 2016/0024021 A1  Jan. 28, 2016

(30) Foreign Application Priority Data

Mar. 15, 2013 (WO) ............... PCT/CN2013/072690

(51) Int. Cl.
| | |
|---|---|
| *C07D 239/42* | (2006.01) |
| *A61K 31/506* | (2006.01) |
| *C07D 487/04* | (2006.01) |
| *C07D 403/12* | (2006.01) |
| *C07D 405/14* | (2006.01) |
| *C07D 401/12* | (2006.01) |
| *C07D 401/14* | (2006.01) |
| *C07D 403/14* | (2006.01) |
| *C07D 413/12* | (2006.01) |
| *C07D 417/12* | (2006.01) |
| *C07D 471/04* | (2006.01) |
| *C07D 405/10* | (2006.01) |
| *C07D 405/06* | (2006.01) |
| *C07D 405/12* | (2006.01) |

(52) U.S. Cl.
CPC ......... *C07D 487/04* (2013.01); *C07D 239/42* (2013.01); *C07D 401/12* (2013.01); *C07D 401/14* (2013.01); *C07D 403/12* (2013.01); *C07D 403/14* (2013.01); *C07D 405/06* (2013.01); *C07D 405/10* (2013.01); *C07D 405/12* (2013.01); *C07D 405/14* (2013.01); *C07D 413/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | | |
|---|---|---|---|---|
| 2006/0247250 A1* | 11/2006 | Cao | .................. | C07D 239/48 514/252.14 |
| 2007/0149508 A1* | 6/2007 | Noronha | .............. | C07D 239/42 514/218 |
| 2008/0027070 A1* | 1/2008 | Noronha | .............. | C07D 239/48 514/252.18 |
| 2009/0318468 A1* | 12/2009 | Buttar | .................. | C07D 231/14 514/254.05 |
| 2010/0160283 A1* | 6/2010 | Chaffee | ................ | C07D 213/74 514/210.02 |
| 2014/0142084 A1 | 5/2014 | Kameda et al. | | |
| 2015/0031703 A1 | 1/2015 | Suzuki et al. | | |

FOREIGN PATENT DOCUMENTS

| | | |
|---|---|---|
| WO | WO 2004/065378 A1 | 8/2004 |
| WO | WO 2006/101977 A2 | 9/2006 |
| WO | WO 2007/056075 A2 | 5/2007 |
| WO | WO 2008/008234 A1 | 1/2008 |
| WO | WO 2008/060907 | 5/2008 |
| WO | WO 2010/086646 A1 | 8/2010 |
| WO | WO 2013/129369 A1 | 9/2013 |
| WO | WO 2013/133351 A1 | 9/2013 |

OTHER PUBLICATIONS

International Search Report from the International Searching Authority mailed on Dec. 19, 2013, for International Application No. PCT/CN2013/072690 (4 pgs.).
International Search Report from the International Searching Authority mailed on May 28, 2014, for International Application No. PCT/CN2014/073444 (3 pgs.).
Extended European Search Report for European Patent Application No. 14764299.5, mailed Aug. 2, 2016 (7 pages).

* cited by examiner

*Primary Examiner* — Theodore R West
(74) *Attorney, Agent, or Firm* — Finnegan, Henderson, Farabow, Garrett & Dunner LLP

(57) ABSTRACT

The present invention relates to novel pyrimidine and pyridine compounds of formula (I) or a pharmaceutical acceptable salt thereof,

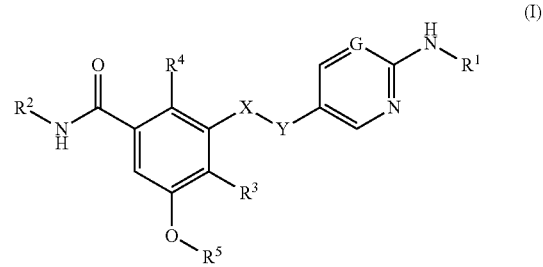

(I)

wherein $R^1$, $R^2$, $R^3$, $R^4$, $R^5$, X, Y and G are as defined in the description, to pharmaceutical compositions containing them, a process for preparing them, and their use in therapy of a disease responsive to inhibition of FGFR, for example, cancer.

23 Claims, No Drawings

PYRIMIDINE AND PYRIDINE COMPOUNDS AND THEIR USAGE

FIELD OF THE INVENTION

The present invention relates to novel pyrimidine and pyridine compounds, pharmaceutical compositions containing them, a process for preparing them, and their use in therapy.

BACKGROUND OF THE INVENTION

Fibroblast growth factor (FGF) has been recognized as an important mediator in many physiological processes. The fibroblast growth factor receptor family of receptor tyrosine kinases consists of four members (FGFR1, FGFR2, FGFR3, and FGFR4). Fibroblast growth factors (FGF) and their receptors (FGFR) play important roles in cell proliferation, cell differentiation, cell migration, cell survival, protein synthesis, and angiogenesis. There are many evidences directly linking FGF signaling to cancer. Dysregulation of FGFR signaling has been implicated in a number of cancers, including squamous non-small cell lung cancer (NSCLC), small cell lung cancer (SCLC), gastric, liver, breast, ovarian, endometrial, and bladder carcinomas, such as FGFR1 has been be found to be amplified in 22% squamous NSCLC, FGFR2 amplifications have been reported in up to 10% gastric cancers, and FGFR3 mutation have been found in approximately 50-60% nonmuscle invasion and 17% of high-grade bladder cancers, fueling significant interest in FGFRs as targets for therapeutic intervention.

Accordingly, new compounds and methods for modulating FGFR genes and treating proliferation disorders, including cancer, are needed. The present invention, addresses these needs.

SUMMARY OF THE INVENTION

The present invention provides a compound of formula (I):

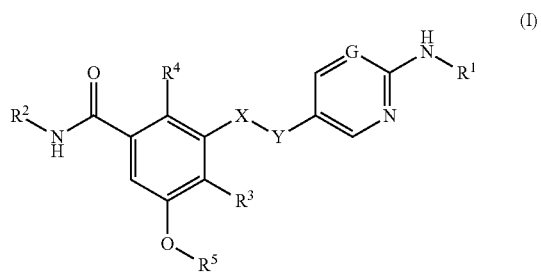

and/or its prodrug, enantiomers, diastereomers, tautomers, or their mixtures in any ratio, or a pharmaceutically acceptable salt thereof;
wherein
X is $CH_2$, Y is selected from $CH_2$, O or $S(O)_2$; or X and Y together with the bond there-between form —CH═CH— or —C≡C—;
G is N or CH;
$R^1$ is aryl or heteroaryl, which is optionally substituted with one or more substituents independently selected from halo, —$NR^6R^7$, —$OR^8$, —$S(O)_nR^9$, —$(CH_2)_r$—$C(O)R^{10}$, —CN, —$C(O)NR^6R^7$, —$NR^6C(O)R^{10}$, —$NR^6S(O)_nR^9$, —$NR^6S(O)_nNR^{11}R^{12}$, —$NR^6C(O)OR^8$, —$NR^6C(O)$ $NR^{11}R^{12}$, —$NO_2$, —$S(O)_nNR^6R^7$, oxo, optionally substituted alkyl, —$(CH_2)_p$-optionally substituted cycloalkyl, —$(CH_2)_m$-optionally substituted heterocyclyl, —$(CH_2)_q$-optionally substituted heteroaryl, optionally substituted alkenyl, and optionally substituted alkynyl;
$R^2$ is independently chosen from optionally substituted $C_1$-$C_6$ alkyl, optionally substituted $C_1$-$C_6$ alkoxy, or optionally substituted $C_3$-$C_8$ cycloalkyl;
$R^3$, $R^4$ are independently chosen from hydrogen, halogen, —CN, or optionally substituted $C_1$-$C_6$ alkyl,
$R^5$ is $C_1$-$C_6$ alkyl,
or $R^3$ and $R^5$ together with the O atom to which $R^5$ is attached and the bond there-between form a 5- or 6-membered oxy-containing heterocyclic ring;
n is 1 or 2;
m, p, q and r are independently chosen from 0, 1, 2, 3, 4, 5, 6;
$R^6$, $R^7$, $R^8$, $R^9$, $R^{10}$, $R^{11}$ and $R^{12}$ are independently selected from hydrogen, alkyl, cycloalkyl, aryl, heteroaryl, heterocyclyl, each of which except for hydrogen, is optionally substituted with one or more substituents independently selected from halo, hydroxyl, mercapto, oxo, alkyl, cycloalkyl, heterocyclyl, optionally substituted amino, and optionally substituted amide,
wherein each optionally substituted group above for which the substituent(s) is (are) not specifically designated, can be unsubstituted or independently substituted with one or more, such as one, two or three, substituents independently chosen from $C_1$-$C_6$ alkyl, $C_2$-$C_6$ alkenyl, $C_2$-$C_6$ alkynyl, cycloalkyl, aryl, heterocyclyl, heteroaryl, aryl-$C_1$-$C_6$ alkyl-, heteroaryl-$C_1$-$C_6$ alkyl-, $C_1$-$C_6$ haloalkyl-, —$OC_1$-$C_6$ alkyl, —$OC_2$-$C_6$ alkenyl, —$OC_1$-$C_6$ alkylphenyl, —$C_1$-$C_6$ alkyl-OH, —$C_1$-$C_6$ alkyl-SH, —$C_1$-$C_6$ alkyl-O—$C_1$-$C_6$ alkyl, —$OC_1$-$C_6$ haloalkyl, halo, —OH, mercapto, —$NH_2$, —$C_1$-$C_6$ alkyl-$NH_2$, —$N(C_1$-$C_6$ alkyl)$_2$, —$NH(C_1$-$C_6$ alkyl), —$N(C_1$-$C_6$ alkyl)($C_1$-$C_6$ alkylphenyl), —$NH(C_1$-$C_6$ alkylphenyl), cyano, nitro, oxo, —C(O)—OH, —C(O)O$C_1$-$C_6$ alkyl, —CON($C_1$-$C_6$ alkyl)$_2$, —CONH($C_1$-$C_6$ alkyl), —$CONH_2$, —NHC(O)($C_1$-$C_6$ alkyl), —NHC(O)(phenyl), —N($C_1$-$C_6$ alkyl)C(O)($C_1$-$C_6$ alkyl), —N($C_1$-$C_6$ alkyl)C(O) (phenyl), —C(O)$C_1$-$C_6$ alkyl, —C(O)$C_1$-$C_6$ alkylphenyl, —C(O)$C_1$-$C_6$ haloalkyl, —OC(O)$C_1$-$C_6$ alkyl, —$S(O)_2$—$C_1$-$C_6$ alkyl, —S(O)—$C_1$-$C_6$ alkyl, —$S(O)_2$-phenyl, —$S(O)_2$—$C_1$-$C_6$ haloalkyl, —$S(O)_2NH_2$, —$S(O)_2$NH($C_1$-$C_6$ alkyl), —$S(O)_2$NH(phenyl), —NHS$(O)_2$($C_1$-$C_6$ alkyl), —NHS$(O)_2$(phenyl), and —NHS$(O)_2$($C_1$-$C_6$ haloalkyl), in which each of phenyl, aryl, heterocyclyl, and heteroaryl is optionally substituted by one or more substituents chosen from halo, cycloalkyl, heterocyclyl, $C_1$-$C_4$ alkyl, $C_1$-$C_6$ haloalkyl-, —$OC_1$-$C_6$ alkyl, $C_1$-$C_6$ alkyl-OH, —$C_1$-$C_6$ alkyl-O—$C_1$-$C_6$ alkyl, —$OC_1$-$C_6$ haloalkyl, cyano, nitro, —$NH_2$, —C(O)—OH, —C(O)O$C_1$-$C_6$ alkyl, —CON($C_1$-$C_6$ alkyl)$_2$, —CONH($C_1$-$C_6$ alkyl), —$CONH_2$, —NHC(O)($C_1$-$C_6$ alkyl), —NH($C_1$-$C_6$ alkyl)C(O)($C_1$-$C_6$ alkyl), —$SO_2$($C_1$-$C_6$ alkyl), —$SO_2$(phenyl), —$SO_2$($C_1$-$C_6$ haloalkyl), —$SO_2NH_2$, —$SO_2$NH($C_1$-$C_6$ alkyl), —$SO_2$NH(phenyl), —NHS$O_2$($C_1$-$C_6$ alkyl), —NHS$O_2$(phenyl), and —NHS$O_2$ ($C_1$-$C_6$ haloalkyl).

Also provided is a pharmaceutical composition, comprising at least one compound of formula (I) and/or at least one pharmaceutically acceptable salt thereof described herein and optionally at least one pharmaceutically acceptable carrier.

Also provided is a method of in vivo or in vitro inhibiting the activity of FGFR comprising contacting FGFR with an effective amount of at least one compound of formual (I) and/or at least one pharmaceutically acceptable salt thereof described herein.

Also provided is a method of treating a disease responsive to inhibition of FGFR comprising administering to a subject in need thereof an effective amount to treat said disease of at least one compound of formula (I) and/or at least one pharmaceutically acceptable salt thereof described herein.

Also provided is use of at least one compound of formula (I) and/or at least one pharmaceutically acceptable salt thereof described herein for treating a disease responsive to inhibition of FGFR.

Also provided is use of at least one compound of formula (I) and/or at least one pharmaceutically acceptable salt thereof described herein in the manufacture of a medicament for treating a disease responsive to inhibition of FGFR.

DETAILED DESCRIPTION OF THE INVENTION

Definitions

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom.

The term "alkyl" as used herein refers to a straight or branched saturated hydrocarbon radical, containing 1-18, preferably 1-12, more preferably 1-6, further preferably 1-4, especially 1-3 carbon atoms. Examples of alkyl groups include, but are not limited to, methyl, ethyl, n-propyl, i-propyl, n-butyl, i-butyl, s-butyl and t-butyl.

The term "alkoxy" as used herein refers to the group —O-alkyl, wherein the alkyl is as defined above. Examples of alkoxy groups include, but are not limited to, methoxy, ethoxy, n-propyloxy, i-propyloxy, n-butyloxy, i-butyloxy, t-butyloxy, pentyloxy, hexyloxy, including their isomers.

The term "alkenyl" as used herein refers to a straight or branched hydrocarbon radical, containing one or more C=C double bonds and 2-10, preferably 2-6, more preferably 2-4 carbon atoms. Examples of alkenyl groups include, but are not limited to, vinyl, 2-propenyl, and 2-butenyl.

The term "alkynyl" as used herein refers to a straight or branched hydrocarbon radical, containing one or more C≡C triple bonds and 2-10, preferably 2-6, more preferably 2-4 carbon atoms. Examples of alkynyl groups include, but are not limited to, ethynyl, 2-propynyl, and 2-butynyl.

The term "cycloalkyl" as used herein refers to saturated and partially unsaturated cyclic hydrocarbon radical having 3 to 12, preferably 3 to 8, more preferably 3 to 6 carbon atoms. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The ring of the cycloalkyl group may be saturated or has one or more, for example, one or two double bonds (i.e. partially unsaturated), but not fully conjugated, and not aryl as defined herein.

The term "aryl" as used herein refers to 5- and 6-membered monocyclic carbocyclic aromatic hydrocarbon radical and 8- to 12-membered bicyclic carbocyclic hydrocarbon radical wherein at least one ring is aromatic, for example, phenyl, naphthalenyl, 1,2,3,4-tetrahydronaphthalenyl, indenyl, indanyl, azulenyl.

The term "halo" as used herein includes fluoro, chloro, bromo, and iodo, and the term "halogen" as used herein includes fluorine, chlorine, bromine, and iodine.

The term "heteroaryl" as used herein refers to 5- to 6-membered monocyclic aromatic hydrocarbon radical containing one or more, for example, from 1 to 4, or, in some embodiments, from 1 to 3, in some embodiments, 1 or 2 heteroatoms independently selected from N, O, and S, with the remaining ring atoms being carbon; and 8- to 12-membered bicyclic hydrocarbon radical containing one or more, for example, from 1 to 4, or, in some embodiments, from 1 to 3, in some embodiments, 1 or 2 heteroatoms independently selected from N, O, and S, with the remaining ring atoms being carbon, wherein at least one of the rings is aromatic. For example, the bicyclic heteroaryl includes a 5- to 6-membered heterocyclic aromatic ring fused to a 5- to 6-membered cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the heteroaryl group is not more than 1.

The heteroaryl group also includes those wherein the N heteroatom occurs as N-oxide, such as pyridinyl N-oxides.

Examples of the heteroaryl group include, but are not limited to, pyridyl, pyridyl N-oxide, such as pyrid-2-yl, pyrid-3-yl, pyrid-4-yl or N-oxide thereof; pyrazinyl, such as pyrazin-2-yl, pyrazin-3-yl; pyrimidinyl, such as pyrimidin-2-yl, pyrimidin-4-yl; pyrazolyl, such as pyrazol-1-yl, pyrazol-3-yl, pyrazol-4-yl, pyrazol-5-yl; imidazolyl, imidazol-2-yl, imidazolin-4-yl; oxazolyl; isoxazolyl; thiazolyl; isothiazolyl; thiadiazolyl; tetrazolyl; triazolyl, such as 1H-1,2,4-triazolyl, 4H-1,2,4-triazolyl, 1H-1,2,3-triazolyl, 2H-1,2,3-triazolyl; thienyl; furyl; pyranyl; pyrrolyl; pyridazinyl; bezodioxolyl, such as benzo[d][1,3]dioxolyl; benzoxazolyl, such as benzo[d]oxazolyl; imidazopyridinyl, such as imidazo[1,2-a]pyridinyl; triazolopyridinyl, such as [1,2,4]triazolo[4,3-a]pyridinyl and [1,2,4]triazolo[1,5-a]pyridinyl; indazolyl, 2H-indazolyl; pyrazolopyrimidinyl, such as pyrazolo[1,5-a]pyrimidinyl; tetrazolopyridinyl, such as tetrazolo[1,5-a]pyridinyl; benzothienyl; benzofuryl; benzoimidazolinyl; indolyl; indolinyl; quinolinyl, isoquinolinyl, 1,2,3,4-tetrahydroquinolinyl and 5,6,7,8-tetrahydroisoquinolinyl.

The term "heterocyclyl" as used herein refers to 3- to 14-membered, preferably 4- to 12-membered, monocyclic, bicyclic or tricyclic saturated or partially unsaturated hydrocarbon radical containing at least 2 carbon atoms and 1, 2 or 3 heteroatoms independently selected from oxygen, sulfur, and nitrogen. More preferably, "heterocyclyl" refers to 4- to 8-membered, especially 4-, 5- or 6-membered monocyclic heterocyclyl group containing 1 or 2 heteroatoms independently selected from N, O, and S. "Heterocyclyl" also refers to an aliphatic spirocyclic ring containing one or more heteroatoms independently selected from N, O, and S. The rings may be saturated or have one or more double bonds (i.e. partially unsaturated). The point of the attachment may be carbon or heteroatom in the heterocyclyl group. However, any of the rings in the heterocylyl group is not aromatic so that the heterocylyl group is not a heteroaryl as defined herein. The heterocyclyl group also includes those wherein the N or S heteroatom occurs as oxide thereof. Examples of heterocyclyl include, but are not limited to, oxetanyl, such as oxetan-2-yl or oxetan-3-yl; azetidinyl, such as azetidin-2-yl or azetidin-3-yl; pyrrolidinyl, such as pyrrolidin-1-yl, pyrrolidin-2-yl, pyrrolidin-3-yl; tetrahydrofuranyl, such as tetrahydrofuran-2-yl, tetrahydrofuran-3-yl; tetrahydropyranyl, such as tetrahydropyran-2-yl, tetrahydropyran-3-yl, tetrahydropyran-4-yl; dioxolanyl, such as 1,3-dioxolanyl; dioxanyl, such as 1,4-dioxanyl, 1,3-dioxanyl; morpholinyl, morpholinyl-N-oxide, such as morpholin-2-yl, morpholin-3-yl, morpholin-4-yl (morpholino) (numbered wherein the oxygen is assigned priority 1); thiomorpholinyl, 1-oxo-thiomorpholin-4-yl, 1,1-dioxo-thiomorpholin-4-yl; imidazolinyl, such as imidazolidin-2-yl, imidazolidin-4-yl; pyrazolidinyl, such as pyrazolidin-2-yl, pyrazolidin-3-yl; piperidinyl or piperidinyl N-oxide, such as piperidin-1-yl and piperidin-2-yl, piperidin-3-yl, piperidin-4-yl or N-oxide thereof; and piperazinyl, such as piperazin-1-yl, piperazin-2-yl, piperazin-3-yl; octahydropyrrolo[3,4-b]pyrrolyl.

The term "5- or 6-membered oxy-containing heterocyclic ring" as used herein refers to a 5- or 6-membered unsaturated ring optionally containing one or two heteroatoms independently selected from N, O or S, in addition to the oxy heteroatom linking the phenyl ring and the group $R^5$ in formula (I), with the remaining ring atoms being carbon. "5- or 6-membered oxy-containing heterocyclic ring" is preferably furan, dihydrofuran, pyran or dihydropyran.

"Hydroxyl" refers to the —OH radical.
"Nitro" refers to the —NO$_2$ radical.
"Mercapto" refers to the —SH radical.
"Cyano" refers to the —CN radical.
"Oxo" refers to the =O radical.
"Carboxyl" refers to the —C(O)—OH radical.

The term "optional" or "optionally" means that the subsequently described event or circumstance may or may not occur, and that the description includes instances where the event or circumstance occurs and instances in which it does not. For example, "optionally substituted alkyl" encompasses both "unsubstituted alkyl" and "substituted alkyl" as defined herein. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term "substituted", as used herein, means that one or more hydrogens on the designated atom or group are replaced with one or more selections from the indicated group of substituents, provided that the designated atom's normal valence is not exceeded. When a substituent is oxo (i.e., =O), then 2 hydrogens on a single atom are replaced. Combinations of substituents and/or variables are permissible only if such combinations result in a chemically correct and stable compound. A chemically correct and stable compound is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The term "substituted with one or more substitutents" as used herein means that one or more hydrogens on the designated atom or group are independently replaced with one or more selections from the indicated group of substituents. In some embodiments, "substituted with one or more substitutents" means that the designated atom or group is substituted with two substituents independently selected from the indicated group of substituents. In some embodiments, "substituted with one or more substitutents" means that the designated atom or group is substituted with three substituents independently selected from the indicated group of substituents. In some embodiments, "substituted with one or more substitutents" means that the designated atom or group is substituted with four substituents independently selected from the indicated group of substituents.

It will be appreciated by those skilled in the art that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by those skilled in the art that the present invention includes all the individual stereoisomers (e.g. enantiomers), racemic mixtures or partially resolved mixtures of the compounds of formula (I) and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

"Pharmaceutically acceptable salt" include, but are not limited to, acid addition salts formed by the compound of formula (I) with an inorganic acid, such as hydrochloride, hydrobromide, carbonate, bicarbonate, phosphate, sulfate, sulfite, nitrate and the like; as well as with an organic acid, such as formate, acetate, malate, maleate, fumarate, tartrate, succinate, citrate, lactate, methanesulfonate, p-toluenesulfonate, 2-hydroxyethylsulfonate, benzoate, salicylate, stearate, and salts with alkane-dicarboxylic acid of formula HOOC—(CH$_2$)$_n$—COOH where n is 0-4, and the like. Also, "pharmaceutically acceptable salt" includes base addition salts formed by the compound of formula (I) carring an acidic moiety with pharmaceutically acceptable cations, for example, sodium, potassium, calcium, aluminum, lithium, and ammonium. In addition, if a compound described herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable acid addition salts.

The term "solvates" means solvent addition forms that contain either stoichiometric or non stoichiometric amounts of solvent. Some compounds have a tendency to trap a fixed molar ratio of solvent molecules in the solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrates, for example, hemihydrates, monohydrate and dihydrate.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. For example, an ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester.

As used herein, the terms "group", "radical" and "moiety" are synonymous and are intended to indicate functional groups or fragments of molecules attachable to other fragments of molecules.

The terms "treating", "treat" or "treatment" of a disease or disorder refers to administering one or more pharmaceutical substances, especially at least one compound of formula (I) and/or at least one pharmaceutically acceptable salt thereof described herein to a subject that has the disease or disorder, or has a symptom of a disease or disorder, or has a predisposition toward a disease or disorder, with the purpose to cure, heal, alleviate, relieve, alter, remedy, ameliorate, improve, or affect a disease or disorder, the symptoms of the disease or disorder, or the predisposition toward the disease or disorder. In some embodiments, the disease or disorder is cancer.

The terms "treating", "contacting" and "reacting" when referring to a chemical reaction mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount of at least one compound of formula (I) and/or at least one pharmaceutically acceptable salt thereof described herein effective to "treat", as defined above, a disease or disorder in a subject responsive to the inhibition of FGFR. The effective amount may cause any of the changes observable or measurable in a subject as described in the definition of "treating" "treat" or "treatment" above. For example, in the case of cancer, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of FGFR. The term "effective amount" may also refer to an amount of at least one compound of formula (I) and/or at least one pharmaceutically acceptable salt described herein effective to inhibit the activity of FGFR in a subject responsive to the inhibition of FGFR.

The term "inhibition" or "inhibiting" indicates a decrease in the baseline activity of a biological activity or process. "Inhibition of FGFR" refers to a decrease in the activity of FGFR as a direct or indirect response to the presence of at least one compound of formula (I) and/or at least one pharmaceutically acceptable salt thereof described herein, relative to the activity of FGFR in the absence of the at least one compound of formula (I) and/or the at least one pharmaceutically acceptable salt thereof. The decrease in activity may be due to the direct interaction of the at least one compound of formula (I) and/or at least one pharmaceutically acceptable salt thereof described herein with the FGFR, or due to the interaction of the at least one compound of formula (I) and/or at least one pharmaceutically acceptable salt thereof described herein, with one or more other factors that in turn affect the FGFR activity. For example, the presence of at least one compound of formula (I) and/or at least one pharmaceutically acceptable salt thereof described herein, may decrease the FGFR activity by directly binding to the FGFR, by causing (directly or indirectly) another factor to decrease the FGFR activity, or by (directly or indirectly) decreasing the amount of FGFR present in the cell or organism.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The term "pharmaceutically acceptable" means that the substance following this term is useful in preparing a pharmaceutical composition and is generally safe, non-toxic, and neither biologically nor otherwise undesirable, especially for human pharmaceutical use.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein and not specifically defined have the meaning commonly understood by those skilled in the art to which the present invention pertains.

Embodiments of the Invention

In one aspect, the present invention provides a compound of formula (I):

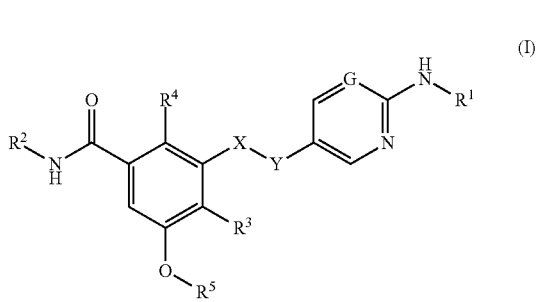

and/or prodrug, its enantiomers, diastereomers, tautomers, or their mixtures in any ratio, or a pharmaceutically acceptable salt thereof;
wherein
X is $CH_2$, Y is selected from $CH_2$, O or $S(O)_2$; or X and Y together with the bond there-between form —CH═CH— or —C≡C—;

G is N or CH;

$R^1$ is aryl or heteroaryl, each of which is optionally substituted with one or more substituents independently selected from halo, —$NR^6R^7$, —$OR^8$, —$S(O)_nR^9$, —$(CH_2)_r$—$C(O)R^{10}$, —CN, —$C(O)NR^6R$, —$NR^6C(O)R^{10}$, —$NR^6S(O)_nR^9$, —$NR^6S(O)_nNR^{11}R^{12}$, —$NR^6C(O)OR^8$, —$NR^6C(O)NR^{11}R^{12}$, —$NO_2$, —$S(O)_nNR^6R^7$, oxo, optionally substituted alkyl, —$(CH_2)_p$-optionally substituted cycloalkyl, —$(CH_2)_m$-optionally substituted heterocyclyl, —$(CH_2)_q$-optionally substituted heteroaryl, optionally substituted alkenyl, and optionally substituted alkynyl;

$R^2$ is independently chosen from optionally substituted $C_1$-$C_6$ alkyl, optionally substituted $C_1$-$C_6$ alkoxy, or optionally substituted $C_3$-$C_8$ cycloalkyl;

$R^3$, $R^4$ are independently chosen from hydrogen, halogen, —CN, or optionally substituted $C_1$-$C_6$ alkyl, $R^5$ is $C_1$-$C_6$ alkyl, or $R^3$ and $R^5$ together with the O atom to which $R^5$ is attached and the bond there-between form a 5- or 6-membered oxy-containing heterocyclic ring;

n is 1 or 2;

m, p, q and r are independently chosen from 0, 1, 2, 3, 4, 5, 6;

$R^6$, $R^7$, $R^8$, $R^9$, $R^{10}$, $R^{11}$ and $R^{12}$ are independently selected from hydrogen, alkyl, cycloalkyl, aryl, heteroaryl, heterocyclyl, each of which except for hydrogen, is optionally substituted with one or more substituents independently selected from halo, hydroxyl, mercapto, oxo, alkyl, cycloalkyl, heterocyclyl, optionally substituted amino, and optionally substituted amide, wherein each optionally substituted group above for which the substituent(s) is (are) not specifically designated, can be unsubstituted or independently substituted with one or more, such as one, two or three, substituents independently chosen from $C_1$-$C_6$ alkyl, $C_2$-$C_6$ alkenyl, $C_2$-$C_6$ alkynyl, cycloalkyl, aryl, heterocyclyl, heteroaryl, aryl-$C_1$-$C_6$ alkyl-, heteroaryl-$C_1$-$C_6$ alkyl-, $C_1$-$C_6$ haloalkyl-, —$OC_1$-$C_6$ alkyl, —$OC_2$-$C_6$ alkenyl, —$OC_1$-$C_6$ alkylphenyl, —$C_1$-$C_6$ alkyl-OH, —$C_1$-$C_6$ alkyl-SH, —$C_1$-$C_6$ alkyl-O-$C_1$-$C_6$ alkyl, —$OC_1$-$C_6$ haloalkyl, halo, —OH, mercapto, —$NH_2$, —$C_1$-$C_6$ alkyl-$NH_2$, —$N(C_1$-$C_6$ alkyl)$_2$, —$NH(C_1$-$C_6$ alkyl), —$N(C_1$-$C_6$ alkyl)($C_1$-$C_6$ alkylphenyl), —$NH(C_1$-$C_6$ alkylphenyl), cyano, nitro, oxo, —C(O)—OH, —$C(O)OC_1$-$C_6$ alkyl, —$CON(C_1$-$C_6$ alkyl)$_2$, —$CONH(C_1$-$C_6$ alkyl), —$CONH_2$, —$NHC(O)(C_1$-$C_6$ alkyl), —NHC(O)(phenyl), —$N(C_1$-$C_6$ alkyl)$C(O)(C_1$-$C_6$ alkyl), —$N(C_1$-$C_6$ alkyl)C(O)(phenyl), —$C(O)C_1$-$C_6$ alkyl, —$C(O)C_1$-$C_6$ alkylphenyl, —$C(O)C_1$-$C_6$haloalkyl, —$OC(O)C_1$-$C_6$ alkyl, —$S(O)_2$—$C_1$-$C_6$ alkyl, —S(O)—$C_1$-$C_6$alkyl, —$S(O)_2$-phenyl, —$S(O)_2$—$C_1$-$C_6$ haloalkyl, —$S(O)_2NH_2$, —$S(O)_2NH(C_1$-$C_6$ alkyl), —$S(O)_2NH$(phenyl), —$NHS(O)_2(C_1$-$C_6$ alkyl), —$NHS(O)_2$(phenyl), and —$NHS(O)_2(C_1$-$C_6$ haloalkyl).

In an embodiment of the compound of formula (I), each optionally substituted group above can be unsubstituted or independently substituted with one or more substituents independently chosen from hydroxyl, mercapto, halo, $C_1$-$C_6$ alkyl, $C_2$-$C_6$ alkenyl, $C_2$-$C_6$ alkynyl, —$OC_1$-$C_6$alkyl, —$NH_2$, —$N(C_1$-$C_6$alkyl)$_2$, —$NH(C_1$-$C_6$ alkyl), cyano, nitro, oxo, —$S(O)_2$—$C_1$-$C_6$ alkyl, —S(O)—$C_1$-$C_6$ alkyl, —$S(O)_2$—$C_1$-$C_6$ haloalkyl, —C(O)—OH, —$C_1$-$C_6$ alkyl-OH, —$C_1$-$C_6$ alkyl-SH, heterocyclyl.

In an embodiment of the compound of formula (I), $R^1$ is aryl or heteroaryl, each of which is optionally substituted by one or more substituents independently selected from halo, oxo, optionally substituted alkyl, —$(CH_2)_m$-optionally substituted heterocyclyl, —$(CH_2)_p$-optionally substituted cycloalkyl, —$(CH_2)_q$-optionally substituted heteroaryl, —$S(O)_nR^9$, —$(CH_2)_r$—$C(O)R^{10}$, optionally substituted alkenyl, optionally substituted alkynyl, —$OR^8$, wherein n is 1 or 2; m, p, q and r are independently chosen from 0, 1, 2, 3, 4, 5, 6; $R^8$, $R^9$ and $R^{10}$ are independently selected from hydrogen, alkyl, heterocyclyl, each of which except for hydrogen, is optionally substituted with one or more substituents independently selected from alkyl, oxo, heterocyclyl; wherein "optionally substituted alkyl", "optionally substituted heterocyclyl", "optionally substituted cycloalkyl", "optionally substituted heteroaryl", "optionally substituted alkenyl" and "optionally substituted alkynyl" in $R^1$ above can be unsubstituted or independently substituted with one or more substituents independently chosen from hydroxyl, mercapto, halo, $C_1$-$C_6$ alkyl, $C_2$-$C_6$ alkenyl, $C_2$-$C_6$ alkynyl, —$OC_1$-$C_6$ alkyl, —$NH_2$, —$N(C_1$-$C_6$ alkyl)$_2$, —$NH(C_1$-$C_6$ alkyl), cyano, nitro, oxo, —$S(O)_2$—$C_1$-$C_6$ alkyl, —S(O)—$C_1$-$C_6$ alkyl, —$S(O)_2$—$C_1$-$C_6$ haloalkyl, —C(O)—OH, —$C_1$-$C_6$ alkyl-OH, —$C_1$-$C_6$ alkyl-SH, heterocyclyl.

In an embodiment of the compound of formula (I), $R^1$ is aryl or heteroaryl, each of which is optionally substituted with one or more substituents independently selected from: (1) halo; (2) oxo; (3) alkyl optionally substituted with one or more substitutents independently selected from hydroxyl, mercapto, halo, —$OC_1$-$C_6$ alkyl, —$NH_2$, —$N(C_1$-$C_6$ alkyl)$_2$, —$NH(C_1$-$C_6$ alkyl), cyano, nitro, —$S(O)_2$—$C_1$-$C_6$ alkyl, —S(O)—$C_1$-$C_6$ alkyl, —C(O)—OH; (4) —$(CH_2)_m$-heterocyclyl optionally substituted with one or more substitutents independently selected from $C_1$-$C_6$ alkyl, —$C_1$-$C_6$ alkyl-OH, —$C_1$-$C_6$ alkyl-SH and oxo, wherein m is 0, 1, 2, 3, 4, 5 or 6; (5) —$(CH_2)_p$-unsubstituted cycloalkyl, wherein p is 0, 1, 2, 3, 4, 5 or 6; (6) —$(CH_2)_q$-heteroaryl optionally substituted with one or more substituents independently selected from $C_1$-$C_6$ alkyl, wherein q is 0, 1, 2, 3, 4, 5 or 6; (7) —$S(O)_nR^9$, wherein $R^9$ is $C_1$-$C_6$ alkyl, and n is 1 or 2; (8) —$(CH_2)_r$—$C(O)R^{10}$, wherein $R^{10}$ is heterocyclyl optionally substituted with one or more substitutents independently selected from $C_1$-$C_6$ alkyl and oxo, wherein r is 0, 1, 2, 3, 4, 5 or 6; (9) unsubstituted $C_2$-$C_6$ alkenyl; (10) unsubstituted $C_2$-$C_6$ alkynyl; (11) —$OR^8$, wherein $R^8$ is selected from hydrogen, alkyl optionally substituted with one or more substituents independently selected from heterocyclyl.

In an embodiment of the compound of formula (I), $R^1$ is aryl or heteroaryl, each of which is optionally substituted with one or more substituents independently selected from:
  (1) halo;
  (2) —$NR^6R^7$, wherein $R^6$ and $R^7$ are independently selected from hydrogen and $C_1$-$C_6$ alkyl optionally substituted with amino which is optionally substituted with $C_1$-$C_6$ alkyl;
  (3) —$OR^8$, wherein $R^8$ is selected from hydrogen and $C_1$-$C_6$ alkyl optionally substituted with one or more substituents independently selected from: heterocyclyl optionally substituted with —OH or mercapto, and amino optionally substituted with $C_1$-$C_6$ alkyl, (4) —S(O)$_n$R$^9$, wherein R$^9$ is $C_1$-$C_6$ alkyl, and n is 1 or 2;

(5) —(CH$_2$)$_r$—C(O)R$^{10}$, wherein R$^{10}$ is $C_1$-$C_6$ alkyl, or heterocyclyl optionally substituted with one or more substitutents independently selected from $C_1$-$C_6$ alkyl and oxo, wherein r is 0, 1, 2, 3, 4, 5 or 6;

(6) —CN;

(7) —C(O)NR$^6$R$^7$, wherein R$^6$ and R$^7$ are independently selected from hydrogen and $C_1$-$C_6$ alkyl optionally substituted with amino which is optionally substituted with $C_1$-$C_6$ alkyl;

(8) —NR$^6$C(O)R$^{10}$, wherein R$^6$ is H, and R$^{10}$ is $C_1$-$C_6$ alkyl;

(9) oxo;

(10) alkyl optionally substituted with one or more substituents independently selected from hydroxyl, mercapto, halo, —O$C_1$-$C_6$ alkyl, —NH$_2$, —N($C_1$-$C_6$ alkyl)$_2$, —NH($C_1$-$C_6$alkyl), cyano, nitro, —S(O)$_2$—$C_1$-$C_6$alkyl, —S(O)—$C_1$-$C_6$alkyl, —C(O)—OH;

(11) —(CH$_2$)$_p$-unsubstituted cycloalkyl, wherein p is 0, 1, 2, 3, 4, 5 or 6;

(12) —(CH$_2$)$_m$-heterocyclyl optionally substituted with one or more substitutents independently selected from $C_1$-$C_6$ alkyl, $C_3$-$C_8$ cycloalkyl, —$C_1$-$C_6$ alkyl-OH, —$C_1$-$C_6$ alkyl-SH, —$C_1$-$C_6$ alkyl-O—$C_1$-$C_6$ alkyl, —NH$_2$, —N($C_1$-$C_6$alkyl)$_2$, —NH($C_1$-$C_6$alkyl), oxo, —C(O)$C_1$-$C_6$alkyl, wherein m is 0, 1, 2, 3, 4, 5 or 6;

(13) —(CH$_2$)$_q$-heteroaryl optionally substituted with one or more substituents independently selected from $C_1$-$C_6$ alkyl, wherein q is 0, 1, 2, 3, 4, 5 or 6;

(14) unsubstituted $C_2$-$C_6$ alkenyl;

(15) unsubstituted $C_2$-$C_6$ alkynyl.

In any one of the preceding embodiments, R$^1$ is a radical of the ring or ring system chosen from

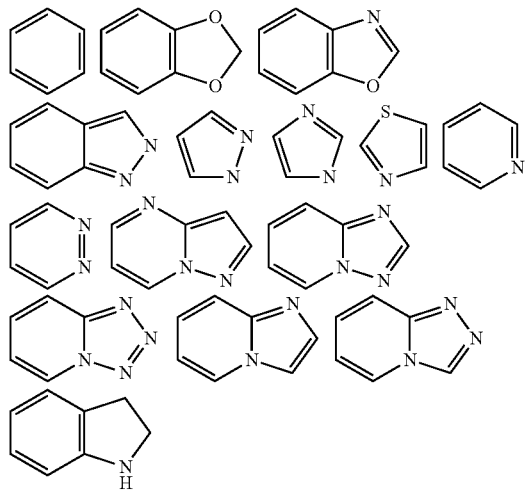

each of which is optionally substituted as defined above.

In any one of the preceding embodiments, R$^1$ is chosen from

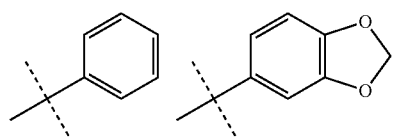

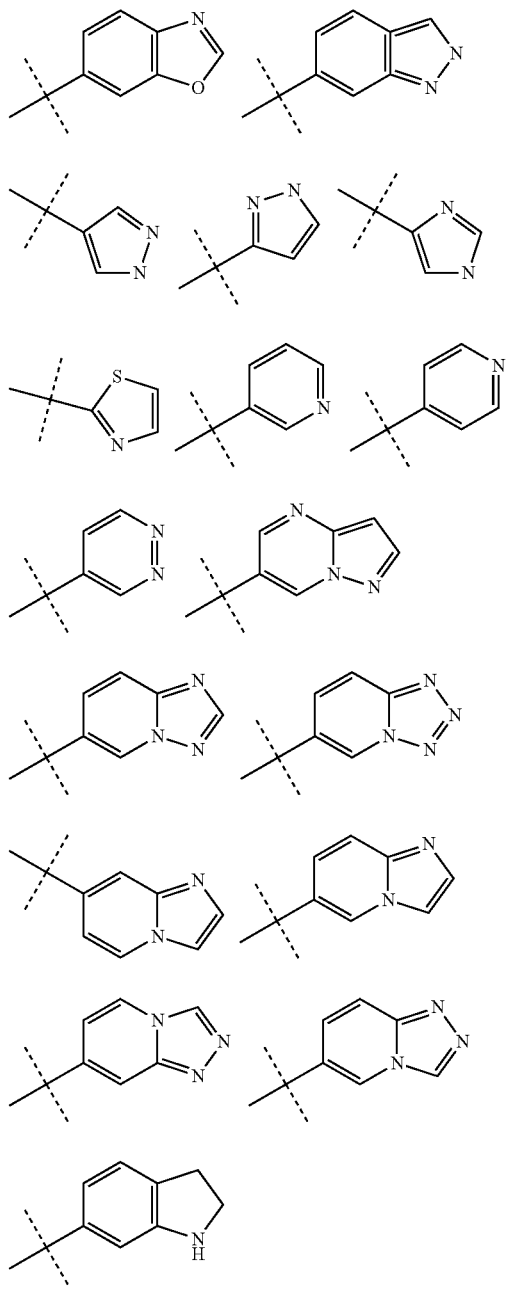

each of which is optionally substituted as defined above.

In an embodiment of the compound of formula (I), R$^8$ is hydrogen or $C_1$-$C_6$ alkyl optionally substituted with heterocyclyl.

In an embodiment of the compound of formula (I), R$^{10}$ is heterocyclyl optionally substituted with one or more substituents independently selected from $C_1$-$C_6$ alkyl and oxo.

In an embodiment of the compound of formula (I), R$^1$ is phenyl optionally substituted by one or more substituents independently selected from: (1) halo; (2) alkyl optionally substituted with —C(O)—OH; (3) —(CH$_2$)$_m$-heterocyclyl optionally substituted with one or more substitutents independently selected from $C_1$-$C_6$ alkyl, —$C_1$-$C_6$ alkyl-OH, —$C_1$-$C_6$ alkyl-SH and oxo, wherein m is 0, 1, 2, 3, 4, 5 or 6; (4) —(CH$_2$)$_q$-heteroaryl optionally substituted with one or more substituents independently selected from $C_1$-$C_6$ alkyl, wherein q is 0; (5) —$(CH_2)_r$—$C(O)R^{10}$, wherein $R^{10}$ is heterocyclyl optionally substituted with one or more substitutents independently selected from $C_1$-$C_6$ alkyl and oxo, wherein r is 0; (6) unsubstituted $C_2$-$C_6$ alkenyl; (7) unsubstituted $C_2$-$C_6$ alkynyl; (8) —$OR^8$, wherein $R^8$ is selected from hydrogen, alkyl optionally substituted with one or more substituents independently selected from heterocyclyl.

In an embodiment of the compound of formula (I), $R^1$ is phenyl substituted by piperazinyl, which piperizinyl is optionally substituted by one or more $C_1$-$C_6$ alkyl or $C_3$-$C_8$ cycloalkyl, preferably $C_1$-$C_6$ alkyl, more preferably, $R^1$ is phenyl substituted by piperazinyl, which is optionally substituted by one or more methyl or ethyl. In a specific embodiment, $R^1$ is phenyl substituted by piperazinyl, which piperizinyl is optionally substituted by one or more $C_1$-$C_6$ alkyl. In a more specific embodiment, $R^1$ is phenyl substituted by piperazinyl, which is optionally substituted by one or more methyl or ethyl.

In an embodiment of the compound of formula (I), $R^1$ is pyrazolyl, which is optionally substituted with one or more substituents selected from: (1) alkyl optionally substituted with one or more substitutents independently selected from hydroxyl, mercapto, halo, —$OC_1$-$C_6$ alkyl, —$NH_2$, —$N(C_1$-$C_6$ alkyl$)_2$, —$NH(C_1$-$C_6$ alkyl), —$S(O)_2$—$C_1$-$C_6$ alkyl, —$S(O)$—$C_1$-$C_6$ alkyl; (2) —$(CH_2)_m$-heterocyclyl optionally substituted with one or more substitutents independently selected from $C_1$-$C_6$ alkyl, wherein m is 0, 1, 2, 3, 4, 5 or 6; (3) —$(CH_2)_p$-unsubstituted cycloalkyl, wherein p is 0, 1, 2, 3, 4, 5 or 6; (4) —$(CH_2)_q$-heteroaryl optionally substituted with one or more substituents independently selected from $C_1$-$C_6$ alkyl, wherein q is 0, 1, 2, 3, 4, 5 or 6; (5) —$S(O)_nR^9$, wherein $R^9$ is $C_1$-$C_6$ alkyl, and n is 1 or 2; (6) —$(CH_2)_r$—$C(O)R^{10}$, wherein $R^{10}$ is heterocyclyl optionally substituted with one or more substitutents independently selected from $C_1$-$C_6$ alkyl and oxo, wherein r is 0, 1, 2, 3, 4, 5 or 6.

In any one of the preceding embodiments, $R^2$ is chosen from $C_1$-$C_6$ alkyl, $C_1$-$C_6$ alkoxy optionally substituted with hydroxyl, or $C_3$-$C_8$ cycloalkyl (preferably $C_3$-$C_6$ cycloalkyl).

In a specific embodiment, $R^2$ is methyl, ethyl, methoxy, ethoxy substituted with hydroxyl, isopropoxy or cyclopropyl. In a specific embodiment, $R^2$ is methyl.

In any one of the preceding embodiments, $R^3$, $R^4$ are independently chosen from hydrogen, halogen, —CN, or unsubstituted $C_1$-$C_6$ alkyl (preferably unsubstituted $C_1$-$C_3$ alkyl), $R^5$ is $C_1$-$C_6$ alkyl, preferably $C_1$-$C_3$ alkyl, or $R^3$ and $R^5$ together with the O atom to which $R^5$ is attached and the bond there-between form a 5- or 6-membered oxy-containing heterocyclic ring. In a specific embodiment, $R^3$ is hydrogen, F, Cl, Br, —CN, methyl, $R^4$ is hydrogen or F, $R^5$ is methyl or ethyl. In another specific embodiment, $R^4$ is hydrogen, and $R^3$ and $R^5$ together with the O atom to which $R^5$ is attached and the bond there-between form furan or dihydrofuran ring.

In a specific embodiment, the compound of formula (I) is selected from Compounds 1-309 prepared in the Examples.

In another aspect, the present invention provided a pharmaceutical composition, comprising at least one compounds of formula (I) and/or at least one pharmaceutically acceptable salt thereof described herein and optionally at least one pharmaceutically acceptable carrier.

In another aspect, the present invention provides a method of in vivo or in vitro inhibiting the activity of FGFR, comprising contacting FGFR with an effective amount of at least one compound of formula (I) and/or at least one pharmaceutically acceptable salt thereof described herein.

In another aspect, the present invention provides a method of treating a disease responsive to inhibition of FGFR, comprising administering to a subject in need thereof an effective amount to treat said disease of at least one compound of formula (I) and/or at least one pharmaceutically acceptable salt thereof described herein.

In another aspect, the present invention provides use of at least one compound of formula (I) and/or at least one pharmaceutically acceptable salt thereof described herein for treating a disease responsive to inhibition of FGFR.

In another aspect, the present invention provides use of at least one compound of formula (I) and/or at least one pharmaceutically acceptable salt thereof described herein in the manufacture of a medicament for treating a disease responsive to inhibition of FGFR.

In some embodiments, said disease responsive to inhibition of FGFR is cancer, for example, lung cancer, stomach cancer, liver cancer, breast cancer, ovarian cancer, endometrial carcinoma, or bladder carcinoma.

The compound of formula (I) described herein and/or a pharmaceutically acceptable salt thereof described herein can be synthesized from commercially available starting materials by methods well known in the art, taken together with the disclosure in this patent application. The following schemes illustrate methods for preparation of some of the compounds disclosed herein.

Scheme I

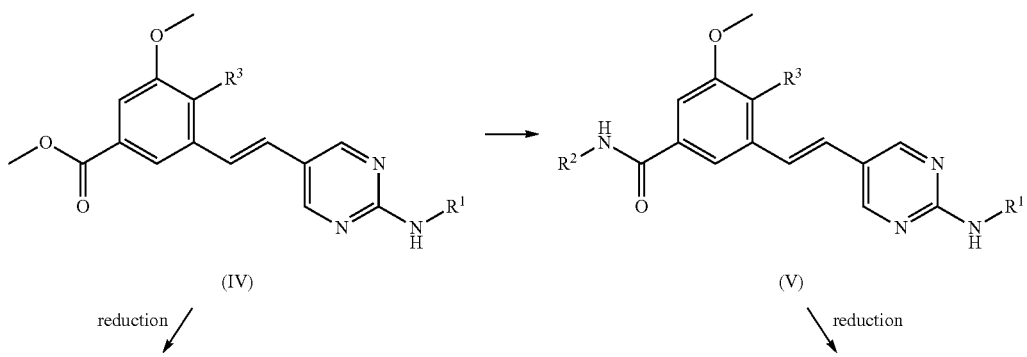

(IV)    (V)

reduction    reduction

-continued


(III)    (II)    (I)

As shown in Scheme I, compounds of formula (I) can be obtained from the reduction of compounds of formula (V). The reduction could be conducted with hydrogen in the presence of a catalyst such as palladium or platinum etc, or conducted with other reductants such as 4-methylbenzene-sulfonohydrazide etc. Compounds of formula (V) can be obtained from compounds of formula (IV) with the aminolysis reaction without or with other reagent such as trimethylaluminum. In other embodiments compounds of formula (I) can be obtained from compounds of formula (III), which can be obtained from the reduction of compounds of formula (IV), with the method of hydrolysis reaction and then the coupling reaction or with other suitable methods that could be recognized by one skilled in the art. And $R^1$, $R^2$ and $R^3$ are as defined hereinbefore.

Pharmaceutical Compositions and Utility

A composition comprising at least one compounds of formula (I) and/or at least one pharmaceutically acceptable salt thereof described herein can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are Scheme II


(VI)    (VII)    (VIII)

As shown in Scheme II, compounds of formula (VIII) can be obtained from the compounds of formula (VI) under the conditions described in Scheme I. And $R^1$, $R^2$, $R^3$ and Y are as defined hereinbefore. The compounds thus obtained can be further modified at their peripheral positions to provide the desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the compound of formula (I) and/or a pharmaceutically acceptable salt thereof described herein can be purified by column chromatography, high performance liquid chromatography, crystallization or other suitable methods.

also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable Intermediate can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the Intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compound of formula (I) and/or a pharmaceutically acceptable salt thereof described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the compound of formula (I) and/or a pharmaceutically acceptable salt thereof described herein, in inhibiting the activity of FGFR kinase. The compound of formula (I) and/or a pharmaceutically acceptable salt thereof described herein can further be examined for efficacy in treating inflammatory disease by in vivo assays. For example, the compound of formula (I) and/or a pharmaceutically acceptable salt thereof described herein can be administered to an animal (e.g., a mouse model) having inflammatory disease and its therapeutic effects can be accessed. Based on the results, an appropriate dosage range and administration route for animals, such as humans, can also be determined.

The compound of formula (I) and/or a pharmaceutically acceptable salt thereof described herein can be used to achieve a beneficial therapeutic or prophylactic effect, for example, in subjects with cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the examples of the cancer to be treated include, but are not limited to lung cancer (such as squamous non-small cell lung cancer (NSCLC), small cell lung cancer (SCLC)), stomach cancer, liver cancer, breast cancer, ovarian cancer, endometrial carcinoma, and bladder carcinomas.

In some embodiments, the compound of formula (I) and/or a pharmaceutically acceptable salt thereof described herein is administered in conjunction with another therapeutic agent. In some embodiments, the other therapeutic agent is one that is normally administered to patients with the disease or condition being treated. The compound of formula (I) and/or a pharmaceutically acceptable salt thereof described herein may be administered with the other therapeutic agent in a single dosage form or as a separate dosage form. When administered as a separate dosage form, the other therapeutic agent may be administered prior to, at the same time as, or following administration of the compound of formula (I) and/or a pharmaceutically acceptable salt thereof described herein.

In some embodiments, the compound of formula (I) and/or a pharmaceutically acceptable salt thereof described herein is administered in conjunction with an anti-neoplastic agent. As used herein, the term "anti-neoplastic agent" refers to any agent that is administered to a subject with cancer for purposes of treating the cancer. Nonlimiting examples anti-neoplastic agents include: radiotherapy; immunotherapy;

DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees Centigrade, and pressure is at or near atmospheric. All MS data were checked by agilent 6120 and/or agilent 1100. $^1$H-NMR spectra were recorded on an instrument operating at 400 MHz. NMR spectra were obtained as CDCl$_3$ solutions (reported in ppm), using chloroform as the reference standard (7.26 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), q (quarter), br (broadened), dd (doublet of doublets) dt (doublet of triplets). Coupling constants, when given, are reported in Herz (Hz). All reagents, except intermediates, used in this invention are commercially available. All compound names except the reagents were generated by Chemdraw.

In addition, for convenience and as clearly understood by those skilled in the art, not all hydrogen atoms have been expressly indicated as bonding to each carbon and/or nitrogen atom. For example, Compound 16 is depicted by the formula

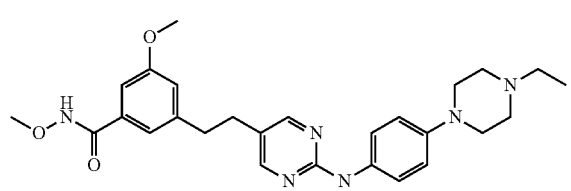 [SMILES: CCN1CCN(c2ccc(Nc3ncc(CCc4cc(OC)cc(C(=O)NOC)c4)cn3)cc2)CC1]

in Example 3 below, wherein one hydrogen atom bonding to the nitrogen atom between the pyrimidine ring and the phenyl ring has been omitted. Correspondingly, this formula represents the same compound as the formula

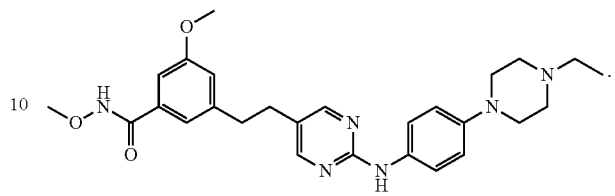

In the following examples, the abbreviations below are used:
AIBN a,a'-azo-isobutyronnitrile
CCl$_4$ perchloromethane
DCM dichloromethane
DEAD Diethyl azodicarboxylate
DIPEA N,N-diisopropylethylamine
DMF N,N-dimethylformamide
EA ethyl acetate
h hour(s)
HATU O-(7-azabenzotriazol-1-yl)-N,N,N',N'-tetra-methyluronium hexafluorophosphate
ISCO combiflash chromatograph
KHMDS potassium bis(trimethylsilyl)amide
mL milliliter(s)
min minute(s)
MeOH methanol
NBS N-bromosuccinimide
NIS N-iodosuccinimide
PE petroleum ether
Pd(dppf)Cl$_2$.CH$_2$Cl$_2$ 1,1'-Bis(diphenylphosphino)ferrocene-palladium(II)dichloride dichloromethane complex
Pd(PPh$_3$)$_4$ tetrakis(triphenylphosphine)palladium(0)
PdCl$_2$(PPh$_3$)$_2$ bis(triphenylphosphine)palladium(II)dichloride
PPh$_3$ triphenylphosphine
PTLC preparative thin-layer chromatography
THF tetrahydrofuran
TFA trifluoroacetic acid
Xantphos 4,5-Bis(diphenylphosphino)-9,9-dimethylxanthene Intermediate 1

Methyl 3-bromo-4-fluoro-5-methoxybenzoate

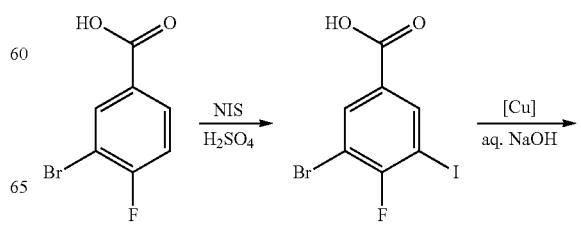

-continued

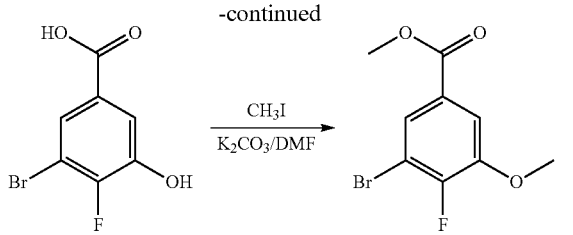

(A) 3-bromo-4-fluoro-5-iodobenzoic acid

To a mixture of 3-bromo-4-fluorobenzoic acid (45 g, 0.21 mol) in $H_2SO_4$ (96%, 150 mL) was added NIS (50 g, 0.22 mol) in portions at 0° C. in 30 min. The mixture was stirred at room temperature for 2 h. Then the mixture was diluted by ice water, filtered. The filter cake was washed by ice water, dried to afford the title compound as a yellow solid (60 g, 84.7% yield). MS (m/z): 342.7, 344.7 (M–H)⁻.

(B) 3-bromo-4-fluoro-5-hydroxybenzoic acid

A mixture of 3-bromo-4-fluoro-5-iodobenzoic acid (60 g, 0.17 mol), $Cu_2O$ (3.0 g, 0.021 mol) and NaOH (35 g, 0.88 mol) in water (600 mL) was heated at 100° C. for 16 h. The reaction mixture was then cooled to room temperature and filtered. The filtrate was acidified with aq. HCl (5N) and extracted with EA. The organic layer was separated, concentrated and dried to afford the title compound as a yellow solid (35 g, 85.6% yield).

(C) Methyl 3-bromo-4-fluoro-5-methoxybenzoate

To a mixture of 3-bromo-4-fluoro-5-hydroxybenzoic acid (35 g, 0.15 mol) and $K_2CO_3$ (45 g, 0.32 mol) in DMF (150 mL) was added iodomethane (45 g, 0.32 mol) at room temperature. The mixture was stirred at 80° C. for 4 h. The mixture was then diluted by water, extracted by EA. The organic layer was separated and concentrated, and the residue was then purified via silica gel chromatography (PE/EA) to afford the title compound as a white solid (15 g, 38.3% yield). MS (m/z): 263.2, 265.2 (M+H)⁺.

The following intermediates were prepared according to the procedures of intermediate 1 using the corresponding intermediates and reagents under appropriate conditions that could be recognized by one skilled in the art.

| Intermediate | Structure | MS (m/z) (M + H)⁺ |
|---|---|---|
| 2 | | 199.1 |
| 3 | | 215.0 |
| 4 | 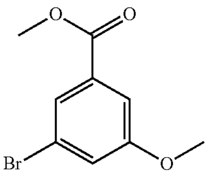 | 245.0/247.0 |
| 5 | 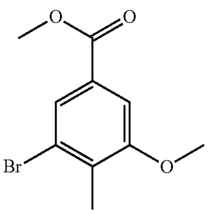 | 259.0/261.0 |
| 6 | 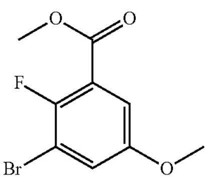 | 262.8/264.8 |
| 7 | 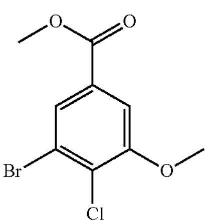 | 278.9/280.9 |
| 8 | 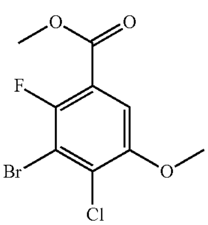 | 297.0/299.0 |

Intermediate 9

Methyl 4-bromo-3-iodo-5-methoxybenzoate

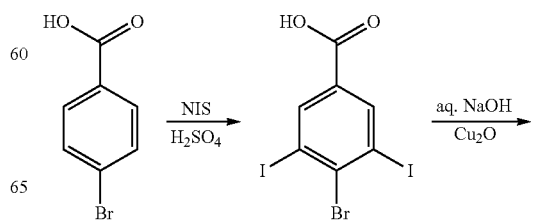

-continued

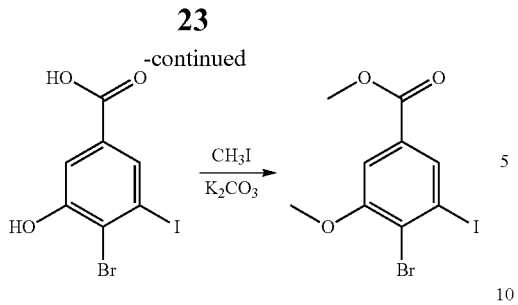

(A) 4-bromo-3,5-diiodobenzoic acid

To a mixture of 4-bromobenzoic acid (2.7 g, 13 mmol) in H$_2$SO$_4$ (96%, 50 mL) was added NIS (7.5 g, 33 mmol) in portions at 0° C. in 15 min and the resulting mixture was stirred at room temperature for 2 h. Then the mixture was diluted by ice water, followed by Na$_2$SO$_3$ aqueous solution. Then the mixture was filtered. The filter cake was washed by ice water, dried to afford the title compound as a slight pink solid (5.8 g, 95.4% yield). MS (m/z): 450.5, 452.5 (M−H)$^-$.

(B) 4-bromo-3-hydroxy-5-iodobenzoic acid

A mixture of 4-bromo-3,5-diiodobenzoic acid (3.0 g, 6.6 mmol), Cu$_2$O (0.10 g, 0.70 mmol) and NaOH (1.4 g; 35 mmol) in water (30 mL) was heated at 80° C. for 3 h. The reaction mixture was then diluted by water, acidified by aq. HCl (10 N), then filtered. The filter cake was washed by ice water and dried to afford the title compound as a yellow solid (1.8 g, 79.2% yield). MS (m/z): 340.6, 342.6 (M−H)$^-$.

(C) Methyl 4-bromo-3-iodo-5-methoxybenzoate

To a mixture of 4-bromo-3-hydroxy-5-iodobenzoic acid (1.8 g, 5.3 mmol) and K$_2$CO$_3$ (1.8 g, 13 mmol) in DMF (30 mL) was added iodomethane (1.7 g, 12 mmol) at room temperature and then the mixture was stirred at 80° C. for 4 h. The mixture was then diluted by water, extracted by EA. The organic layer was separated and concentrated to afford the title compound as a grey solid (1.9 g, 97.6% yield). MS (m/z): 370.7, 372.7 (M+H)$^+$.

Intermediate 10

3-bromo-N,5-dimethoxybenzamide

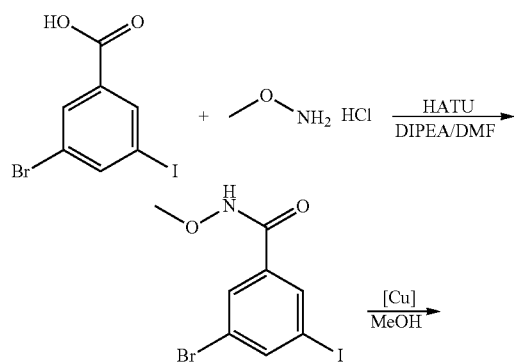

-continued

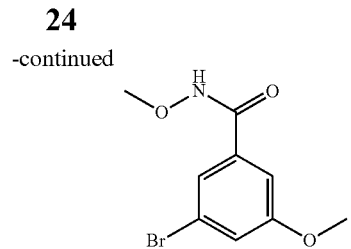

(A) 3-bromo-5-iodo-N-methoxybenzamide

To a solution of 3-bromo-5-iodobenzoic acid (5.0 g, 15 mmol) and methoxylamine hydrochloride (1.3 g, 16 mmol) in DCM (70 mL) was added HATU (7.0 g, 18 mmol) and DIPEA (4.0 g, 31 mmol). The resulting mixture was stirred at room temperature for 16 h, diluted by water and extracted by DCM. The combined organic layers were concentrated and the residue was purified via silica gel chromatography (DCM/MeOH) to afford the title compound as a white solid (4.2 g, 77.1% yield). MS (m/z): 356.2, 358.2 (M+H)$^+$.

(B) 3-bromo-N,5-dimethoxybenzamide

A mixture of 3-bromo-5-iodo-N-methoxybenzamide (3.6 g, 10 mmol), CuI (0.20 g, 1.1 mmol), 1, 10-phenanthroline (0.38 g, 2.1 mmol) and Cs$_2$CO$_3$ (4.6 g, 14 mmol) in MeOH (20 mL) was heated at 100° C. for 1 h under microwave. The mixture was then filtered and the filter cake was washed by MeOH (20 mL). The filtrate was concentrated and the residue was purified via silica gel chromatography (PE/EA) to afford the title compound as a coffee solid (1.1 g, 41.8% yield). MS (m/z): 262.0, 260.0 (M+H)$^+$.

Intermediate 11

Methyl 2,4-difluoro-5-methoxy-3-methylbenzoate

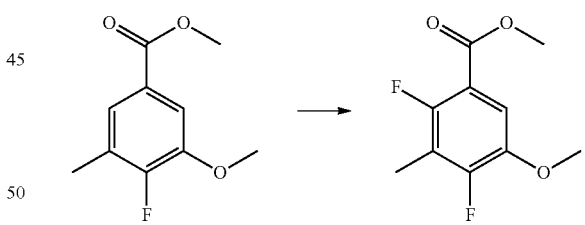

(A) Methyl 2,4-difluoro-5-methoxy-3-methylbenzoate

To a solution of methyl 4-fluoro-3-methoxy-5-methylbenzoate (5.0 g, 25.23 mmol) and 1-(chloromethyl)-4-fluoro-1,4-diazabicyclo[2.2.2]octane-1,4-diium tetrafluoroborate (9.8 g, 27.66 mmol) in acetonitrile (150 mL) was added acetic acid (30 mL) and the resulting mixture was stirred at 70° C. for 18 h under nitrogen atmosphere. The volatiles were removed under reduced pressure and the residue was purified via silica gel column chromatography (eluted with EA in PE 0~100%) to afford the title compound as a white solid (1.50 g, 27.5% yield). MS (m/z): 217.0 (M+H)$^+$.

Intermediate 12

Methyl 3-(bromomethyl)-4-chloro-5-methoxybenzoate

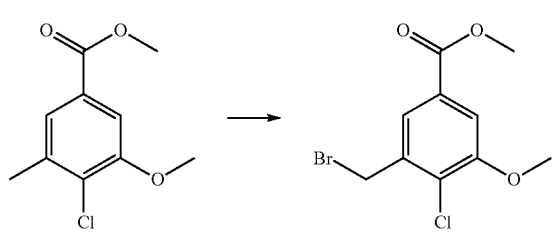

(A) Methyl 3-(bromomethyl)-4-chloro-5-methoxybenzoate

To a solution of methyl 4-chloro-3-methoxy-5-methylbenzoate (2.00 g, 9.32 mmol) in CCl$_4$ (40 mL) were added NBS (1.99 g, 11.18 mmol) and AIBN (153 mg, 0.93 mmol). Then the mixture was stirred at 70° C. for overnight. After cooled to room temperature, the mixture was partitioned between DCM and water. The aqueous layer was extracted with DCM. The combined organic layers was washed with water and brine, dried over anhydrous sodium sulfate and concentrated. The residue was suspended in PE (5 mL) and stirred for 1 h at room temperature. After filtration, the filter cake was washed with PE (2*2 mL), dried under reduced pressure at 60° C. for 1 h to give a yellow solid (2.66 g, 97.3% yield). MS (m/z): 293.0/295.0 (M+H)$^+$.

The following intermediate was prepared according to the procedures of intermediate 12 using the corresponding intermediates and reagents under appropriate conditions that could be recognized by one skilled in the art.

| Intermediate | Structure | MS (m/z) (M + H)$^+$ |
|---|---|---|
| 13 | ![structure] | 277.0/279.0 |
| 14 | ![structure] | 295.3/297.3 |

Intermediate 15

1-ethyl-1H-pyrazol-4-amine

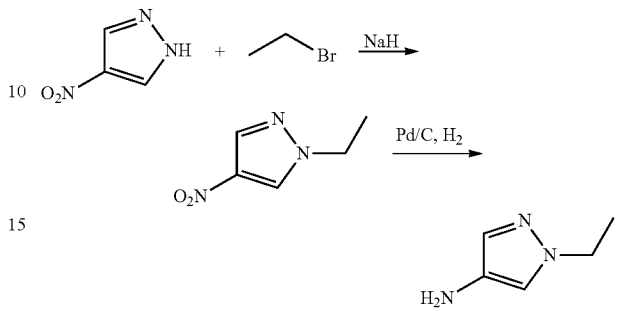

(A) 1-Ethyl-1H-pyrazol-4-amine

To a solution of 4-nitro-1H-pyrazole (500 mg, 4.42 mmol) in anhydrous THF (20 mL) was added NaH (60% dispersion in mineral oil, 353 mg, 8.84 mmol) in portions at 0° C. The resulting mixture was stirred at 0° C. for 10 min. Then 1-bromoethane (723 mg, 6.64 mmol) in anhydrous THF (2 mL) was added dropwise at 0° C. The mixture was stirred at ambient temperature for 16 h. Then reaction was quenched with H$_2$O (20 mL) and the volatiles were removed under reduced pressure. The resulting aqueous layer was extracted with EA (2*30 mL). The combined extracts were concentrated under reduced pressure. The residue was dissolved in MeOH (30 mL) and then Pd/C (10%, 100 mg) was added. The mixture was stirred at ambient temperature under hydrogen atmosphere for 16 h. The catalyst was filtered off. The filtrate was concentrated and the residue was purified via ISCO (eluted with MeOH in H$_2$O 0~100%) to afford the title compound as brown oil (260 mg, 52.9% yield, 2 steps). MS (m/z): 112.1 (M+H)$^+$.

Intermediate 16

(R)-tert-butyl 3-(4-amino-1H-pyrazol-1-yl)piperidine-1-carboxylate

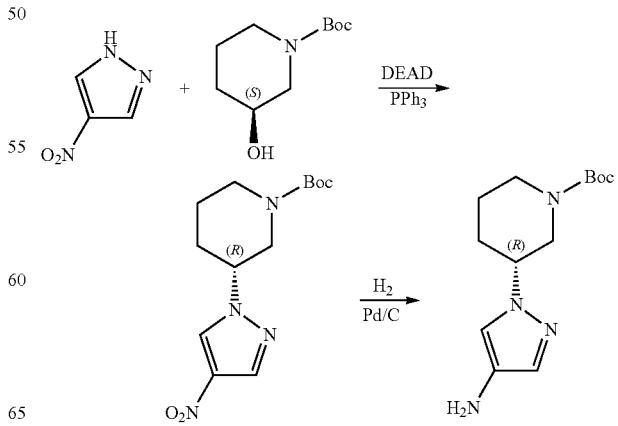

(A) (R)-tert-butyl 3-(4-nitro-1H-pyrazol-1-yl)piperidine-1-carboxylate

To a solution of 4-nitro-1H-pyrazole (1, 2.0 g, 17.7 mmol), (S)-tert-butyl 3-hydroxypiperidine-1-carboxylate (4.2 g, 21.2 mmol) and PPh$_3$ (6.9 g, 26.6 mmol) in THF (35 mL) was added DEAD (4.6 g, 26.6 mmol) dropwise with ice-water bath cooling. After addition, the mixture was stirred at room temperature for further 12 h. The resulting mixture was concentrated in vacuo. The residue was purified via silica gel chromatography (eluted with EA in PE 0-60%) to give a yellow oil (2.5 g, 47.7% yield). MS (m/z): 197.0 (M+H-100)$^+$.

(B) (R)-tert-butyl 3-(4-amino-1H-pyrazol-1-yl)piperidine-1-carboxylate

A mixture of (R)-tert-butyl 3-(4-nitro-1H-pyrazol-1-yl)piperidine-1-carboxylate (1.0 g, 3.37 mmol) and Pd/C (5%, 200 mg) in MeOH (20 mL) was stirred under 1 atm of H$_2$ at room temperature for 12 h. The resulting mixture was filtered and the filtrate was concentrated in vacuo to give a brown oil (920 mg, quantative yield). MS (m/z): 267.0 (M+H)$^+$.

The following intermediates were prepared according to the procedures of intermediate 16 using the corresponding intermediates and reagents under appropriate conditions that could be recognized by one skilled in the art.

| Intermediate | Structure | MS (m/z) (M + H)$^+$ |
|---|---|---|
| 17 | 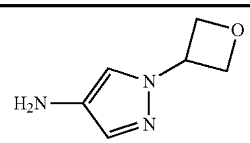 | 140.0 |
| 18 | 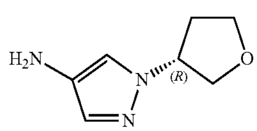 | 154.0 |
| 19 | 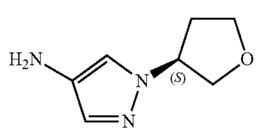 | 154.1 |
| 20 | 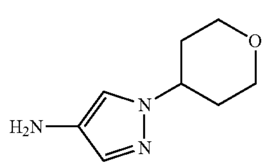 [SMILES: Nc1cnn(C2CCOCC2)c1] | 168.0 |
| 21 | 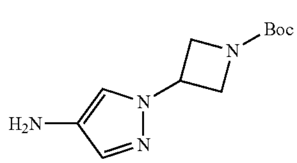 [SMILES: CC(C)(C)OC(=O)N1CC(n2cc(N)cn2)C1] | 182.9(M + H − 56)$^+$ |
| 22 | 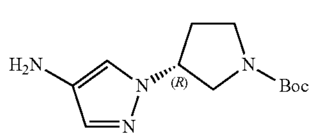 | 153.0(M + H − 100)$^+$ |
| 23 | | 153.1(M + H − 100)$^+$ |
| 24 | | 167.0(M + H − 100)$^+$ |
| 25 | | 267.1 |

Intermediate 26

(R)-1-(4-amino-1H-pyrazol-1-yl)propan-2-ol

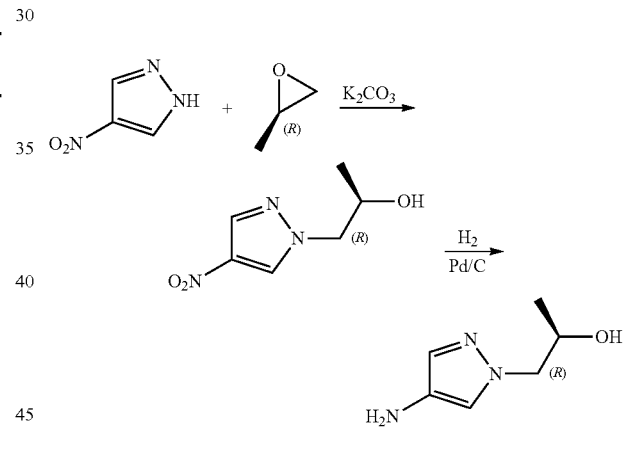

(A) (R)-1-(4-Nitro-1H-pyrazol-1-yl)propan-2-ol

To a solution of 4-nitro-1H-pyrazole (500 mg, 4.42 mmol) in DMF (5 mL) was added (R)-2-methyloxirane (282 mg, 4.86 mmol) and K$_2$CO$_3$ (1.2 g, 8.84 mmol). The resulting mixture was stirred at 60° C. in a sealed tube for 16 h. The reaction mixture was partitioned between H$_2$O (30 mL) and EA (30 mL). The organic layer was concentrated and purified via ISCO (PE/EA) to afford the title compound as a colorless oil (360 mg, 47.6% yield). MS (m/z): 171.9 (M+H)$^+$

(B) (R)-1-(4-Amino-1H-pyrazol-1-yl)propan-2-ol

To a solution of (R)-1-(4-nitro-1H-pyrazol-1-yl) propan-2-ol (140 mg, 0.82 mmol) in MeOH (30 mL) was added Pd/C (10%, 50 mg). The mixture was stirred at ambient temperature under hydrogen atmosphere for 16 h. The catalyst was filtered off and the filtrate was concentrated to afford the title compound as a brown oil (115 mg, 0.82 mmol, quantative yield). MS (m/z): 142.1 (M+H)⁺.

The following intermediate was prepared according to the procedures of intermediate 26 using the corresponding intermediates and reagents under appropriate conditions that could be recognized by one skilled in the art.

| Intermediate | Structure | MS (m/z) (M + H)⁺ |
|---|---|---|
| 27 | 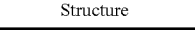 | 142.0 |

Intermediate 28

3-(4-ethylpiperazin-1-yl)aniline

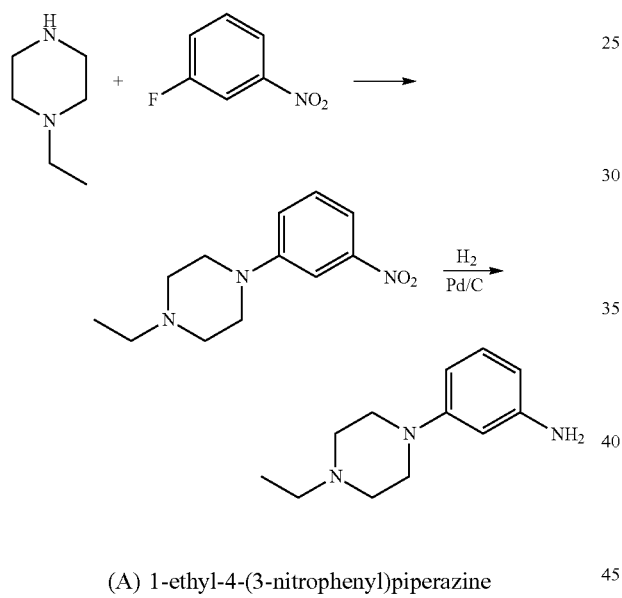

(A) 1-ethyl-4-(3-nitrophenyl)piperazine

A mixture of 1-ethylpiperazine (3.23 g, 0.0283 mol) and 1-fluoro-3-nitrobenzene (2.0 g, 0.0142 mol) was heated at reflux for 2 days. The resulting mixture was cooled and concentrated in vacuo. The residue was poured into water (50 mL), extracted with EA (2*50 mL). The combined extracts were washed with brine, concentrated in vacuo. The residue was purified via ISCO (eluted with EA in PE 0-70%) to give a yellow solid (1.80 g, 54.0% yield). MS (m/z): 236.1 (M+H)⁺.

(B) 3-(4-ethylpiperazin-1-yl)aniline

A mixture of 1-ethyl-4-(3-nitrophenyl)piperazine (1.8 g, 0.00765 mol) and Rany-Ni (1.0 g) in MeOH (20 mL) was stirred under 1 atm of H₂ at room temperature for 6 h. The resulting mixture was filtered and the filtrate was concentrated in vacuo to give a grey slurry (1.5 g, 95.5% yield). MS (m/z): 206.2 (M+H)⁺.

The following intermediates were prepared according to the procedures of intermediate 28 using the corresponding intermediates and reagents under appropriate conditions that could be recognized by one skilled in the art.

| Intermediate | Structure | MS (m/z) (M + H)⁺ |
|---|---|---|
| 29 | 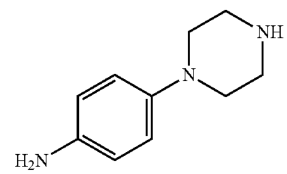 [SMILES: Nc1ccc(N2CCNCC2)cc1] | 178.1 |
| 30 | 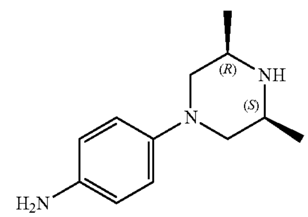 | 206.1 |

Intermediate 31

5-bromo-N-(4-((3R,5S)-3,5-dimethylpiperazin-1-yl)phenyl)pyrimidin-2-amine (A) 5-bromo-N-(4-((3R,5S)-3,5-dimethylpiperazin-1-yl)phenyl)pyrimidin-2-amine A mixture of 5-bromo-2-chloropyrimidine (392 mg, 2.03 mmol), 4-((3R,5S)-3,5-dimethylpiperazin-1-yl)aniline (416 mg, 1.968 mmol) and TFA (0.5 mL, 6.09 mmol) in propan-2-ol (5 mL) was stirred at 150° C. for 80 min under microwave. The resulting mixture was concentrated, basified with ammonia water, purified via ISCO (DCM/MeOH) to afford the title compound as a yellow solid (550 mg, 74.9% yield). MS (m/z): 362.0 (M+H)⁺.

The following intermediates were prepared according to the procedures of intermediate 31 using the corresponding intermediates and reagents under appropriate conditions that could be recognized by one skilled in the art.

| Intermediate | Structure | MS (m/z) (M + H)+ |
|---|---|---|
| 32 | HO-pyrimidine-NH-(1-ethylpyrazol-4-yl) | 206.1 |
| 33 | Br-pyrimidine-NH-(1-ethylpyrazol-4-yl) | 267.9/269.9 |
| 34 | Br-pyridine-NH-phenyl-(4-ethylpiperazin-1-yl) | 361.1/363.1 |
| 35 | Br-pyrimidine-NH-(3-(4-ethylpiperazin-1-yl)phenyl) | 362.1/364.1 |
| 36 | Br-pyrimidine-NH-(4-(4-ethylpiperazin-1-yl)phenyl) | 362.1/364.1 |

Intermediate 37

4-((6-bromopyridin-3-yl)methyl)morpholine

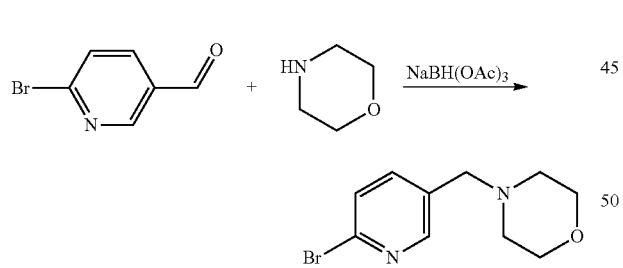

(A) 4-((6-bromopyridin-3-yl)methyl)morpholine

To a solution of 6-bromonicotinaldehyde (1.0 g, 5.4 mmol) and morpholine (0.50 g, 5.7 mmol) in 1,2-dichloroethane (30 mL) was added sodium triacetoxyborohydride (1.8 g, 8.5 mmol) and the resulting mixture was stirred at room temperature for 2 h. The mixture was concentrated and purified via ISCO (eluted with MeOH in H$_2$O 0~100%) to afford the title compound as a yellow solid (0.80 g, 57.9% yield). MS (m/z): 256.9/258.9 (M+H)$^+$.

Intermediate 38

1-(4-aminophenyl)pyridin-2(1H)-one

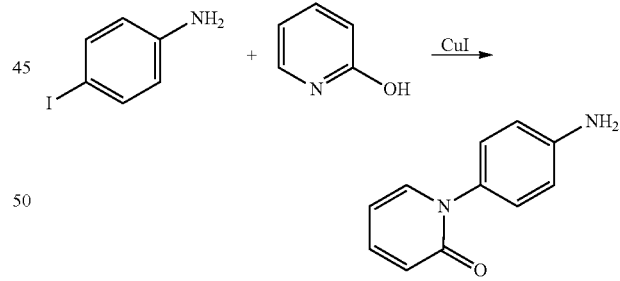

(A) 1-(4-aminophenyl)pyridin-2(1H)-one

A mixture of pyridin-2-ol (2.00 g, 21.0 mmol), 4-iodoaniline (4.61 g, 21.0 mmol), 8-quinolinol (0.61 g, 4.2 mmol), CuI (0.80 g, 4.2 mmol) and Cs$_2$CO$_3$ (10.26 g, 31.5 mmol) in DMSO (50 mL) was stirred at 120° C. for overnight. After filtration, the filtrate was partitioned between EA and water and the aqueous layer was further extracted with EA. The combined organic layers was washed with water and brine, dried over anhydrous sodium sulfate and concentrated to afford the title compound as a green solid (1.56 g, 39.8% yield). MS (m/z): 186.9 (M+H)$^+$.

Intermediate 39

(E)-Methyl 4-chloro-3-methoxy-5-(2-(4,4,5,5-tetramethyl-1,3,2-dioxaborolan-2-yl)vinyl)benzoate

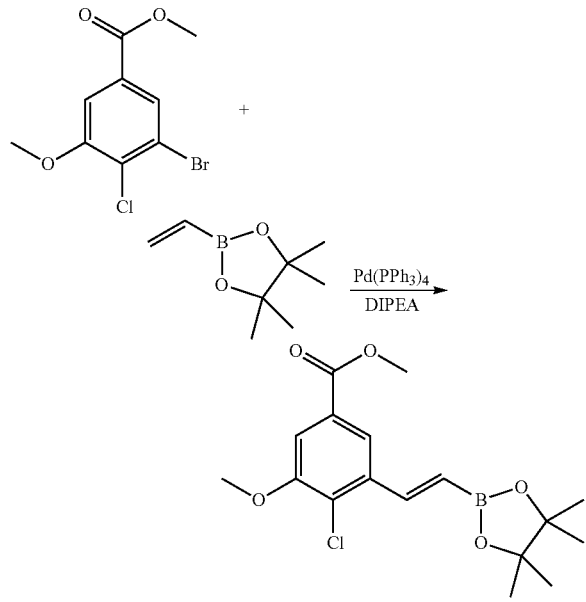

(A) (E)-Methyl 4-chloro-3-methoxy-5-(2-(4,4,5,5-tetramethyl-1,3,2-dioxaborolan-2-yl)vinyl)benzoate A mixture of methyl 3-bromo-4-chloro-5-methoxybenzoate (24 g, 86 mmol), 4,4,5,5-tetramethyl-2-vinyl-1,3,2-dioxaborolane (26.5 g, 172 mmol), Pd(PPh$_3$)$_4$ (6 g, 5.16 mmol) and DIPEA (27.7 g, 215 mmol) in anisole (450 mL) was stirred at 140° C. under nitrogen atmosphere for 16 h. The volatiles were removed under reduced pressure and the residue was purified via silica gel chromatography (eluted with PE/EA=10:1). The crude product after the purification was washed with PE again to afford the title compound as a yellow solid (14.5 g, 47.9% yield). MS (m/z): 353.1 (M+H)$^+$.

The following intermediates were prepared according to the procedures of intermediate 39 using the corresponding intermediates and reagents under appropriate conditions that could be recognized by one skilled in the art.

| Intermediate | Structure | MS (m/z) (M + H)$^+$ |
|---|---|---|
| 40 | 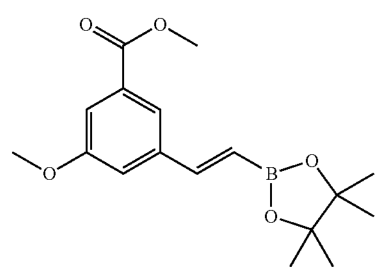 | 319.2 |
| 41 | 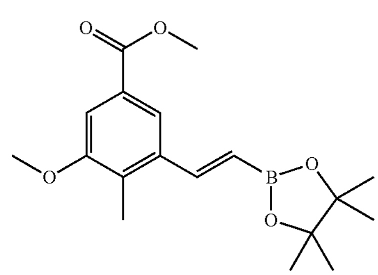 | 333.2 |
| 42 | 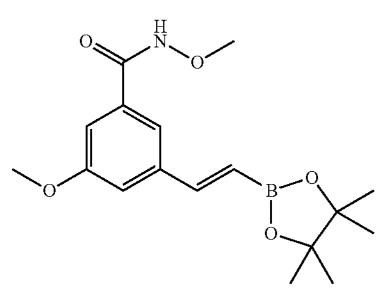 | 334.5 |

-continued

| Intermediate | Structure | MS (m/z) (M + H)+ |
|---|---|---|
| 43 | 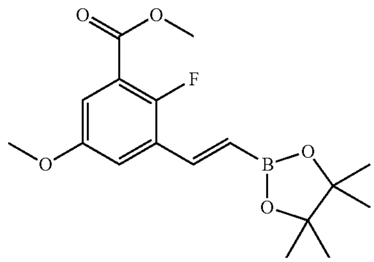 | 337.0 |
| 44 | 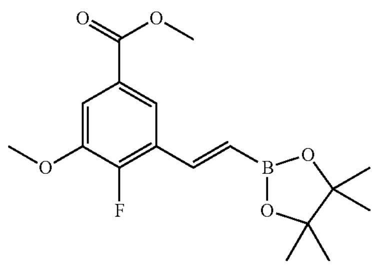 | 337.4 |
| 45 | 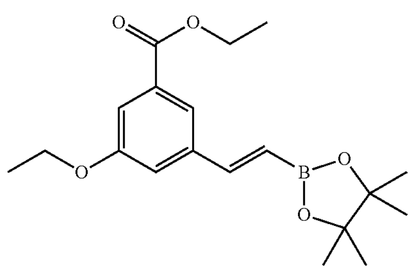 [SMILES: CCOC(=O)c1cc(/C=C/B2OC(C)(C)C(C)(C)O2)cc(OCC)c1] | 347.2 |
| 46 | 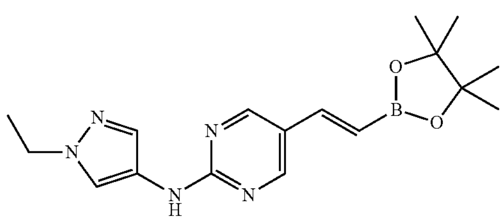 [SMILES: CCn1cc(Nc2ncc(/C=C/B3OC(C)(C)C(C)(C)O3)cn2)cn1] | 342.1 |
| 47 | 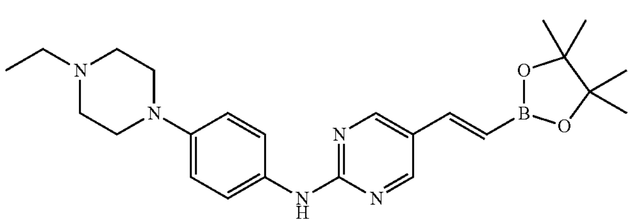 [SMILES: CCN1CCN(c2ccc(Nc3ncc(/C=C/B4OC(C)(C)C(C)(C)O4)cn3)cc2)CC1] | 436.3 |

Intermediate 48

(E)-Methyl 4-chloro-3-(2-(2-chloropyrimidin-5-yl)vinyl)-5-methoxybenzoate

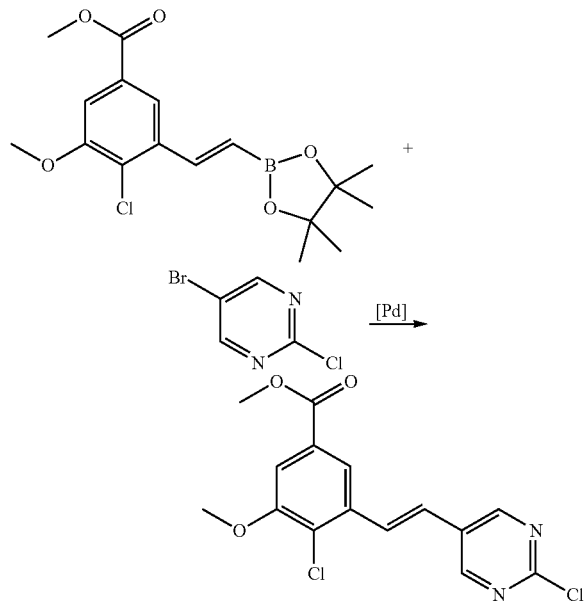

(A) (E)-methyl 4-chloro-3-(2-(2-chloropyrimidin-5-yl)vinyl)-5-methoxybenzoate A mixture of (E)-methyl 4-chloro-3-methoxy-5-(2-(4,4,5,5-tetramethyl-1,3,2-dioxaborolan-2-yl)vinyl)benzoate (8.0 g, 23 mmol), 5-bromo-2-chloropyrimidine (5.5 g, 28 mmol), $K_2CO_3$ (7.8 g, 56 mmol) and $Pd(dppf)Cl_2·CH_2Cl_2$ (0.80 g, 1.1 mmol) in dioxane (100 mL) and water (20 mL) was heated at 80° C. for 30 min. Then the mixture was concentrated and the residue was partitioned between water (400 mL) and DCM (300 mL). The aqueous layer was extracted with DCM (2*150 mL). The combined organic layers were concentrated. Then the residue was dispersed in ethanol (50 mL) and filtered. The filter cake was washed by ethanol (3*20 mL) and then dried to afford the title compound as a yellow solid (5.5 g, 71.5% yield). MS (m/z): 338.9 $(M+H)^+$.

The following intermediates were prepared according to the procedures of intermediate 48 using the corresponding intermediates and reagents under appropriate conditions that could be recognized by one skilled in the art.

| Intermediate | Structure | MS (m/z) (M + H)⁺ |
|---|---|---|
| 49 | 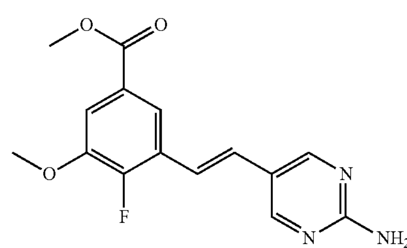 | 304.0 |
| 50 | 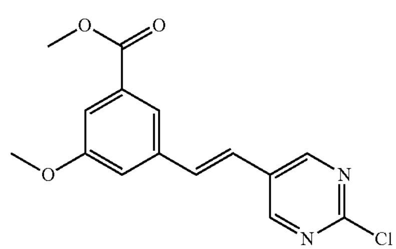 [SMILES: COC(=O)c1cc(/C=C/c2cnc(Cl)nc2)cc(OC)c1] | 305.0 |
| 51 | 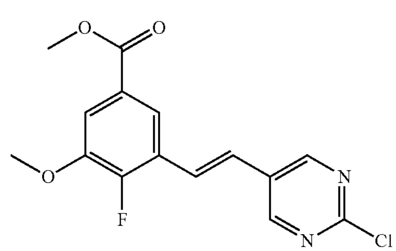 [SMILES: COC(=O)c1cc(/C=C/c2cnc(Cl)nc2)c(F)c(OC)c1] | 323.0 |

| Intermediate | Structure | MS (m/z) (M + H)+ |
|---|---|---|
| 52 | 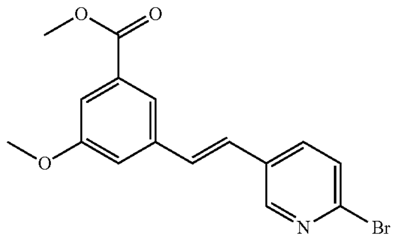 [SMILES: COC(=O)c1cc(/C=C/c2ccc(Br)nc2)cc(OC)c1] | 348.0/350.0 |
| 53 | 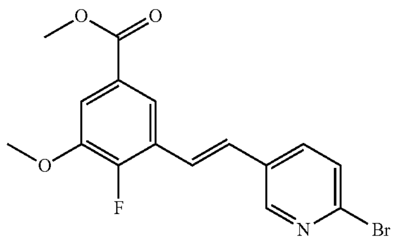 [SMILES: COC(=O)c1cc(/C=C/c2ccc(Br)nc2)c(F)c(OC)c1] | 365.8/367.8 |
Example 1: Synthesis of Compounds 1-8
Compound 1
3-(2-(2-((4-(4-ethylpiperazin-1-yl)phenyl)amino)pyrimidin-5-yl)ethyl)-5-methoxy-N-methylbenzamide
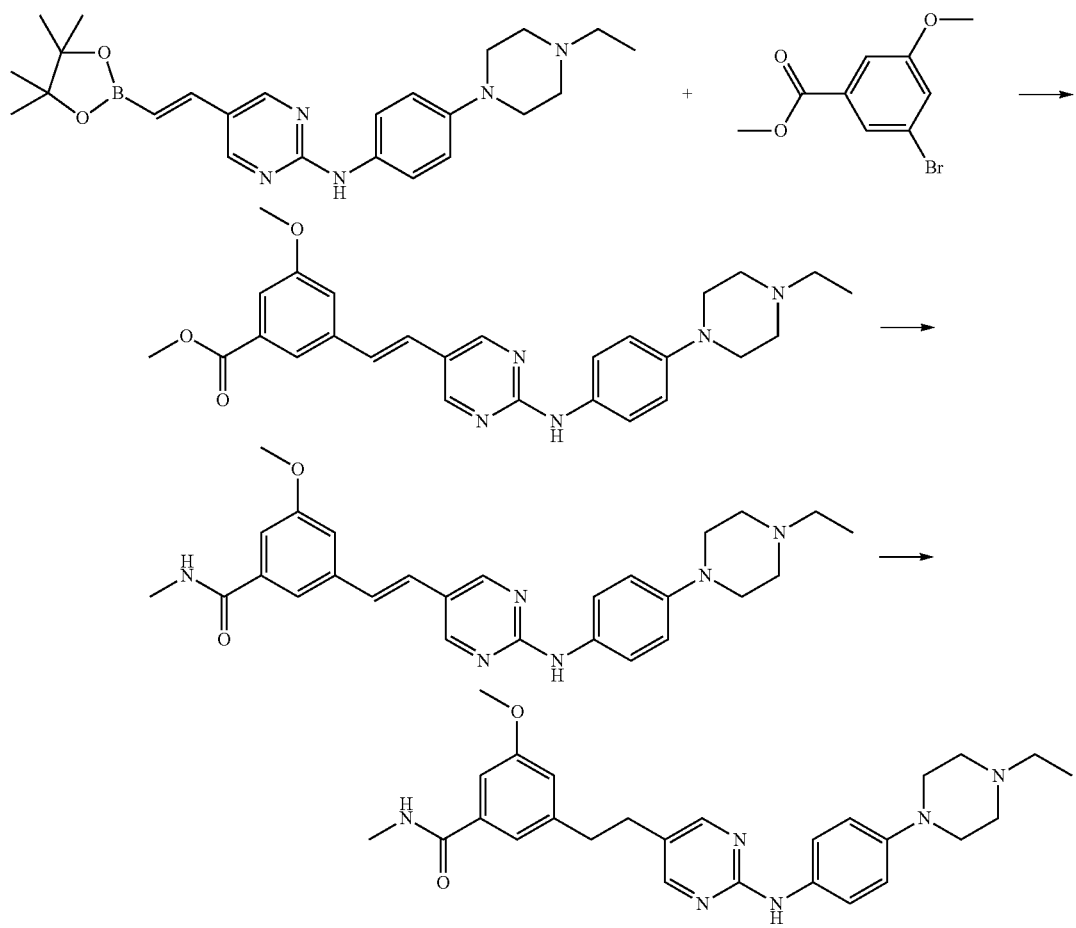

(A) (E)-methyl 3-(2-(2-(4-(4-ethylpiperazin-1-yl) phenylamino) pyrimidin-5-yl)vinyl)-5-methoxybenzoate A mixture of (E)-N-(4-(4-ethylpiperazin-1-yl)phenyl)-5-(2-(4,4,5,5-tetramethyl-1,3,2-dioxaborolan-2-yl)vinyl)pyrimidin-2-amine (170 mg, 0.39 mmol), methyl 3-bromo-5-methoxybenzoate (96 mg, 0.39 mmol), Pd(dppf)Cl$_2$.CH$_2$Cl$_2$ (16 mg, 0.020 mmol) and Na$_2$CO$_3$ (103 mg, 0.975 mmol) in 1,4-dioxane (4 mL) and water (1 mL) was stirred at 120° C. for 30 min under microwave. The resulting mixture was partitioned between 2N HCl (20 mL) and EA (30 mL). Then the aqueous layer was based with 2N NaOH to pH=8 and extracted with EA (2*30 mL). The combined extracts were concentrated to afford the title compound as an orange solid (100 mg, 54.1% yield). MS (m/z): 474.0 (M+H)$^+$.

(B) (E)-3-(2-(2-(4-(4-ethylpiperazin-1-yl)phenylamino)pyrimidin-5-yl)vinyl)-5-meth oxy-N-methylbenzamide A mixture of (E)-methyl 3-(2-(2-(4-(4-ethylpiperazin-1-yl)phenylamino)pyrimidin-5-yl)vinyl)-5-methoxybenzoate (100 mg, 0.211 mmol) and methylamine (5 mL, 35% solution in ethanol) was stirred at 120° C. for 50 min under microwave. The resulting mixture was partitioned between water (20 mL) and EA (20 mL). The aqueous layer was extracted with EA (2*20 mL). The combined organic layer was concentrated to afford the title compound as a yellow solid (60 mg, 60.1% yield). MS (m/z): 472.9 (M+H)$^+$.

(C) 3-(2-(2-(4-(4-ethylpiperazin-1-yl)phenylamino) pyrimidin-5-yl)ethyl)-5-methoxy-N-methylbenzamide To a mixture of (E)-3-(2-(2-(4-(4-ethylpiperazin-1-yl)phenylamino)pyrimidin-5-yl)vinyl)-5-methoxy-N-methylbenzamide (60 mg, 0.127 mmol) in MeOH (20 mL) was added Pd/C(10%, 20 mg). The resulting mixture was stirred at ambient temperature under hydrogen atmosphere for overnight. The resulting mixture was filtered through celite, the filtrate was concentrated, purified via PTLC (DCM/MeOH=15:1) to afford the title compound as a yellow solid (19 mg, 31.5% yield). MS (m/z): 474.9 (M+H)$^+$. $^1$H NMR (400 MHz, CD$_3$OD) δ 8.11 (s, 2H), 7.44 (d, J=9.0 Hz, 2H), 7.21 (s, 1H), 7.19 (s, 1H), 6.95 (d, J=9.0 Hz, 2H), 6.88 (s, 1H), 3.79 (s, 3H), 3.18-3.12 (m, 4H), 2.94 (t, J=7.4 Hz, 2H), 2.92 (s, 3H), 2.82 (t, J=7.4 Hz, 2H), 2.67-2.62 (m, 4H), 2.49 (q, J=7.2 Hz, 2H), 1.14 (t, J=7.2 Hz, 3H).

The following compounds were prepared according to the procedures of Compound 1 using the corresponding intermediates and reagents under appropriate conditions that could be recognized by one skilled in the art.

| Compound | Structure | LC-MS (m/z) (M + H)$^+$ | $^1$H NMR |
|---|---|---|---|
| 2 | 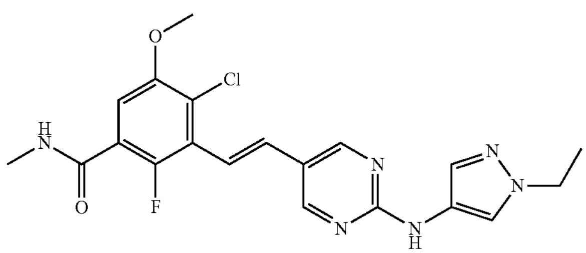 [SMILES: CCn1cc(Nc2ncc(/C=C/c3c(F)c(C(=O)NC)cc(OC)c3Cl)cn2)cn1] | 431.2 | $^1$H NMR (400 MHz, CDCl$_3$) δ 8.58 (s, 2H), 7.91 (s, 1H), 7.58 (d, J = 6.6 Hz, 1H), 7.53 (s, 1H), 7.12 (s, 2H), 6.96 (s, 1H), 6.78 (d, J = 9.3 Hz, 1H), 4.18 (q, J = 7.3 Hz, 2H), 3.96 (s, 3H), 3.06 (d, J = 4.8 Hz, 3H), 1.52 (t, J = 7.4 Hz, 3H). |
| 3 | 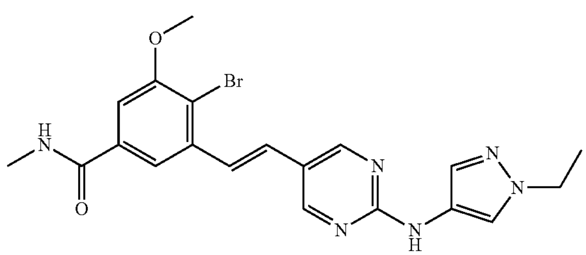 [SMILES: CCn1cc(Nc2ncc(/C=C/c3cc(C(=O)NC)cc(OC)c3Br)cn2)cn1] | 457.1/ 459.1 | $^1$H NMR (400 MHz, CD$_3$OD) δ 8.59 (s, 2H), 7.94 (s, 1H), 7.71 (d, J = 1.8 Hz, 1H), 7.57 (s, 1H), 7.44 (d, J = 16.3 Hz, 1H), 7.32 (d, J = 1.6 Hz, 1H), 7.00 (d, J = 16.3 Hz, 1H), 4.17 (q, J = 7.3 Hz, 2H), 3.98 (s, 3H), 2.99 (s, 3H), 1.51 (t, J = 7.3 Hz, 3H). |
| 4 | 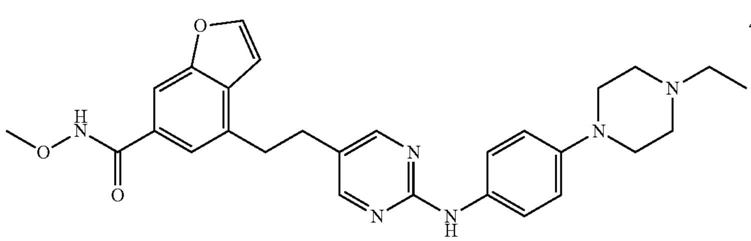 [SMILES: CCN1CCN(c2ccc(Nc3ncc(CCc4cc(C(=O)NOC)cc5occc45)cn3)cc2)CC1] | 485.2 | $^1$H NMR (400 MHz, CD$_3$OD) δ 8.06 (s, 2H), 7.85-7.82 (m, 2H), 7.55-7.52 (m, 1H), 7.46 (d, J = 9.0 Hz, 2H), 6.97 (d, J = 9.0 Hz, 2H), 6.91-6.89 (m, 1H), 3.40-3.32 (m, 4H), 3.27-3.23 (m, 4H), 3.19 (t, J = 7.6 Hz, 2H), 3.07 (q, J = 7.6 Hz, 2H), 2.95-2.90 (m, 5H), 1.33 (t, J = 7.6 Hz, 3H). |

| Compound | Structure | LC-MS (m/z) (M + H)+ | 1H NMR |
|---|---|---|---|
| 5 | 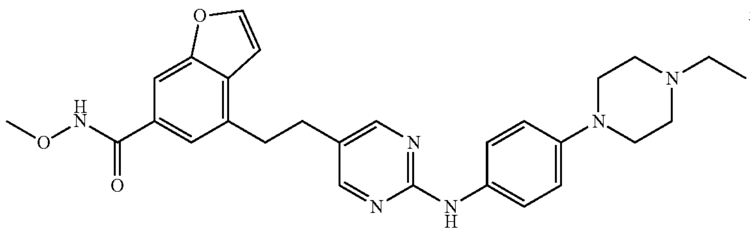 [SMILES: CCN1CCN(c2ccc(Nc3ncc(CCc4cc(C(=O)NOC)cc5occc45)cn3)cc2)CC1] | 501.2 | 1H NMR (400 MHz, CD3OD) δ 8.05 (s, 2H), 7.86 (s, 1H), 7.78 (s, 1H), 7.50-7.39 (m, 3H), 6.98-6.88 (m, 3H), 3.80 (s, 3H), 3.21-3.08 (m, 6H), 2.90 (t, J = 7.2 Hz, 2H), 272-2.61 (m, 4H), 2.51 (q, J = 7.1 Hz, 2H), 1.14 (t, J = 7.1 Hz, 3H). |
| 6 | 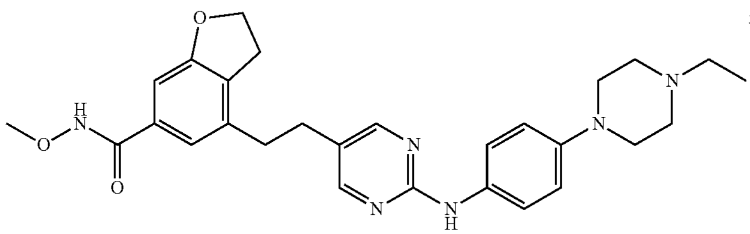 [SMILES: CCN1CCN(c2ccc(Nc3ncc(CCc4cc(C(=O)NOC)cc5c4CCO5)cn3)cc2)CC1] | 503.1 | 1H NMR (400 MHz, CD3OD) δ 8.00 (s, 2H), 7.35 (d, J = 9.0 Hz, 2H), 7.00 (d, J = 2.4 Hz, 1H), 6.89-6.84 (m, 3H), 4.42 (t, J = 8.7 Hz, 2H), 3.68 (s, 3H), 3.08-3.06 (m, 4H), 2.96 (t, J = 8.7 Hz, 2H), 2.79-2.69 (m, 4H), 2.59-2.56 (m, 4H), 2.42 (q, J = 7.2 Hz, 2H), 1.06 (t, J = 7.2 Hz, 3H). |
| 7 | 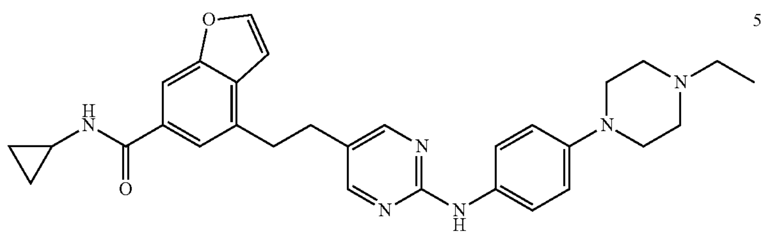 [SMILES: CCN1CCN(c2ccc(Nc3ncc(CCc4cc(C(=O)NC5CC5)cc5occc45)cn3)cc2)CC1] | 511.2 | 1H NMR (400 MHz, CD3OD) δ 8.05 (s, 2H), 7.85-7.83 (m, 2H), 7.53-7.50 (m, 1H), 7.42 (d, J = 7.2 Hz, 2H), 6.94 (d, J = 7.2 Hz, 2H), 6.91-6.89 (m, 1H), 3.18-3.14 (m, 6H), 2.90 (t, J = 7.5 Hz, 2H), 2.88-2.83 (m, 1H), 2.66-2.64 (m, 4H), 2.50 (q, J = 7.2 Hz, 2H), 1.14 (t, J = 7.2 Hz, 3H), 0.81-0.78 (m, 2H), 0.65-0.63 (m, 2H). |
| 8 | 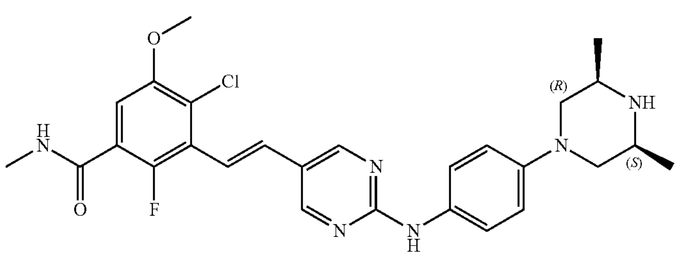 | 525.3 | 1H NMR (400 MHz, CDCl3) δ 8.56 (s, 2H), 7.57 (d, J = 6.5 Hz, 1H), 7.47 (d, J = 8.8 Hz, 2H), 7.13 (s, 1H), 7.11 (s, 2H), 6.94 (d, J = 8.8 Hz, 2H), 6.78 (d, J = 7.8 Hz, 1H), 3.96 (s, 3H), 3.51-3.44 (m, 2H), 3.12-3.07 (m, 2H), 3.06 (d, J = 4.7 Hz, 3H), 2.31 (t, J = 11.0 Hz, 2H), 1.16 (d, J = 6.3 Hz, 6H). |

Example 2: Synthesis of Compounds 9-13

Compound 9
3-(2-(2-((3-(4-ethylpiperazin-1-yl)phenyl)amino)pyrimidin-5-yl)ethyl)-5-methoxy-N-methylbenzamide

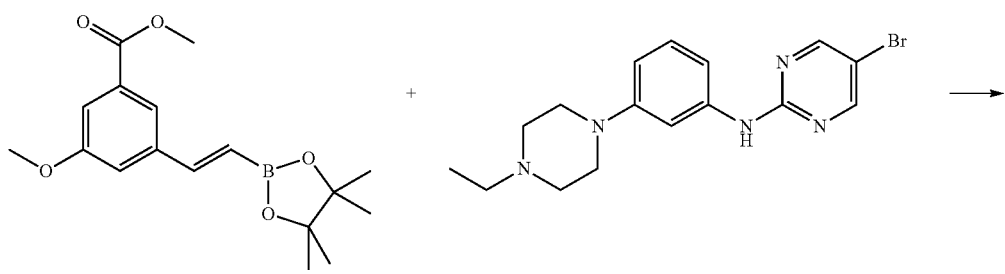

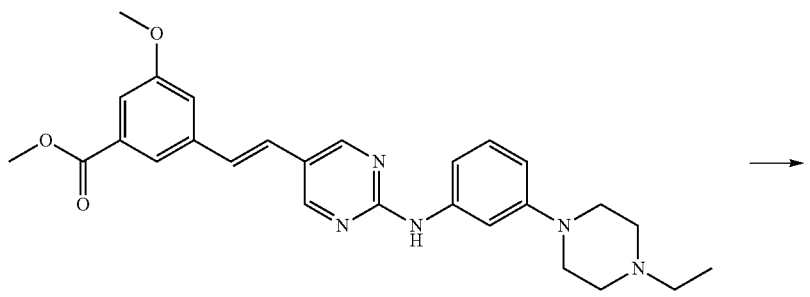

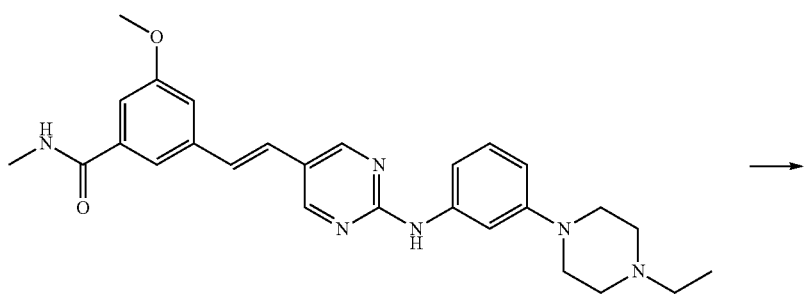

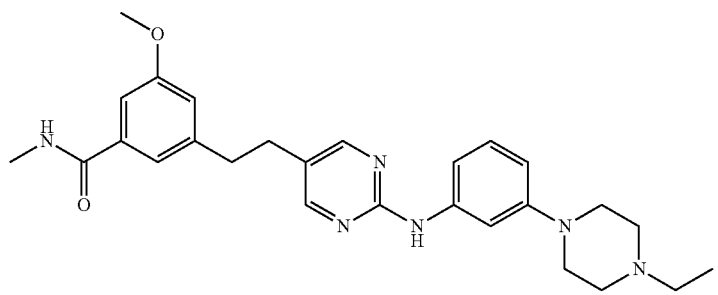

(A) (E)-methyl 3-(2-(2-((3-(4-ethylpiperazin-1-yl)phenyl)amino)pyrimidin-5-yl)vinyl)-5-methoxybenzoate A mixture of 5-bromo-N-(3-(4-ethylpiperazin-1-yl)phenyl)pyrimidin-2-amine (113 mg, 0.31 mmol), (E)-methyl 3-methoxy-4-(2-(4,4,5,5-tetramethyl-1,3,2-dioxaborolan-2-yl)vinyl)benzoate (100 mg, 0.31 mmol), $K_2CO_3$ (87 mg, 0.63 mmol), Pd(dffp)$_2$Cl$_2$·CH$_2$Cl$_2$ (20 mg, 0.022 mmol) and water (1 mL) in dioxane (5 mL) was heated at 100° C. for 1 h under microwave. The resulting mixture was cooled and concentrated in vacuo. The residue was dissolved in DCM (10 mL) and washed with water and brine. The organic layer was concentrated, purified via ISCO (eluted with MeOH in DCM 0-10%) to give a yellow solid (70 mg, 47.4% yield). MS (m/z): 462.2 (M+H)$^+$.

(B) (E)-3-(2-(2-((3-(4-ethylpiperazin-1-yl)phenyl)amino)pyrimidin-5-yl)vinyl)-5-methoxy-N-methyl-benzamide A mixture of (E)-methyl 3-(2-(2-((3-(4-ethylpiperazin-1-yl)phenyl)amino)pyrimidin-5-yl)vinyl)-5-methoxybenzoate (70 mg, 0.15 mmol) in methylamine (5 mL, 35% solution in ethanol) was heated at 120° C. for 30 min under microwave. The resulting mixture was cooled and concentrated in vacuo to give a yellow solid (70 mg, quantative yield). MS (m/z): 473.2 (M+H)$^+$.

(C) 3-(2-(2-((3-(4-ethylpiperazin-1-yl)phenyl)amino)pyrimidin-5-yl)ethyl)-5-methoxy-N-methyl-benzamide A mixture of (E)-3-(2-(2-((3-(4-ethylpiperazin-1-yl)phenyl)amino)pyrimidin-5-yl)vinyl)-5-methoxy-N-methylbenzamide (70 mg, 0.15 mmol) and Pd/C (5%, 25 mg) in MeOH (15 mL) was stirred under 1 atm of H$_2$ at 40° C. for 12 h. The resulting mixture was filtered and the filtrate was concentrated in vacuo. The residue was purified via PTLC (DCM/MeOH=10:1) to give the title compound as a white solid (23.0 mg, 32.8% yield). MS (m/z): 475.2 (M+H)$^+$. $^1$H NMR (400 MHz, CD$_3$OD) δ 8.18 (s, 2H), 7.37 (s, 1H), 7.24-7.21 (m, 2H), 7.18-7.11 (m, 2H), 6.89 (s, 1H), 6.65 (d, J=8.1 Hz) 3.83 (s, 3H), 3.31-3.26 (m, 4H), 2.95-2.82 (m, 1H), 2.75-2.67 (m, 2H), 1.23 (t, J=7.2 Hz, 3H).

The following compounds were prepared according to the procedures of Compound 9 using the corresponding intermediates and reagents under appropriate conditions that could be recognized by one skilled in the art.

| Compound | Structure | LC-MS (m/z) (M + H)+ | 1H NMR |
|---|---|---|---|
| 10 | 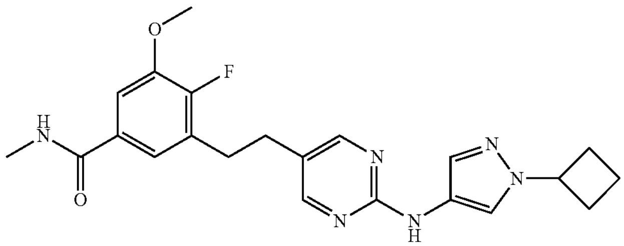 [SMILES: CNC(=O)c1cc(CCc2cnc(Nc3cnn(C4CCC4)c3)nc2)c(F)c(OC)c1] | 425.0 | 1H NMR (400 MHz, CDCl3) δ 8.15 (s, 2H), 7.91 (s, 1H), 7.44 (s, 1H), 7.32 (d, J = 6.0 Hz, 1H), 7.21 (s, 1H), 7.00 (d, J = 4.3 Hz, 1H), 4.77-4.69 (m, 1H), 3.90 (s, 3H), 2.97 (d, J = 4.6 Hz, 3H), 2.91 (t, J = 7.4 Hz, 2H), 2.79 (t, J = 7.3 Hz, 2H), 2.62-2.41 (m, 4H), 1.92-1.83 (m, 2H). |
| 11 | 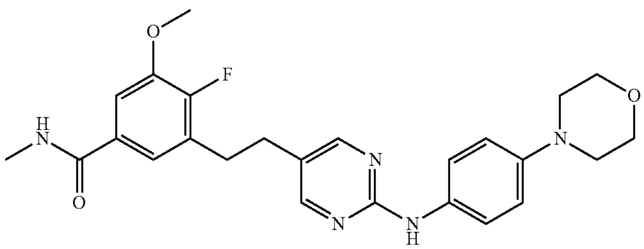 [SMILES: CNC(=O)c1cc(CCc2cnc(Nc3ccc(N4CCOCC4)cc3)nc2)c(F)c(OC)c1] | 465.9 | 1H NMR (400 MHz, DMSO-d6) δ 9.20 (s, 1H), 8.38 (d, J = 4.6 Hz, 1H), 8.20 (s, 2H), 7.53 (d, J = 9.1 Hz, 2H), 7.42 (d, J = 7.8 Hz, 1H), 7.37 (d, J = 4.3 Hz, 1H), 6.85 (d, J = 9.1 Hz, 2H), 3.83 (s, 3H), 3.75-3.67 (m, 4H), 3.03-2.96 (m, 4H), 2.88 (t, J = 7.3 Hz, 2H), 2.76-2.72 (m, 5H). |
| 12 | 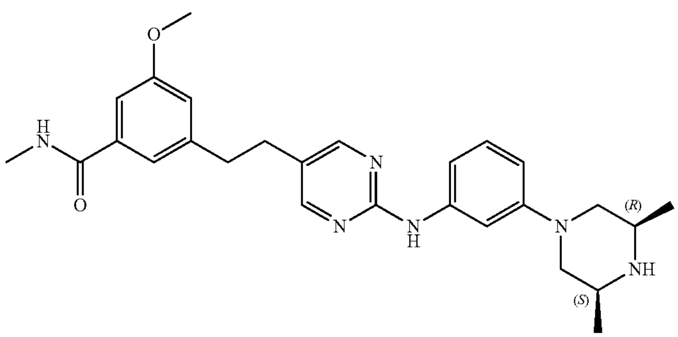 | 475.1 | 1H NMR (400 MHz, CD3OD) δ 8.17 (s, 2H), 7.29 (s, 1H), 7.22 (s, 1H), 7.20 (s, 1H), 7.15-7.08 (m, 2H), 6.88 (s, 1H), 6.62 (d, J = 7.7 Hz, 1H), 3.79 (s, 3H), 3.56-3.50 (m, 2H), 3.02-2.96 (m, 2H), 2.93-2.90 (m, 2H), 2.89 (s, 3H), 2.87-2.82 (m, 2H), 2.27 (t, J = 11.2 Hz, 2H), 1.14 (d, J = 6.4 Hz, 6H). |
| 13 | 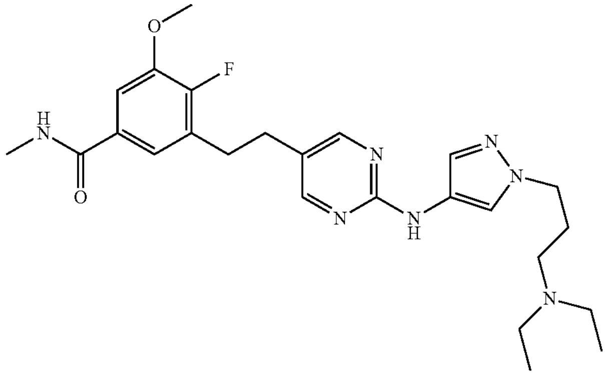 [SMILES: CCN(CC)CCCn1cc(Nc2ncc(CCc3cc(C(=O)NC)cc(OC)c3F)cn2)cn1] | 483.9 | 1H NMR (400 MHz, CD3OD) δ 8.14 (s, 2H), 7.95 (s, 1H), 7.53 (s, 1H), 7.41 (dd, J = 7.8 Hz, 2.1 Hz, 1H), 7.27 (dd, J = 6.0 Hz, 2.1 Hz, 1H), 4.15-4.09 (m, 2H), 3.88 (s, 3H), 2.94 (t, J = 7.6 Hz, 2H), 2.89 (s, 3H), 2.81 (t, J = 7.6 Hz, 2H), 2.55 (q, J = 7.2 Hz, 4H), 2.50-2.43 (m, 2H), 2.02-1.99 (m, 2H), 1.01 (t, J = 7.2 Hz, 6H). |

Example 3: Synthesis of Compounds 14-17

Compound 14
3-(2-(2-((3-(4-ethylpiperazin-1-yl)phenyl)amino)pyrimidin-5-yl)ethyl)-N,5-dimethoxybenzamide

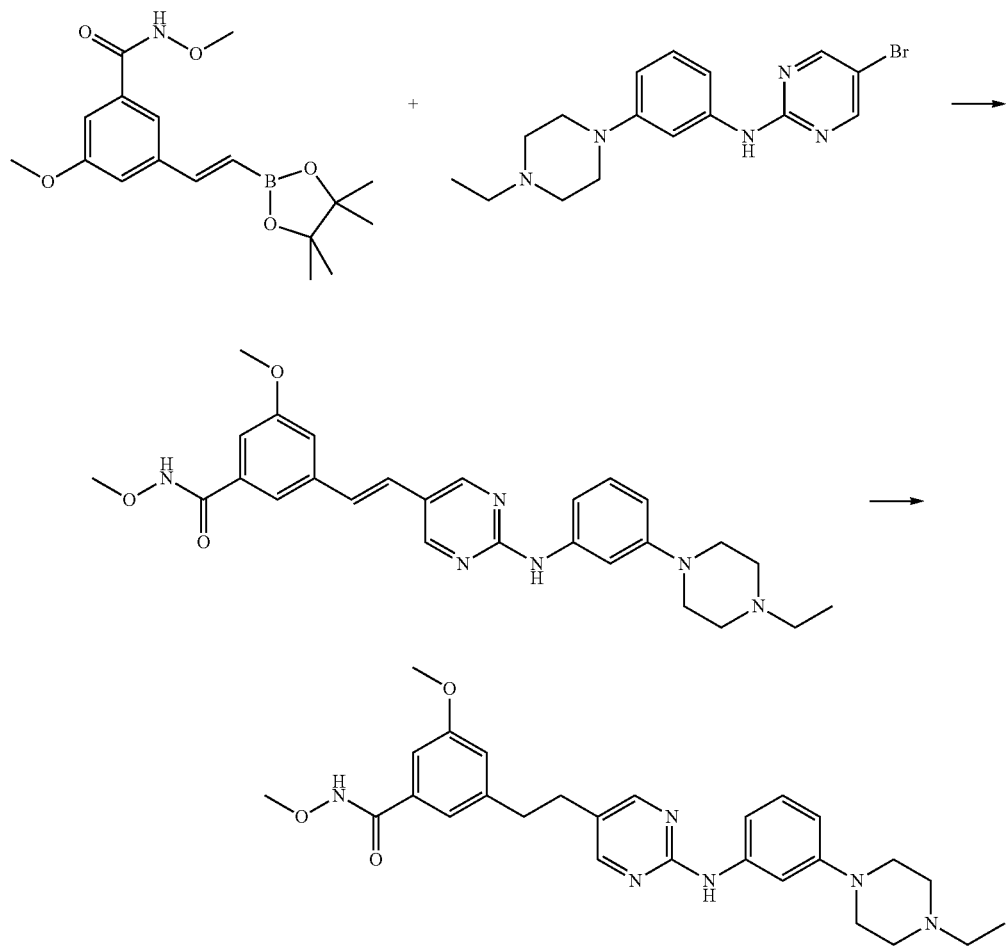

(A) (E)-3-(2-(2-((3-(4-ethylpiperazin-1-yl)phenyl)amino)pyrimidin-5-yl)vinyl)-N,5-dimethoxybenzamide A mixture of (E)-N,3-dimethoxy-5-(2-(4,4,5,5-tetramethyl-1,3,2-dioxaborolan-2-yl)vinyl)benzamide (0.10 g, 0.30 mmol), 5-bromo-N-(3-(4-ethylpiperazin-1-yl) phenyl) pyrimidin-2-amine (0.11 g, 0.30 mmol), Na$_2$CO$_3$ (0.07 g, 0.66 mmol) and Pd(dffp)$_2$Cl$_2$·CH$_2$Cl$_2$ (0.025 g, 0.034 mmol) in dioxane (5 mL) and water (1 mL) was heated at 100° C. for 30 min under microwave. Then the mixture was filtered and the filtrate was purified via ISCO (eluted with MeOH in H$_2$O 0~100%) directly to afford the title compound as a yellow solid (0.036 g, 24.6% yield). MS (m/z): 489.7 (M+H)$^+$.

(B) 3-(2-(2-((3-(4-ethylpiperazin-1-yl)phenyl)amino)pyrimidin-5-yl)ethyl)-N,5-dimethoxybenzamide A solution of (E)-3-(2-(2-((3-(4-ethylpiperazin-1-yl)phenyl)amino)pyrimidin-5-yl) vinyl)-N,5-dimethoxybenzamide (0.036 g, 0.078 mmol) in MeOH (15 mL) was added Pd/C (10%, 0.04 g) and the mixture was stirred at 35° C. for 40 h under hydrogen atmosphere. The mixture was filtered and the filtrate was concentrated. The residue was purified via PTLC (DCM/MeOH) to afford the title compound as a yellow solid (0.020 g, 55.3% yield). MS (m/z): 491.7 (M+H)$^+$. $^1$H NMR (400 MHz, CD$_3$OD) δ 8.19 (s, 2H), 7.34 (s, 1H), 7.22 (s, 1H), 7.19-7.08 (m, 3H), 6.68-6.59 (m, 2H), 3.76 (s, 3H), 3.71 (s, 3H), 3.23-3.17 (m, 4H), 2.89-2.79 (m, 4H), 2.68-2.61 (m, 4H), 2.49 (q, J=7.3 Hz, 2H), 1.14 (t, J=7.2 Hz, 3H).

The following compounds were prepared according to the procedures of Compound 14 using the corresponding intermediates and reagents under appropriate conditions that could be recognized by one skilled in the art.

| Compound | Structure | LC-MS (m/z) (M + H)+ | 1H NMR |
|---|---|---|---|
| 15 | 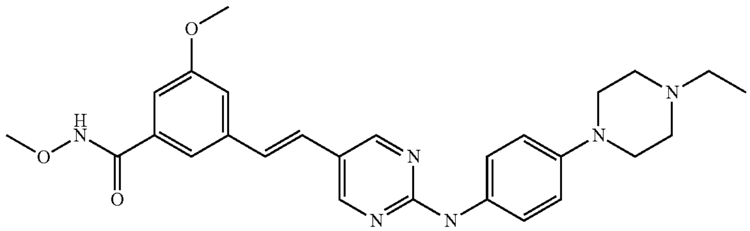 [SMILES: CCN1CCN(c2ccc(Nc3ncc(/C=C/c4cc(OC)cc(C(=O)NOC)c4)cn3)cc2)CC1] | 489.2 | 1H NMR (400 MHz, CD3OD) δ 8.58 (s, 2H), 7.55-7.51 (m, 3H), 7.24 (s, 1H), 7.09-6.96 (m, 5H), 3.83 (s, 3H), 3.72 (s, 3H), 3.18-3.17 (m, 4H), 2.67-2.64 (m, 4H), 2.50 (q, J = 7.1 Hz, 2H), 1.14 (t, J = 7.1 Hz, 3H). |
| 16 | 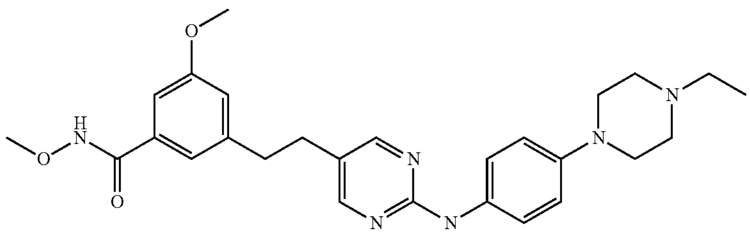 [SMILES: CCN1CCN(c2ccc(Nc3ncc(CCc4cc(OC)cc(C(=O)NOC)c4)cn3)cc2)CC1] | 491.2 | 1H NMR (400 MHz, CD3OD) δ 8.12 (s, 2H), 7.49 (d, J = 9.0 Hz, 2H), 7.13-7.12 (m, 2H), 6.97 (d, J = 9.0 Hz, 2H), 6.90 (s, 1H), 3.78 (s, 3H), 3.77 (s, 3H), 3.36-3.31 (m, 4H), 3.12 (q, J = 7.3 Hz, 3H), 2.90 (t, J = 7.3 Hz, 2H), 2.81 (t, J = 7.3 Hz, 2H), 1.33 (t, J = 7.3 Hz, 3H). |
| 17 | 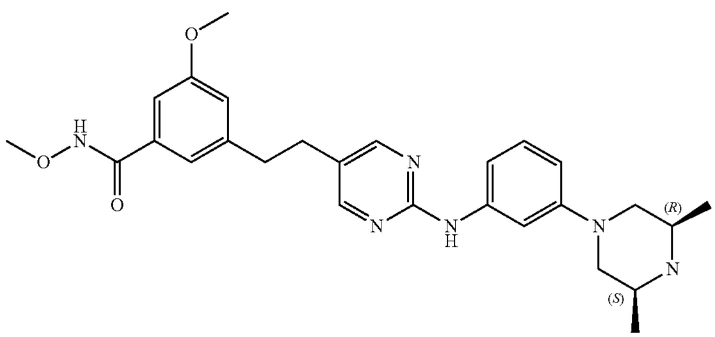 | 491.4 | 1H NMR (400 MHz, CD3OD) δ 8.17 (s, 2H), 7.29 (s, 1H), 7.24-7.06 (m, 4H), 6.75 (s, 1H), 6.61 (s, 1H), 3.76 (s, 3H), 3.73 (s, 3H), 3.57-3.48 (m, 2H), 3.03-2.92 (m, 2H), 2.92-2.76 (m, 4H), 2.25 (t, J = 10.6 Hz, 2H), 1.13 (d, J = 6.0 Hz, 6H). |
Example 4: Synthesis of Compound 18
Compound 18
3-(2-(2-((4-(4-(2-hydroxyethyl)piperazin-1-yl)phenyl)amino)pyrimidin-5-yl)ethyl)-N,5-dimethoxybenzamide
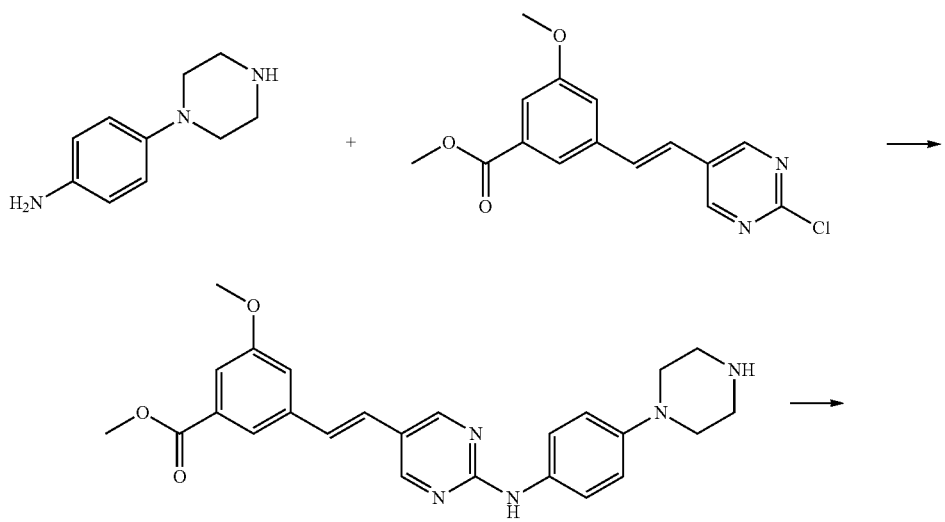

-continued

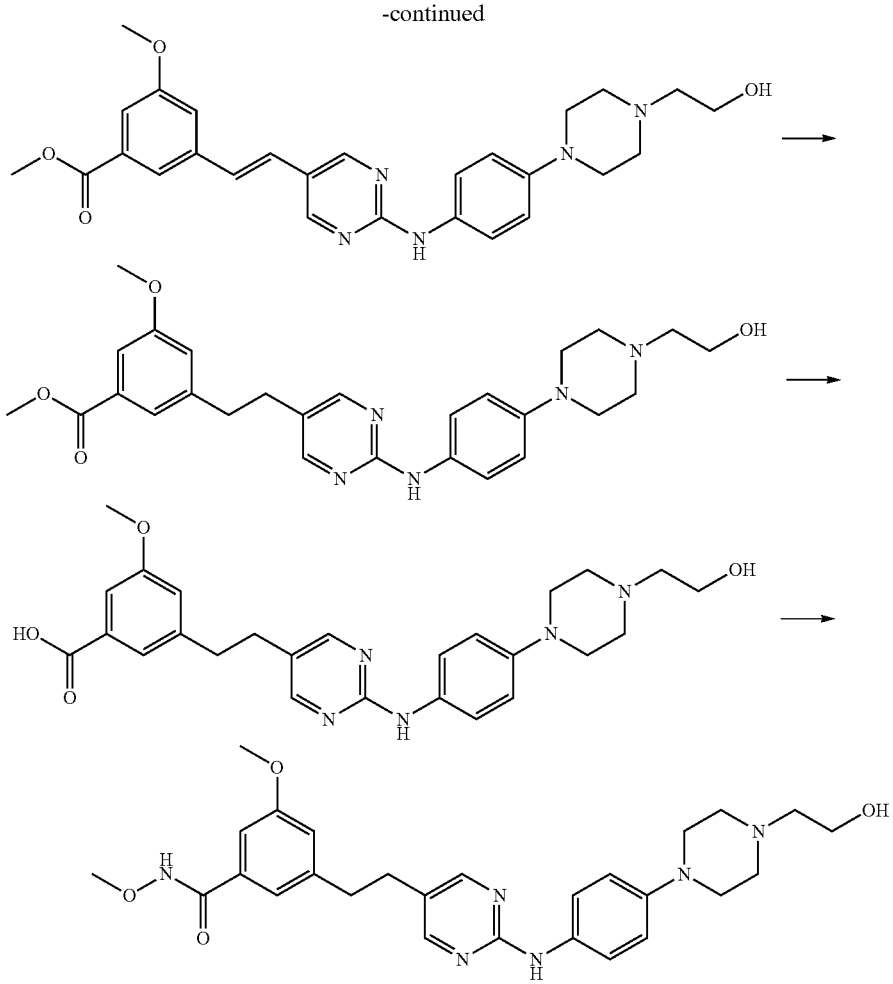

(A) (E)-methyl 3-methoxy-5-(2-(2-(4-(piperazin-1-yl)phenylamino)pyrimidin-5-yl)vinyl)benzoate A mixture of 4-(piperazin-1-yl)aniline (348 mg, 1.968 mmol), (E)-methyl 3-(2-(2-chloropyrimidin-5-yl)vinyl)-5-methoxybenzoate (600 mg, 1.968 mmol) and TFA (672 mg, 5.904 mmol) in propan-2-ol (30 mL) was stirred at 150° C. for 40 min under microwave. The resulting mixture was concentrated, basified with ammonia water, purified via ISCO (DCM/MeOH) to afford the title compound as a yellow solid (320 mg, 36.6% yield). MS (m/z): 446.3 (M+H)$^+$.

(B) (E)-methyl 3-(2-(2-(4-(4-(2-hydroxyethyl)piperazin-1-yl)phenylamino) pyrimidin-5-yl)vinyl)-5-methoxybenzoate A mixture of (E)-methyl 3-methoxy-5-(2-(2-(4-(piperazin-1-yl)phenylamino)pyrimidin-5-yl)vinyl)benzoate (260 mg, 0.584 mmol), 2-bromoethanol (146 mg, 1.167 mmol) and K$_2$CO$_3$ (242 mg, 1.752 mmol) in DMF (5 mL) was stirred at 65° C. for overnight. The resulting mixture was partitioned between water (30 mL) and EA (30 mL). The organic phase was concentrated to afford the title compound as a brown oil (200 mg, 70.0% yield). MS (m/z): 490.2 (M+H)$^+$.

(C) Methyl 3-(2-(2-(4-(4-(2-hydroxyethyl)piperazin-1-yl)phenylamino) pyrimidin-5-yl)ethyl)-5-methoxybenzoate To a mixture of (E)-methyl 3-(2-(2-(4-(4-(2-hydroxyethyl)piperazin-1-yl)phenylamino) pyrimidin-5-yl)vinyl)-5-methoxybenzoate (200 mg, 0.409 mmol) in MeOH (8 mL) and THF (2 mL) was added Pd/C (10%,100 mg). The resulting mixture was stirred at ambient temperature for 20 h and 50° C. for 6 h under hydrogen atmosphere. The resulting mixture was filtered through celite. The filtrate was concentrated and the residue was purified via ISCO (eluted with MeOH in H$_2$O 0-100%) to afford the title compound as a yellow solid (85 mg, 42.3% yield). MS (m/z): 492.2 (M+H)$^+$.

(D) 3-(2-(2-(4-(4-(2-hydroxyethyl)piperazin-1-yl)phenylamino)pyrimidin-5-yl)ethyl)-5-methoxybenzoic acid A mixture of methyl 3-(2-(2-(4-(4-(2-hydroxyethyl)piperazin-1-yl)phenylamino) pyrimidin-5-yl)ethyl)-5-methoxybenzoate (85 mg, 0.173 mmol) and a solution of 30% sodium hydroxide (0.8 mL, 6.00 mmol) in MeOH (10 mL) was stirred at 40° C. for 3 h. The resulting mixture was concentrated, adjusted to pH=7 with 2N HCl, concentrated, purified via ISCO (eluted with MeOH in H$_2$O 0-100%) to afford the title compound as a brown oil (70 mg, 84.8% yield). MS (m/z): 478.2 (M+H)+.

(E) 3-(2-(2-(4-(4-(2-hydroxyethyl)piperazin-1-yl)phenylamino)pyrimidin-5-yl)ethyl)-N,5-dimethoxybenzamide A mixture of 3-(2-(2-(4-(4-(2-hydroxyethyl)piperazin-1-yl)phenylamino)pyrimidin-5-yl)ethyl)-5-methoxybenzoic acid (70 mg, 0.173 mmol), O-methylhydroxylamine (18 mg, 0.220 mmol), HATU (168 mg, 0.441 mmol) and DIPEA (57 mg, 0.441 mmol) in DMF (3 mL) was stirred at ambient temperature for 20 min. The resulting mixture was concentrated, purified via ISCO (eluted with MeOH in H$_2$O 0~100%) to afford the title compound as a yellow solid (60 mg, 80.8% yield). MS (m/z): 507.2 (M+H)+. $^1$H NMR (400 MHz, CD$_3$OD) δ 8.11 (s, 2H), 7.47 (d, J=9.0 Hz, 2H), 7.12-7.11 (m, 2H), 6.96 (d, J=9.0 Hz, 2H), 6.90 (s, 1H), 3.85 (t, J=5.6 Hz, 2H), 3.78 (s, 3H), 3.76 (s, 3H), 3.32-3.30 (m, 2H), 3.11 (t, J=5.6 Hz, 2H), 2.89 (t, J=7.3 Hz, 2H), 2.81 (t, J=7.3 Hz, 2H).

Example 5: Synthesis of Compound 19

Compound 19
3-(2-(2-((4-(4-ethylpiperazin-1-yl)phenyl)amino)pyrimidin-5-yl)ethyl)-N-(2-hydroxyethoxy)-5-methoxybenzamide

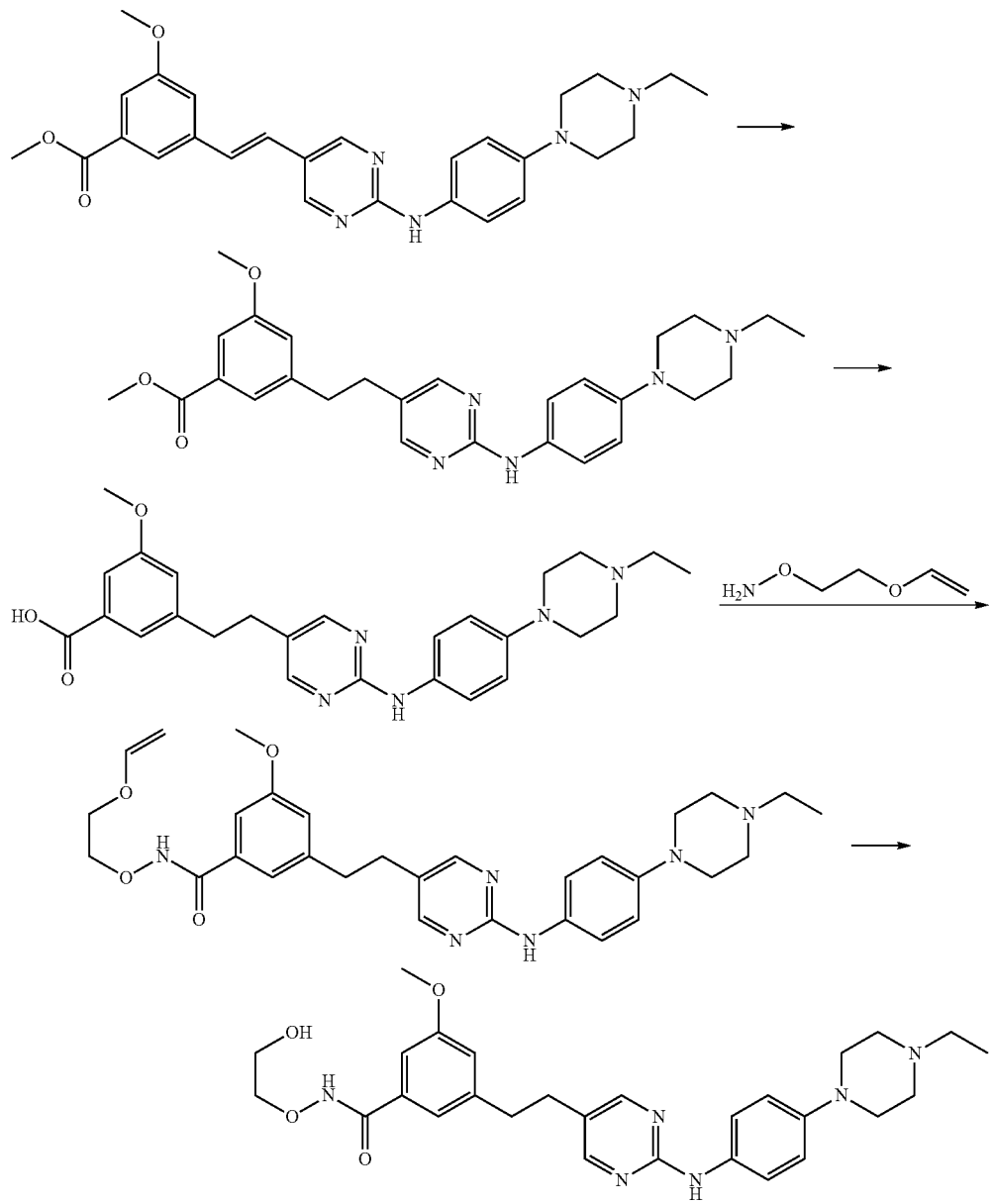

(A) Methyl 3-(2-(2-((4-(4-ethylpiperazin-1-yl)phenyl)amino)pyrimidin-5-yl)ethyl)-5-methoxybenzoate To a solution of (E)-methyl 3-(2-(2-((4-(4-ethylpiperazin-1-yl)phenyl)amino) pyrimidin-5-yl)vinyl)-5-methoxybenzoate (0.91 g, 1.9 mmol) in THF (30 mL) was added Pd/C (10%, 0.5 g) and the mixture was stirred at 40° C. for 24 h under hydrogen (1 atm). The mixture was filtered and the filtrate was concentrated to afford the title compound as a yellow solid (0.68 g, 74.4% yield). MS (m/z): 476.3 (M+H)+.

(B) 3-(2-(2-((4-(4-ethylpiperazin-1-yl)phenyl)amino)pyrimidin-5-yl)ethyl)-5-methoxybenzoic acid To a solution of methyl 3-(2-(2-((4-(4-ethylpiperazin-1-yl)phenyl)amino)pyrimidin-5-yl)ethyl)-5-methoxybenzoate (0.68 g, 1.4 mmol) in THF (20 mL) was added aqueous LiOH solution (0.20 g LiOH in 5 mL H₂O). The mixture was stirred at 40° C. for 2 h, then purified via ISCO (eluted with MeOH in H₂O 0~100%) directly to afford the title compound as a yellow solid (0.503 g, 76.2% yield). MS (m/z): 462.2 (M+H)+.

(C) 3-(2-(2-(4-(4-ethylpiperazin-1-yl)phenylamino)pyrimidin-5-yl)ethyl)-5-methoxy-N-(2-(vinyloxy)ethoxy)benzamide A mixture of 3-(2-(2-(4-(4-ethylpiperazin-1-yl)phenylamino)pyrimidin-5-yl)ethyl)-5-methoxybenzoic acid (100 mg, 0.210 mmol), O-(2-(vinyloxy)ethyl)hydroxylamine (32 mg, 0.315 mmol), HATU (240 mg, 0.630 mmol) and DIPEA (81 mg, 0.630 mmol) in DMF (3 mL) was stirred at ambient temperature for 30 min. The resulting mixture was partitioned between water (30 mL) and EA (30 mL). The organic phase was concentrated and the residue was purified via ISCO (eluted with MeOH in H₂O 0~100%) to afford the title compound as a yellow solid (70 mg, 59.1% yield). MS (m/z): 547.3 (M+H)+.

(D) 3-(2-(2-(4-(4-ethylpiperazin-1-yl)phenylamino)pyrimidin-5-yl)ethyl)-N-(2-hydroxyethoxy)-5-methoxybenzamide To a mixture of 3-(2-(2-(4-(4-ethylpiperazin-1-yl)phenylamino)pyrimidin-5-yl) ethyl)-5-methoxy-N-(2-(vinyloxy)ethoxy)benzamide (70 mg, 0.128 mmol) in MeOH (4 mL) was added 2N HCl (1 mL, 2.0 mmol). The mixture was stirred at ambient temperature for 1 h. The resulting mixture was concentrated, basified with ammonia water, concentrated, purified via ISCO (eluted with MeOH in H₂O 0~100%) to afford the title compound as a yellow solid (35 mg, 52.5% yield). MS (m/z): 521.2 (M+H)+. ¹H NMR (400 MHz, CD₃OD) δ 8.11 (s, 2H), 7.48 (d, J=9.0 Hz, 2H), 7.14 (s, 1H), 7.13 (s, 1H), 6.96 (d, J=9.0 Hz, 2H), 6.91 (s, 1H), 4.00 (t, J=4.5 Hz, 2H), 3.78 (s, 3H), 3.73 (t, J=4.5 Hz, 2H), 3.33-3.31 (m, 4H), 3.25-3.22 (m, 4H), 3.10 (q, J=7.3 Hz, 2H), 2.90 (t, J=7.3 Hz, 2H), 2.81 (t, J=7.3 Hz, 2H), 1.32 (t, J=7.3 Hz, 3H).

Example 6: Synthesis of Compounds 20-59

Compound 20
3-(2-(2-((4-((3R,5S)-3,5-dimethylpiperazin-1-yl)phenyl)amino)pyrimidin-5-yl)ethyl)-4-fluoro-5-methoxy-N-methylbenzamide

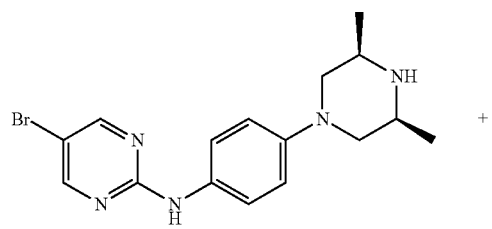

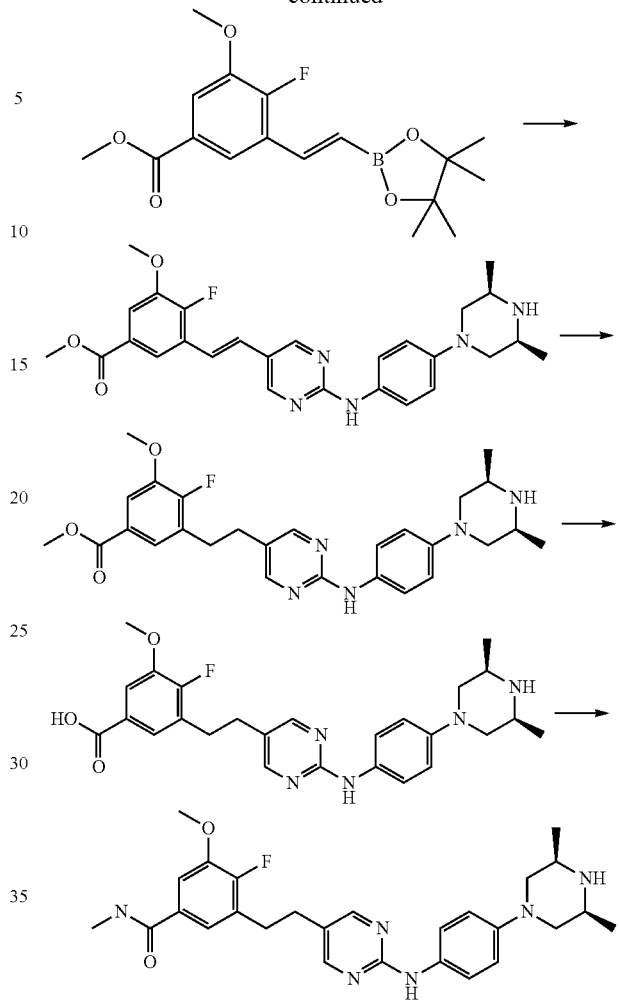

(A) Methyl 3-((E)-2-(2-(4-((3R,5S)-3,5-dimethylpiperazin-1-yl)phenylamino) pyrimidin-5-yl)vinyl)-4-fluoro-5-methoxybenzoate A mixture of (E)-methyl 4-fluoro-3-methoxy-5-(2-(4,4,5,5-tetramethyl-1,3,2-dioxaborolan-2-yl)vinyl)benzoate (278 mg, 0.828 mmol), 5-bromo-N-(4-((3R,5S)-3,5-dimethylpiperazin-1-yl)phenyl)pyrimidin-2-amine (300 mg, 0.828 mmol), Pd(dffp)₂Cl₂.CH₂Cl₂ (34 mg, 0.041 mmol) and Na₂CO₃ (220 mg, 2.07 mmol) in 1,4-dioxane (4 mL) and water (1 mL) was stirred at 110° C. for 25 min under microwave.

The resulting mixture was concentrated, purified via ISCO (eluted with MeOH in H₂O 0~100%) to afford the title compound as a yellow solid (170 mg, 41.8% yield). MS (m/z): 492.2 (M+H)+.

(B) Methyl 3-(2-(2-(4-((3R,5S)-3,5-dimethylpiperazin-1-yl)phenylamino) pyrimidin-5-yl)ethyl)-4-fluoro-5-methoxybenzoate To a mixture of methyl 3-((E)-2-(2-(4-((3R,5S)-3,5-dimethylpiperazin-1-yl) phenylamino)pyrimidin-5-yl)vinyl)-4-fluoro-5-methoxybenzoate (170 mg, 0.346 mmol) in MeOH (10 mL) and THF (4 mL) was added Pd/C (10%, 50 mg). The mixture was stirred at 50° C. for 4 h under hydrogen atmosphere. The resulting mixture was filtered through celite. The filtrate was concentrated to afford the title compound as a yellow oil (150 mg, 87.9% yield). MS (m/z): 494.2 (M+H)+.

(C) 3-(2-(2-(4-((3R,5S)-3,5-dimethylpiperazin-1-yl)phenylamino)pyrimidin-5-yl) ethyl)-4-fluoro-5-methoxybenzoic acid A mixture of methyl 3-(2-(2-(4-((3R,5S)-3,5-dimethyl-piperazin-1-yl)phenylamino) pyrimidin-5-yl)ethyl)-4-fluoro-5-methoxybenzoate (150 mg, 0.304 mmol) and a solution of 30% sodium hydroxide (1 mL, 7.50 mmol) in MeOH (10 mL) was stirred at 40° C. for 3 h. The resulting mixture was cooled to ambient temperature, adjusted to pH=7 with 2N HCl, concentrated, purified via ISCO (eluted with MeOH in H₂O 0~100%) to afford the title compound as a brown oil (60 mg, 41.2% yield). MS (m/z): 480.2 (M+H)⁺.

(D) 3-(2-(2-(4-((3R,5S)-3,5-dimethylpiperazin-1-yl)phenylamino)pyrimidin-5-yl) ethyl)-4-fluoro-5-methoxy-N-methylbenzamide A mixture of 3-(2-(2-(4-((3R,5S)-3,5-dimethylpiperazin-1-yl)phenylamino) pyrimidin-5-yl)ethyl)-4-fluoro-5-methoxybenzoic acid (40 mg, 0.083 mmol), methylamine hydrochloride (8.4 mg, 0.125 mmol), HATU (95 mg, 0.250 mmol) and DIPEA (32 mg, 0.250 mmol) in DMF (3 mL) was stirred at ambient temperature for 30 min. The resulting mixture was purified via ISCO (eluted with MeOH in H₂O 0~100%) and then PTLC (DCM/MeOH=15:1) to afford the title compound as a yellow solid (29 mg, 70.6% yield). MS (m/z): 493.2 (M+H)⁺. ¹H NMR (400 MHz, CD₃OD) δ 8.11 (s, 2H), 7.42 (d, J=9.0 Hz, 2H), 7.41 (dd, J=6.0 Hz, 2.0 Hz, 1H), 7.28 (dd, J=6.0 Hz, 2.0 Hz, 1H), 6.95 (d, J=9.0 Hz, 2H), 3.90 (s, 3H), 3.48-3.43 (m, 2H), 3.05-2.98 (m, 2H), 2.95 (t, J=7.3 Hz, 2H), 2.90 (s, 3H), 2.82 (t, J=7.3 Hz, 2H), 2.28-2.22 (m, 2H), 1.15 (t, J=6.4 Hz, 3H).

The following compounds were prepared according to the procedures of Compound 20 using the corresponding intermediates and reagents under appropriate conditions that could be recognized by one skilled in the art.

| Compound | Structure | LC-MS (m/z) (M + H)⁺ | ¹H NMR |
|---|---|---|---|
| 21 | 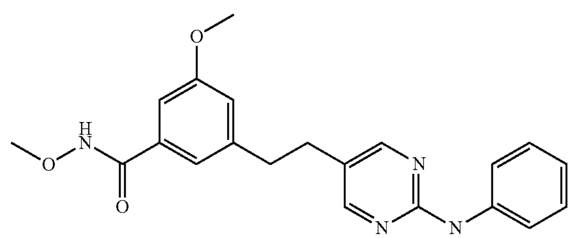 [SMILES: CONC(=O)c1cc(CCc2cnc(Nc3ccccc3)nc2)cc(OC)c1] | 379.1 | ¹H NMR (400 MHz, CD₃OD) δ 8.18 (s, 2H), 7.58 (dd, J = 8.6 Hz, 1.0 Hz, 2H), 7.27-7.21 (m, 2H), 7.20 (s, 1H), 7.15 (dd, J = 2.2 Hz, 1.4 Hz, 1H), 6.97-6.91 (m, 1H), 6.72-6.69 (m, 1H), 3.75 (s, 3H), 3.71 (s, 3H), 2.87-2.82 (m, 4H). |
| 22 | 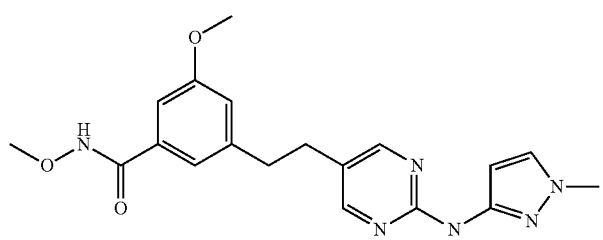 | 383.1 | ¹H NMR (400 MHz, CD₃OD) δ 8.16 (s, 2H), 7.42 (d, J = 2.0 Hz, 1H), 7.15 (s, 1H), 7.12 (s, 1H), 6.90 (s, 1H), 6.48 (d, J = 2.1 Hz, 1H), 3.81-3.76 (m, 9H), 2.89 (t, J = 6.9 Hz, 2H), 2.83 (t, J = 6.8 Hz, 2H). |
| 23 | 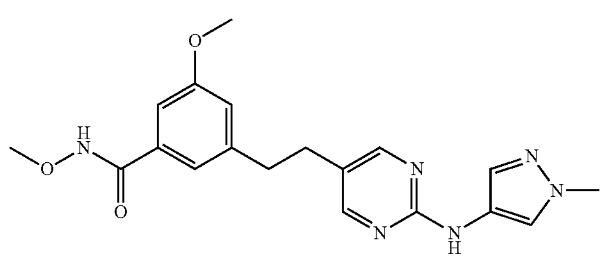 | 383.5 | ¹H NMR (400 MHz, CD₃OD) δ 8.16 (s, 2H), 7.89 (s, 1H), 7.51 (s, 1H), 7.14 (d, J = 7.8 Hz, 2H), 6.90 (s, 1H), 3.84 (s, 3H), 3.79 (s, 6H), 2.90 (t, J = 6.8 Hz, 2H), 2.82 (t, J = 6.8 Hz, 2H). |
| 24 | 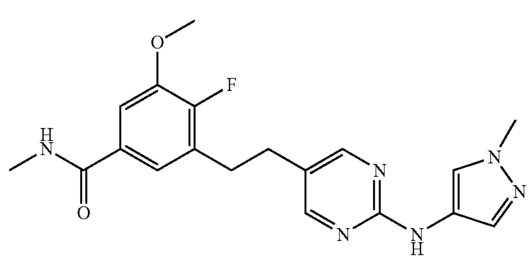 [SMILES: CNC(=O)c1cc(CCc2cnc(Nc3cnn(C)c3)nc2)c(F)c(OC)c1] | 385.1 | ¹H NMR (400 MHz, CD₃OD) δ 8.13 (s, 2H), 7.87 (s, 1H), 7.50 (s, 1H), 7.40 (dd, J = 7.8 Hz, 2.1 Hz, 1H), 7.27 (dd, J = 5.9 Hz, 2.1 Hz, 1H), 3.88 (s, 3H), 3.84 (s, 3H), 2.93 (t, J = 7.3 Hz, 2H), 2.89 (s. 3H), 2.81 (t, J = 7.4 Hz, 2H). |

| Compound | Structure | LC-MS (m/z) (M + H)+ | 1H NMR |
|---|---|---|---|
| 25 | 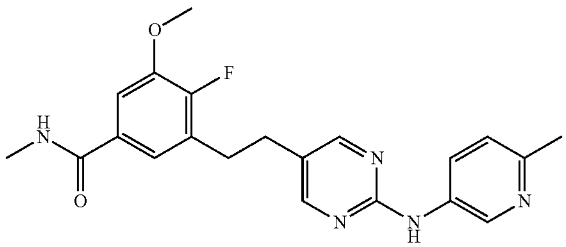 | 396.0 | 1H NMR (400 MHz, CD3OD) δ 8.67 (d, J = 2.1 Hz, 1H), 8.19 (s, 2H), 8.07 (dd, J = 8.5 Hz, 2.7 Hz, 1H), 7.40 (dd, J = 7.8 Hz, 2.1 Hz, 1H), 7.26 (dd, J = 6.0 Hz, 2.2 Hz, 1H), 7.19 (d, J = 8.5 Hz, 1H), 3.87 (s, 3H), 2.95 (t, J = 7.5 Hz, 2H), 2.87 (s, 3H), 2.83 (t, J = 7.5 Hz, 2H), 2.45 (s, 3H). |
| 26 | 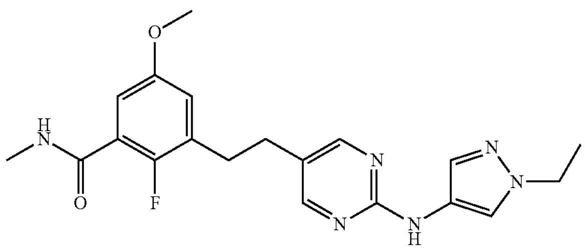 [SMILES: CCn1cc(Nc2ncc(CCc3cc(OC)cc(C(=O)NC)c3F)cn2)cn1] | 398.9 | 1H NMR (400 MHz, CD3OD) δ 8.14 (s, 2H), 7.91 (s, 1H), 7.52 (s, 1H), 7.06 (s, 1H), 6.85 (s, 1H), 4.12 (q, J = 6.7 Hz, 2H), 3.74 (s, 3H), 2.99-2.91 (m, 2H), 2.87 (s, 3H), 2.84-2.75 (m, 2H), 1.43 (t, J = 6.6 Hz, 3H). |
| 27 | 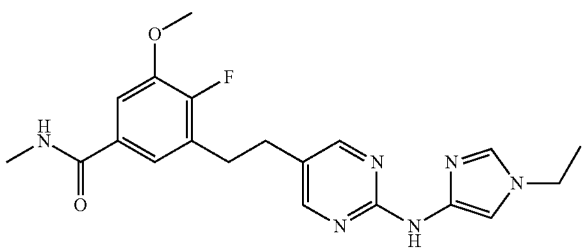 [SMILES: CCn1cnc(Nc2ncc(CCc3cc(C(=O)NC)cc(OC)c3F)cn2)c1] | 395.2 | 1H NMR (400 MHz, CD3OD) δ 8.17 (s, 2H), 7.46-7.38 (m, 2H), 7.33-7.22 (m, 2H), 4.02 (q, J = 6.9 Hz, 2H), 3.88 (s, 3H), 2.96-2.92 (m, 2H), 2.89 (s, 3H), 2.86-2.80 (m, 2H), 1.44 (t, J = 7.2 Hz, 3H). |
| 28 | 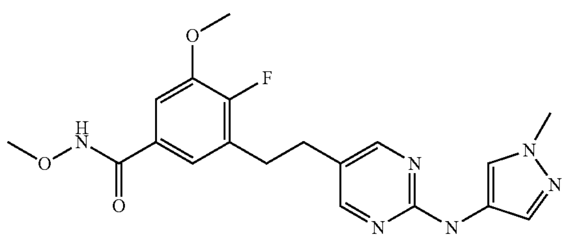 [SMILES: CONC(=O)c1cc(CCc2cnc(Nc3cnn(C)c3)nc2)c(F)c(OC)c1] | 401.4 | 1H NMR (400 MHz, CD3OD) δ 8.13 (s, 2H), 7.87 (s, 1H), 7.50 (s, 1H), 7.35 (dd, J = 7.8 Hz, 2.0 Hz, 1H), 7.21 (dd, J = 6.0 Hz, 2.0 Hz, 1H), 3.89 (s, 3H), 3.84 (s, 3H), 3.78 (s, 3H), 2.94 (t, J = 7.3 Hz, 2H), 2.81 (t, J = 7.4 Hz, 2H). |
| 29 | 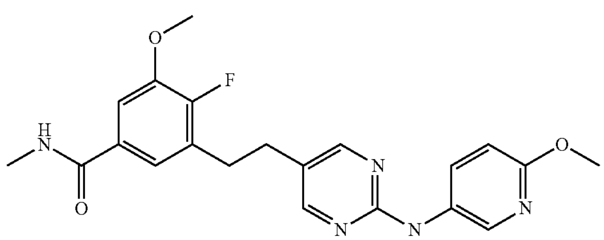 | 411.9 | 1H NMR (400 MHz, CD3OD) 8.33 (d, J = 2.8 Hz, 1H), 8.16 (s, 2H), 7.94 (dd, J = 8.9 Hz, 2.8 Hz, 1H), 7.42 (dd, J = 7.8 Hz, 2.1 Hz, 1H), 7.29 (dd, J = 6.0 Hz, 2.1 Hz, 1H), 6.77 (d, J = 8.9 Hz, 1H), 3.91 (s, 3H), 3.90 (s, 3H), 2.96 (t, J = 7.4 Hz, 2H), 2.92 (s, 3H), 2.84 (t, J = 7.4 Hz, 2H). |
| 30 | 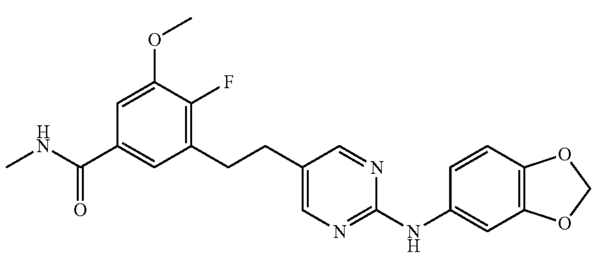 [SMILES: CNC(=O)c1cc(CCc2cnc(Nc3ccc4c(c3)OCO4)nc2)c(F)c(OC)c1] | 425.1 | 1H NMR (400 MHz, CD3OD) δ 8.11 (s, 2H), 7.41 (dd, J = 7.6 Hz, 2.0 Hz, 1H), 7.27 (dd, J = 7.6 Hz, 2.0 Hz, 1H), 7.23 (d, J = 2.1 Hz, 1H), 6.89 (dd, J = 8.3 Hz, 2.0 Hz, 1H), 6.72 (d, J = 8.3 Hz, 1H), 5.90 (s, 2H), 3.89 (s, 3H), 2.95 (t, J = 7.5 Hz, 2H), 2.89 (s, 3H), 2.81 (t, J = 7.5 Hz, 2H). |

| Compound | Structure | LC-MS (m/z) (M + H)+ | 1H NMR |
|---|---|---|---|
| 31 | 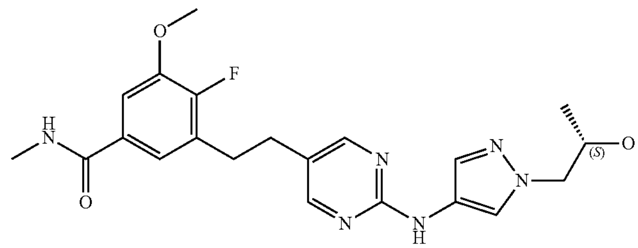 | 429.2 | 1H NMR (400 MHz, CD3OD) δ 8.12 (s, 2H), 7.91 (s, 1H), 7.53 (s, 1H), 7.40 (dd, J = 7.8 Hz, 2.1 Hz, 1H), 7.26 (dd, J = 5.9 Hz, 2.1 Hz, 1H), 4.12-4.08 (m, 1H), 4.05-3.95 (m, 2H), 3.88 (s, 3H), 2.94 (t, J = 7.4 Hz, 2H), 2.88 (s, 3H), 2.81 (t, J = 7.3 Hz, 2H), 1.15 (d, J = 6.2 Hz, 3H). |
| 32 | 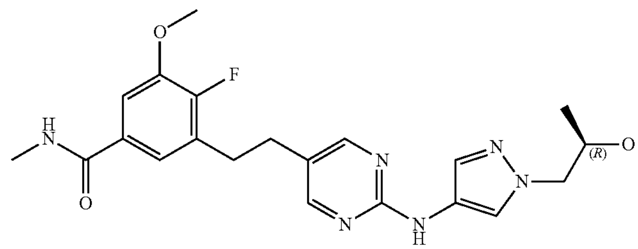 | 429.2 | 1H NMR (400 MHz, CD3OD) δ 8.12 (s, 2H), 7.90 (s, 1H), 7.53 (s, 1H), 7.40 (d, J = 7.6 Hz, 1H), 7.26 (d, J = 5.0 Hz, 1H), 4.15-4.06 (m, 1H), 4.05-3.94 (m, 2H), 3.88 (s, 3H), 2.93 (t, J = 7.0 Hz, 2H), 2.88 (s, 3H), 2.80 (t, J = 7.1 Hz, 2H), 1.15 (d, J = 6.0 Hz, 3H). |
| 33 | 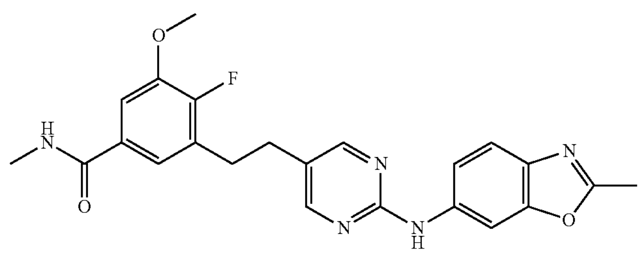 | 436.1 | 1H NMR (400 MHz, CD3OD) δ 8.22 (d, J = 2.1 Hz, 1H), 8.20 (s, 2H), 7.45 (d, J = 8.6 Hz, 1H), 7.40 (dd, J = 7.6 Hz, 2.1 Hz, 1H), 7.35 (dd, J = 8.6 Hz, 2.1 Hz, 1H), 7.27 (dd, J = 6.0 Hz, 2.1 Hz, 1H), 3.88 (s, 2H), 2.96 (t, J = 7.2 Hz, 2H), 2.87 (s, 3H), 2.84 (t, J = 7.2 Hz, 2H), 2.59 (s, 3H). |
| 34 | 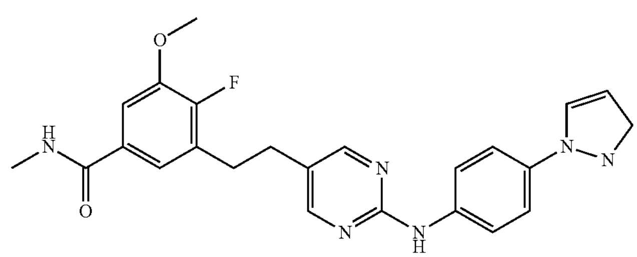 [SMILES: CNC(=O)c1cc(CCc2cnc(Nc3ccc(N4C=CCN4)cc3)nc2)c(F)c(OC)c1] | 447.0 | 1H NMR (400 MHz, CD3OD) δ 8.19 (s, 2H), 8.11 (d, J = 2.5 Hz, 1H), 7.77 (d, J = 9.2 Hz, 2H), 7.67-7.65 (m, 1H), 7.59 (d, J = 9.2 Hz, 2H), 7.40 (dd, J = 7.8 Hz, 2.1 Hz, 1H), 7.27 (dd, J = 6.0 Hz, 2.1 Hz, 1H), 6.49-6.48 (m, 1H), 3.88 (s, 3H), 2.96 (t, J = 7.3 Hz, 2H), 2.88 (s, 3H), 2.84 (t, J = 7.3 Hz, 2H). |
| 35 | 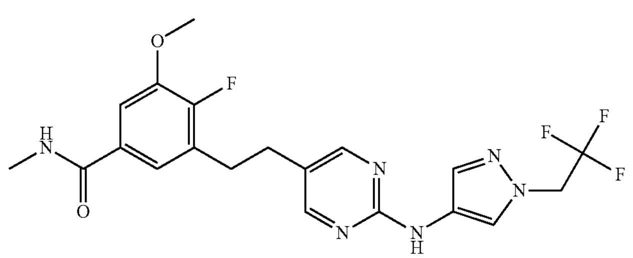 [SMILES: CNC(=O)c1cc(CCc2cnc(Nc3cnn(CC(F)(F)F)c3)nc2)c(F)c(OC)c1] | 453.0 | 1H NMR (400 MHz, CD3OD) δ 8.16 (s, 2H), 8.08 (s, 1H), 7.62 (s, 1H), 7.39 (s, 1H), 7.26 (s, 1H), 4.82-4.80 (m, 2H), 3.86 (s, 3H), 2.96-2.90 (m, 2H), 2.87 (s, 3H), 2.83-2.77 (m, 2H). |
| 36 | 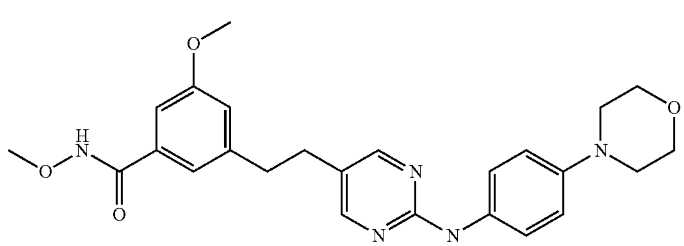 [SMILES: CONC(=O)c1cc(CCc2cnc(Nc3ccc(N4CCOCC4)cc3)nc2)cc(OC)c1] | 464.2 | 1H NMR (400 MHz, CD3OD) δ 8.09 (s, 2H), 7.45-7.41 (m, 2H), 7.15 (s, 1H), 7.12 (s, 1H), 6.93-6.89 (m, 2H), 6.87 (s, 1H), 3.82-3.79 (m, 4H), 3.77 (s, 3H), 3.76 (s, 3H), 3.07-3.03 (m, 4H), 2.87 (t, J = 6.8 Hz, 3H), 2.78 (t, J = 6.8 Hz, 2H). |

| Compound | Structure | LC-MS (m/z) (M+H)+ | 1H NMR |
|---|---|---|---|
| 37 | 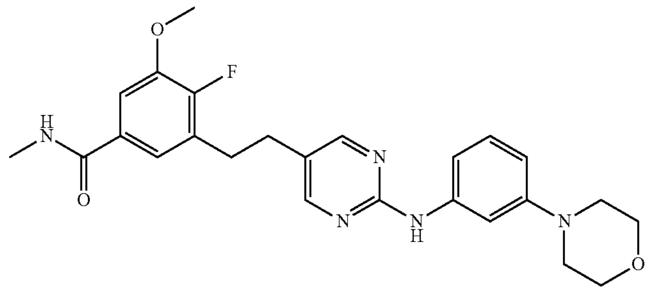 [SMILES: CNC(=O)c1cc(CCc2cnc(Nc3cccc(N4CCOCC4)c3)nc2)c(F)c(OC)c1] | 466.2 | 1H NMR (400 MHz, CD3OD) δ 8.19 (s, 2H), 7.44 (dd, J = 7.8 Hz, 2.1 Hz, 1H), 7.35 (t, J = 2.1 Hz, 1H), 7.31 (dd, J = 6.0 Hz, 2.1 Hz, 1H), 7.21-7.17 (m, 1H), 7.17-7.14 (m, 1H), 6.67-6.65 (m, 1H), 3.92 (s, 2H), 3.88-3.85 (m, 4H), 3.17-3.15 (m, 4H), 2.98 (t, J = 7.5 Hz, 2H) 2.92 (s, 3H), 2.85 (t, J = 7.5 Hz, 2H). |
| 38 | 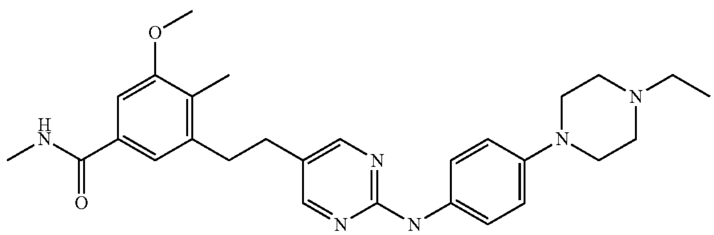 | 489.3 | 1H NMR (400 MHz, CD3OD) δ 8.09 (s, 2H), 7.44 (d, J = 8.7 Hz, 2H), 7.24 (s, 1H), 7.20 (s, 1H), 6.95 (d, J = 8.9 Hz, 2H), 3.86 (s, 3H), 3.20-3.11 (m, 4H), 2.97-2.91 (m, 2H), 2.89 (s, 3H), 2.78-2.74 (m, 2H), 2.69-2.61 (m, 4H), 2.53-2.45 (m, 2H), 2.14 (s, 3H), 1.14 (t, J = 7.1 Hz, 3H). |
| 39 | 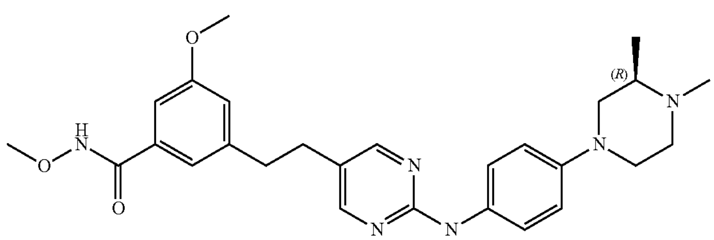 | 491.2 | 1H NMR (400 MHz, CD3OD) δ 8.12 (s, 2H), 7.45 (d, J = 9.0 Hz, 2H), 7.16-7.13 (m, 2H), 6.97-6.90 (m, 3H), 3.78 (s, 3H), 3.78 (s, 3H), 3.53-3.46 (m, 2H), 3.14-3.04 (m, 1H), 2.93-2.84 (m, 3H), 2.84-2.78 (m, 2H), 2.68-2.59 (m, 1H), 2.59-2.50 (m, 2H), 2.48 (s, 3H), 1.22 (d, J = 6.0 Hz, 3H). |
| 40 | 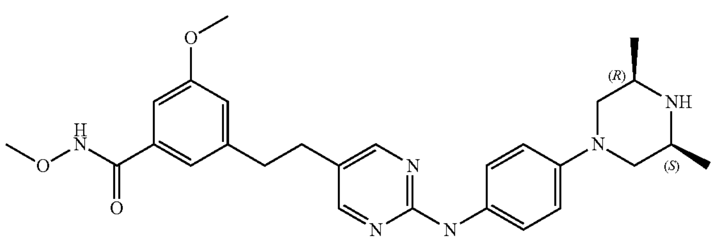 | 491.2 | 1H NMR (400 MHz, CD3OD) δ 8.13 (s, 2H), 7.50 (d, J = 8.9 Hz, 2H), 7.15 (s, 1H), 7.13 (s, 1H), 6.98 (d, J = 9.0 Hz, 2H), 6.92 (s, 1H), 3.80 (s, 3H), 3.78 (s, 3H), 3.76-3.71 (m, 2H), 3.53-3.44 (m, 2H), 2.91 (t, J = 7.0 Hz, 2H), 2.85-2.79 (m, 2H), 2.68-2.58 (m, 2H), 1.37 (d, J = 6.6 Hz, 6H). |
| 41 | 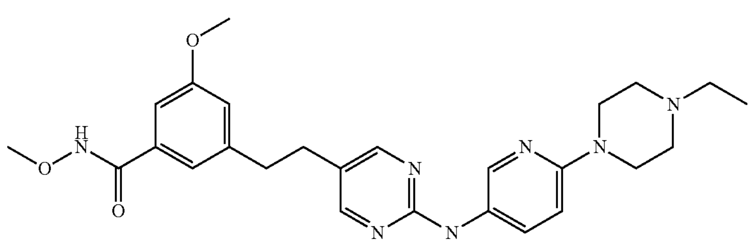 [SMILES: CCN1CCN(c2ccc(Nc3ncc(CCc4cc(OC)cc(C(=O)NOC)c4)cn3)cn2)CC1] | 492.3 | 1H NMR (400 MHz, CD3OD) δ 8.48 (s, 1H), 8.24 (s, 2H), 8.01 (d, J = 7.0 Hz, 1H), 7.25 (s, 1H), 7.23 (s, 1H), 7.10-6.89 (m, 2H), 3.91-3.87 (m, 4H), 3.79 (s, 3H), 3.40 (s, 3H), 3.37-3.24 (m, 4H), 3.17 (q, J = 7.0 Hz, 2H), 3.05-2.97 (m, 2H), 2.97-2.87 (m, 2H), 1.43 (t, J = 7.0 Hz, 3H). |
| 42 | 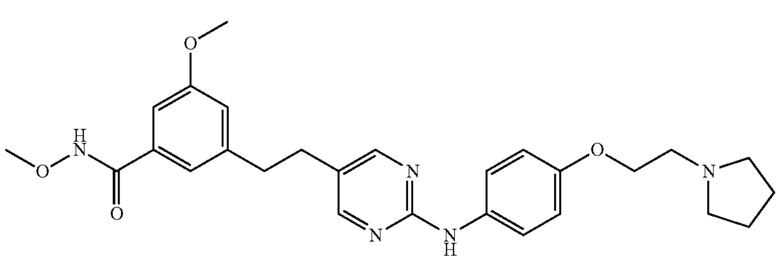 [SMILES: CONC(=O)c1cc(CCc2cnc(Nc3ccc(OCCN4CCCC4)cc3)nc2)cc(OC)c1] | 492.5 | 1H NMR (400 MHz, CD3OD) δ 8.13 (s, 2H), 7.51 (d, J = 9.0 Hz, 2H), 7.17-7.11 (m, 2H), 6.96 (d, J = 9.0 Hz, 2H), 6.93-6.90 (m, 1H), 4.29 (t, J = 8.0 Hz, 2H), 3.79 (s, 3H), 3.74 (s, 3H), 3.61 (t, J = 8.0 Hz, 2H), 3.49-3.39 (m, 4H), 2.91 (t, J = 7.0 Hz, 2H), 2.83 (t, J = 7.0 Hz, 2H), 2.13-2.09 (m, 4H). |

-continued

| Compound | Structure | LC-MS (m/z) (M + H)+ | 1H NMR |
|---|---|---|---|
| 43 | 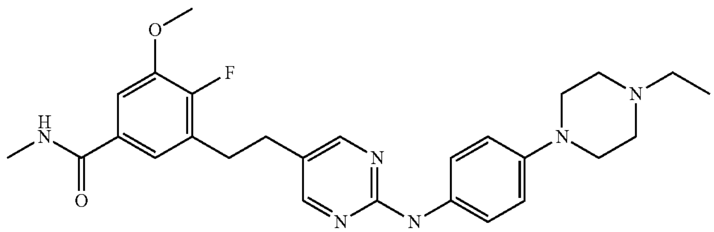 [SMILES: CCN1CCN(c2ccc(Nc3ncc(CCc4cc(C(=O)NC)cc(OC)c4F)cn3)cc2)CC1] | 493.3 | 1H NMR (400 MHz, CD3OD) δ 8.08 (s, 2H), 7.53-7.33 (m, 3H), 7.25 (d, J = 4.3 Hz, 1H), 6.93 (d, J = 8.9 Hz, 2H), 3.87 (s, 3H), 3.18-3.09 (m, 4H), 2.91 (t, J = 7.0 Hz, 2H), 2.87 (s, 3H), 2.78 (t, J = 7.3 Hz, 2H), 2.69-2.59 (m, 4H), 2.48 (q, J = 7.1 Hz, 2H), 1.12 (t, J = 7.2 Hz, 3H). |
| 44 | 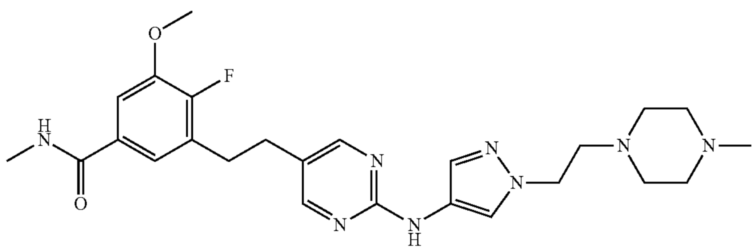 | 497.3 | 1H NMR (400 MHz, CD3OD) δ 8.13 (s, 2H), 7.96 (s, 1H), 7.52 (s, 1H), 7.40 (d, J = 7.7 Hz, 1H), 7.27 (d, J = 5.8 Hz, 1H), 4.21 (t, J = 6.5 Hz, 2H), 3.88 (s, 3H), 2.93 (t, J = 7.2 Hz, 2H), 2.88 (s, 3H), 2.82-2.78 (m, 4H), 2.62-2.35 (m, 8H), 2.25 (s, 3H). |
| 45 | 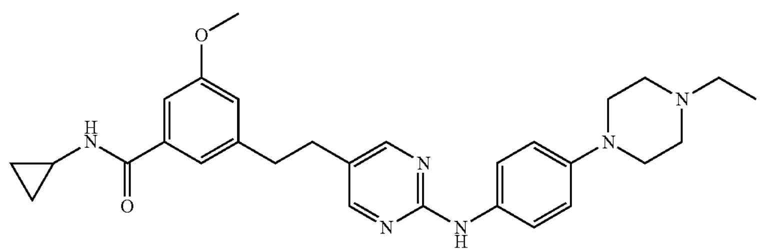 [SMILES: CCN1CCN(c2ccc(Nc3ncc(CCc4cc(OC)cc(C(=O)NC5CC5)c4)cn3)cc2)CC1] | 501.2 | 1H NMR (400 MHz, CD3OD) δ 8.12 (s, 2H), 7.49 (d, J = 8.8 Hz, 2H), 7.19 (s, 1H), 7.18 (s, 1H), 6.97 (d, J = 8.8 Hz, 2H), 6.87 (s, 1H), 3.78 (s, 3H), 3.37-3.31 (m, 4H), 3.27-3.18 (m, 4H), 3.08 (q, J = 7.1 Hz, 2H), 2.94-2.85 (m, 2H), 2.86-2.80 (m, 2H), 2.80-2.70 (m, 1H), 1.32 (t, J = 7.3 Hz, 3H), 0.86-0.71 (m, 2H), 0.69-0.54 (m, 2H). |
| 46 | 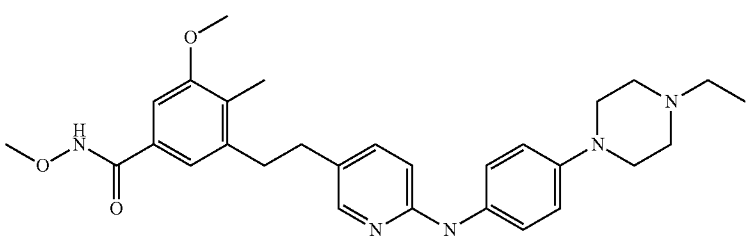 [SMILES: CCN1CCN(c2ccc(Nc3ccc(CCc4cc(C(=O)NOC)cc(OC)c4C)cn3)cc2)CC1] | 504.3 | 1H NMR (400 MHz, CD3OD) δ 7.74 (s, 1H), 7.29 (d, J = 8.3 Hz, 1H), 7.24 (d, J = 8.0 Hz, 2H), 7.15 (s, 1H), 7.13 (s, 1H), 6.93 (d, J = 8.1 Hz, 2H), 6.65 (d, J = 8.1 Hz, 1H), 3.83 (8. 3H), 3.77 (s, 3H), 3.20-3.08 (m. 4H), 2.94-2.83 (m, 2H), 2.76-2.68 (m, 2H), 2.68-2.56 (m, 4H), 2.48 (q, J = 6.5 Hz, 2H), 2.12 (s, 3H), 1.13 (t, J = 6.6 Hz, 3H). |
| 47 | 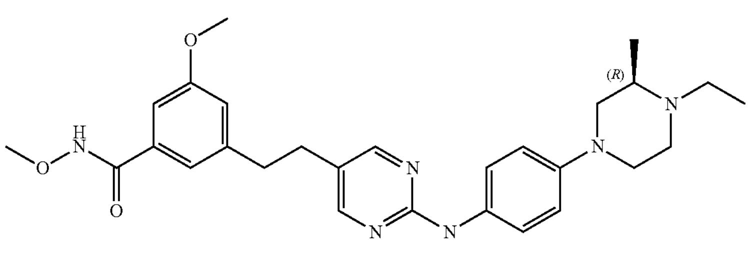 | 505.2 | 1H NMR (400 MHz, CD3OD) δ 8.12 (s, 2H), 7.45 (d, J = 8.8 Hz, 2H), 7.16 (s, 1H), 7.15 (s, 1H), 6.94 (d, J = 8.8 Hz, 2H), 6.91 (s, 1H), 3.80 (s, 3H), 3.79 (s, 3H), 3.46-3.38 (m, 2H), 3.04-2.98 (m, 1H), 2.98-2.87 (m, 4H), 2.86-2.77 (m, 2H), 2.64-2.55 (m, 2H), 2.53-2.43 (m, 2H), 1.16 (d, J = 6.0 Hz, 3H), 1.11 (t, J = 7.2 Hz, 3H). |
| 48 | 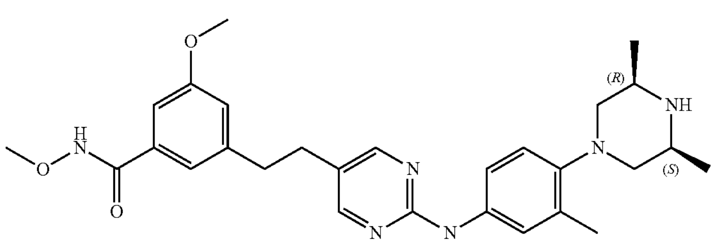 | 505.3 | 1H NMR (400 MHz, CD3OD) δ 8.14 (s, 2H), 7.37-7.35 (m, 2H), 7.17 (s, H), 7.15 (s, 1H), 6.97 (d, J = 9.2 Hz, 1H), 6.91 (s, 1H), 3.80 (s, 3H), 3.79 (s, 3H), 3.08-2.99 (m, 2H), 2.96-2.87 (m, 4H), 2.86-2.80 (m, 2H), 2.34-2.25 (m, 5H), 1.12 (d, J = 6.4 Hz, 6H). |

| Compound | Structure | LC-MS (m/z) (M + H)+ | 1H NMR |
|---|---|---|---|
| 49 | 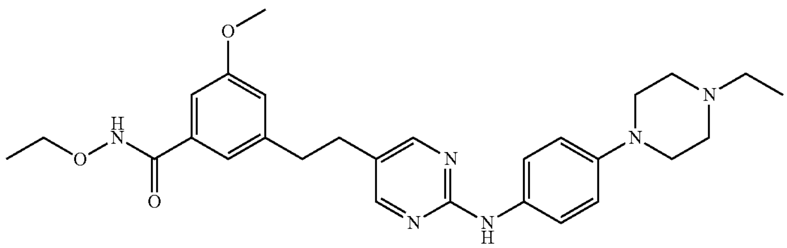 [SMILES: CCONC(=O)c1cc(CCc2cnc(Nc3ccc(N4CCN(CC)CC4)cc3)nc2)cc(OC)c1] | 505.3 | 1H NMR (400 MHz, CD3OD) δ 8.10 (s, 2H), 7.44 (d, J = 8.8 Hz, 2H), 7.15 (s, 1H), 7.14-7.08 (m, 1H), 6.93 (d, J = 8.9 Hz, 2H), 6.89 (s, 1H), 3.98 (q, J = 7.0 Hz, 2H), 3.78 (s, 3H), 3.19-3.08 (m, 4H), 2.91-2.84 (m, 2H), 2.82-2.75 (m, 2H), 2.68-2.58 (m, 4H), 2.48 (q, J = 7.1 Hz, 2H), 1.28 (t, J = 7.0 Hz, 3H), 1.13 (t, J = 7.2 Hz, 3H). |
| 50 | 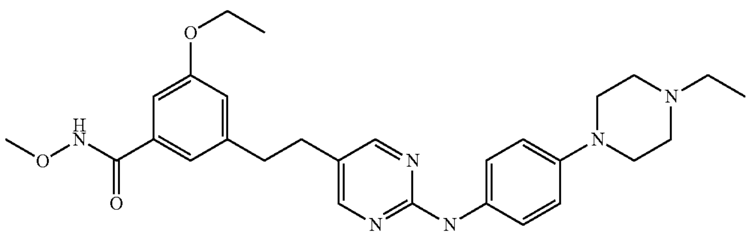 [SMILES: CCOc1cc(CCc2cnc(Nc3ccc(N4CCN(CC)CC4)cc3)nc2)cc(C(=O)NOC)c1] | 505.3 | 1H NMR (400 MHz, CD3OD) δ 8.10 (s, 2H), 7.47 (d, J = 8.8 Hz, 2H), 7.12 (s, 1H), 7.09 (s, 1H), 6.94 (d, J = 8.8 Hz, 2H), 6.86 (s, 1H), 4.00 (q, J = 7.0 Hz, 2H), 3.77 (s, 3H), 3.45-3.29 (m, 6H), 3.25-3.08 (m, 3H), 3.00-2.73 (m, 5H), 1.36-1.34 (m, 3H), 1.33-1.32 (m, 3H). |
| 51 | 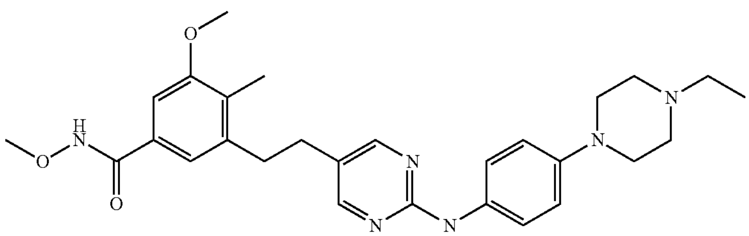 [SMILES: CCN1CCN(c2ccc(Nc3ncc(CCc4cc(C(=O)NOC)cc(OC)c4C)cn3)cc2)CC1] | 505.4 | 1H NMR (400 MHz, CD3OD) δ 8.08 (s, 2H), 7.44 (d, J = 6.1 Hz, 2H), 7.18 (s, 1H), 7.13 (s, 1H), 6.94 (d, J = 5.5 Hz, 2H), 3.85 (s, 3H), 3.77 (s, 3H), 3.24-3.08 (m, 4H), 2.99-2.86 (m, 2H), 2.82-2.71 (m, 2H), 2.71-2.56 (m, 4H), 2.56-2.42 (m, 2H), 2.14 (s, 3H), 1.13 (t, J = 9.8 Hz, 3H). |
| 52 | 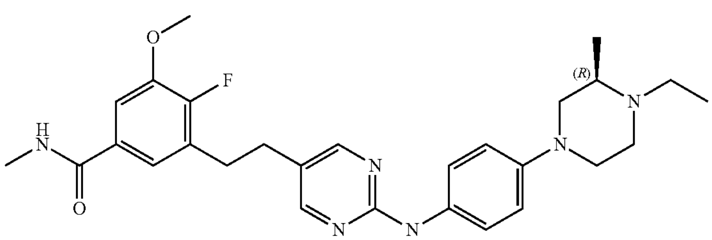 | 507.2 | 1H NMR (400 MHz, CD3OD) δ 8.09 (s, 2H), 7.43 (d, J = 8.8 Hz, 2H), 7.39 (s, 1H), 7.26 (d, J = 4.6 Hz, 1H), 6.93 (d, J = 8.8 Hz, 2H), 3.88 (s, 3H), 3.48-3.36 (m, 2H), 3.06-2.91 (m, 4H), 2.88 (s, 3H), 2.86-2.73 (m, 3H), 2.67-2.38 (m, 4H), 1.15 (d, J = 5.4 Hz, 3H), 1.10 (t J = 6.8 Hz, 3H). |
| 53 | 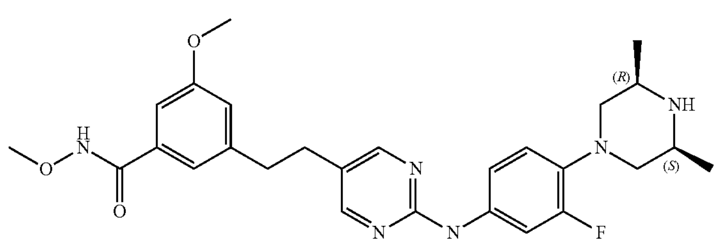 | 509.2 | 1H NMR (400 MHz, CD3OD) δ 8.16 (s, 2H), 7.58 (dd, J = 15.0 Hz, 2.5 Hz, 1H), 7.22-7.18 (m, 1H), 7.16-7.15 (m, 1H), 7.13-7.12 (m, 1H), 6.97-6.91 (t, J = 8.0 Hz, 1H), 6.89 (s, 1H), 3.78 (s, 3H), 3.77 (s, 3H), 3.24-3.16 (m, 2H), 3.07-2.98 (m, 2H), 2.92-2.86 (m, 2H), 2.86-2.78 (m, 2H), 2.28 (t, J = 11.0 Hz, 2H), 1.10 (d, J = 6.5 Hz, 6H). |
| 54 | 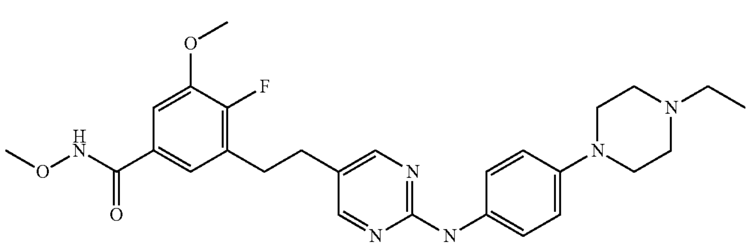 [SMILES: CCN1CCN(c2ccc(Nc3ncc(CCc4cc(C(=O)NOC)cc(OC)c4F)cn3)cc2)CC1] | 509.3 | 1H NMR (400 MHz, CD3OD) δ 8.09 (s, 2H), 7.42 (d, J = 8.5 Hz, 2H), 7.33 (d, J = 7.2 Hz, 1H), 7.20 (d, J = 4.5 Hz, 1H), 6.92 (d, J = 8.5 Hz, 2H), 3.86 (s, 3H), 3.76 (s, 3H), 3.18-3.08 (m, 4H), 2.90 (t, J = 6.9 Hz, 2H), 2.78 (t, J = 7.2 Hz, 2H), 2.68-2.59 (m, 4H), 2.48 (q, J = 6.9 Hz, 2H), 1.12 (t, J = 7.1 Hz, 3H). |

-continued

| Compound | Structure | LC-MS (m/z) (M + H)+ | 1H NMR |
|---|---|---|---|
| 55 | 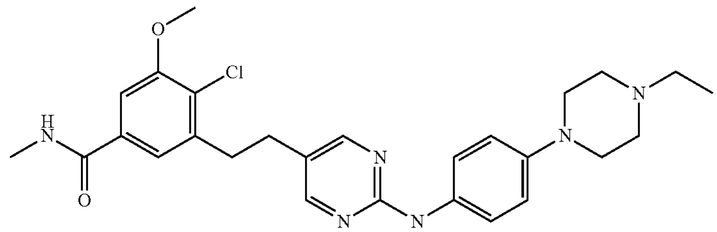 | 509.2 | 1H NMR (400 MHz, CD3OD) δ 8.09 (s, 2H), 7.58-7.20 (m, 4H), 6.93 (d, J = 8.5 Hz, 2H), 3.90 (s, 3H), 3.20-3.09 (m, 4H), 3.02 (t, J = 7.3 Hz, 2H), 2.88 (s, 3H), 2.80 (t, J = 7.3 Hz, 2H), 2.69-2.59 (m, 4H), 2.48 (q, J = 7.1 Hz, 2H), 1.13 (t, J = 7.0 Hz, 3H). |
| 56 | 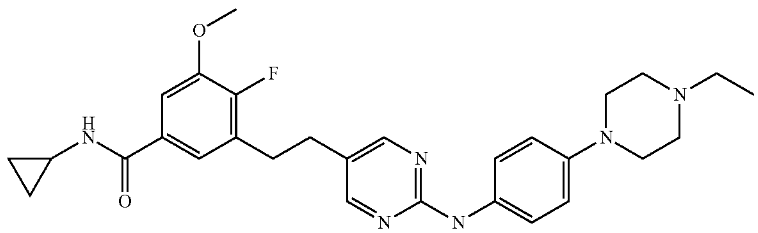 [SMILES: CCN1CCN(c2ccc(Nc3ncc(CCc4cc(C(=O)NC5CC5)cc(OC)c4F)cn3)cc2)CC1] | 519.3 | 1H NMR (400 MHz, CD3OD) δ 8.08 (s, 2H), 7.42 (d, J = 8.9 Hz, 2H), 7.38 (d, J = 7.8 Hz, 1H), 7.24 (d, J = 4.1 Hz, 1H), 6.93 (d, J = 8.9 Hz, 2H), 3.86 (s, 3H), 3.18-3.09 (m, 4H), 3.06-2.98 (m, 1H), 2.91 (t, J = 7.0 Hz, 2H), 2.80-2.75 (m, 2H), 2.67-2.59 (m, 4H), 2.47 (q, J = 7.2 Hz, 2H), 1.12 (t, J = 7.2 Hz, 3H), 0.81-0.72 (m, 2H), 0.64-0.57 (m, 2H). |
| 57 | 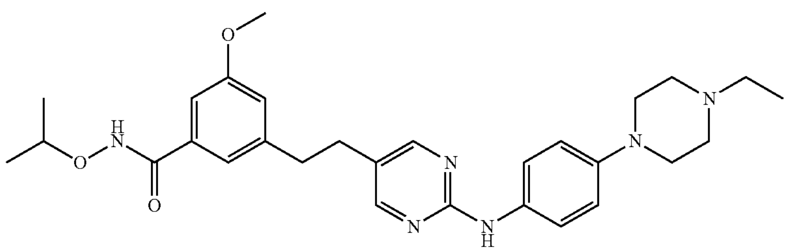 [SMILES: CCN1CCN(c2ccc(Nc3ncc(CCc4cc(OC)cc(C(=O)NOC(C)C)c4)cn3)cc2)CC1] | 519.3 | 1H NMR (400 MHz, CD3OD) δ 8.10 (s, 2H), 7.44 (d, J = 6.5 Hz, 2H), 7.13 (s, 2H), 7.05-6.73 (m, 3H), 4.26-4.08 (m, 1H), 3.78 (s, 3H), 3.23-3.04 (m, 4H), 2.95-2.75 (m, 4H), 2.74-2.57 (m, 4H), 2.57-2.42 (m, 2H), 1.25 (d, J = 4.1 Hz, 6H), 1.13 (t, J = 12.3 Hz, 3H). |
| 58 | 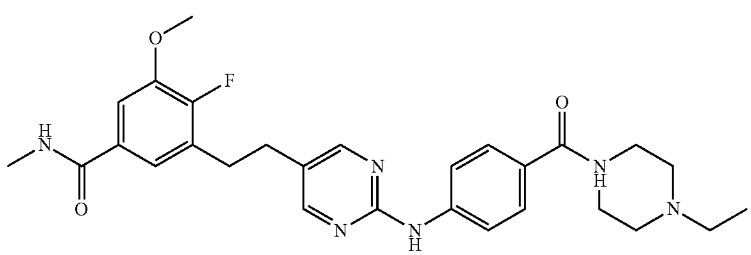 [SMILES: CCN1CCN(C(=O)c2ccc(Nc3ncc(CCc4cc(C(=O)NC)cc(OC)c4F)cn3)cc2)CC1] | 523.0 | 1H NMR (400 MHz, CD3OD) δ 8.22 (s, 2H), 7.81-7.71 (m, 4H), 7.40 (dd, J = 7.5 Hz, 1.6 Hz, 1H), 7.27 (dd, J = 5.8 Hz, 1.6 Hz, 1H), 3.88 (s, 3H), 3.49 (t, J = 7.4 Hz, 2H), 2.97 (t, J = 7.4 Hz, 2H), 2.88 (s, 3H), 2.85 (t, J = 7.2 Hz, 2H), 2.72 (t, J = 7.2 Hz, 2H), 2.65 (q, J = 7.1 Hz, 4H), 1.09 (t, J = 7.1 Hz, 6H). |
| 59 | 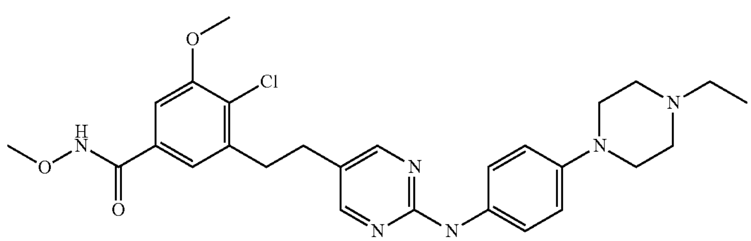 [SMILES: CCN1CCN(c2ccc(Nc3ncc(CCc4cc(C(=O)NOC)cc(OC)c4Cl)cn3)cc2)CC1] | 525.2 | 1H NMR (400 MHz, CD3OD) δ 8.10 (s, 2H), 7.43 (d, J = 8.1 Hz, 2H), 7.30 (s, 1H), 7.22 (s, 1H), 6.93 (d, J = 8.1 Hz, 2H), 3.90 (s, 3H), 3.76 (s, 3H), 3.20-3.09 (m, 4H), 3.09-2.96 (m, 2H), 2.86-2.73 (m, 2H), 2.71-2.58 (m, 4H), 2.48 (q, J = 6.8 Hz, 2H), 1.13 (t, J = 6.7 Hz, 3H). |

Example 7: Synthesis of Compounds 60-76

Compound 60

4-fluoro-3-methoxy-N-methyl-5-(2-(2-((2-methylpyridin-4-yl)amino)pyrimidin-5-yl)ethyl)benzamide

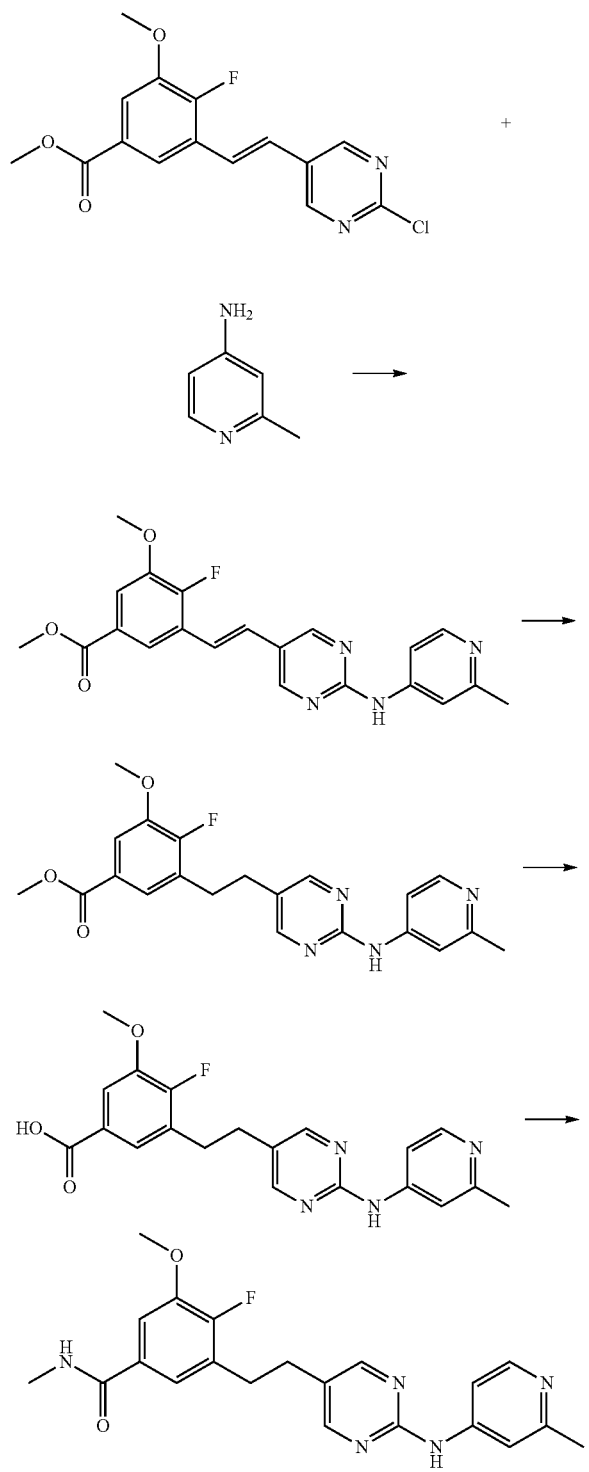

(A) (E)-methyl 4-fluoro-3-methoxy-5-(2-(2-((2-methylpyridin-4-yl)amino) pyrimidin-5-yl)vinyl) benzoate To a solution of (E)-methyl 3-(2-(2-chloropyrimidin-5-yl) vinyl)-4-fluoro-5-methoxybenzoate (232 mg, 0.72 mmol) in 1,4-dioxane (12 mL) were added 2-methylpyridin-4-amine (93 mg, 0.86 mmol), palladium(I)acetate (16 mg, 0.072 mmol), Xantphos (83 mg, 0.14 mmol) and $Cs_2CO_3$ (703 mg, 2.16 mmol). Then the mixture was stirred under microwave at 150° C. for 20 min. The mixture was then concentrated and purified via ISCO (eluted with MeOH in DCM 0%~15%) directly to give a yellow solid (143 mg, 50.4% yield). MS (m/z): 395.1 $(M+H)^+$.

(B) Methyl 4-fluoro-3-methoxy-5-(2-(2-((2-methyl-pyridin-4-yl) amino)pyrimidin-5-yl)ethyl)benzoate To a solution of (E)-methyl 4-fluoro-3-methoxy-5-(2-(2-((2-methylpyridin-4-yl)amino) pyrimidin-5-yl)vinyl)benzoate (143 mg, 0.36 mmol) in a mixed solvent of MeOH/THF (10 mL/10 mL) was added Pd/C (10%, 50 mg). Then the mixture was purged with hydrogen and stirred overnight at 35° C. under hydrogen atmosphere. After filtration, the filtrate was concentrated and the residue (119 mg, 82.8% yield) was used directly in the next step without further purification. MS (m/z): 397.1 $(M+H)^+$.

(C) 4-fluoro-3-methoxy-5-(2-(2-((2-methylpyridin-4-yl)amino)pyrimidin-5-yl)ethyl) benzoic acid To a solution of methyl 4-fluoro-3-methoxy-5-(2-(2-((2-methylpyridin-4-yl)amino) pyrimidin-5-yl)ethyl)benzoate (119 mg, 0.30 mmol) in MeOH (10 mL) was added aqueous NaOH (2 N, 4 mL, 8 mmol). Then the mixture was stirred overnight at room temperature. After concentration, the residue was purified via ISCO (eluted with MeOH in $H_2O$ 0%~100%) to give a yellow solid (110 mg, 95.8% yield). MS (m/z): 383.1 $(M+H)^+$.

(D) 4-fluoro-3-methoxy-N-methyl-5-(2-(2-((2-methylpyridin-4-yl)amino)pyrimidin-5-yl)ethyl)benzamide To a solution of 4-fluoro-3-methoxy-5-(2-(2-((2-methylpyridin-4-yl)amino) pyrimidin-5-yl)ethyl)benzoic acid (55 mg, 0.14 mmol) in DMF (5 mL) were added methanamine hydrochloride (19 mg, 0.29 mmol), HATU (164 mg, 0.43 mmol) and DIPEA (74 mg, 0.58 mmol). The mixture was stirred for 2 h at room temperature. Then the mixture was purified with ISCO (eluted with MeOH in $H_2O$ 0~100%) directly to afford the title compound as a yellow solid (17.5 mg, 30.8% yield). MS (m/z): 396.1 $(M+H)^+$. $^1$H NMR (400 MHz, $CD_3OD$) δ 8.29 (s, 2H), 8.13 (d, J=5.9 Hz, 1H), 7.61 (d, J=2.1 Hz, 1H), 7.59 (dd, J=5.8 Hz, 2.3 Hz, 1H), 7.41 (dd, J=7.8 Hz, 2.1 Hz, 1H), 7.28 (dd, J=6.0 Hz, 2.1 Hz, 1H), 3.88 (s, 3H), 2.98 (t, J=7.5 Hz, 3H), 2.91-2.86 (m, 5H), 2.45 (s, 3H).

The following compounds were prepared according to the procedures of Compound 60 using the corresponding intermediates and reagents under appropriate conditions that could be recognized by one skilled in the art.

| Compound | Structure | LC-MS (m/z) (M + H)+ | 1H NMR |
|---|---|---|---|
| 61 | 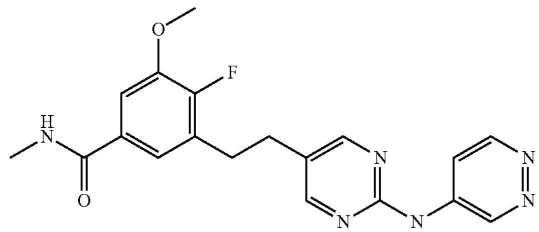 [SMILES: CNC(=O)c1cc(CCc2cnc(Nc3ccnnc3)nc2)c(F)c(OC)c1] | 383.1 | 1H NMR (400 MHz, CD3OD) δ 9.51 (s, 1H), 9.05-8.90 (m, 1H), 8.56 (s, 2H), 8.52-8.45 (m, 1H), 7.60 (dd, J = 7.8 Hz, 2.1 Hz, 1H), 7.48 (dd, J = 6.0 Hz, 2.1 Hz, 1H), 4.08 (s, 3H), 3.19 (t, J = 7.4 Hz, 2H), 3.11 (t, J = 7.4 Hz, 2H), 3.08 (s, 3H). |
| 62 | 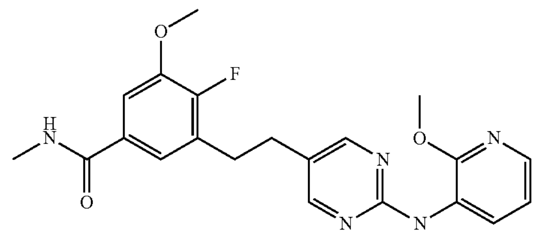 [SMILES: CNC(=O)c1cc(CCc2cnc(Nc3cccnc3OC)nc2)c(F)c(OC)c1] | 411.9 | 1H NMR (400 MHz, CD3OD) δ 8.63 (dd, J = 7.8 Hz, 1.6 Hz, 1H), 8.24 (s, 2H), 7.71 (dd, J = 5.0 Hz, 1.7 Hz, 1H), 7.40 (dd, J = 7.8 Hz, 2.0 Hz, 1H), 7.27 (dd, J = 6.0 Hz, 2.0 Hz, 1H), 6.92 (dd, J = 7.8 Hz, 5.0 Hz, 1H), 4.01 (s, 3H), 3.88 (s, 3H), 2.97 (t, J = 7.4 Hz, 2H), 2.88 (s, 3H), 2.86 (t, J = 7.4 Hz, 2H). |
| 63 | 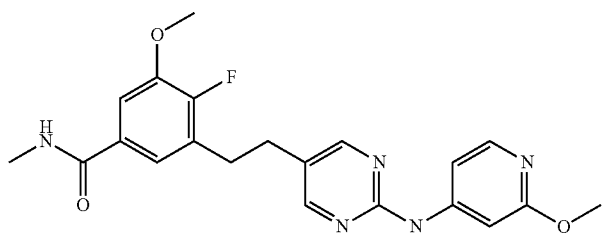 | 412.0 | 1H NMR (400 MHz, CD3OD) δ 8.28 (s, 2H), 7.86 (d, J = 5.9 Hz, 1H), 7.40 (dd, J = 7.7 Hz, 2.1 Hz, 1H), 7.38 (d, J = 1.9 Hz, 1H), 7.27 (dd, J = 5.9 Hz, 2.1 Hz, 1H), 7.15 (dd, J = 5.9 Hz, 2.1 Hz, 1H), 3.88 (s, 3H), 3.86 (s, 3H), 2.97 (t, J = 7.5 Hz, 2H), 2.99-2.85 (m, 5H). |
| 64 | 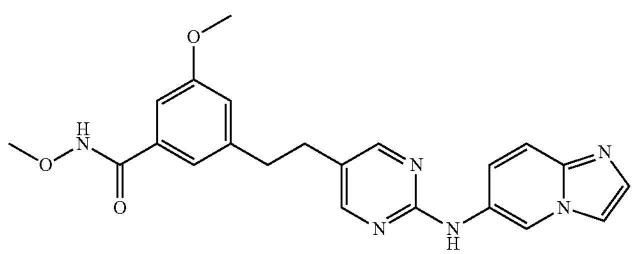 [SMILES: CONC(=O)c1cc(CCc2cnc(Nc3ccc4nccn4c3)nc2)cc(OC)c1] | 419.1 | 1H NMR (400 MHz, CD3OD) δ 9.19 (s, 1H), 8.16 (s, 2H), 7.70 (s, 1H), 7.40 (s, 1H), 7.36 (d, J = 9.6 Hz, 1H), 7.22 (dd, J = 9.6 Hz, 2.0 Hz, 1H), 7.11 (s, 1H), 7.07 (dd, J = 2.4 Hz, 1.4 Hz, 1H), 6.68 (dd, J = 2.2 Hz, 1.4 Hz, 1H), 3.68 (s, 3H), 3.64 (s, 3H), 2.83-2.76 (m, 4H). |
| 65 | 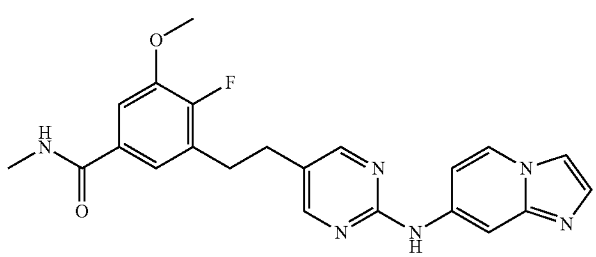 [SMILES: CNC(=O)c1cc(CCc2cnc(Nc3ccn4ccnc4c3)nc2)c(F)c(OC)c1] | 421.1 | 1H NMR (400 MHz, CD3OD) δ 8.73-8.62 (m, 1H), 8.53-8.43 (m, 1H), 8.36 (s, 2H), 7.94-7.80 (m, 1H), 7.75-7.59 (m, 1H), 7.41 (dd, J = 7.8 Hz, 2.1 Hz, 1H), 7.33 (d, J = 7.2 Hz, 1H), 7.29 (dd, J = 5.9 Hz, 2.0 Hz, 1H), 3.88 (s, 3H), 3.01 (t, J = 6.7 Hz, 2H), 2.95-2.90 (t, J = 6.7 Hz, 2H), 2.89 (s, 3H). |
| 66 | 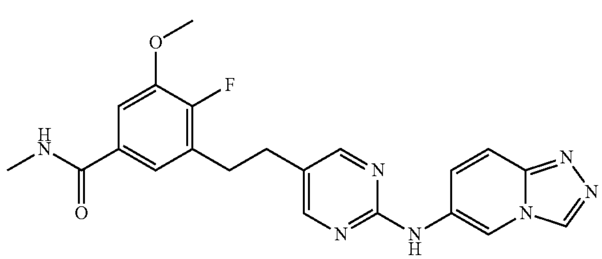 [SMILES: CNC(=O)c1cc(CCc2cnc(Nc3ccc4nncn4c3)nc2)c(F)c(OC)c1] | 422 | 1H NMR (400 MHz, CD3OD) δ 9.72 (dd, J = 1.9 Hz, 0.8 Hz, 1H), 8.29 (s, 1H), 8.28 (s, 2H), 7.70 (dd, J = 9.5 Hz, 2.0 Hz, 1H), 7.66 (dd, J = 9.5 Hz, 0.7 Hz, 1H), 7.40 (dd, J = 7.8 Hz, 2.1 Hz, 1H), 7.28 (dd, J = 6.0 Hz, 2.1 Hz, 1H), 3.87 (s, 3H), 2.97 (t, J = 7.4 Hz, 2H), 2.89-2.85 (m, 5H). |

-continued

| Compound | Structure | LC-MS (m/z) (M + H)+ | 1H NMR |
|---|---|---|---|
| 67 | 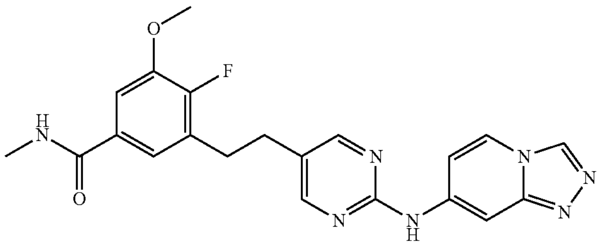 [SMILES: CNC(=O)c1cc(CCc2cnc(Nc3ccn4cnnc4c3)nc2)c(F)c(OC)c1] | 422.1 | 1H NMR (400 MHz, CD3OD) δ 8.93 (d, J = 0.7 Hz, 1H), 8.51-8.47 (m, 1H), 8.32 (s, 2H), 8.30-8.28 (m, 1H), 7.40 (dd, J = 7.7 Hz, 2.0 Hz, 1H), 7.28 (dd, J = 6.0 Hz, 2.0 Hz, 1H), 7.08 (dd, J = 7.5 Hz, 2.0 Hz, 1H), 3.87 (s, 3H), 2.98 (t, J = 7.3 Hz, 2H), 2.91-2.86 (m, 5H). |
| 68 | 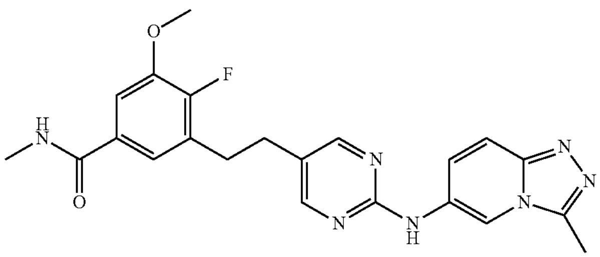 [SMILES: CNC(=O)c1cc(CCc2cnc(Nc3ccc4nnc(C)n4c3)nc2)c(F)c(OC)c1] | 436.1 | 1H NMR (400 MHz, CD3OD) δ 9.59 (dd, J = 2.0 Hz, 0.7 Hz, 1H), 8.26 (s, 2H), 7.65 (dd, J = 9.5 Hz, 2.1 Hz, 1H), 7.54 (dd, J = 9.5 Hz, 0.6 Hz, 1H), 7.40 (dd, J = 7.8 Hz, 2.1 Hz, 1H), 7.27 (dd, J = 6.0 Hz, 2.1 Hz, 1H), 3.87 (s, 3H), 2.97 (t, J = 7.1 Hz, 2H), 2.89-2.84 (m, 5H), 2.49 (s, 3H). |
| 69 | 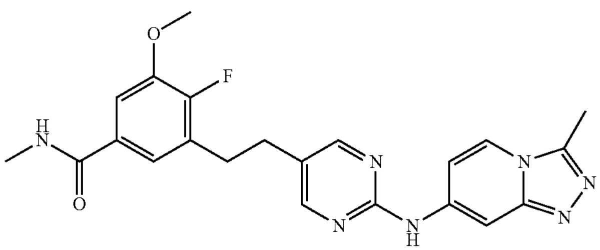 [SMILES: CNC(=O)c1cc(CCc2cnc(Nc3ccn4c(C)nnc4c3)nc2)c(F)c(OC)c1] | 436.1 | 1H NMR (400 MHz, CD3OD) δ 8.37-8.34 (m, 1H), 8.24 (s, 2H), 8.03 (d, J = 7.5 Hz, 1H), 7.32 (dd, J = 7.8 Hz, 2.0 Hz, 1H), 7.20 (dd, J = 5.9 Hz, 2.0 Hz, 1H), 7.01 (dd, J = 7.5 Hz, 2.0 Hz, 1H), 3.79 (s, 3H), 2.90 (t, J = 7.3 Hz, 2H), 2.83-2.79 (m, 5H), 2.59 (s, 3H). |
| 70 | 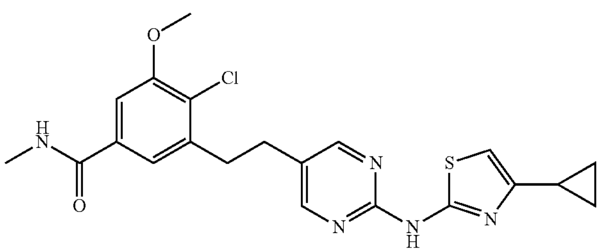 [SMILES: CNC(=O)c1cc(CCc2cnc(Nc3nc(C4CC4)cs3)nc2)c(Cl)c(OC)c1] | 444.2 | 1H NMR (400 MHz, DMSO-d6) δ 11.39 (br s, 1H), 8.45 (br s, 1H), 8.42 (s, 2H), 7.44 (s, 1H), 7.42 (s, 1H), 6.62 (s, 1H), 3.89 (s, 3H), 3.03 (t, J = 7.5 Hz, 2H), 2.85 (t, J = 7.6 Hz, 2H), 2.79 (d, J = 3.4 Hz, 3H), 2.01-1.89 (m, 1H), 0.86-0.73 (m, 4H). |
| 71 | 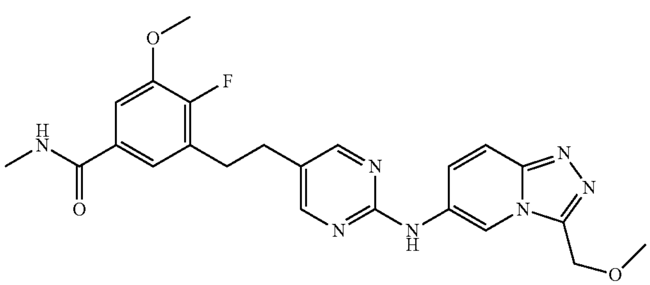 | 466.1 | 1H NMR (400 MHz, CDCl3) δ 9.68 (d, J = 1.3 Hz, 1H), 8.22 (s, 2H), 7.61 (d, J = 9.4 Hz, 1H), 7.36 (dd, J = 9.5 Hz, 2.1 Hz, 1H), 7.33 (dd, J = 7.7 Hz, 1.9 Hz, 1H), 7.08 (dd, J = 5.8 Hz, 1.9 Hz, 1H), 4.74 (s, 2H), 3.91 (s, 3H), 3.54 (s, 3H), 2.98 (s, 3H), 2.97-2.93 (t, J = 7.3 Hz, 2H), 2.87-2.82 (t, J = 7.3 Hz, 2H). |
| 72 | 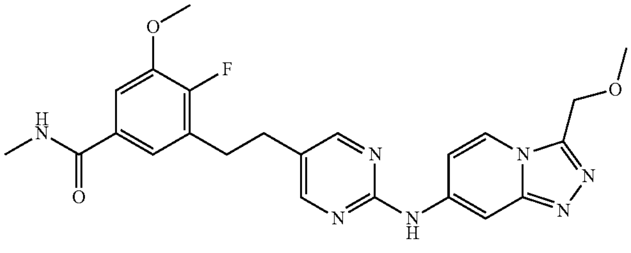 | 466.1 | 1H NMR (400 MHz, CD3OD) δ 8.44 (dd, J = 2.0 Hz, 0.8 Hz, 1H), 8.25 (s, 2H), 8.18 (dd, J = 7.5 Hz, 0.8 Hz, 1H), 7.33 (dd, J = 7.8 Hz, 2.1 Hz, 1H), 7.20 (dd, J = 6.0 Hz, 2.2 Hz, 1H), 7.05 (dd, J = 7.5 Hz, 2.1 Hz, 1H), 4.84 (s, 2H), 3.80 (s, 3H), 3.31 (s, 3H), 2.94-2.89 (t, J = 7.0 Hz, 2H), 2.83 (t, J = 7.0 Hz, 2H), 2.80 (s, 3H). |

| Compound | Structure | LC-MS (m/z) (M + H)+ | 1H NMR |
|---|---|---|---|
| 73 | 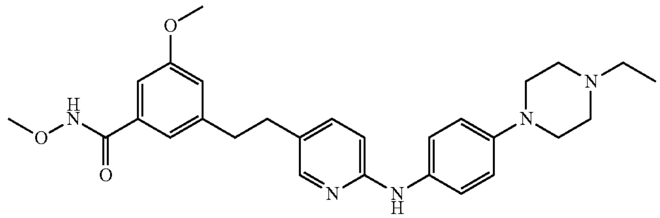 [SMILES: CCN1CCN(c2ccc(Nc3ccc(CCc4cc(OC)cc(C(=O)NOC)c4)cn3)cc2)CC1] | 490.3 | 1H NMR (400 MHz, CD3OD) δ 7.74 (s, 1H), 7.31 (dd, J = 8.5 Hz, 2.0 Hz, 1H), 7.25 (d, J = 8.7 Hz, 2H), 7.16-7.09 (m, 2H), 6.92 (d, J = 8.2 Hz, 2H), 6.86 (s, 1H), 6.65 (d, J = 8.5 Hz, 1H), 3.77 (s, 3H), 3.76 (s, 3H), 3.19-3.08 (m, 4H), 2.90-2.83 (m, 2H), 2.82-2.74 (m, 2H), 2.69-2.60 (m, 4H), 2.50 (q, J = 7.2 Hz, 2H), 1.13 (t, J = 7.2 Hz, 3H). |
| 74 | 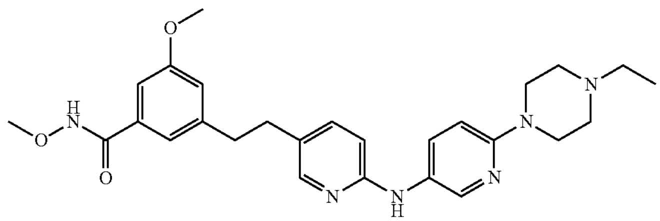 [SMILES: CCN1CCN(c2ccc(Nc3ccc(CCc4cc(OC)cc(C(=O)NOC)c4)cn3)cn2)CC1] | 491.3 | 1H NMR (400 MHz, CD3OD) δ 8.27 (s, 1H), 7.86-7.68 (m, 2H), 7.38 (d,J = 8.4 Hz, 1H), 7.13 (s, 1H), 7.10 (s, 1H), 6.92-6.83 (m, 2H), 6.76-6.59 (m, 1H), 3.77 (s, 3H), 3.76 (s, 3H), 3.76-3.64 (m, 4H), 3.38-3.29 (m, 4H), 3.20 (q, J = 7.1 Hz, 2H), 2.89-2.76 (m, 4H), 1.34 (t, J = 7.0 Hz, 3H). |
| 75 | 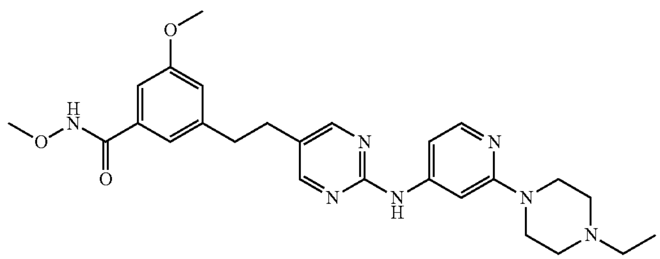 [SMILES: CCN1CCN(c2cc(Nc3ncc(CCc4cc(OC)cc(C(=O)NOC)c4)cn3)ccn2)CC1] | 492.3 | 1H NMR (400 MHz, CD3OD) δ 8.28 (s, 2H), 7.86 (d, J = 5.9 Hz, 1H), 7.35 (d, J = 1.7 Hz, 1H), 7.20 (t, J = 1.4 Hz, 1H), 7.15 (dd, J = 2.5 Hz, 1.3 Hz, 1H), 7.01 (dd, J = 5.9 Hz, 1.8 Hz, 1H), 6.62 (dd, J = 2.4 Hz, 1.6 Hz, 1H), 3.74 (s, 3H), 3.69 (s, 3H), 3.50-3.46 (m, 4H), 2.86 (m, 4H), 2.61-2.57 (m, 4H), 2.48 (q, J = 7.3 Hz, 2H), 1.14 (t, J = 7.2 Hz, 3H). |
| 76 | 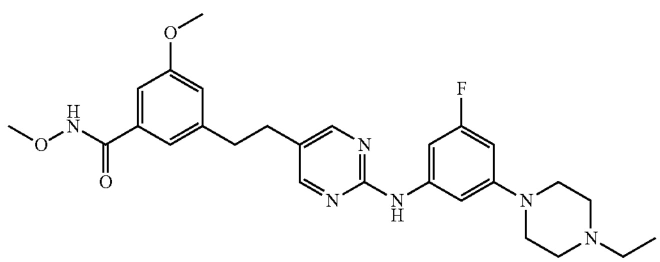 [SMILES: CCN1CCN(c2cc(F)cc(Nc3ncc(CCc4cc(OC)cc(C(=O)NOC)c4)cn3)c2)CC1] | 509.2 | 1H NMR (400 MHz, CD3OD) δ 8.20 (s, 2H), 7.19 (s, 1H), 7.16-7.09 (m, 2H), 6.96 (s, 1H), 6.70 (s, 1H), 6.29 (dt, J = 11.9 Hz, 2.0 Hz, 1H), 3.75 (s, 3H), 3.71 (s, 3H), 3.22-3.17 (t, J = 4.9 Hz, 4H), 2.84 (m, 4H), 2.62-2.58 (t, J = 4.9 Hz, 4H), 2.47 (q, J = 7.2 Hz, 2H), 1.12 (t, J = 7.2 Hz, 3H). |

Example 8: Synthesis of Compounds 77

Compound 77

4-((5-(2-fluoro-3-methoxy-5-(methylcarbamoyl)phenethyl)pyrimidin-2-yl)amino)-2-methylpyridine 1-oxide

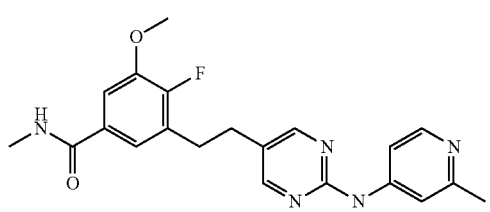

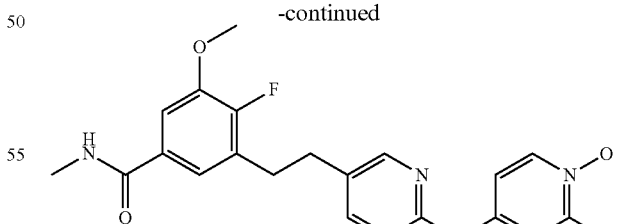

(A) 4-((5-(2-fluoro-3-methoxy-5-(methylcarbamoyl)phenethyl)pyrimidin-2-yl)amino)-2-methylpyridine 1-oxide To a solution of 4-fluoro-3-methoxy-N-methyl-5-(2-(2-((2-methylpyridin-4-yl)amino) pyrimidin-5-yl)ethyl)benzamide (18 mg, 0.046 mmol) in DCM (6 mL) was added 3-chlorobenzoperoxoic acid (8 mg, 0.046 mmol) in one portion. The resulting mixture was stirred for 2 h at 0° C. Then the reaction mixture was diluted with DCM and washed with 10% aqueous $K_2CO_3$ solution. After removal of the solvent, the residue was purified via PTLC (DCM/MeOH=20:1) to afford the title compound as a yellow solid (6.7 mg, 35.8% yield). MS (m/z): 412.1 $(M+H)^+$. $^1H$ NMR (400 MHz, $CD_3OD$) δ 8.30 (s, 2H), 8.12 (d, J=7.3 Hz, 1H), 7.89 (d, J=3.1 Hz, 1H), 7.80 (dd, J=7.3 Hz, 3.1 Hz, 1H), 7.40 (dd, J=7.8 Hz, 2.1 Hz, 1H), 7.27 (dd, J=6.0 Hz, 2.1 Hz, 1H), 3.87 (s, 3H), 2.97 (t, J=7.3 Hz, 2H), 2.91-2.85 (m, 5H), 2.49 (s, 3H).

Example 9: Synthesis of Compounds 78-103

Compound 78
4-chloro-3-(2-(2-((4-((3S,5R)-3,5-dimethylpiperazin-1-yl)phenyl)amino)pyrimidin-5-yl)ethyl)-5-methoxy-N-methylbenzamide

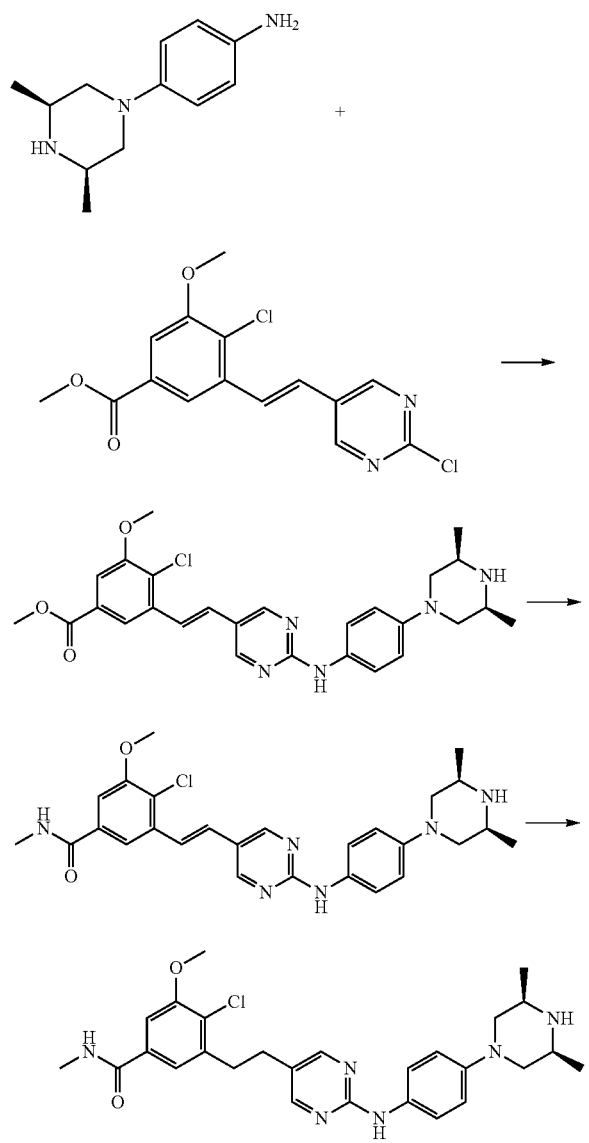

(A) Methyl 4-chloro-3-((E)-2-(2-(4-((3S,5R)-3,5-dimethylpiperazin-1-yl) phenylamino)pyrimidin-5-yl)vinyl)-5-methoxybenzoate A mixture of (E)-methyl 4-chloro-3-(2-(2-chloropyrimidin-5-yl)vinyl)-5-methoxy benzoate (150 mg, 0.442 mmol), 4-((3S,5R)-3,5-dimethylpiperazin-1-yl)aniline (109 mg, 0.531 mmol) and TFA (0.1 mL, 1.326 mmol) in propan-2-ol (5 mL) was stirred at 150° C. for 1 h under microwave. The resulting mixture was concentrated, basified with ammonia water, purified via ISCO (DCM/MeOH) to afford the title compound as a yellow solid (130 mg, 57.9% yield). MS (m/z): 508.2 $(M+H)^+$.

(B) 4-chloro-3-((E)-2-(2-(4-((3S,5R)-3,5-dimethylpiperazin-1-yl)phenylamino)pyrimidin-5-yl)vinyl)-5-methoxy-N-methylbenzamide A mixture of methyl 4-chloro-3-((E)-2-(2-(4-((3S,5R)-3,5-dimethylpiperazin-1-yl) phenylamino)pyrimidin-5-yl)vinyl)-5-methoxybenzoate (250 mg, 0.492 mmol) and methylamine (6 mL, 35% solution in ethanol) was stirred at 145° C. for 22 min under microwave. The resulting mixture was concentrated, purified via ISCO (DCM/MeOH) to afford the title compound as a yellow solid (145 mg, 58.1% yield). MS (m/z): 506.9 $(M+H)^+$.

(C) 4-chloro-3-(2-(2-(4-((3S,5R)-3,5-dimethylpiperazin-1-yl)phenylamino)pyrimidin-5-yl)ethyl)-5-methoxy-N-methylbenzamide A mixture of 4-chloro-3-((E)-2-(2-(4-((3S,5R)-3,5-dimethylpiperazin-1-yl) phenylamino)pyrimidin-5-yl)vinyl)-5-methoxy-N-methylbenzamide (120 mg, 0.237 mmol), 4-methylbenzenesulfonohydrazide (528 mg, 2.84 mmol) and sodium acetate (233 mg, 2.84 mmol) in THF (6 mL) and water (6 mL) was stirred overnight at 100° C. under nitrogen atmosphere. The resulting mixture was concentrated. The residue was partitioned between 2N HCl (15 mL) and EA (15 mL). The aqueous layer was then adjusted to pH=8 with 30% NaOH and extracted with DCM (2*15 mL). The combined extracts were concentrated and the residue was purified via ISCO (eluted with MeOH in $H_2O$ 0~100%) to afford the title compound as a yellow solid (50 mg, 41.5% yield). MS (m/z): 509.0 $(M+H)^+$. $^1H$ NMR (400 MHz, $CD_3OD$) δ 8.11 (s, 2H), 7.44 (d, J=9.1 Hz, 2H), 7.37 (d, J=2.0 Hz, 1H), 7.30 (d, J=2.0 Hz, 1H), 6.95 (d, J=9.1 Hz, 2H), 3.93 (s, 3H), 3.53-3.44 (m, 2H), 3.10-2.99 (m, 4H), 2.90 (s, 3H), 2.82 (t, J=7.6 Hz, 2H), 2.25 (t, J=7.5 Hz, 2H), 1.16 (d, J=6.4 Hz, 6H).

The following compounds were prepared according to the procedures of Compound 78 using the corresponding intermediates and reagents under appropriate conditions that could be recognized by one skilled in the art.

| Compound | Structure | LC-MS (m/z) (M + H)+ | 1H NMR |
|---|---|---|---|
| 79 | 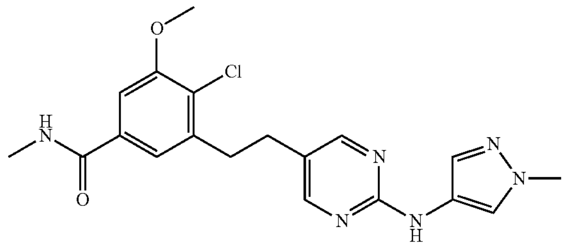 | 401.1 | 1H NMR (400 MHz, CD3OD) δ 8.17 (s, 2H), 7.87 (s, 1H), 7.52 (s, 1H), 7.37 (s, 1H), 7.31 (s, 1H), 3.94 (s, 3H), 3.86 (s, 3H), 3.09-3.02 (m, 2H), 2.92 (s, 3H), 2.86-2.80 (m, 2H). |
| 80 | 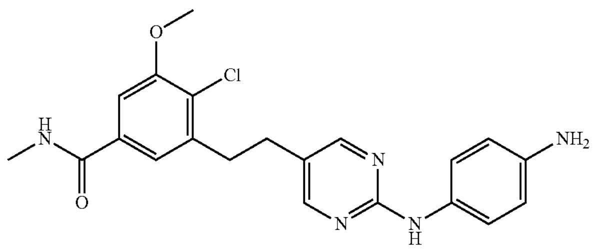 [SMILES: CNC(=O)c1cc(CCc2cnc(Nc3ccc(N)cc3)nc2)c(Cl)c(OC)c1] | 411.8 | 1H NMR (400 MHz, DMSO-d6) δ 8.89 (s, 1H), 8.45 (br, 1H), 8.19 (s, 2H), 7.45 (d, J = 1.9 Hz, 1H), 7.43 (d, J = 1.9 Hz, 1H), 7.29 (d, J = 8.7 Hz, 2H), 6.51 (d, J = 8.7 Hz, 2H), 4.68 (s, 2H), 3.91 (s, 3H), 3.02-2.96 (m, 2H), 2.80 (d, J = 4.5 Hz, 3H), 2.78-2.73 (m, 2H). |
| 81 | 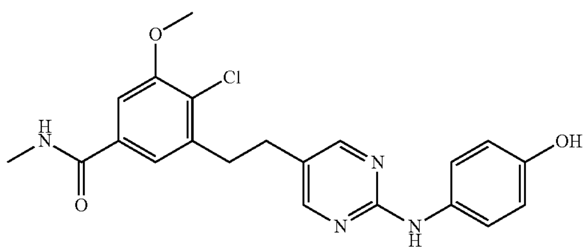 [SMILES: CNC(=O)c1cc(CCc2cnc(Nc3ccc(O)cc3)nc2)c(Cl)c(OC)c1] | 412.8 | 1H NMR (400 MHz, DMSO-d6) δ 9.07 (s, 1H), 8.44 (br, 1H), 8.21 (s, 2H), 7.46-7.43 (m, 2H), 7.43-7.40 (m, 2H), 6.67 (d, J = 8.8 Hz, 2H), 3.89 (s, 3H), 3.01-2.96 (m, 2H), 2.78 (d, J = 4.4 Hz, 3H), 2.78-2.73 (m, 2H). |
| 82 | 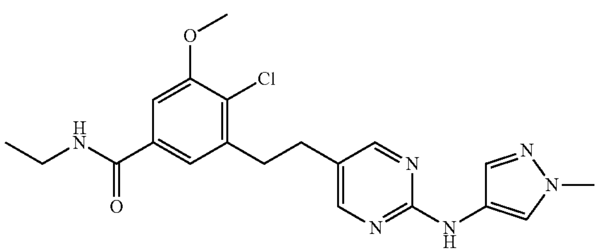 [SMILES: CCNC(=O)c1cc(CCc2cnc(Nc3cnn(C)c3)nc2)c(Cl)c(OC)c1] | 414.9 | 1H NMR (400 MHz, CD3OD) δ 8.15 (s, 2H), 7.88 (s, 1H), 7.50 (s, 1H), 7.37 (s, 1H), 7.30 (s, 1H), 3.93 (s, 3H), 3.84 (s, 3H), 3.38 (q, J = 6.5 Hz, 2H), 3.10-3.01 (m, 2H), 2.87-2.77 (m, 2H), 1.20 (t, J = 6.8 Hz, 3H). |
| 83 | 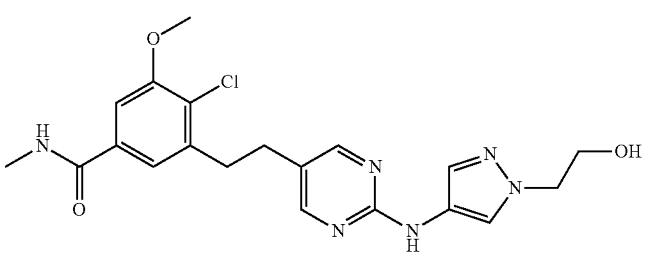 [SMILES: CNC(=O)c1cc(CCc2cnc(Nc3cnn(CCO)c3)nc2)c(Cl)c(OC)c1] | 431.0 | 1H NMR (400 MHz, CD3OD) δ 8.13 (s, 2H), 7.93 (s, 1H), 7.54 (s, 1H), 7.36 (d, J = 1.8 Hz, 1H), 7.29 (d, J = 1.9 Hz, 1H), 4.16 (t, J = 5.4 Hz, 2H), 3.91 (s, 3H), 3.86 (t, J = 5.2 Hz, 2H), 3.04 (t, J = 7.6 Hz, 2H), 2.89 (s, 3H), 2.81 (t, J = 7.6 Hz, 2H). |
| 84 | 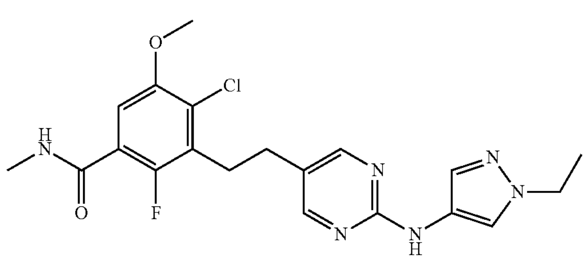 | 433.2 | 1H NMR (400 MHz, CD3OD) δ 8.13 (s, 2H), 7.90 (s, 1H), 7.52 (s, 1H), 7.26 (d, J = 5.5 Hz, 1H), 4.13 (q, J = 7.2 Hz, 2H), 3.88 (s, 3H), 3.10 (t, J = 6.9 Hz, 2H), 2.90 (s, 3H), 2.79 (t, J = 7.0 Hz, 2H), 1.43 (t, J = 7.3 Hz, 3H). |

-continued

| Compound | Structure | LC-MS (m/z) (M + H)+ | 1H NMR |
|---|---|---|---|
| 85 | 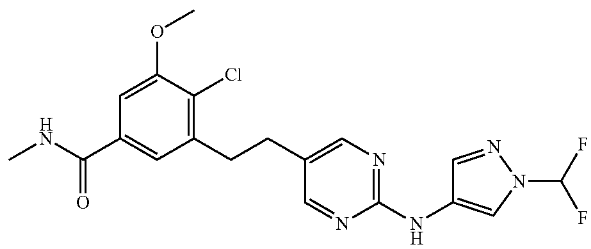 [SMILES: CNC(=O)c1cc(CCc2cnc(Nc3cnn(C(F)F)c3)nc2)c(Cl)c(OC)c1] | 436.9 | 1H NMR (400 MHz, CD3OD) δ 8.33 (s, 1H), 8.22 (s, 2H), 7.76 (s, 1H), 7.38 (t, J = 59.8 Hz, 1H), 7.37 (d, J = 2.0 Hz, 1H), 7.31 (d, J = 1.6 Hz, 1H), 3.93 (s, 3H), 3.07 (t, J = 7.6 Hz, 2H), 2.89 (s, 3H), 2.85 (t, J = 7.6 Hz, 2H). |
| 86 | 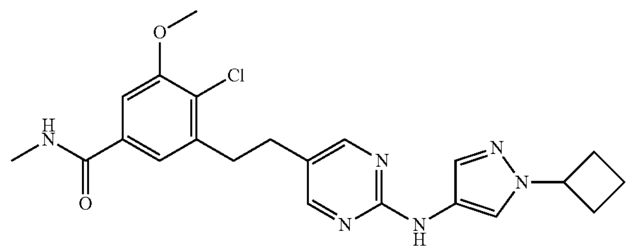 | 441.0 | 1H NMR (400 MHz, CDCl3) δ 8.16 (s, 2H), 7.91 (s, 1H), 7.43 (s, 1H), 7.28 (s, 1H), 7.23 (s, 1H), 7.03 (s, 1H), 4.77-4.69 (m, 1H), 3.95 (s, 3H), 3.01 (t, J = 7.6 Hz, 2H), 2.97 (d, J = 4.7 Hz, 3H), 2.79 (t, J = 7.6 Hz, 2H), 2.62-2.40 (m, 4H), 1.92-1.83 (m, 2H). |
| 87 | 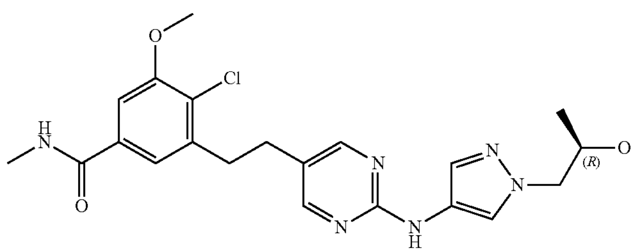 | 445.2 | 1H NMR (400 MHz, CD3OD) δ 8.13 (s, 2H), 7.93 (s, 1H), 7.54 (s, 1H), 7.36 (s, 1H), 7.30 (s, 1H), 4.19-3.97 (m, 3H), 3.91 (s, 3H), 3.04 (t, J = 7.0 Hz, 2H), 2.89 (s, 3H), 2.81 (d, J = 7.0 Hz, 2H), 1.15 (d, J = 5.2 Hz, 3H). |
| 88 | 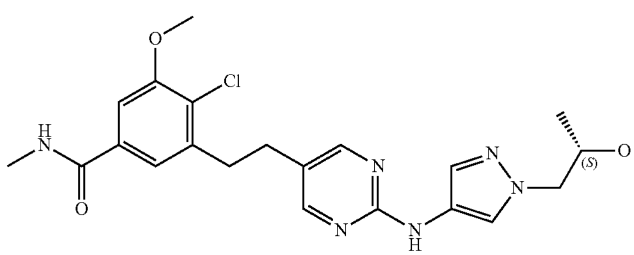 | 445.3 | 1H NMR (400 MHz, CD3OD) δ 8.13 (s, 2H), 7.91 (s, 1H), 7.54 (s, 1H), 7.36 (d, J = 1.9 Hz, 1H), 7.30 (d, J = 1.9 Hz, 1H), 4.14-4.06 (m, 1H), 4.05-3.96 (m, 2H), 3.92 (s, 3H), 3.05 (t, J = 7.6 Hz, 2H), 2.89 (s, 3H), 2.82 (t, J = 7.6 Hz, 2H), 1.15 (d, J = 6.2 Hz, 3H). |
| 89 | 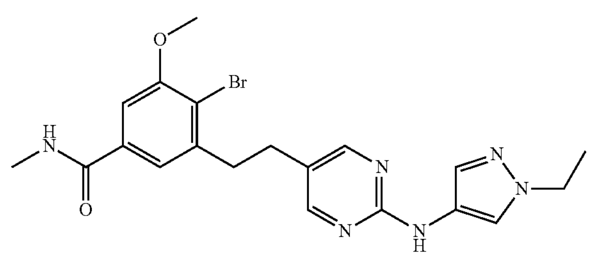 | 458.9 460.9 | 1H NMR (400 MHz, CD3OD) δ 8.15 (s, 2H), 7.91 (s, 1H), 7.52 (s, 1H), 7.30 (s, 1H), 7.29 (s, 1H), 4.12 (q, J = 6.8 Hz, 2H), 3.91 (s, 3H), 3.12-3.02 (m, 2H), 2.89 (s, 3H), 2.81 (t, J = 9.1 Hz, 2H), 1.43 (t, J = 6.9 Hz, 3H). |
| 90 | 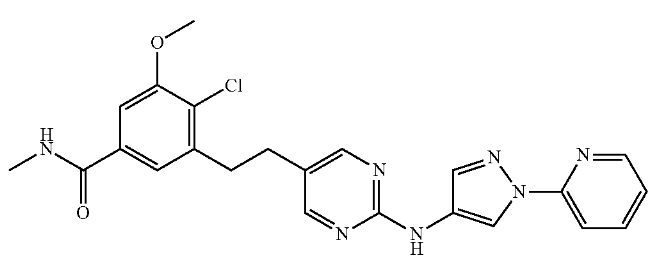 [SMILES: CNC(=O)c1cc(CCc2cnc(Nc3cnn(-c4ccccn4)c3)nc2)c(Cl)c(OC)c1] | 463.9 | 1H NMR (400 MHz, CD3OD) δ 8.86 (s, 1H), 8.38 (s, 1H), 8.21 (s, 2H), 7.93-7.80 (m, 3H), 7.33 (s, 1H), 7.29 (s, 1H), 7.23-7.16 (m, 1H), 3.91 (s, 3H), 3.09-2.98 (m, 2H), 2.89 (s, 3H), 2.87-2.77 (m, 2H). |

| Compound | Structure | LC-MS (m/z) (M + H)+ | 1H NMR |
|---|---|---|---|
| 91 | 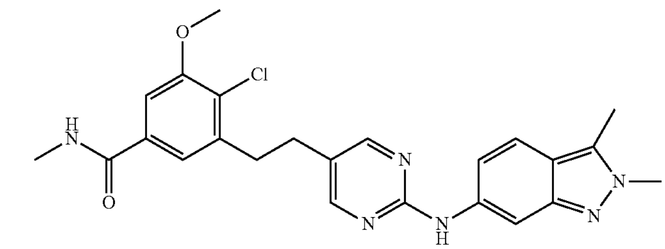 | 464.9 | 1H NMR (400 MHz, CD3OD) δ 8.22 (s, 2H), 8.09 (s, 1H), 7.51 (d, J = 9.0 Hz, 1H), 7.38 (d, J = 1.9 Hz, 1H), 7.32 (d, J = 1.9 Hz, 1H), 7.06 (dd, J = 9.0 Hz, 1.8 Hz, 1H), 4.02 (s, 3H), 3.93 (s, 3H), 3.08 (t, J = 7.2 Hz, 2H), 2.89 (s, 3H), 2.86 (t, J = 7.2 Hz, 2H), 2.59 (s, 3H). |
| 92 | 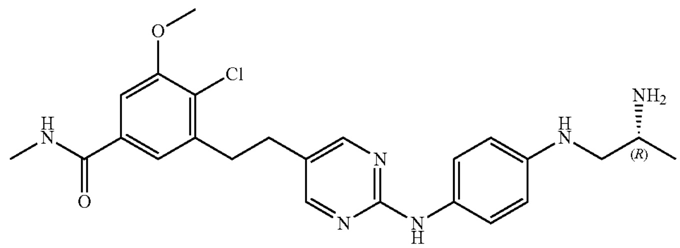 | 468.9 | 1H NMR (400 MHz, DMSO-d6) δ 8.91 (s, 1H), 8.45 (br, 1H), 8.18 (s, 2H), 7.44 (d, J = 1.9 Hz, 1H), 7.42 (d, J = 1.9 Hz, 1H), 7.33 (d, J = 8.8 Hz, 2H), 6.52 (d, J = 8.8 Hz, 2H), 5.20 (t, J = 5.9 Hz, 1H), 3.89 (s, 3H), 3.02-2.93 (m, 3H), 2.91-2.84 (m, 1H), 2.79 (d, J = 4.5 Hz, 3H), 2.76-2.71 (m, 3H), 1.01 (d, J = 6.3 Hz, 3H). |
| 93 | 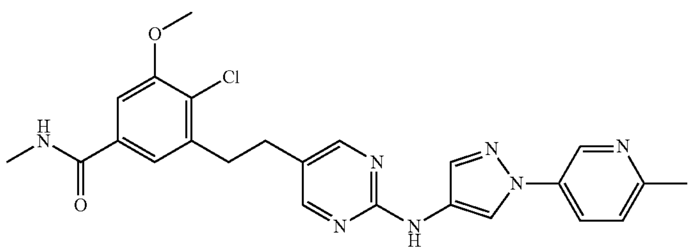 | 477.9 | 1H NMR (400 MHz, CD3OD) δ 8.82 (s, 1H), 8.55 (s, 1H), 8.24 (s, 2H), 8.05 (d, J = 6.9 Hz, 1H), 7.85 (s, 1H), 7.40 (d, J = 7.2 Hz, 1H), 7.38 (s, 1H), 7.33 (s, 1H), 3.94 (s, 3H), 3.08 (t, J = 7.8 Hz, 2H), 2.92 (s, 3H), 2.89-2.83 (m, 2H), 2.58 (s, 3H). |
| 94 | 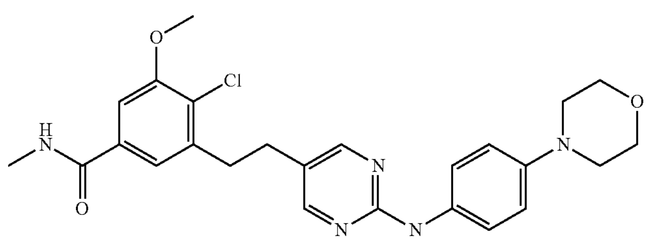 | 481.8 | 1H NMR (400 MHz, CDCl3) δ 8.09 (s, 2H), 7.39 (d, J = 7.5 Hz, 2H), 7.22 (d, J = 1.8 Hz, 1H), 6.99 (s, 1H), 6.93 (d, J = 1.8 Hz, 1H), 6.85 (s, 2H), 5.95 (s, 1H), 3.89 (s, 3H), 3.82-3.78 (m, 4H), 3.07-3.03 (m, 4H), 2.97-2.92 (m, 2H), 2.90 (d, J = 4.8 Hz, 3H), 2.78-2.72 (m, 2H). |
| 95 | 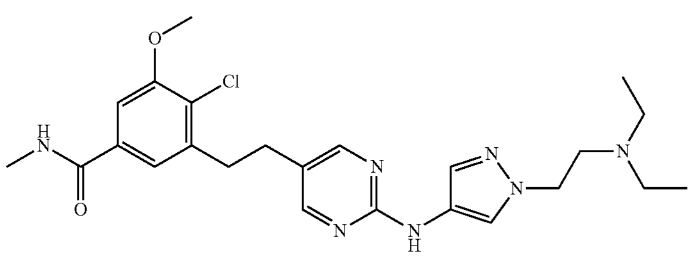 | 485.9 | 1H NMR (400 MHz, CD3OD) δ 8.15 (s, 2H), 7.97 (s, 1H), 7.54 (s, 1H), 7.37 (d, J = 1.8 Hz, 1H), 7.31 (d, J = 1.8 Hz, 1H), 4.19 (t, J = 7.0 Hz, 2H), 3.92 (s, 3H), 3.06 (t, J = 7.6 Hz, 2H), 2.93-2.87 (m, 5H), 2.83 (t, J = 7.5 Hz, 2H), 2.58 (q, J = 7.1 Hz, 4H), 1.04 (t, J = 7.1 Hz, 6H). |
| 96 | 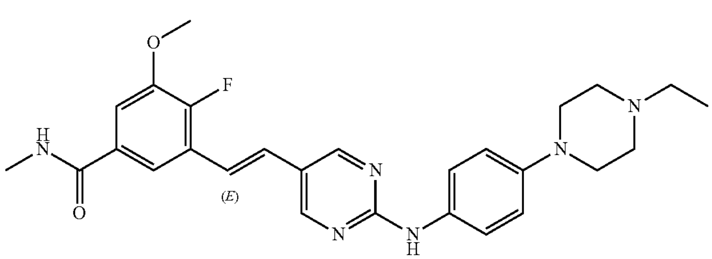 [SMILES: CCN1CCN(c2ccc(Nc3ncc(/C=C/c4cc(C(=O)NC)cc(OC)c4F)cn3)cc2)CC1] | 491.2 | 1H NMR (400 MHz, CDCl3) δ 8.55 (s, 2H), 7.47 (d, J = 8.9 Hz, 2H), 7.34 (dd, J = 7.9 Hz, 1.9 Hz, 1H), 7.14 (d, J = 16.6 Hz, 1H), 7.08 (s, 1H), 7.02 (d, J = 16.5 Hz, 1H), 6.95 (d, J = 8.7 Hz, 2H), 6.14 (s, 1H), 3.95 (s, 3H), 3.24-3.16 (m, 4H), 3.04 (d, J = 4.9 Hz, 3H), 2.66-2.59 (m, 4H), 2.49 (q, J = 7.1 Hz, 2H), 1.14 (t, J = 7.2 Hz, 3H). |

| Compound | Structure | LC-MS (m/z) (M + H)+ | 1H NMR |
|---|---|---|---|
| 97 | 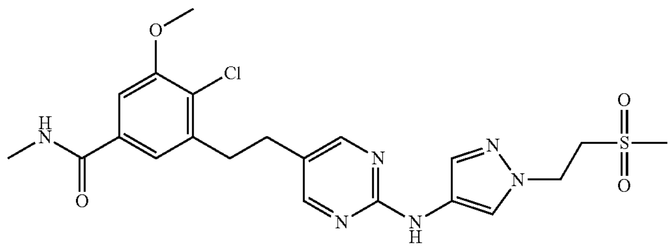 | 492.9 | 1H NMR (400 MHz, DMSO-d6) δ 9.33 (s, 1H), 8.47 (s, 1H), 8.23 (s, 2H), 7.97 (s, 1H), 7.51 (s, 1H), 7.42 (s, 1H), 7.40 (s, 1H), 4.47 (t, J = 6.9 Hz, 2H), 3.87 (s, 3H), 3.64 (t, J = 6.5 Hz, 2H), 2.97 (t, J = 7.4 Hz, 2H), 2.83 (s, 3H), 2.78-2.71 (m, 5H). |
| 98 | 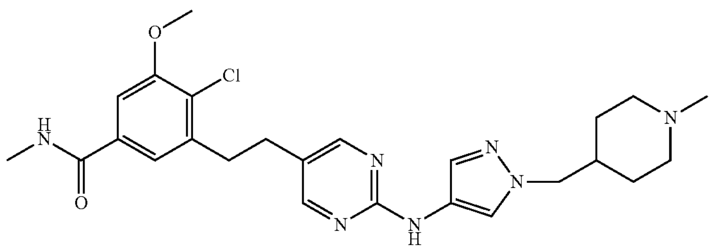 | 498.0 | 1H NMR (400 MHz, CD3OD) δ 8.15 (s, 2H), 7.98 (s, 1H), 7.55 (s, 1H), 7.37 (d, J = 1.9 Hz, 1H), 7.30 (d, J = 1.9 Hz, 1H), 4.07 (d, J = 6.9 Hz, 2H), 3.93 (s, 3H), 3.06 (t, J = 7.5 Hz, 2H), 2.90 (s, 3H), 2.84 (t, J = 7.5 Hz, 2H), 2.79 (s, 3H), 2.20-2.16 (m, 2H), 2.08-1.99 (m, 1H), 1.86-1.82 (m, 2H), 1.60-1.46 (m, 4H). |
| 99 | 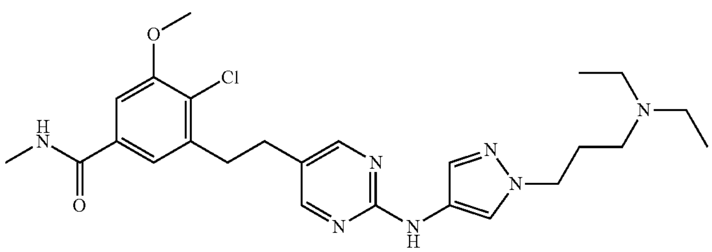 [SMILES: CCN(CC)CCCn1cc(Nc2ncc(CCc3cc(C(=O)NC)cc(OC)c3Cl)cn2)cn1] | 500.0 | 1H NMR (400 MHz, CD3OD) δ 8.15 (s, 2H), 7.95 (s, 1H), 7.53 (s, 1H), 7.37 (d, J = 1.9 Hz, 1H), 7.31 (d, J = 1.9 Hz, 1H), 4.12 (t, J = 6.7 Hz, 2H), 3.92 (s, 3H), 3.05 (t, J = 7.6 Hz, 2H), 2.90 (s, 3H), 2.82 (t, J = 7.6 Hz, 2H), 2.55 (q, J = 7.2 Hz, 4H), 2.51-2.42 (m, 2H), 2.06-1.93 (m, 2H), 1.01 (t, J = 7.2 Hz, 6H). |
| 100 | 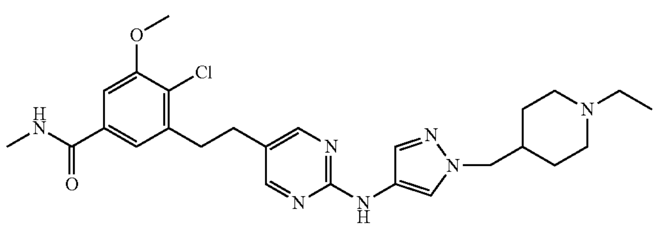 [SMILES: CCN1CCC(Cn2cc(Nc3ncc(CCc4cc(C(=O)NC)cc(OC)c4Cl)cn3)cn2)CC1] | 511.9 | 1H NMR (400 MHz, CD3OD) δ 8.16 (s, 2H), 7.92 (s, 1H), 7.54 (s, 1H), 7.37 (d, J = 1.9 Hz, 1H), 7.31 (d, J = 1.9 Hz, 1H), 3.98 (d, J = 7.2 Hz, 2H), 3.93 (s, 3H), 3.06 (t, J = 7.6 Hz, 2H), 2.98-2.92 (m, 2H), 2.90 (s, 3H), 2.83 (t, J = 7.6 Hz, 2H), 2.42 (q, J = 7.4 Hz, 2H), 2.02-1.90 (m, 3H), 1.64-1.56 (m, 2H), 1.37-1.34 (m, 2H), 1.08 (t, J = 7.4 Hz, 3H). |
| 101 | 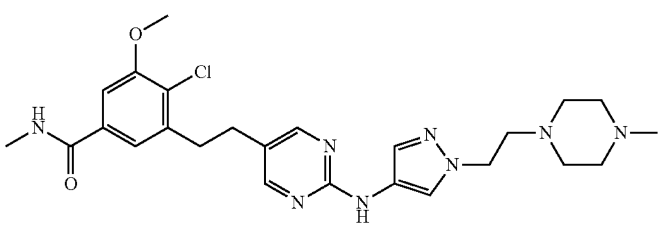 | 513.0 | 1H NMR (400 MHz, CD3OD) δ 8.15 (s, 2H), 7.97 (s, 1H), 7.53 (s, 1H), 7.36 (s, 1H), 7.30 (s, 1H), 4.21 (t, J = 6.6 Hz, 2H), 3.92 (s, 3H), 3.05 (t, J = 7.6 Hz, 2H), 2.89 (s, 3H), 2.89-2.78 (m, 4H), 2.62-2.40 (m, 8H), 2.26 (s, 3H). |
| 102 | 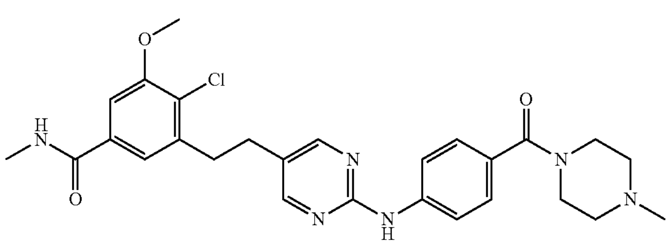 | 523.3 | 1H NMR (400 MHz, CD3OD) δ 8.23 (s, 2H), 7.77 (d, J = 8.8 Hz, 2H), 7.38-7.35 (m, 3H), 7.31 (d, J = 2.0 Hz, 1H), 3.93 (s, 3H), 3.79-3.54 (m, 4H), 3.08 (t, J = 7.6 Hz, 2H), 2.89-2.85 (m, 5H), 2.53-2.41 (m, 4H), 2.32 (s, 3H). |

| Compound | Structure | LC-MS (m/z) (M + H)+ | 1H NMR |
|---|---|---|---|
| 103 | 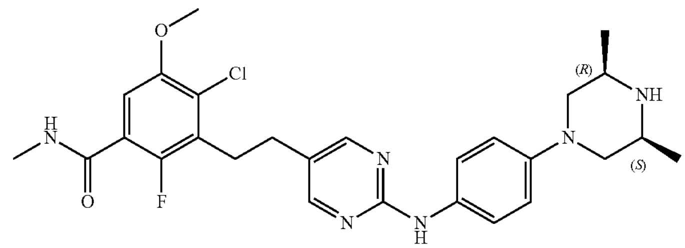 | 527.3 | 1H NMR (400 MHz, CD3OD) δ 8.01 (s, 2H), 7.34 (d, J = 8.5 Hz, 2H), 7.18 (d, J = 6.2 Hz, 1H), 6.85 (d, J = 8.6 Hz, 2H), 3.80 (s, 3H), 3.43-3.32 (m, 2H), 3.02 (t, J = 7.2 Hz, 2H), 2.96-2.87 (m, 2H), 2.81 (s, 3H), 2.70 (t, J = 7.4 Hz, 2H), 2.15 (t, J = 11.0 Hz, 2H), 1.05 (d, J = 6.4 Hz, 6H). |

Example 10: Synthesis of Compounds 104-111

Compound 104
4-fluoro-3-methoxy-N-methyl-5-(2-(2-((5-(morpholinomethyl)pyridin-2-yl)amino)pyrimidin-5-yl)ethyl)benzamide

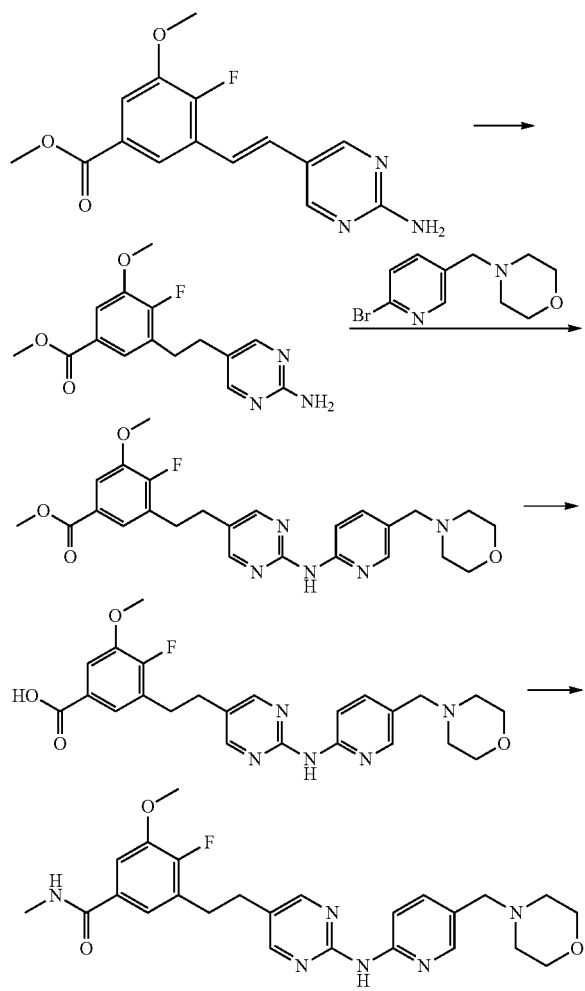

(A) Methyl 3-(2-(2-aminopyrimidin-5-yl)ethyl)-4-fluoro-5-methoxybenzoate

To a solution of (E)-methyl 3-(2-(2-aminopyrimidin-5-yl)vinyl)-4-fluoro-5-methoxybenzoate (0.26 g, 0.86 mmol) in THF (40 mL) was added Pd/C (10%, 0.14 g). The mixture was stirred at 35° C. for 48 h under hydrogen (1 atm). The mixture was filtered and the filtrate was concentrated. The residue was then purified via ISCO (eluted with MeOH in H2O 0~100%) to afford the title compound as a yellow solid (0.11 g, 42.0% yield). MS (m/z): 306.1 (M+H)+.

(B) Methyl 4-fluoro-3-methoxy-5-(2-(2-((5-(morpholinomethyl)pyridin-2-yl)amino) pyrimidin-5-yl) ethyl)benzoate A mixture of methyl 3-(2-(2-aminopyrimidin-5-yl)ethyl)-4-fluoro-5-methoxybenzoate (0.09 g, 0.30 mmol), 4-((6-bromopyridin-3-yl)methyl)morpholine (0.12 g, 0.47 mmol), Cs2CO3 (0.20 g, 0.62 mmol), palladium(I)acetate (0.02 g, 0.089 mmol) and Xantphos (0.02 g, 0.035 mmol) in dioxane (6 mL) was heated at 130° C. under microwave for 15 min. Then the mixture was concentrated and the residue was purified via ISCO (eluted with MeOH in H2O 0~100%) to afford the title compound as a yellow solid (0.06 g, 42.3% yield). MS (m/z): 482.3 (M+H)+.

(C) 4-fluoro-3-methoxy-5-(2-(2-((5-(morpholinomethyl)pyridin-2-yl)amino)pyrimidin-5-yl)ethyl)benzoic acid A mixture of methyl 4-fluoro-3-methoxy-5-(2-(2-((5-(morpholinomethyl)pyridin-2-yl) amino)pyrimidin-5-yl) ethyl)benzoate (0.06 g, 0.12 mmol) in THF (4 mL) and aqueous LiOH solution (0.02 g in 1 mL H2O) was stirred at 40° C. for 2 h. Then the reaction mixture was purified via ISCO (eluted with MeOH in H2O 0~100%) directly to afford the title compound as a yellow solid (0.042 g, 72.1% yield). MS (m/z): 468.2 (M+H)+.

(D) 4-fluoro-3-methoxy-N-methyl-5-(2-(2-((5-(morpholinomethyl)pyridin-2-yl)amino)pyrimidin-5-yl) ethyl)benzamide A mixture of 4-fluoro-3-methoxy-5-(2-(2-((5-(morpholinomethyl)pyridin-2-yl) amino)pyrimidin-5-yl)ethyl)benzoic acid (0.042 g, 0.090 mmol), methylamine hydrochloride (0.010 g, 0.15 mmol), DIPEA (0.032 g, 0.25 mmol) and HATU (0.070 g, 0.18 mmol) in DMF (8 mL) was stirred at room temperature for 0.5 h. Then the reaction mixture was purified via ISCO (eluted with MeOH in H2O 0~100%) directly to afford the title compound as a yellow solid (0.015 g, 34.7% yield). MS (m/z): 481.2 (M+H)+. 1H NMR (400 MHz, CD3OD) δ 8.30 (s, 2H), 8.17 (s, 1H), 7.73 (s, 1H), 7.72 (s, 1H), 7.42 (d, J=7.2 Hz, 1H), 7.30 (d, J=7.1 Hz, 1H), 3.91 (s, 3H), 3.80-3.66 (m, 4H), 3.54-3.47 (m, 2H), 3.00 (t, J=9.1 Hz, 2H), 2.92 (s, 3H), 2.91-2.82 (m, 2H), 2.57-2.40 (m, 4H).

The following compounds were prepared according to the procedures of Compound 104 using the corresponding intermediates and reagents under appropriate conditions that could be recognized by one skilled in the art.

| Compound | Structure | LC-MS (m/z) (M + H)+ | $^1$H NMR |
|---|---|---|---|
| 105 | 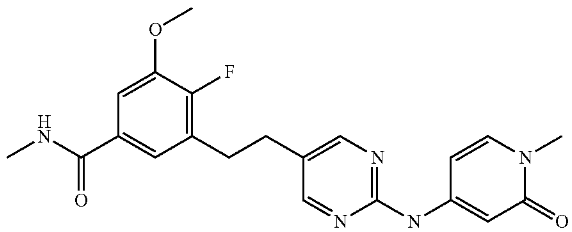 [SMILES: CNC(=O)c1cc(CCc2cnc(Nc3ccn(C)c(=O)c3)nc2)c(F)c(OC)c1] | 412.0 | $^1$H NMR (400 MHz, CD$_3$OD) δ 8.29 (s, 2H), 7.46 (d, J = 7.5 Hz, 1H), 7.40 (dd, J = 7.8 Hz, 2.0 Hz, 1H), 7.30 (d, J = 2.4 Hz, 1H), 7.27 (dd, J = 5.9 Hz, 2.0 Hz, 1H), 6.64 (dd, J = 7.5 Hz, 2.4 Hz, 1H), 3.88 (s, 3H), 3.48 (s, 3H), 2.97 (t, J = 7.2 Hz, 2H), 2.88 (s, 3H), 2.87 (t, J = 7.2 Hz, 2H). |
| 106 | 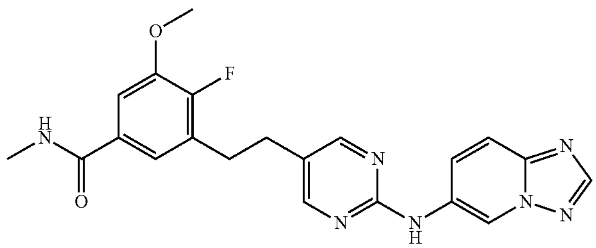 [SMILES: CNC(=O)c1cc(CCc2cnc(Nc3ccc4ncnn4c3)nc2)c(F)c(OC)c1] | 421.9 | $^1$H NMR (400 MHz, CDCl$_3$) δ 9.72 (s, 1H), 8.30 (s, 1H), 8.25 (s, 2H), 7.69 (d, J = 9.4 Hz, 1H), 7.36 (dd, J = 9.4 Hz, 2.0 Hz, 1H), 7.32 (dd, J = 7.7 Hz, 2.0 Hz, 1H), 7.16 (s, 1H), 7.06 (dd, J = 5.9 Hz, 2.0 Hz, 1H), 6.06 (s, 1H), 3.92 (s, 3H), 2.98 (d, J = 4.8 Hz, 3H), 2.96-2.93 (m, 2H), 2.86 (t, J = 7.4 Hz, 2H). |
| 107 | 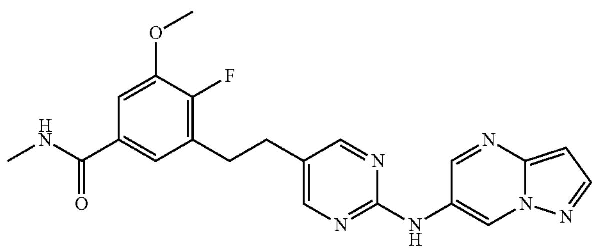 [SMILES: CNC(=O)c1cc(CCc2cnc(Nc3cnc4ccnn4c3)nc2)c(F)c(OC)c1] | 422.0 | $^1$H NMR (400 MHz, CD$_3$OD) δ 9.74 (s, 1H), 8.60 (s, 1H), 8.27 (s, 2H), 8.03 (s, 1H), 7.41 (d, J = 7.7 Hz, 1H), 7.29 (d, J = 4.3 Hz, 1H), 6.63 (s, 1H), 3.89 (s, 3H), 2.98 (t, J = 7.3 Hz, 2H), 2.92-2.84 (m, 5H). |
| 108 | 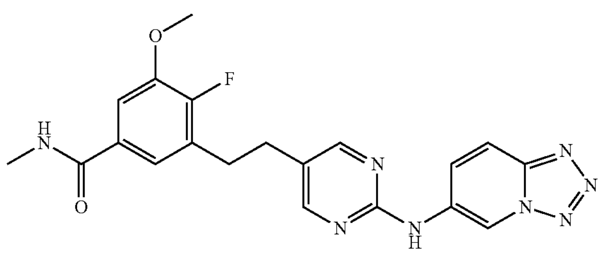 [SMILES: CNC(=O)c1cc(CCc2cnc(Nc3ccc4nnnn4c3)nc2)c(F)c(OC)c1] | 422.9 | $^1$H NMR (400 MHz, DMSO-d6) δ 10.24 (s, 1H), 9.91 (s, 1H), 8.45 (s, 2H), 8.38 (d, J = 4.4 Hz, 1H), 8.13 (d, J = 9.6 Hz, 1H), 7.89 (dd, J = 9.6 Hz, 1.8 Hz, 1H), 7.42 (dd, J = 7.9 Hz, 2.0 Hz, 1H), 7.38 (dd, J = 7.9 Hz, 2.0 Hz, 1H), 3.82 (s, 3H), 2.93 (t, J = 7.4 Hz, 2H), 2.84 (t, J = 7.5 Hz, 2H), 2.74 (d, J = 4.5 Hz, 3H). |
| 109 | 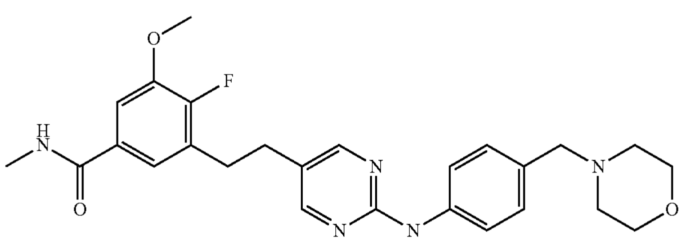 [SMILES: CNC(=O)c1cc(CCc2cnc(Nc3ccc(CN4CCOCC4)cc3)nc2)c(F)c(OC)c1] | 480.0 | $^1$H NMR (400 MHz, CD$_3$OD) δ 8.17 (s, 2H), 7.58 (d, J = 8.6 Hz, 2H), 7.42 (dd, J = 7.7 Hz, 2.2 Hz, 1H), 7.28 (dd, J = 5.9 Hz, 2.2 Hz, 1H), 7.25 (d, J = 8.6 Hz, 2H), 3.90 (s, 3H), 3.69 (t, J = 4.5 Hz, 4H), 3.48 (s, 2H), 2.97 (t, J = 7.4 Hz, 2H), 2.90 (s, 3H), 2.84 (t, J = 7.4 Hz, 2H), 2.46 (t, J = 4.5 Hz, 4H). |
| 110 | 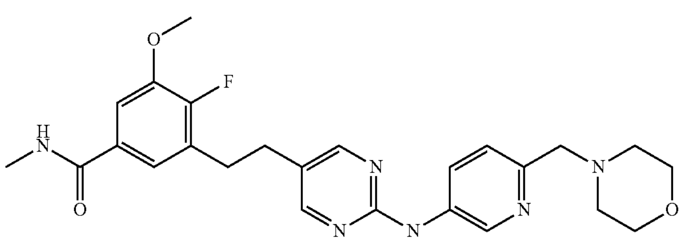 [SMILES: CNC(=O)c1cc(CCc2cnc(Nc3ccc(CN4CCOCC4)nc3)nc2)c(F)c(OC)c1] | 481.0 | $^1$H NMR (400 MHz, CD$_3$OD) δ 8.80 (d, J = 2.6 Hz, 1H), 8.23-8.21 (m, 3H), 7.43-7.39 (m, 2H), 7.27 (dd, J = 6.0 Hz, 2.1 Hz, 1H), 3.88 (s, 3H), 3.77 (s, 2H), 3.75-3.72 (m, 4H), 2.97 (t, J = 7.3 Hz, 2H), 2.88 (s, 3H), 2.85 (t, J = 7.3 Hz, 2H), 2.70-2.65 (m, 4H). |

| Compound | Structure | LC-MS (m/z) (M + H)+ | 1H NMR |
|---|---|---|---|
| 111 | 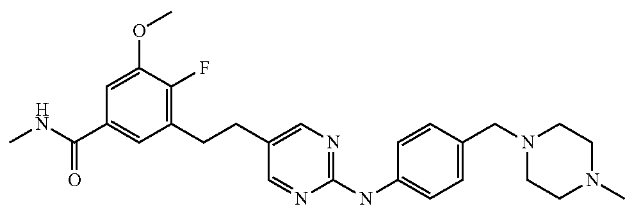 | 493.0 | 1H NMR (400 MHz, CD3OD) δ 8.18 (s, 2H), 7.63 (d, J = 8.3 Hz, 2H), 7.43-7.41 (m, 1H), 7.30-7.26 (m, 3H), 3.89 (s, 3H), 3.69 (s, 2H), 3.14-3.06 (m, 4H), 2.97 (t, J = 7.8 Hz, 2H), 2.90 (s, 3H), 2.86-2.78 (m, 6H), 2.73 (s, 3H). |

Example 11: Synthesis of Compounds 112-161

Compound 112

3-(2-(2-((1-ethyl-1H-pyrazol-4-yl)amino)pyrimidin-5-yl)ethyl)-4-fluoro-5-methoxy-N-methylbenzamide

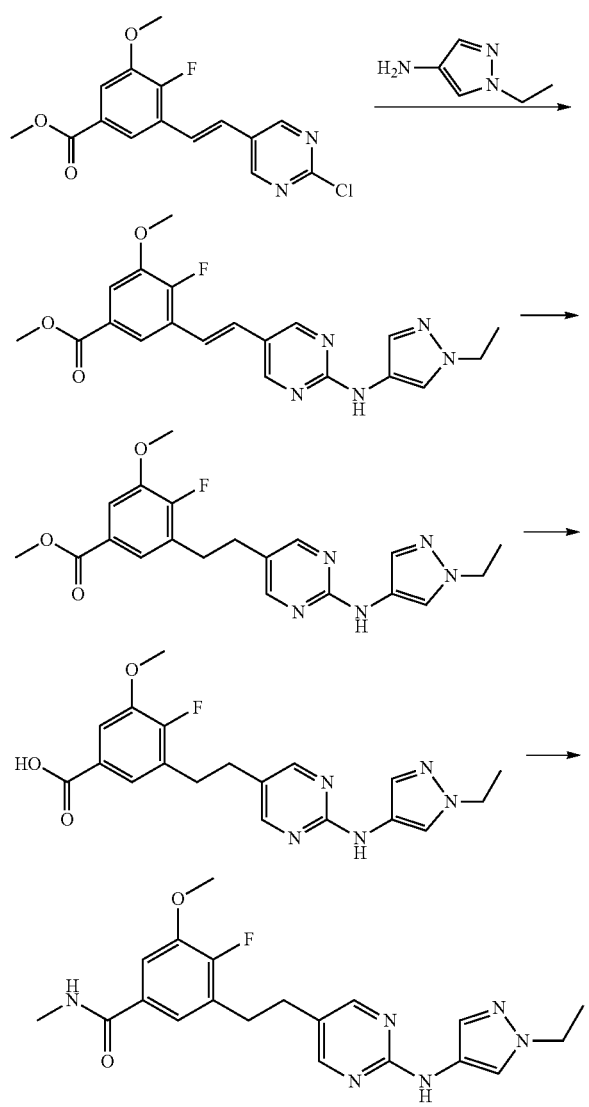

(A) (E)-Methyl 3-(2-(2-((1-ethyl-1H-pyrazol-4-yl)amino)pyrimidin-5-yl)vinyl)-4-fluoro-5-methoxybenzoate A mixture of (E)-methyl 3-(2-(2-chloropyrimidin-5-yl)vinyl)-4-fluoro-5-methoxybenzoate (150 mg, 0.46 mmol), 1-Ethyl-1H-pyrazol-4-amine (103 mg, 0.93 mmol) and p-toluenesulfonic acid (79 mg, 0.46 mmol) in propan-2-ol (20 mL) was stirred at 150° C. under microwave for 40 min. The volatiles were removed under reduced pressure and the residue was partitioned between saturated aqueous NaHCO3 (20 mL) and DCM (60 mL). The organic layer was concentrated and purified via ISCO (DCM/MeOH) to afford the title compound as a yellow solid (130 mg, 70.4% yield).

(B) Methyl 3-(2-(2-((1-ethyl-1H-pyrazol-4-yl)amino)pyrimidin-5-yl)ethyl)-4-fluoro-5-methoxybenzoate To a solution of (E)-methyl 3-(2-(2-((1-ethyl-1H-pyrazol-4-yl)amino)pyrimidin-5-yl) vinyl)-4-fluoro-5-methoxybenzoate (130 mg, 0.33 mmol) in THF (30 mL) and MeOH (20 mL) was added Pd/C (10%, 100 mg). The mixture was stirred at 40° C. under hydrogen atmosphere for 16 h. The catalyst was filtered off and the filtrate was concentrated to afford the title compound as a yellow solid (130 mg, quantative yield). MS (m/z): 400.0 (M+H)+.

(C) 3-(2-(2-((1-Ethyl-1H-pyrazol-4-yl)amino)pyrimidin-5-yl)ethyl)-4-fluoro-5-methoxybenzoic acid To a solution of Methyl 3-(2-(2-((1-ethyl-1H-pyrazol-4-yl)amino)pyrimidin-5-yl)ethyl)-4-fluoro-5-methoxybenzoate (130 mg, 0.33 mmol) in MeOH (10 mL) was added aq NaOH (66 mg, 1.65 mmol in 4 mL H2O). The reaction was stirred at 40° C. for 3 h. The volatiles were removed under reduced pressure and the residue was purified via ISCO (eluted with MeOH in H2O 0~100%) to afford the title compound as a white solid (100 mg, 79.7% yield). MS (m/z): 386.0 (M+H)+.

(D) 3-(2-(2-((1-Ethyl-1H-pyrazol-4-yl)amino)pyrimidin-5-yl)ethyl)-4-fluoro-5-methoxy-N-methylbenzamide To a solution of 3-(2-(2-((1-ethyl-1H-pyrazol-4-yl)amino)pyrimidin-5-yl)ethyl)-4-fluoro-5-methoxybenzoic acid (100 mg, 0.26 mmol) in dry DMF (4 mL) was added DIPEA (10 drops), HATU (296 mg, 0.78 mmol) and methylamine hydrochloride (52 mg, 0.78 mmol). The reaction was stirred at ambient temperature for 30 min and then purified via ISCO (eluted with MeOH in H2O 0~100%) directly to afford the title compound as a white solid (78 mg, 75.4% yield). MS (m/z): 399.1 (M+H)+. 1H NMR (400 MHz, CD3OD) δ

8.12 (s, 2H), 7.89 (s, 1H), 7.50 (s, 1H), 7.39 (dd, J=7.7 Hz, 1.9 Hz, 1H), 7.25 (dd, J=5.9 Hz, 2.0 Hz, 1H), 4.11 (q, J=7.3 Hz, 2H), 3.87 (s, 3H), 2.92 (t, J=7.4 Hz, 2H), 2.87 (s, 3H), 2.79 (t, J=7.5 Hz, 2H), 1.42 (t, J=7.3 Hz, 3H).

The following compounds were prepared according to the procedures of Compound 112 using the corresponding intermediates and reagents under appropriate conditions that could be recognized by one skilled in the art.

| Compound | Structure | LC-MS (m/z) (M + H)+ | 1H NMR |
|---|---|---|---|
| 113 | 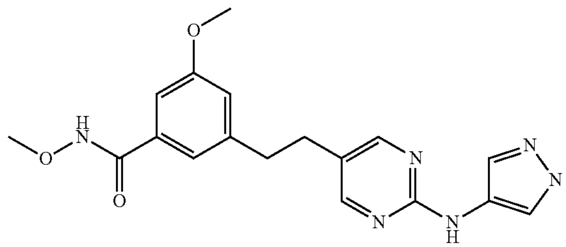 [SMILES: CONC(=O)c1cc(CCc2cnc(Nc3cn[nH]c3)nc2)cc(OC)c1] | 369.1 | 1H NMR (400 MHz, CD3OD) δ 8.14 (s, 2H), 7.77 (s, 2H), 7.16-7.13 (m, 2H), 6.91 (s, 1H), 3.79-3.78 (m, 6H), 2.89-2.88 (m, 2H), 2.83-2.82 (m, 2H). |
| 114 | 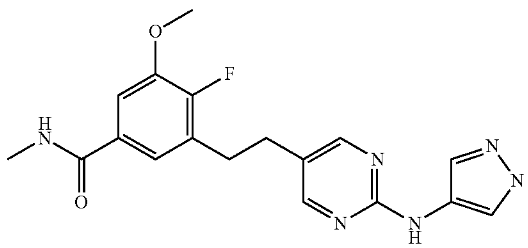 [SMILES: CNC(=O)c1cc(CCc2cnc(Nc3cn[nH]c3)nc2)c(F)c(OC)c1] | 371.1 | 1H NMR (400 MHz, CD3OD) δ 8.13 (s, 2H), 7.75 (s, 2H), 7.40 (dd, J = 7.7 Hz, 2.0 Hz, 1H), 7.26 (dd, J = 5.9 Hz, 2.0 Hz, 1H), 3.87 (s, 3H), 2.93 (t, J = 7.4 Hz, 2H), 2.88 (s, 3H), 2.80 (t, J = 7.4 Hz, 2H). |
| 115 | 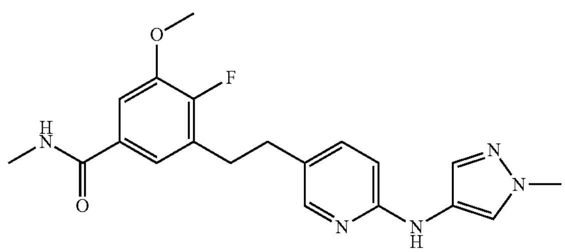 | 384.1 | 1H NMR (400 MHz, CD3OD) δ 7.76 (d, J = 3.1 Hz, 2H), 7.39 (d, J = 0.7 Hz, 1H), 7.37 (dd, J = 7.8 Hz, 2.2 Hz, 1H), 7.30 (dd, J = 8.6 Hz, 2.4 Hz, 1H), 7.24 (dd, J = 6.0 Hz, 2.1 Hz, 1H), 6.56 (dd, J = 8.5 Hz, 0.6 Hz, 1H), 3.87 (s, 3H), 3.83 (s, 3H), 2.93-2.88 (t, J = 7.5 Hz, 2H), 2.87 (s, 3H), 2.78 (t, J = 7.5 Hz, 2H). |
| 116 | 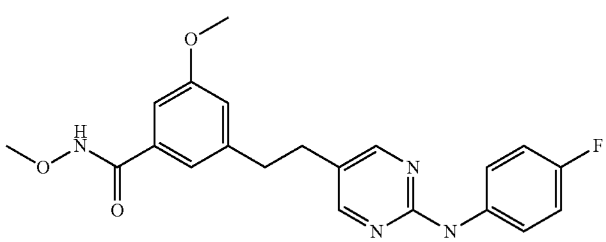 [SMILES: CONC(=O)c1cc(CCc2cnc(Nc3ccc(F)cc3)nc2)cc(OC)c1] | 397.2 | 1H NMR (400 MHz, CD3OD) δ 8.16 (s, 2H), 7.58 (dd, J = 9.0 Hz, 4.8 Hz, 2H), 7.16 (s, 1H), 7.13 (s, 1H), 7.05-6.95 (m, 2H), 6.91 (s, 1H), 3.79 (s, 3H), 3.78 (s, 3H), 2.94-2.87 (m, 2H), 2.86-2.79 (m, 2H). |
| 117 | 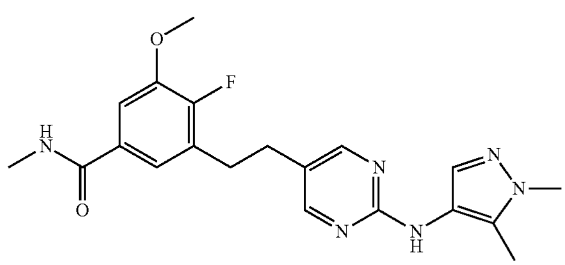 | 399.1 | 1H NMR (400 MHz, CD3OD) δ 8.02 (s, 2H), 7.40 (s, 1H), 7.38 (d, J = 2.0 Hz, 1H), 7.24 (dd, J = 5.9 Hz, 2.0 Hz, 1H), 3.86 (s, 3H), 3.75 (s, 3H), 2.91 (t, J = 7.4 Hz, 2H), 2.88 (s, 3H), 2.77 (t, J = 7.3 Hz, 2H), 2.11 (s, 3H). |

-continued

| Compound | Structure | LC-MS (m/z) (M + H)+ | 1H NMR |
|---|---|---|---|
| 118 | 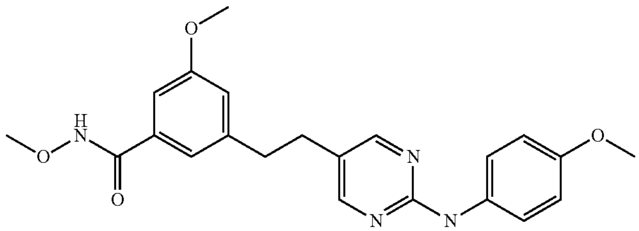 | 409.2 | 1H NMR (400 MHz, CD3OD) δ 8.06 (s, 2H), 7.38 (d, J = 7.8 Hz, 2H), 7.11 (s, 1H), 7.09 (s, 1H), 6.86 (s, 1H), 6.81 (d, J = 7.9 Hz, 2H), 3.84-3.62 (m, 9H), 2.84 (t, J = 6.2 Hz, 2H), 2.77 (t, J = 6.2 Hz, 2H). |
| 119 | 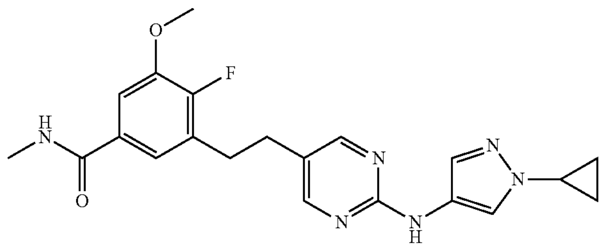 [SMILES: CNC(=O)c1cc(CCc2cnc(Nc3cnn(C4CC4)c3)nc2)c(F)c(OC)c1] | 411.0 | 1H NMR (400 MHz, CD3OD) δ 8.13 (s, 2H), 7.92 (s, 1H), 7.49 (s, 1H), 7.40 (dd, J = 7.7 Hz, 2.1 Hz, 1H), 7.26 (dd, J = 6.0 Hz, 2.1 Hz, 1H), 3.88 (s, 3H), 3.57-3.54 (m, 1H), 2.94 (t, J = 7.3 Hz, 2H), 2.88 (s, 3H), 2.81 (t, J = 7.3 Hz, 2H), 1.07-0.97 (m, 4H). |
| 120 | 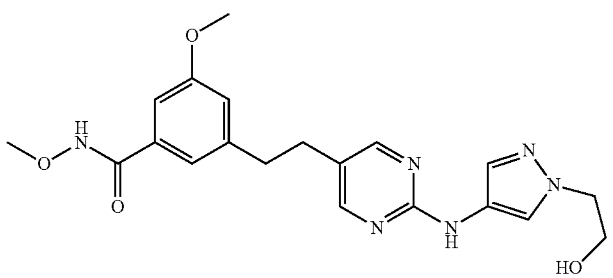 [SMILES: CONC(=O)c1cc(CCc2cnc(Nc3cnn(CCO)c3)nc2)cc(OC)c1] | 413.1 | 1H NMR (400 MHz, CD3OD) δ 8.13 (s, 2H), 8.13 (s, 2H), 7.93 (s, 1H), 7.93 (s, 1H), 7.54 (s, 1H), 7.54 (s, 1H), 7.15-7.13 (m, 2H), 6.89 (s, 1H), 4.17 (t, J = 5.4 Hz, 2H), 3.86 (t, J = 5.3 Hz, 2H), 3.78 (s, 6H), 2.89-2.87 (m, 2H), 2.83-2.81 (m, 2H). |
| 121 | 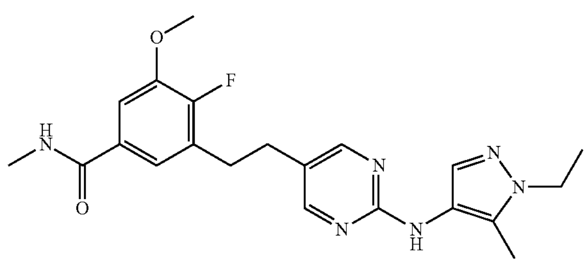 [SMILES: CCn1ncc(Nc2ncc(CCc3cc(C(=O)NC)cc(OC)c3F)cn2)c1C] | 413.0 | 1H NMR (400 MHz, CD3OD) δ 8.03 (s, 2H), 7.44 (s, 1H), 7.40 (dd, J = 7.8 Hz, 1.9 Hz, 1H), 7.26 (dd, J = 5.9 Hz, 1.9 Hz, 1H), 4.10 (q, J = 7.2 Hz, 2H), 3.88 (s, 3H), 2.93 (t, J = 7.4 Hz, 2H), 2.89 (s, 3H), 2.79 (t, J = 7.3 Hz, 2H), 2.14 (s, 3H), 1.38 (t, J = 7.2 Hz, 3H). |
| 122 | 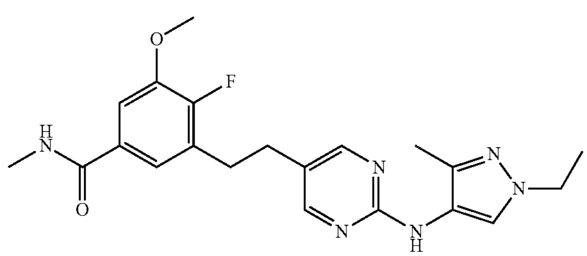 [SMILES: CCn1cc(Nc2ncc(CCc3cc(C(=O)NC)cc(OC)c3F)cn2)c(C)n1] | 413.0 | 1H NMR (400 MHz, CD3OD) δ 8.07 (s, 2H), 7.72 (s, 1H), 7.40 (dd, J = 7.8 Hz, 2.0 Hz, 1H), 7.26 (dd, J = 5.9 Hz, 2.1 Hz, 1H), 4.07 (q, J = 7.3 Hz, 2H), 3.88 (s, 3H), 2.94 (t, J = 7.2 Hz, 2H), 2.89 (s, 3H), 2.80 (t, J = 7.4 Hz, 2H), 2.12 (s, 3H), 1.42 (t, J = 7.3 Hz, 3H). |
| 123 | 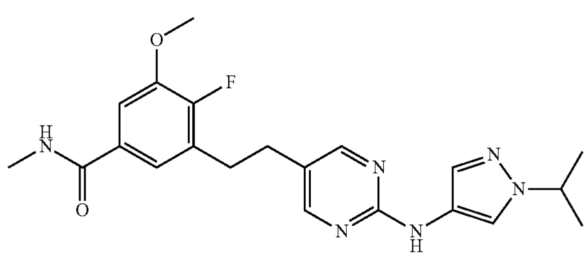 [SMILES: CNC(=O)c1cc(CCc2cnc(Nc3cnn(C(C)C)c3)nc2)c(F)c(OC)c1] | 413.0 | 1H NMR (400 MHz, CD3OD) δ 8.11 (s, 2H), 7.89 (s, 1H), 7.51 (s, 1H), 7.39 (d, J = 7.2 Hz, 1H), 7.25 (d, J = 4.7 Hz, 1H), 4.50-4.36 (m, 1H), 3.86 (s, 3H), 2.92 (t, J = 7.2 Hz, 2H), 2.87 (s, 3H), 2.78 (t, J = 7.1 Hz, 2H), 1.45 (d, J = 6.5 Hz, 6H). |

-continued

| Compound | Structure | LC-MS (m/z) (M + H)⁺ | ¹H NMR |
|---|---|---|---|
| 124 | 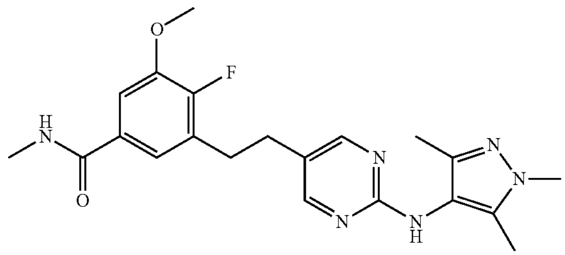 | 413.1 | ¹H NMR (400 MHz, CD₃OD) δ 7.99 (s, 2H), 7.39 (dd, J = 7.8 Hz, 2.0 Hz, 1H), 7.23 (dd, J = 5.9 Hz, 2.0 Hz, 1H), 3.87 (s, 3H), 3.69 (s, 3H), 2.91 (t, J = 7.4 Hz, 2H), 2.88 (s, 3H), 2.78 (t, J = 7.3 Hz, 2H), 2.06 (s, 3H), 2.00 (s, 3H). |
| 125 | 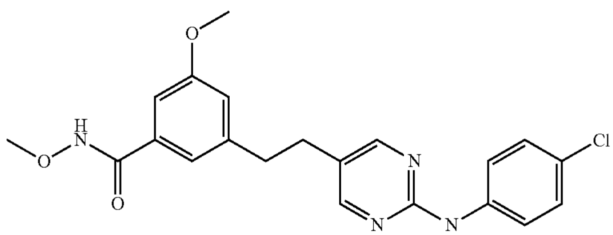 [SMILES: CONC(=O)c1cc(CCc2cnc(Nc3ccc(Cl)cc3)nc2)cc(OC)c1] | 413.2 | ¹H NMR (400 MHz, CD₃OD) δ 8.15 (s, 2H), 7.56 (d, J = 8.9 Hz, 2H), 7.21 (d, J = 8.9 Hz, 2H), 7.16 (s, 1H), 7.13 (s, 1H), 6.81 (s, 1H), 3.79 (s, 3H), 3.77 (s, 3H), 2.92-2.85 (m, 2H), 2.85-2.78 (m, 2H). |
| 126 | 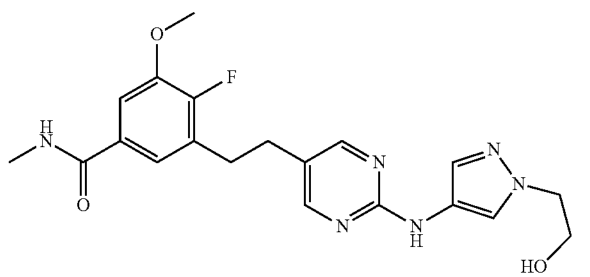 [SMILES: CNC(=O)c1cc(CCc2cnc(Nc3cnn(CCO)c3)nc2)c(F)c(OC)c1] | 415.1 | ¹H NMR (400 MHz, CD₃OD) δ 8.15 (s, 2H), 7.95 (s, 1H), 7.58 (s, 1H), 7.43 (d, J = 7.4 Hz, 1H), 7.30 (d, J = 4.4 Hz, 1H), 4.20 (t, J = 5.2 Hz, 2H), 3.91 (s, 3H), 3.90-3.88 (m, 2H), 2.97-2.95 (m, 2H), 2.92 (s, 3H), 2.84 (t, J = 7.2 Hz, 2H). |
| 127 | 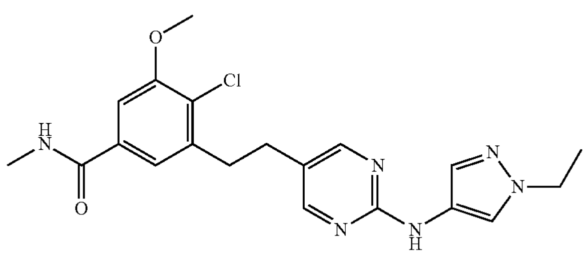 | 414.9 | ¹H NMR (400 MHz, CD₃OD) δ 8.15 (s, 2H), 7.89 (s, 1H), 7.53 (s, 1H), 7.36 (s, 1H), 7.30 (s, 1H), 4.13 (q, J = 7.2 Hz, 2H), 3.92 (s, 3H), 3.04 (t, J = 7.4 Hz, 2H), 2.90 (s, 3H), 2.81 (t, J = 7.6 Hz, 2H), 1.45 (t, J = 7.2 Hz, 3H). |
| 128 | 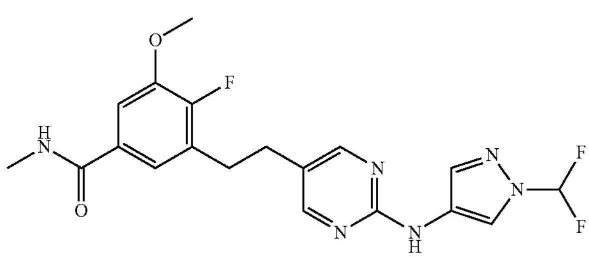 [SMILES: CNC(=O)c1cc(CCc2cnc(Nc3cnn(C(F)F)c3)nc2)c(F)c(OC)c1] | 421.3 | ¹H NMR (400 MHz, CD₃OD) δ 8.33 (s, 1H), 8.21 (s, 2H), 7.76 (s, 1H), 7.41 (dd, J = 7.6 Hz, 2.0 Hz, 1H), 7.38 (t, J = 60.0 Hz, 1H), 7.28 (dd, J = 6.0 Hz, 2.0 Hz, 1H), 3.89 (s, 3H), 2.96 (t, J = 7.3 Hz, 2H), 2.90 (s, 3H), 2.84 (t, J = 7.3 Hz, 2H). |
| 129 | 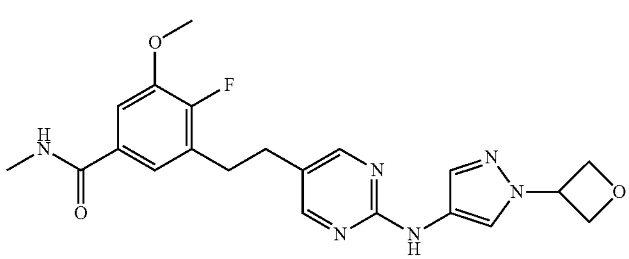 | 426.9 | ¹H NMR (400 MHz, CD₃OD) δ 8.14 (s, 2H), 8.09 (s, 1H), 7.63 (s, 1H), 7.40 (dd, J = 7.7 Hz, 2.1 Hz, 1H), 7.26 (dd, J = 6.0 Hz, 2.0 Hz, 1H), 5.53-5.44 (m, 1H), 5.05-4.98 (m, 4H), 3.88 (s, 3H), 2.94 (t, J = 7.4 Hz, 2H), 2.88 (s, 3H), 2.80 (d, J = 7.3 Hz, 2H). |

| Compound | Structure | LC-MS (m/z) (M + H)+ | 1H NMR |
|---|---|---|---|
| 130 | 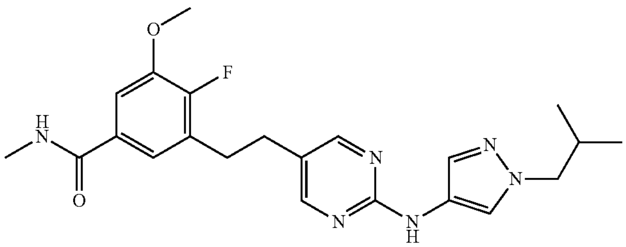 [SMILES: CNC(=O)c1cc(CCc2cnc(Nc3cnn(CC(C)C)c3)nc2)c(F)c(OC)c1] | 427.0 | 1H NMR (400 MHz, CD3OD) δ 8.13 (s, 2H), 7.88 (s, 1H), 7.52 (s, 1H), 7.39 (dd, J = 7.8 Hz, 2.1 Hz, 1H), 7.26 (dd, J = 6.0 Hz, 2.0 Hz, 1H), 3.87 (s, 3H), 3.87 (d, J = 7.2 Hz, 2H), 2.93 (t, J = 7.4 Hz, 2H), 2.88 (s, 3H), 2.80 (t, J = 7.4 Hz, 2H), 2.19-2.09 (m, 1H), 0.89 (d, J = 6.8 Hz, 6H). |
| 131 | 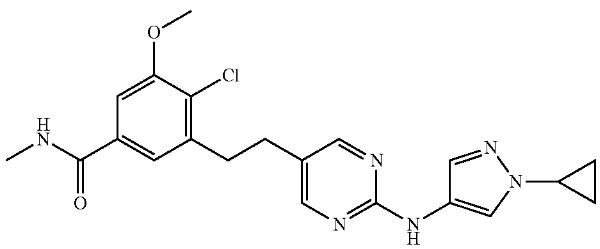 [SMILES: CNC(=O)c1cc(CCc2cnc(Nc3cnn(C4CC4)c3)nc2)c(Cl)c(OC)c1] | 426.9 | 1H NMR (400 MHz, CD3OD) δ 8.14 (s, 2H), 7.92 (s,1H), 7.50 (s, 1H), 7.36 (d, J = 1.9 Hz, 1H), 7.29 (d, J = 1.9 Hz, 1H), 3.91 (s, 3H), 3.57-3.55 (m, 1H), 3.04 (t, J = 7.6 Hz, 2H), 2.89 (s, 3H), 2.81 (t, J = 7.6 Hz, 2H), 1.07-0.97 (m, 4H). |
| 132 | 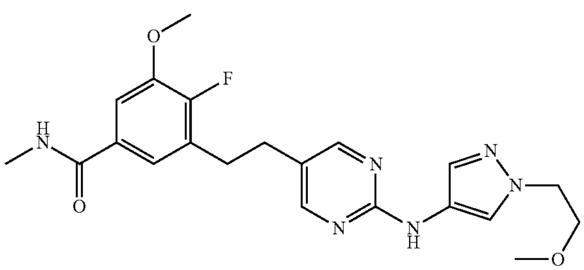 [SMILES: CNC(=O)c1cc(CCc2cnc(Nc3cnn(CCOC)c3)nc2)c(F)c(OC)c1] | 429.0 | 1H NMR (400 MHz, CD3OD) δ 8.12 (s, 2H), 7.91 (s, 1H), 7.53 (s, 1H), 7.39 (dd, J = 7.8 Hz, 1.9 Hz, 1H), 7.25 (dd, J = 5.9 Hz, 1.9 Hz, 1H), 4.22 (t, J = 5.3 Hz, 2H), 3.87 (s, 3H), 3.70 (t, J = 5.3 Hz, 2H), 2.92 (t, J = 7.3 Hz, 2H), 2.87 (s, 3H), 2.79 (t, J = 7.4 Hz, 2H). |
| 133 | 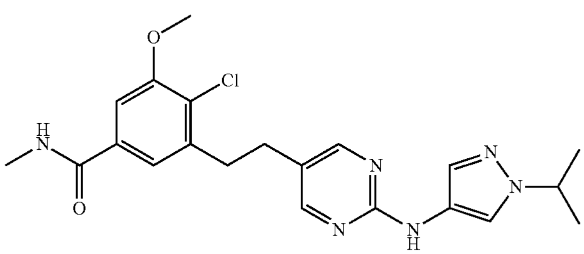 [SMILES: CNC(=O)c1cc(CCc2cnc(Nc3cnn(C(C)C)c3)nc2)c(Cl)c(OC)c1] | 429.1 | 1H NMR (400 MHz, CD3OD) δ 8.14 (s, 2H), 7.90 (s, 1H), 7.52 (s, 1H), 7.36 (s, 1H), 7.29 (s, 1H), 4.49-4.41 (m, 1H), 3.91 (s, 3H), 3.05 (t, J = 7.6 Hz, 2H), 2.89 (s, 3H), 2.81 (t, J = 7.7 Hz, 2H), 1.47 (d, J= 6.7 Hz, 6H). |
| 134 | 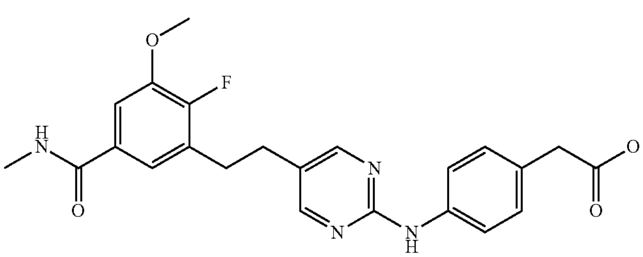 | 439.2 | 1H NMR (400 MHz, DMSO-d6) δ 9.34 (s, 1H), 8.38-8.32 (m, 1H), 8.23 (s, 2H), 7.58 (d, J = 8.4 Hz, 2H), 7.41 (d, J = 6.6 Hz, 1H), 7.37 (d, J = 6.0 Hz, 1H), 7.09 (d, J = 8.4 Hz, 2H), 3.82 (s, 3H), 3.36 (s, 2H), 2.88 (t, J = 7.5 Hz, 2H), 2.78-2.72 (m, 5H). |
| 135 | 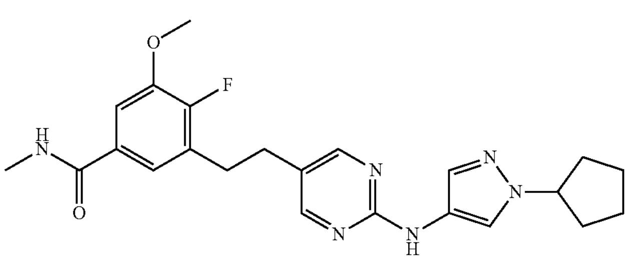 [SMILES: CNC(=O)c1cc(CCc2cnc(Nc3cnn(C4CCCC4)c3)nc2)c(F)c(OC)c1] | 439.0 | 1H NMR (400 MHz, CD3OD) δ 8.12 (s, 2H), 7.90 (s, 1H), 7.52 (s, 1H), 7.39 (d, J = 7.8 Hz, 1H), 7.26 (d, J = 4.0 Hz, 1H), 4.67-4.60 (m, 1H), 3.88 (s, 3H), 2.93 (t, J = 7.4 Hz, 2H), 2.88 (s, 3H), 2.80 (t, J = 7.3 Hz, 2H), 2.21-2.09 (m, 2H), 2.02-1.80 (m, 4H), 1.73-1.70 (m, 2H). |

| Compound | Structure | LC-MS (m/z) (M + H)+ | 1H NMR |
|---|---|---|---|
| 136 | 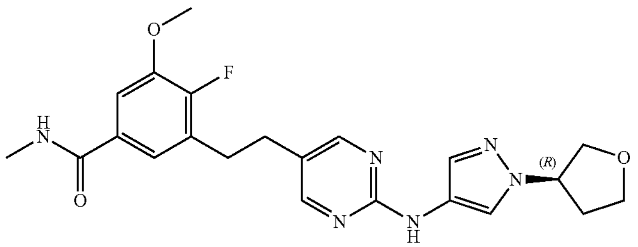 | 440.9 | 1H NMR (400 MHz, CD3OD) δ 8.13 (s, 2H), 7.96 (s, 1H), 7.54 (s, 1H), 7.40 (dd, J = 7.8 Hz, 2.1 Hz, 1H), 7.26 (dd, J = 5.9 Hz, 2.1 Hz, 1H), 5.02-4.94 (m, 1H), 4.15-4.07 (m, 1H), 4.00 (d, J = 4.8 Hz, 2H), 3.94-3.84 (m, 4H), 2.94 (t, J = 7.3 Hz, 2H), 2.88 (s, 3H), 2.81 (t, J = 7.4 Hz, 2H), 2.50-2.41 (m, 1H), 2.35-2.26 (m, 1H). |
| 137 | 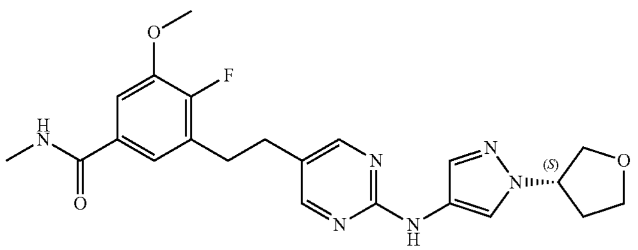 | 441.0 | 1H NMR (400 MHz, CD3OD) δ 8.13 (s, 2H), 7.96 (s, 1H), 7.54 (s, 1H), 7.40 (dd, J = 7.8 Hz, 2.1 Hz, 1H), 7.26 (dd, J = 6.0 Hz, 2.1 Hz, 1H), 5.00-4.93 (m, 1H), 4.14-4.05 (m, 1H), 4.00 (d, J = 4.8 Hz, 2H), 3.92-3.85 (m, 4H), 2.94 (t, J = 7.3 Hz, 2H), 2.88 (s, 3H), 2.81 (t, J = 7.4 Hz, 2H), 2.51-2.40 (m, 1H), 2.35-2.23 (m, 1H). |
| 138 | 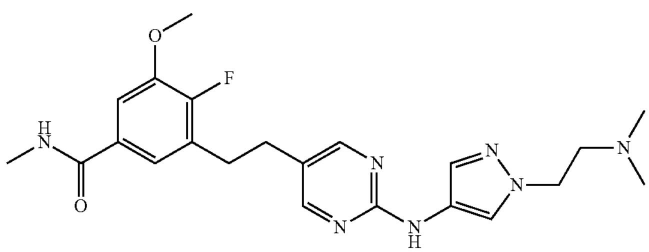 | 442.0 | 1H NMR (400 MHz, CD3OD) δ 8.13 (s, 2H), 7.96 (s, 1H), 7.54 (s, 1H), 7.40 (dd, J = 7.8 Hz, 2.1 Hz, 1H), 7.26 (dd, J = 6.0 Hz, 2.1 Hz, 1H), 4.24 (t, J = 6.8 Hz, 2H), 3.87 (s, 3H), 2.93 (t, J = 7.4 Hz, 2H), 2.90-2.85 (m, 5H), 2.81 (t, J = 7.4 Hz, 2H), 2.34 (s, 6H). |
| 139 | 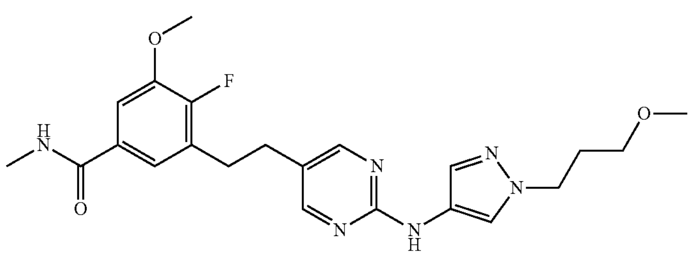 | 443.1 | 1H NMR (400 MHz, CD3OD) δ 8.12 (s, 2H), 7.89 (s, 1H), 7.51 (s, 1H), 7.39 (s, 1H), 7.26 (s, 1H), 4.18-4.12 (m, 2H), 3.86 (s, 3H), 3.33-3.31 (m, 5H), 2.92-2.90 (m, 2H), 2.87 (s, 3H), 2.82-2.74 (m, 2H), 2.07-2.01 (m, 2H). |
| 140 | 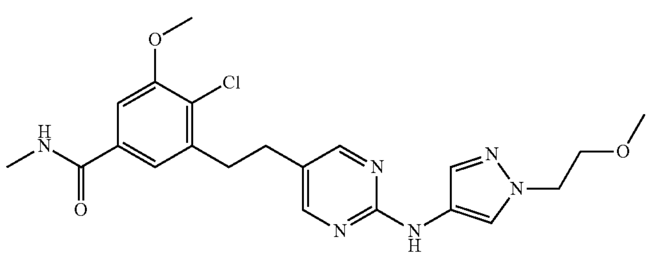 | 444.9 | 1H NMR (400 MHz, CD3OD) δ 8.15 (s, 2H), 7.93 (s, 1H), 7.54 (s, 1H), 7.36 (d, J = 1.8 Hz, 1H), 7.30 (d, J = 1.8 Hz, 1H), 4.23 (t, J = 5.3 Hz, 2H), 3.92 (s, 3H), 3.71 (t, J = 5.2 Hz, 2H), 3.31 (s, 3H), 3.05 (t, J = 7.6 Hz, 2H), 2.89 (s, 3H), 2.82 (t, J = 7.7 Hz, 2H). |
| 141 | 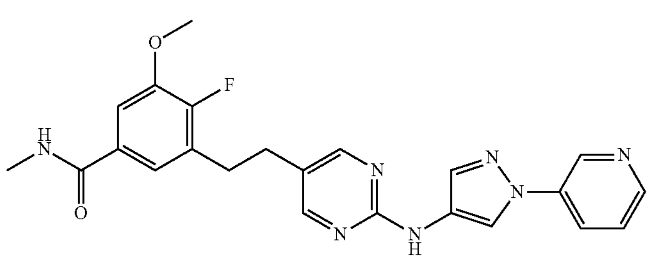 [SMILES: CNC(=O)c1cc(CCc2cnc(Nc3cnn(-c4cccnc4)c3)nc2)c(F)c(OC)c1] | 448.1 | 1H NMR (400 MHz, CD3OD) δ 8.95 (s, 1H), 8.56 (s, 1H), 8.42 (d, J = 4.3 Hz, 1H), 8.21 (s, 2H), 8.13 (d, J = 7.1 Hz, 1H), 7.84 (s, 1H), 7.51 (dd, J = 8.3 Hz, 4.8 Hz, 1H), 7.38 (dd, J = 7.7 Hz, 1.9 Hz, 1H), 7.27 (dd, J = 5.9 Hz, 2.0 Hz, 1H), 3.88 (s, 3H), 2.98-2.91 (m, 2H), 2.89 (s, 3H), 2.83 (t, J = 7.4 Hz, 2H). |

| Compound | Structure | LC-MS (m/z) (M + H)+ | 1H NMR |
|---|---|---|---|
| 142 | 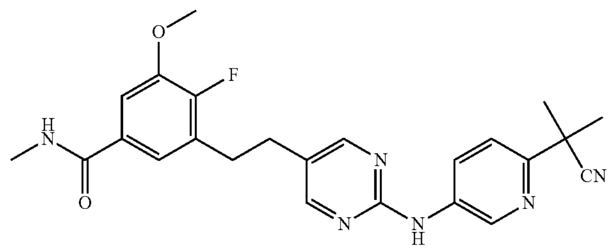 [SMILES: CNC(=O)c1cc(CCc2cnc(Nc3ccc(C(C)(C)C#N)nc3)nc2)c(F)c(OC)c1] | 448.9 | 1H NMR (400 MHz, CD3OD) δ 8.81 (d, J = 2.4 Hz, 1H), 8.28 (dd, J = 8.6 Hz, 2.7 Hz, 1H), 8.24 (s, 2H), 7.51 (d, J = 8.8 Hz, 1H), 7.42 (dd, J = 7.9 Hz, 1.9 Hz, 1H), 7.28 (dd, J = 6.0 Hz, 1.9 Hz, 1H), 3.89 (s, 3H), 3.01-2.95 (m, 2H), 2.89 (s, 3H), 2.89-2.84 (m, 2H), 1.74 (s, 6H). |
| 143 | 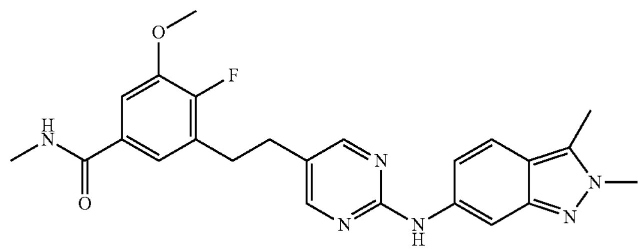 | 448.9 | 1H NMR (400 MHz, CD3OD) δ 8.20 (s, 2H), 8.09 (s, 1H), 7.51 (d, J = 8.9 Hz, 1H), 7.41 (dd, J = 7.6 Hz, 2.0 Hz, 1H), 7.28 (dd, J = 6.0 Hz, 2.0 Hz, 1H), 7.05 (dd, J = 9.0 Hz, 1.7 Hz, 1H), 4.02 (s, 3H), 3.89 (s, 3H), 2.97 (t, J = 7.1 Hz, 2H), 2.89 (s, 3H), 2.85 (t, J = 7.1 Hz, 3H), 2.59 (s, 3H). |
| 144 | 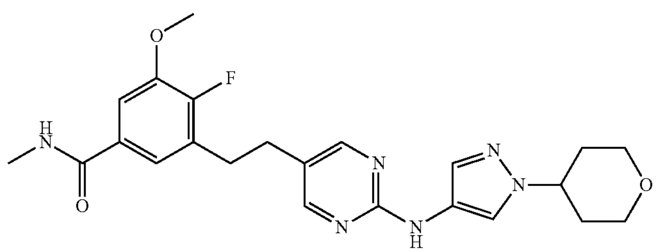 [SMILES: CNC(=O)c1cc(CCc2cnc(Nc3cnn(C4CCOCC4)c3)nc2)c(F)c(OC)c1] | 454.9 | 1H NMR (400 MHz, CD3OD) δ 8.15 (s, 2H), 7.98 (s, 1H), 7.56 (s, 1H), 7.41 (dd, J = 7.8 Hz, 2.1 Hz, 1H), 7.28 (dd, J = 6.0 Hz, 2.1 Hz, 1H), 4.40-4.30 (m, 1H), 4.12-4.02 (m, 2H), 3.89 (s, 3H), 3.62-3.52 (m, 2H), 2.95 (t, J = 7.5 Hz, 2H), 2.90 (s, 3H), 2.82 (t, J = 7.4 Hz, 3H), 2.08-1.98 (m, 4H). |
| 145 | 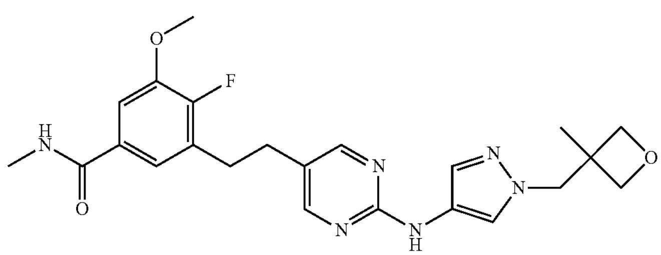 [SMILES: CNC(=O)c1cc(CCc2cnc(Nc3cnn(CC4(C)COC4)c3)nc2)c(F)c(OC)c1] | 455.0 | 1H NMR (400 MHz, CD3OD) δ 8.13 (s, 2H), 7.94 (s, 1H), 7.54 (s, 1H), 7.40 (dd, J = 7.7 Hz, 2.0 Hz, 1H), 7.26 (dd, J = 5.9 Hz, 2.0 Hz, 1H), 4.70 (d, J = 6.1 Hz, 2H), 4.34 (d, J = 6.1 Hz, 2H), 4.29 (s, 2H), 3.88 (s, 3H), 2.94 (t, J = 7.4 Hz, 2H), 2.88 (s, 3H), 2.81 (t, J = 7.4 Hz, 2H), 1.23 (s, 3H). |
| 146 | 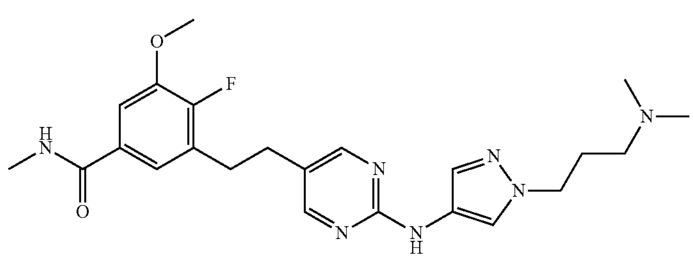 | 456.0 | 1H NMR (400 MHz, CD3OD) δ 8.13 (s, 2H), 7.99 (s, 1H), 7.56 (s, 1H), 7.40 (dd, J = 7.8 Hz, 2.1 Hz, 1H), 7.27 (dd, J = 6.0 Hz, 2.1 Hz, 1H), 4.23 (t, J = 6.4 Hz, 2H), 3.88 (s, 3H), 3.13-3.06 (m, 2H), 2.94 (t, J = 7.2 Hz, 2H), 2.88 (s, 3H), 2.85-2.83 (m, 6H), 2.82-2.79 (m, 2H), 2.28-2.20 (m, 2H). |
| 147 | 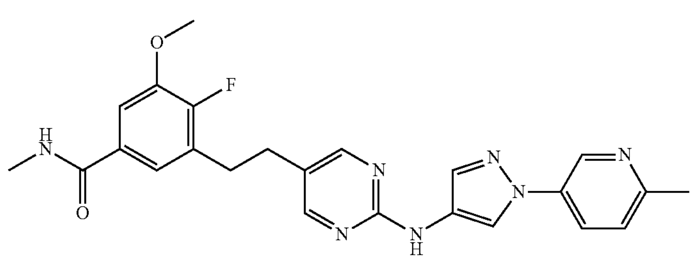 | 462.4 | 1H NMR (400 MHz, CD3OD) δ 8.82 (s, 1H), 8.55 (s, 1H), 8.21 (s, 2H), 8.06 (s, J = 7.2 Hz, 1H), 7.83 (s, 1H), 7.42 (s, 1H), 7.40 (s, 1H), 7.28 (s, 1H), 3.89 (s, 3H), 3.01-2.94 (m, 2H), 2.89 (s, 3H), 2.87-2.79 (m, 2H), 2.57 (s, 3H). |

-continued

| Compound | Structure | LC-MS (m/z) (M + H)+ | 1H NMR |
|---|---|---|---|
| 148 | 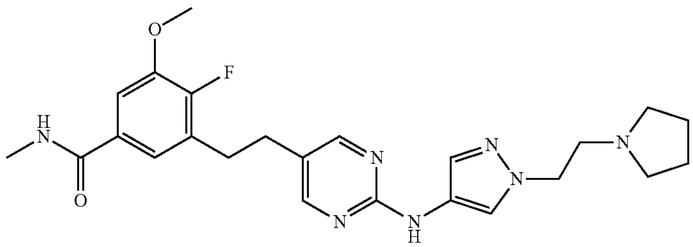 [SMILES: CNC(=O)c1cc(CCc2cnc(Nc3cnn(CCN4CCCC4)c3)nc2)c(F)c(OC)c1] | 468.0 | 1H NMR (400 MHz, CD3OD) δ 8.12 (s, 2H), 7.95 (s, 1H), 7.53 (s, 1H), 7.39 (d, J = 7.2 Hz, 1H), 7.26 (d, J = 4.8 Hz, 1H), 4.23 (t, J = 6.9 Hz, 2H), 3.87 (s, 3H), 2.98-2.88 (m, 4H), 2.87 (s, 3H), 2.80 (t, J = 7.1 Hz, 2H), 2.60-2.50 (m, 4H), 1.84-1.72 (m, 4H). |
| 149 | 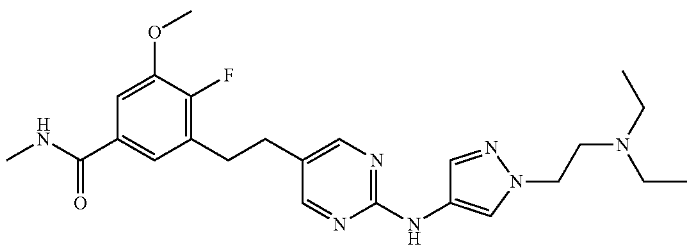 | 469.9 | 1H NMR (400 MHz, CD3OD) δ 8.14 (s, 2H), 7.96 (s, 1H), 7.54 (s, 1H), 7.41 (dd, J = 7.8 Hz, 2.1 Hz, 1H), 7.27 (dd, J = 5.9 Hz, 2.1 Hz, 1H), 4.24-4.13 (m, 2H), 3.89 (s, 3H), 2.97-2.89 (m, 4H), 2.89 (s, 3H), 2.82 (t, J = 7.4 Hz, 2H), 2.58 (q, J = 7.2 Hz, 4H), 1.04 (t, J = 7.2 Hz, 6H). |
| 150 | 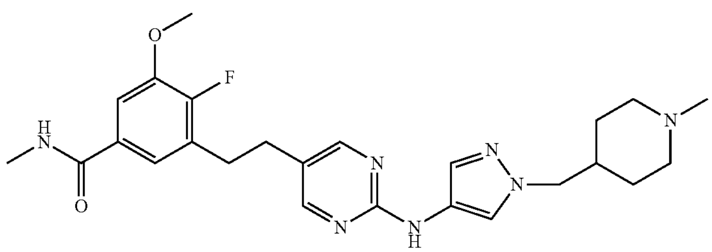 | 482.0 | 1H NMR (400 MHz, CD3OD) δ 8.14 (s, 2H), 7.92 (s, 1H), 7.53 (s, 1H), 7.41 (dd, J = 7.8 Hz, 2.1 Hz, 1H), 7.27 (dd, J = 5.9 Hz, 2.1 Hz, 1H), 3.98 (d, J = 7.2 Hz, 2H), 3.89 (s, 3H), 2.95 (t, J = 7.5 Hz, 2H), 2.89 (s, 3H), 2.81 (t, J = 7.5 Hz, 2H), 2.25 (s, 3H), 2.02-1.93 (m, 2H), 1.93-1.82 (m, 1H), 1.60-1.53 (m, 2H), 1.37-1.28 (m, 4H). |
| 151 | 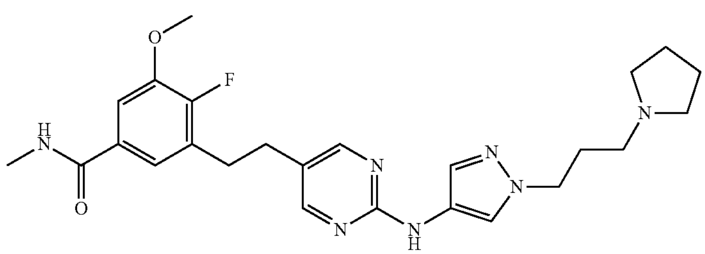 [SMILES: CNC(=O)c1cc(CCc2cnc(Nc3cnn(CCCN4CCCC4)c3)nc2)c(F)c(OC)c1] | 482.1 | 1H NMR (400 MHz, CD3OD) δ 8.05 (s, 2H), 7.86 (s, 1H), 7.44 (s, 1H), 7.31 (d, J = 7.7 Hz, 1H), 7.18 (d, J = 4.1 Hz, 1H), 4.07 (t, J = 6.7 Hz, 2H), 3.79 (s, 3H), 2.86 (t, J = 7.5 Hz, 2H), 2.80 (s, 3H), 2.73 (t, J = 7.2 Hz, 2H), 2.66-2.54 (m, 4H), 2.54-2.45 (m, 2H), 2.05-1.95 (m, 2H), 1.83-1.69 (m, 4H). |
| 152 | 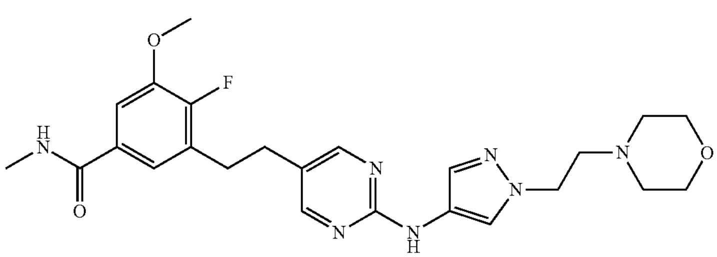 [SMILES: CNC(=O)c1cc(CCc2cnc(Nc3cnn(CCN4CCOCC4)c3)nc2)c(F)c(OC)c1] | 484.0 | 1H NMR (400 MHz, CD3OD) δ 8.11 (s, 2H), 7.96 (s, 1H), 7.51 (s, 1H), 7.39 (dd, J = 7.8 Hz, 2.1 Hz, 1H), 7.26 (dd, J = 6.0 Hz, 2.1 Hz, 1H), 4.21 (t, J = 6.6 Hz, 2H), 3.87 (s, 3H), 3.68-3.58 (m, 4H), 2.93 (t, J = 7.4 Hz, 2H), 2.87 (s, 3H), 2.82-2.78 (m, 2H), 2.77-2.75 (m, 2H), 2.49-2.43 (m, 4H). |
| 153 | 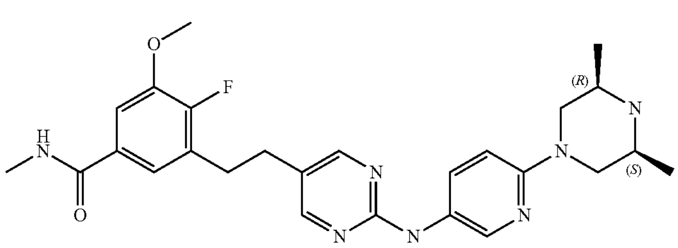 | 494.0 | 1H NMR (400 MHz, CD3OD) δ 8.30 (d, J = 2.7 Hz, 1H), 8.10 (s, 2H), 7.82 (dd, J = 9.1 Hz, 2.7 Hz, 1H), 7.40 (dd, J = 7.8 Hz, 2.1 Hz, 1H), 7.26 (dd, J = 5.9 Hz, 2.0 Hz, 1H), 6.82 (d, J = 9.1 Hz, 1H), 4.12-4.02 (m, 2H), 3.88 (s, 3H), 3.02-2.95 (m, 2H), 2.93 (t, J = 7.4 Hz, 2H), 2.88 (s, 3H), 2.80 (t, J = 7.4 Hz, 2H), 2.43 (dd, J = 12.6 Hz, 11.0 Hz, 2H), 1.18 (d, J = 6.4 Hz, 6H). |

| Compound | Structure | LC-MS (m/z) (M + H)+ | 1H NMR |
|---|---|---|---|
| 154 | 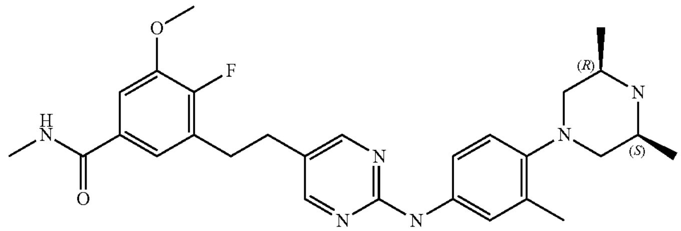 | 506.9 | 1H NMR (400 MHz, CD3OD) δ 8.11 (s, 2H), 7.40 (dd, J = 7.7 Hz, 2.1 Hz, 1H), 7.37-7.32 (m, 2H), 7.26 (dd, J = 6.0 Hz, 2.0 Hz, 1H), 6.95 (d, J = 9.3 Hz, 1H), 3.88 (s, 3H), 3.07-2.98 (m, 2H), 2.97-2.89 (m, 4H), 2.88 (s, 3H), 2.81 (t, J = 7.4 Hz, 2H), 2.28 (t, J = 11.0 Hz, 2H), 2.26 (s, 3H), 1.10 (d, J = 6.4 Hz, 6H). |
| 155 | 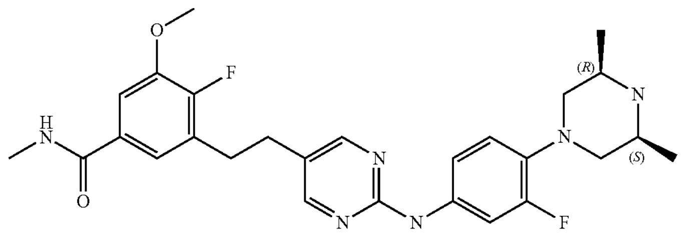 | 510.9 | 1H NMR (400 MHz, CD3OD) δ 8.15 (s, 2H), 7.57 (dd, J = 15.0 Hz, 2.4 Hz, 1H), 7.40 (dd, J = 7.7 Hz, 2.0 Hz, 1H), 7.26 (dd, J = 5.9 Hz, 2.0 Hz, 1H), 7.20 (dd, J = 8.7 Hz, 2.4 Hz, 1H), 6.93 (t, J = 9.2 Hz, 1H), 3.87 (s, 3H), 3.24-3.16 (m, 2H), 3.08-2.98 (m, 2H), 2.94 (t, J = 7.3 Hz, 2H), 2.88 (s, 3H), 2.81 (t, J = 7.4 Hz, 2H), 2.29 (t, J = 10.9 Hz, 2H), 1.10 (d, J = 6.4 Hz, 6H). |
| 156 | 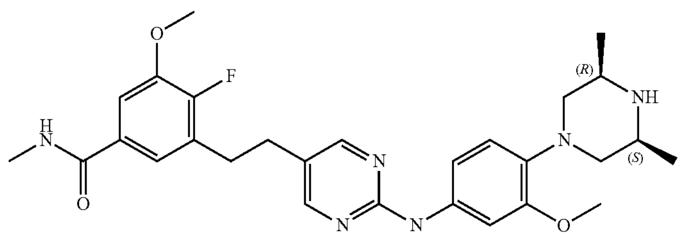 | 523.2 | 1H NMR (400 MHz, CD3OD) δ 8.13 (s, 2H), 7.39 (dd, J = 7.8 Hz, 2.1 Hz, 1H), 7.33 (d, J = 2.3 Hz, 1H), 7.26 (dd, J = 5.9 Hz, 2.1 Hz, 1H), 7.09 (dd, J = 8.6 Hz, 2.3 Hz, 1H), 6.87 (d, J = 8.6 Hz, 1H), 3.87 (s, 3H), 3.84 (s, 3H), 3.25-3.18 (m, 2H), 3.08-3.00 (m, 2H), 2.93 (t, J = 7.5 Hz, 2H), 2.87 (s, 3H), 2.80 (t, J = 7.5 Hz, 2H), 2.21-2.15 (m, 2H), 1.08 (d, J = 6.4 Hz, 6H). |
| 157 | 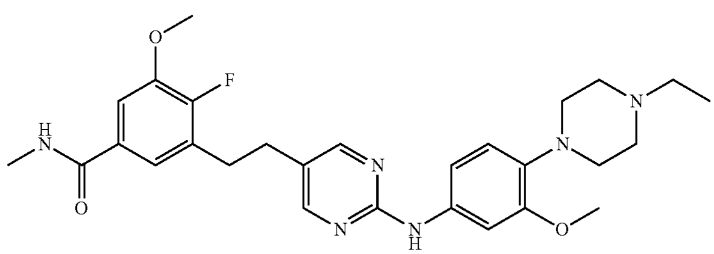 [SMILES: CCN1CCN(c2ccc(Nc3ncc(CCc4cc(C(=O)NC)cc(OC)c4F)cn3)cc2OC)CC1] | 523.4 | 1H NMR (400 MHz, CD3OD) δ 8.13 (s, 2H), 7.39 (dd, J = 7.4 Hz, 1.5 Hz, 1H), 7.33 (d, J = 2.2 Hz, 1H), 7.25 (dd, J = 5.9 Hz, 1.9 Hz, 1H), 7.08 (dd, J = 8.6 Hz, 2.1 Hz, 1H), 6.90 (d, J = 8.6 Hz, 1H), 3.87 (s, 3H), 3.84 (s, 3H), 3.09-2.99 (m, 4H), 2.94 (t, J = 7.4 Hz, 2H), 2.87 (s, 3H), 2.80 (t, J = 7.4 Hz, 2H), 2.69-2.57 (m, 4H), 2.48 (q, J = 7.2 Hz, 2H), 1.12 (t, J = 7.2 Hz, 3H). |
| 158 | 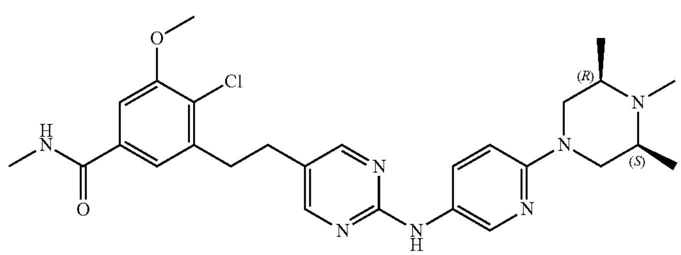 | 524.3 | 1H NMR (400 MHz, CD3OD) δ 8.30 (dd, J = 2.8 Hz, 0.5 Hz, 1H), 8.12 (s, 2H), 7.82 (dd, J = 9.1 Hz, 2.8 Hz, 1H), 7.37 (d, J = 2.0 Hz, 1H), 7.30 (d, J = 2.0 Hz, 1H), 6.81 (dd, J = 9.1 Hz, 0.5 Hz, 1H), 4.02-3.96 (m, 2H), 3.92 (s, 3H), 3.07-3.03 (m, 2H), 2.90 (s, 3H), 2.83 (t, J = 7.6 Hz, 2H), 2.65-2.59 (m, 2H), 2.40-2.33 (m, 2H), 2.33 (s, 3H), 1.19 (d, J = 6.3 Hz, 6H). |
| 159 | 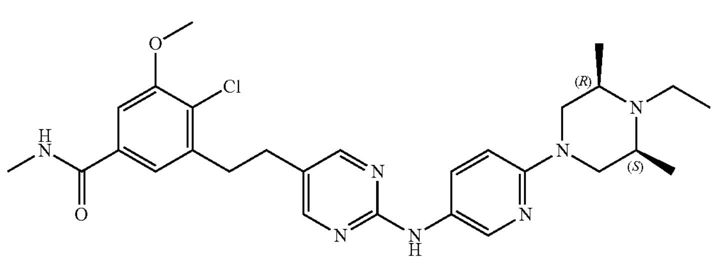 | 538.3 | 1H NMR (400 MHz, CD3OD) δ 8.29 (d, J = 2.6 Hz, 1H), 8.12 (s, 2H), 7.81 (dd, J = 9.1 Hz, 2.6 Hz, 1H), 7.37 (d, J = 1.9 Hz, 1H), 7.30 (d, J = 1.9 Hz, 1H), 6.80 (d, J = 9.1 Hz, 1H), 3.95-4.01 (m, 2H), 3.05 (t, J = 7.5 Hz, 2H), 2.99 (q, J = 7.2 Hz, 2H), 2.89 (s, 3H), 2.82 (t, J = 7.5 Hz, 2H), 2.79-2.71 (m, 2H), 2.63-2.54 (m, 2H), 1.17 (d, J = 6.3 Hz, 6H), 0.96 (t, J = 7.2 Hz, 3H). |

| Compound | Structure | LC-MS (m/z) (M + H)+ | 1H NMR |
|---|---|---|---|
| 160 | 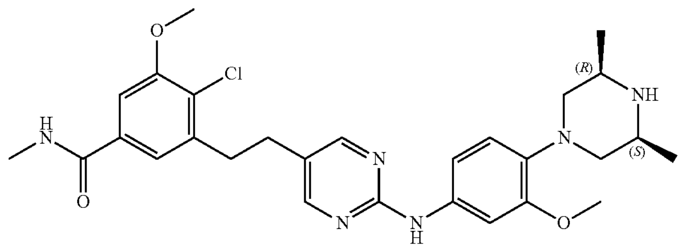 | 539.6 | 1H NMR (400 MHz, CD3OD) δ 8.13 (s, 2H), 7.36-7.31 (m, 2H), 7.28 (s, 1H), 7.09 (dd, J = 8.5 Hz, 2.0 Hz, 1H), 6.87 (dd, J = 8.5 Hz, 1.1 Hz, 1H), 3.90 (s, 3H), 3.83 (s, 3H), 3.23-3.19 (m, 2H), 3.07-2.98 (m, 4H), 2.87 (s, 3H), 2.79 (t, J = 7.5 Hz, 2H), 2.19-2.15 (m, 2H), 1.07 (d, J = 7.3 Hz, 6H). |
| 161 | 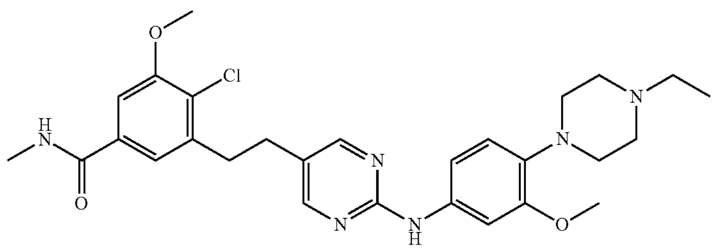 | 539.6 | 1H NMR (400 MHz, CD3OD) δ 8.15 (s, 2H), 7.36-7.35 (m, 2H), 7.29 (d, J = 1.8 Hz, 1H), 7.10 (dd, J = 8.5 Hz, 2.1 Hz, 1H), 6.91 (d, J = 8.6 Hz, 1H), 3.89 (s, 3H), 3.85 (s, 3H), 3.07-3.03 (m, 6H), 2.88 (s, 3H), 2.82 (t, J = 7.6 Hz, 2H), 2.72-2.68 (m, 4H), 2.54 (q, J = 7.0 Hz, 2H), 1.14 (t, J = 7.2 Hz, 3H). |

Example 12: Synthesis of Compound 162

Compound 162
3-(2-(2-((1-(ethylsulfonyl)-1H-pyrazol-4-yl)amino)pyrimidin-5-yl)ethyl)-4-fluoro-5-methoxy-N-methylbenzamide

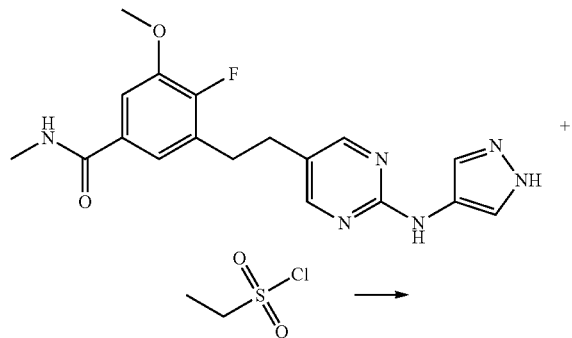

(A) 3-(2-(2-((1-(ethylsulfonyl)-1H-pyrazol-4-yl)amino)pyrimidin-5-yl)ethyl)-4-fluoro-5-methoxy-N-methylbenzamide To a solution of 3-(2-(2-((1H-pyrazol-4-yl)amino)pyrimidin-5-yl)ethyl)-4-fluoro-5-methoxy-N-methylbenzamide (80.0 mg, 0.22 mmol) in THF/DMF (1 mL, 1:1 vol.) was added KHMDS (0.43 mL, 0.22 mmol, 0.5 M in Toluene) dropwise with ice-water bath cooling. After the addition, the mixture was stirred for further 2 min. Then, to the mixture was added ethanesulfonyl chloride (28 mg, 0.22 mmol) dropwise at the same temperature. After the addition, the mixture was stirred for further 2 min and then quenched with water (0.5 mL). The resulting mixture was extracted with DCM (5 mL). The organic layer was concentrated in vacuo and the residue was purified via ISCO (eluted with MeOH in H2O 0-100%) to give the tilted compound as a white solid (7.8 mg, 7.8% yield). MS (m/z): 426.9 (M+H)+. 1H NMR (400 MHz, CD3OD) δ 8.47 (s, 1H), 8.23 (s, 2H), 7.95 (s, 1H), 7.41 (dd, J=7.8 Hz, 2.1 Hz, 1H), 7.28 (dd, J=6.0 Hz, 2.1 Hz, 1H), 3.89 (s, 3H), 3.51 (q, J=7.4 Hz, 2H), 2.97 (t, J=7.4 Hz, 2H), 2.89 (s, 3H), 2.85 (t, J=7.4 Hz, 2H), 1.20 (t, J=7.4 Hz, 3H).

Example 13: Synthesis of Compounds 163-166

Compound 163
3-(2-(2-((1-(cyclopropylmethyl)-1H-pyrazol-4-yl)amino)pyrimidin-5-yl)ethyl)-4-fluoro-5-methoxy-N-methylbenzamide

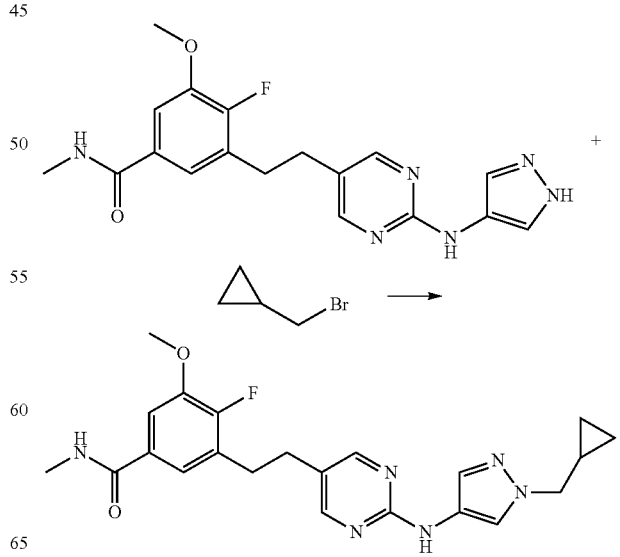

115

(A) 3-(2-(2-((1-(cyclopropylmethyl)-1H-pyrazol-4-yl)amino)pyrimidin-5-yl)ethyl)-4-fluoro-5-methoxy-N-methylbenzamide To a solution of 3-(2-(2-((1H-pyrazol-4-yl)amino)pyrimidin-5-yl)ethyl)-4-fluoro-5-methoxy-N-methylbenzamide (106 mg, 0.29 mmol) and (bromomethyl)cyclopropane (77 mg, 0.57 mmol) in DMF (10 mL) was added $Cs_2CO_3$ (280 mg, 0.86 mmol). The mixture was stirred at 80° C. for overnight. The mixture was then partitioned between EA and water. The organic layer was washed with water and brine, dried over anhydrous sodium sulfate and concentrated. The residue was purified via ISCO (eluted with MeOH in DCM 0~10%) to afford the title compound as an off-white solid (34 mg, 28.0% yield). MS (m/z): 425.1 (M+H)$^+$. $^1$H NMR (400 MHz, $CD_3OD$) δ 8.13 (s, 2H), 7.95 (s, 1H), 7.52 (s, 1H), 7.40 (dd, J=7.8 Hz, 2.1 Hz, 1H), 7.26 (dd, J=5.9 Hz, 2.0 Hz, 1H), 3.93 (d, J=7.1 Hz, 2H), 3.88 (s, 3H), 2.94 (t, J=7.4 Hz, 2H), 2.88 (s, 3H), 2.80 (t, J=7.4 Hz, 2H), 1.28-1.26 (m, 1H), 0.62-0.56 (m, 2H), 0.41-0.34 (m, 2H).

The following compounds were prepared according to the procedures of Compound 163 using the corresponding intermediates and reagents under appropriate conditions that could be recognized by one skilled in the art.

116

Example 14: Synthesis of Compound 167

Compound 167

4-fluoro-3-methoxy-N-methyl-5-(2-(2-((4-(2-oxopiperidin-1-yl)phenyl)amino)pyrimidin-5-yl)ethyl)benzamide

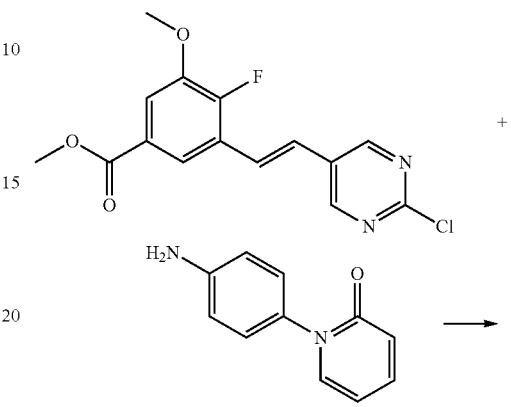

| Compound | Structure | LC-MS (m/z) (M+H)$^+$ | $^1$H NMR |
|---|---|---|---|
| 164 | 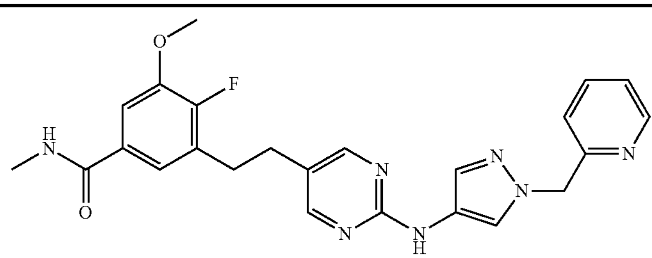 | 462.1 | $^1$H NMR (400 MHz, $CD_3OD$) δ 8.50 (d, J = 4.9 Hz, 1H), 8.13 (s, 2H), 8.07 (s, 1H), 7.77 (td, J = 7.8 Hz, 1.7 Hz, 1H), 7.61 (s, 1H), 7.39 (dd, J = 7.8 Hz, 2.1 Hz, 1H), 7.32 (dd, J = 6.9 Hz, 5.3 Hz, 1H), 7.26 (dd, J = 5.9 Hz, 2.1 Hz, 1H), 7.05 (d, J = 7.9 Hz, 1H), 5.39 (s, 2H), 3.87 (s, 3H), 2.93 (t, J = 7.4 Hz, 2H), 2.87 (s, 3H), 2.80 (t, J = 7.4 Hz, 2H). |
| 165 | 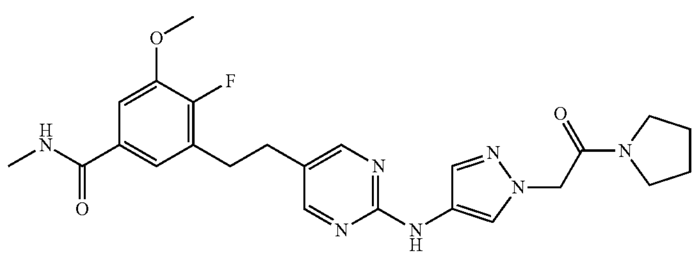 [SMILES: CNC(=O)c1cc(CCc2cnc(Nc3cnn(CC(=O)N4CCCC4)c3)nc2)c(F)c(OC)c1] | 482.2 | $^1$H NMR (400 MHz, $CDCl_3$) δ 8.15 (s, 2H), 7.60 (s, 1H), 7.34 (d, J = 7.5 Hz, 1H), 6.98 (s, 1H), 6.22 (s, 1H), 4.86 (s, 2H), 3.91 (s, 3H), 3.58-3.43 (m, 4H), 2.95 (s, 3H), 2.93-2.87 (m, 2H), 2.85-2.77 (m, 2H), 2.04-1.98 (m, 2H), 1.90-1.84 (m, 2H). |
| 166 | 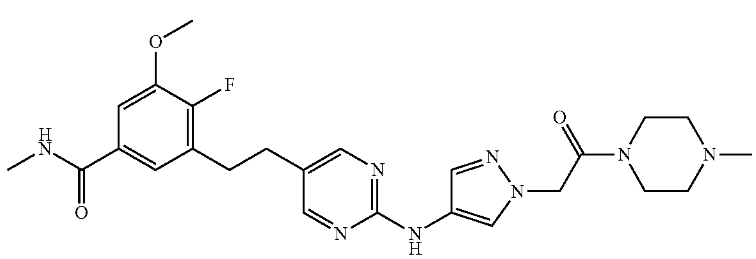 | 511.2 | $^1$H NMR (400 MHz, $CDCl_3$) δ 8.29-7.95 (m, 2H), 7.66-7.45 (m, 1H), 7.33 (d, J = 6.8 Hz, 1H), 7.04-6.96 (m, 1H), 6.32-6.09 (m, 1H), 5.30 (s, 2H), 3.92 (s, 3H), 3.70-3.63 (m, 2H), 3.61-3.55 (m, 2H), 2.97 (d, J = 3.7 Hz, 3H), 2.92 (t, J = 7.0 Hz, 2H), 2.85-2.75 (t, J = 7.0 Hz, 2H), 2.48-2.37 (m, 4H), 2.35-2.29 (m, 3H). |

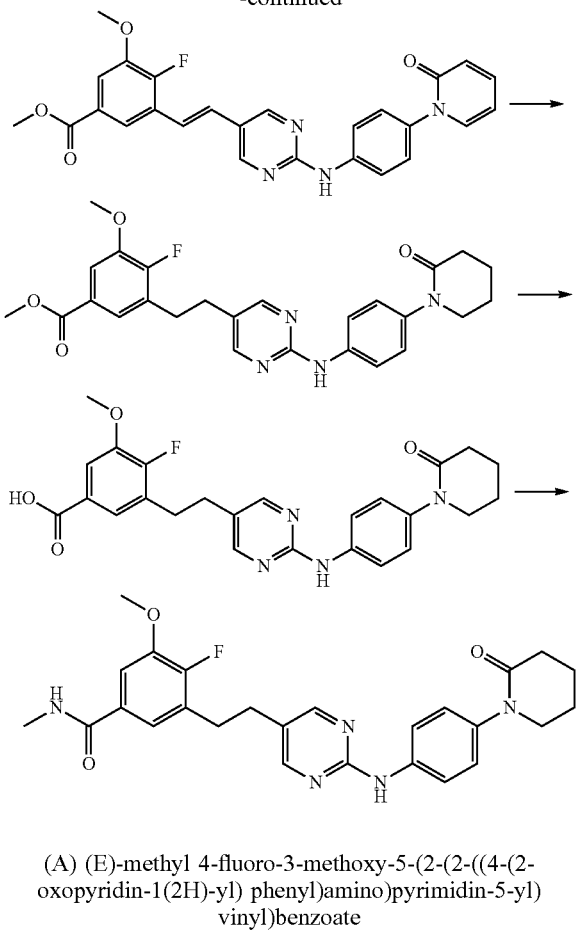

(A) (E)-methyl 4-fluoro-3-methoxy-5-(2-(2-((4-(2-oxopyridin-1(2H)-yl) phenyl)amino)pyrimidin-5-yl) vinyl)benzoate A mixture of 1-(4-aminophenyl)pyridin-2(1H)-one (138 mg, 0.74 mmol), (E)-methyl 3-(2-(2-chloropyrimidin-5-yl) vinyl)-4-fluoro-5-methoxybenzoate (120 mg, 0.37 mmol) and 4-methylbenzenesulfonic acid hydrate (71 mg, 0.37 mmol) in propan-2-ol (4 mL) was stirred at 140° C. for 1 h under microwave. The mixture was filtered and the filter cake was washed with propan-2-ol (3*10 mL). The solid was dried under reduced pressure at 50° C. for 20 min to give the desired compound as a grey solid (150 mg, 85.4% yield). MS (m/z): 473.1 (M+H)+.

(B) Methyl 4-fluoro-3-methoxy-5-(2-(2-((4-(2-oxopiperidin-1-yl)phenyl) amino)pyrimidin-5-yl)ethyl) benzoate To a solution of (E)-methyl 4-fluoro-3-methoxy-5-(2-(2-((4-(2-oxopyridin-1 (2H)-yl) phenyl) amino)pyrimidin-5-yl) vinyl)benzoate (150 mg, 0.32 mmol) in a mixed solvent of THF/MeOH (20 mL/20 mL) was added Pd/C (10%, 100 mg). The mixture was purged with hydrogen and stirred overnight at room temperature under hydrogen atmosphere. The catalyst was fitered off through celite and the filtrate was concentrated to give a light yellow oil (152 mg, quantative yield). MS (m/z): 479.1 (M+H)+.

(C) 4-fluoro-3-methoxy-N-methyl-5-(2-(2-((4-(2-oxopiperidin-1-yl)phenyl)amino)pyrimidin-5-yl) ethyl)benzamide To a solution of methyl 4-fluoro-3-methoxy-5-(2-(2-((4-(2-oxopiperidin-1-yl)phenyl)amino) pyrimidin-5-yl)ethyl) benzoate (152 mg, 0.32 mmol) in MeOH (20 mL) was added aqueous NaOH (2 N, 3 mL, 6 mmol). Then the mixture was stirred overnight at room temperature. After concentration, the residue was adjusted to pH<2 with conc HCl. Then the mixture was concentrated to give a brown solid which was suspended in DMF (10 mL) and then methanamine hydrochloride (43 mg, 0.64 mmol), HATU (183 mg, 0.48 mmol) and DIPEA (165 mg, 1.28 mmol) were added. The resulting mixture was stirred for 2 h at room temperature and then partitioned between EA and water. The organic layer was washed with water and brine, dried over anhydrous sodium sulfate and concentrated. The residue was purified via ISCO (eluted with MeOH in H$_2$O 0~100%) to give the title compound as a slight yellow solid (29.1 mg, 19.2% yield). MS (m/z): 478.2 (M+H)+. $^1$H NMR (400 MHz, CD$_3$OD) δ 8.17 (s, 2H), 7.68 (d, J=8.5 Hz, 2H), 7.42-7.37 (m, 1H), 7.29-7.24 (m, 1H), 7.14 (d, J=8.7 Hz, 2H), 3.87 (s, 3H), 3.65-3.62 (m, 2H), 2.97-2.93 (m, 2H), 2.88 (s, 3H), 2.85-2.80 (m, 2H), 2.51-2.46 (m, 2H), 1.97-1.92 (m, 4H).

Example 15: Synthesis of Compounds 168-178

Compound 168
4-chloro-N,3-dimethoxy-5-(2-(2-((1-methyl-1H-pyrazol-4-yl)amino)pyrimidin-5-yl) ethyl)benzamide

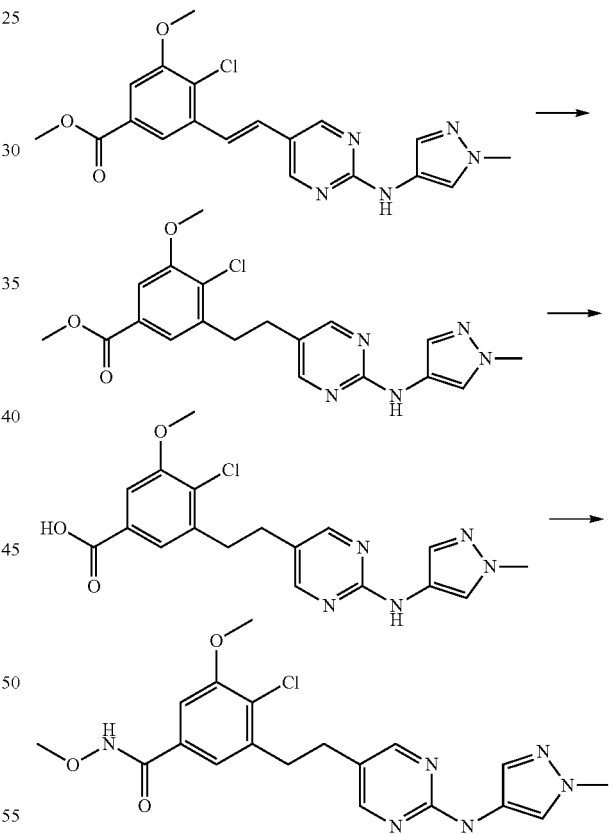

(A) Methyl 4-chloro-3-methoxy-5-(2-(2-((1-methyl-1H-pyrazol-4-yl)amino) pyrimidin-5-yl)ethyl)benzoate A mixture of (E)-methyl 4-chloro-3-methoxy-5-(2-(2-((1-methyl-1H-pyrazol-4-yl)amino)pyrimidin-5-yl)vinyl)benzoate (0.25 g, 0.63 mmol), 4-methylbenzenesulfonohydrazide (1.2 g, 6.4 mmol) and sodium acetate (0.53 g, 6.5 mmol) in THF (15 mL) and H$_2$O (10 mL) was heated at 100° C. for 20 h under nitrogen. Then the volatiles were removed under reduced pressure and the residue was purified via ISCO (eluted with MeOH in H$_2$O 0~100%) to afford the title compound as a yellow solid (0.12 g, 47.8% yield). MS (m/z): 402.3 (M+H)$^+$.

(B) 4-chloro-3-methoxy-5-(2-(2-((1-methyl-1H-pyrazol-4-yl)amino)pyrimidin-5-yl)ethyl)benzoic acid A solution of methyl 4-chloro-3-methoxy-5-(2-(2-((1-methyl-1H-pyrazol-4-yl) amino)pyrimidin-5-yl)benzoate (0.12 g, 0.30 mmol) in THF (3 mL) and MeOH (2 mL) was mixed with aqueous NaOH solution (0.20 g NaOH in 1 mL H$_2$O). The resulting mixture was stirred at room temperature for 2 h, and then purified via ISCO (eluted with MeOH in H$_2$O 0~100%) directly to afford the title compound as a white solid (0.075 g, 64.8% yield). MS (m/z): 388.3 (M+H)$^+$.

(C) 4-chloro-N,3-dimethoxy-5-(2-(2-((1-methyl-1H-pyrazol-4-yl)amino)pyrimidin-5-yl)ethyl)benzamide A mixture of 4-chloro-3-methoxy-5-(2-(2-((1-methyl-1H-pyrazol-4-yl) amino) pyrimidin-5-yl)ethyl)benzoic acid (0.025 g, 0.065 mmol), methoxylamine hydrochloride (0.012 g, 0.14 mmol), DIPEA (0.030 g, 0.23 mmol) and HATU (0.035 g, 0.092 mmol) in DMF (4 mL) was stirred at room temperature for 30 min. Then the reaction mixture was purified via ISCO (eluted with MeOH in H$_2$O 0~100%) directly to afford the title compound as a yellow solid (0.022 g, 81.9% yield). MS (m/z): 417.4 (M+H)$^+$. $^1$H NMR (400 MHz, CD$_3$OD) δ 8.17 (s, 2H), 7.87 (s, 1H), 7.53 (s, 1H), 7.31 (d, J=1.6 Hz, 1H), 7.26 (d, J=1.6 Hz, 1H), 3.95 (s, 3H), 3.87 (s, 3H), 3.82 (s, 3H), 3.06 (t, J=7.7 Hz, 2H), 2.83 (t, J=7.7 Hz, 2H).

The following compound was prepared according to the procedures of Compound 168 using the corresponding intermediates and reagents under appropriate conditions that could be recognized by one skilled in the art.

| Compound | Structure | LC-MS (m/z) (M + H)$^+$ | $^1$H NMR |
|---|---|---|---|
| 169 | 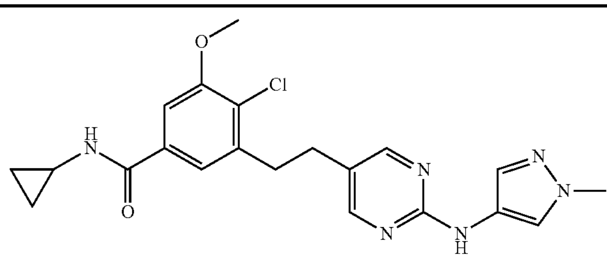 | 427.0 | $^1$H NMR (400 MHz, CD$_3$OD) δ 8.13 (s, 2H), 7.87 (s, 1H), 7.50 (s, 1H), 7.35 (s, 1H), 7.28 (s, 1H), 3.91 (s, 3H), 3.84 (s, 3H), 3.03 (t, J = 9.4 Hz, 2H), 2.91-2.83 (m, 1H), 2.83-2.75 (m, 2H), 0.86-0.70 (m, 2H), 0.70-0.51 (m, 2H). |
| 170 | 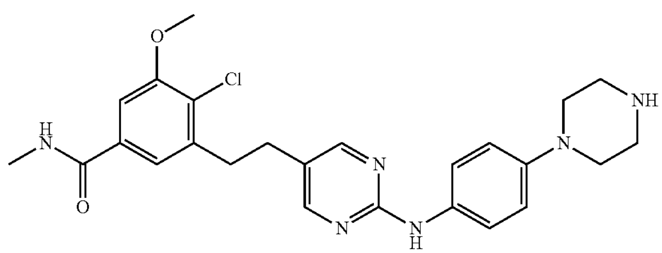 [SMILES: CNC(=O)c1cc(CCc2cnc(Nc3ccc(N4CCNCC4)cc3)nc2)c(Cl)c(OC)c1] | 480.8 | $^1$H NMR (400 MHz, CD$_3$OD) δ 8.10 (s, 2H), 7.43 (d, J = 7.3 Hz, 2H), 7.37-7.34 (m, 1H), 7.30-7.26 (m, 1H), 6.93 (d, J = 7.3 Hz, 2H), 3.91 (s, 3H), 3.09-3.01 (m, 6H), 3.00-2.94 (m, 4H), 2.88 (s, 3H), 2.81 (t, J = 7.4 Hz, 2H). |
| 171 | 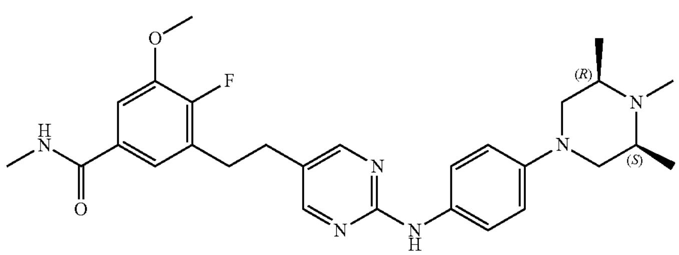 | 506.9 | $^1$H NMR (400 MHz, CD$_3$OD) δ 8.09 (s, 2H), 7.45-7.37 (m, 3H), 7.26 (dd, J = 5.9 Hz, 2.0 Hz, 1H), 6.95-6.88 (m, 2H), 3.88 (s, 3H), 3.44 (d, J = 10.3 Hz, 2H), 2.93 (t, J = 7.4 Hz, 2H), 2.88 (s, 3H), 2.80 (t, J = 7.4 Hz, 2H), 2.52-2.41 (m, 4H), 2.33 (s, 3H), 1.17 (d, J = 5.8 Hz, 6H). |
| 172 | 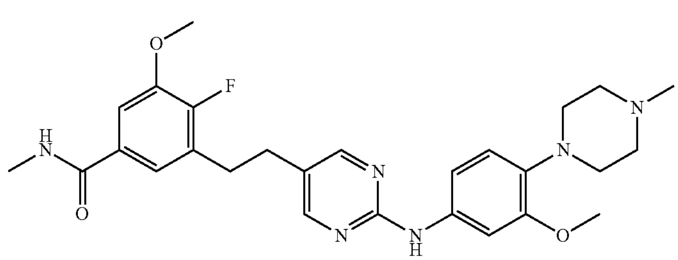 | 509.2 | $^1$H NMR (400 MHz, CD$_3$OD) δ 8.12 (s, 2H), 7.44-7.36 (m, 1H), 7.33 (d, J = 2.0 Hz, 1H), 7.25 (d, J = 4.1 Hz, 1H), 7.08 (dd, J = 8.5 Hz, 2.1 Hz, 1H), 6.88 (d, J = 8.6 Hz, 1H), 3.86 (s, 3H), 3.83 (s, 3H), 3.03-2.99 (m, 4H), 2.93 (t, J = 7.3 Hz, 2H), 2.87 (s, 3H), 2.80 (t, J = 7.3 Hz, 2H), 2.65-2.61 (m, 4H), 2.32 (s, 3H). |

| Compound | Structure | LC-MS (m/z) (M + H)+ | 1H NMR |
|---|---|---|---|
| 173 | 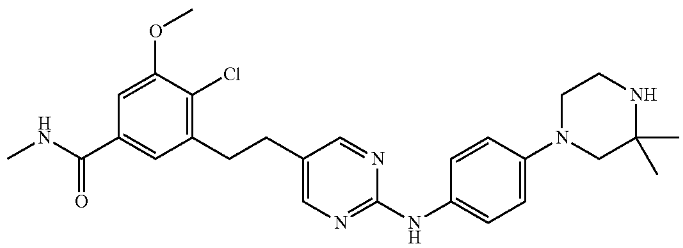 | 508.8 | 1H NMR (400 MHz, CD3OD) δ 8.09 (s, 2H), 7.39 (d, J = 8.8 Hz, 2H), 7.35 (s, 1H), 7.28 (s, 1H), 6.87 (d, J = 8.8 Hz, 2H), 3.91 (s, 3H), 3.06-2.95 (m, 6H), 2.88 (s, 3H), 2.84-2.76 (m, 4H), 1.21 (s, 6H). |
| 174 | 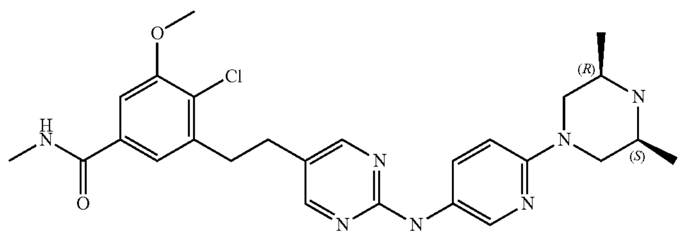 | 510.3 | 1H NMR (400 MHz, CD3OD) δ 8.38 (d, J = 2.6 Hz, 1H), 8.13 (s, 2H), 7.91 (dd, J = 9.0 Hz, 2.7 Hz, 1H), 7.36 (d, J = 1.8 Hz, 1H), 7.29 (d, J = 1.9 Hz, 1H), 6.92 (d, J = 9.1 Hz, 1H), 4.36 (dd, J = 14.0 Hz, 2.4 Hz, 1H), 3.92 (s, 3H), 3.45-3.36 (m, 2H), 3.05 (t, J = 7.6 Hz, 2H), 2.89 (s, 3H), 2.83 (t, J = 7.6 Hz, 2H), 2.75 (dd, J = 13.9 Hz, 11.4 Hz, 2H), 1.37 (d, J = 6.6 Hz, 6H). |
| 175 | 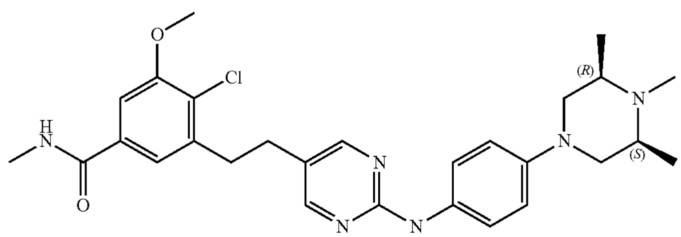 | 522.9 | 1H NMR (400 MHz, CD3OD) δ 8.10 (s, 2H), 7.45-7.40 (m, 2H), 7.36 (d, J = 2.0 Hz, 1H), 7.28 (d, J = 2.0 Hz, 1H), 6.94-6.88 (m, 2H), 3.91 (s, 3H), 3.46-3.40 (m, 2H), 3.03 (t, J = 7.6 Hz, 2H), 2.88 (s, 3H), 2.80 (t, J = 7.6 Hz, 2H), 2.51-2.40 (m, 4H), 2.32 (s, 3H), 1.17 (d, J = 5.9 Hz, 6H). |
| 176 | 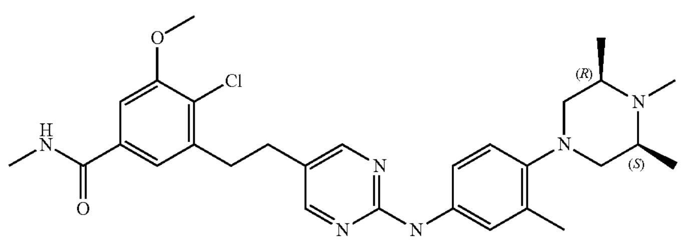 | 523.3 | 1H NMR (400 MHz, CD3OD) δ 8.12 (s, 2H), 7.37-7.32 (m, 3H), 7.30-7.28 (m, 1H), 6.95 (d, J = 9.3 Hz, 1H), 3.91 (s, 3H), 3.07-3.01 (m, 4H), 2.94-2.89 (m, 2H), 2.88 (s, 3H), 2.81 (t, J = 7.6 Hz, 2H), 2.28 (t, J = 10.9 Hz, 2H), 2.26 (s, 3H), 1.09 (d, J = 6.5 Hz, 6H). |
| 177 | 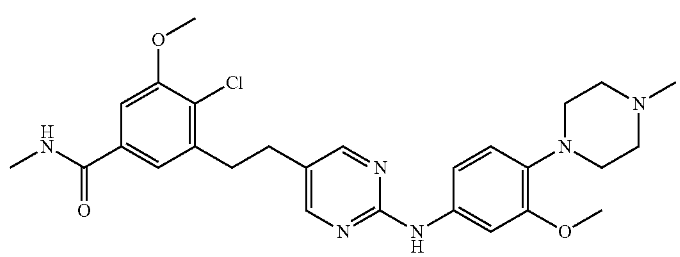 | 525.2 | 1H NMR (400 MHz, CD3OD) δ 8.14 (s, 2H), 7.39-7.31 (m, 2H), 7.29 (s, 1H), 7.08 (d, J = 8.6 Hz, 1H), 6.89 (d, J = 8.5 Hz, 1H), 3.91 (s, 3H), 3.84 (s, 3H), 3.10-2.98 (m, 6H), 2.88 (s, 3H), 2.82 (t, J = 7.5 Hz, 2H), 2.63-2.59 (m, 4H), 2.32 (s, 3H). |
| 178 | 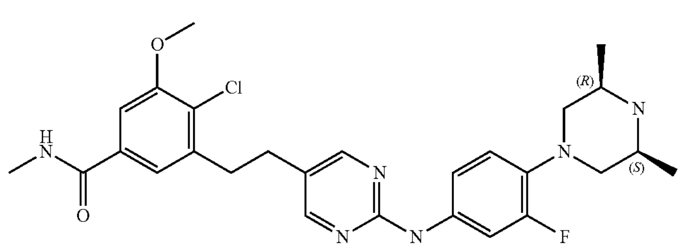 | 527.3 | 1H NMR (400 MHz, CD3OD) δ 8.16 (s, 2H), 7.57 (d, J = 14.2 Hz, 1H), 7.36 (s, 1H), 7.29 (s, 1H), 7.91 (d, J = 8.3 Hz, 1H), 6.93 (t, J = 9.1 Hz, 1H), 3.91 (s, 3H), 3.20 (d, J = 11.0 Hz, 2H), 3.09-2.95 (m, 4H), 2.88 (s, 3H), 2.82 (t, J = 7.1 Hz, 2H), 2.28 (t, J = 10.7 Hz, 2H), 1.10 (d, J = 6.1 Hz, 6H). |

Example 16: Synthesis of Compound 179

Compound 179
4-chloro-3-methoxy-N-methyl-5-(2-(2-((1-(piperidin-4-yl)-1H-pyrazol-4-yl)amino)pyrimidin-5-yl)ethyl)benzamide (B) 4-chloro-3-methoxy-N-methyl-5-(2-(2-((1-(piperidin-4-yl)-1H-pyrazol-4-yl)amino)pyrimidin-5-yl)ethyl)benzamide A mixture of tert-butyl 4-(4-((5-(2-chloro-3-methoxy-5-(methylcarbamoyl)-phenethyl)-pyrimidin-2-yl)amino)-1H-

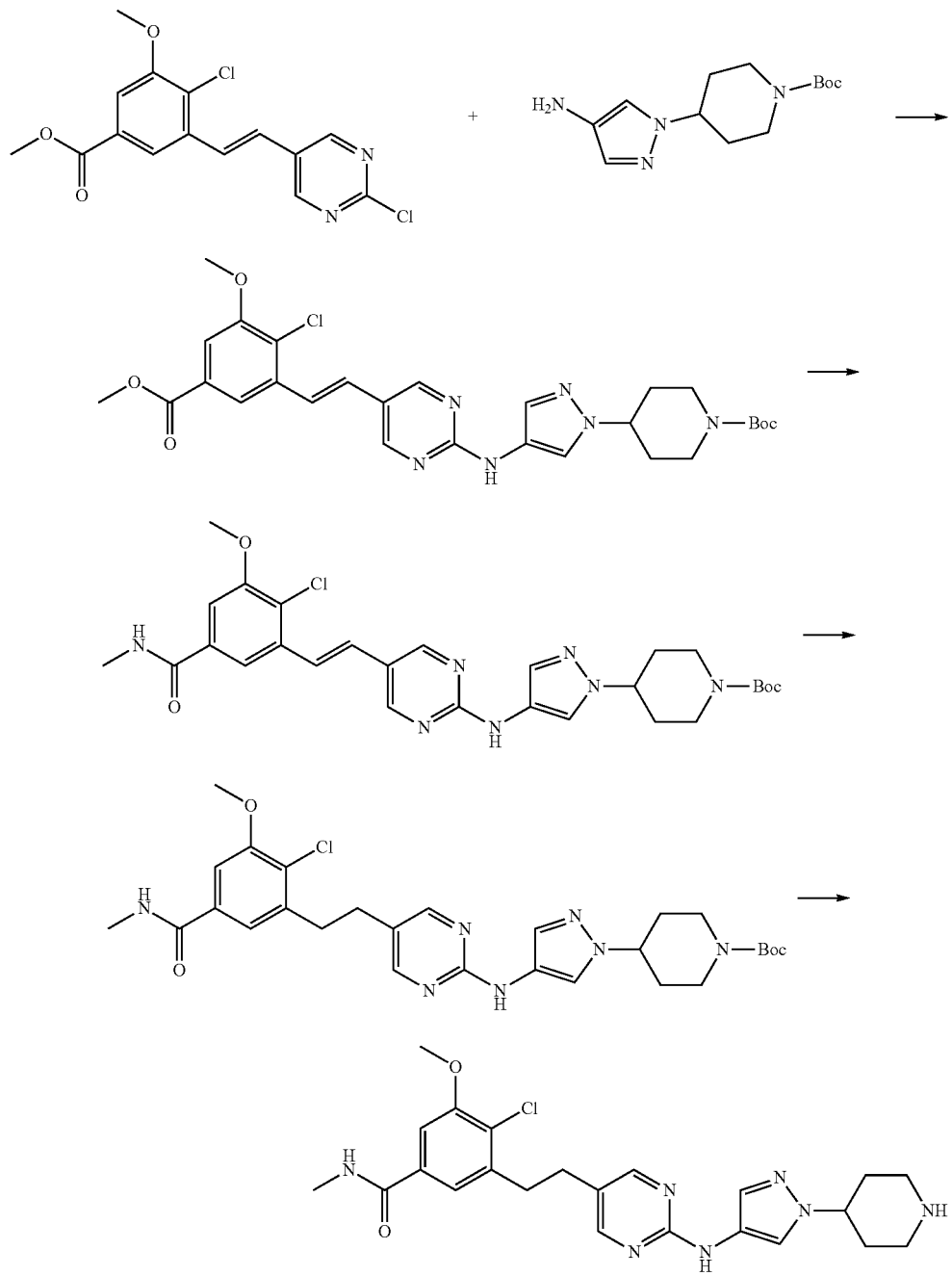 [SMILES: COC(=O)c1cc(/C=C/c2cnc(Cl)nc2)c(Cl)c(OC)c1 ; CC(C)(C)OC(=O)N1CCC(n2cc(N)cn2)CC1 ; COC(=O)c1cc(/C=C/c2cnc(Nc3cnn(C4CCN(C(=O)OC(C)(C)C)CC4)c3)nc2)c(Cl)c(OC)c1 ; CNC(=O)c1cc(/C=C/c2cnc(Nc3cnn(C4CCN(C(=O)OC(C)(C)C)CC4)c3)nc2)c(Cl)c(OC)c1 ; CNC(=O)c1cc(CCc2cnc(Nc3cnn(C4CCN(C(=O)OC(C)(C)C)CC4)c3)nc2)c(Cl)c(OC)c1 ; CNC(=O)c1cc(CCc2cnc(Nc3cnn(C4CCNCC4)c3)nc2)c(Cl)c(OC)c1]

(A) tert-butyl 4-(4-((5-(2-chloro-3-methoxy-5-(methylcarbamoyl)phenethyl)-pyrimidin-2-yl)amino)-1H-pyrazol-1-yl)piperidine-1-carboxylate The title compound was prepared according to the procedures of Example 9 using the corresponding intermediates and reagents.

pyrazol-1-yl)piperidine-1-carboxylate (80 mg, 0.15 mmol) in MeOH (2 mL) was treated with 5 drops of conc. hydrochloric acid. The mixture was concentrated in vacuo (45° C. water bath) and the residue was taken in aq. NaHCO₃ (5 mL) and extracted with DCM (2*10 mL). The organic layers were combined and concentrated in vacuo. The residue was purified via ISCO (eluted with MeOH in H₂O 0-100%) to afford the title compound (46 mg, 69.7% yield). MS (m/z): 470.0 (M+H)+. 1H NMR (400 MHz, CD3OD) δ 8.14 (s, 2H), 8.01 (s, 1H), 7.57 (s, 1H), 7.36 (d, J=1.9 Hz, 1H), 7.30 (d, J=1.9 Hz, 1H), 4.52-4.43 (m, 1H), 3.92 (s, 3H), 3.59-3.50 (m, 2H), 3.23-3.13 (m, 2H), 3.05 (t, J=7.6 Hz, 2H), 2.89 (s, 3H), 2.83 (t, J=7.6 Hz, 2H), 2.33-2.17 (m, 4H).
Example 17: Synthesis of Compounds 180-185
Compound 180
(R)-4-fluoro-3-methoxy-N-methyl-5-(2-(2-((1-(piperidin-3-yl)-1H-pyrazol-4-yl)amino)pyrimidin-5-yl)ethyl)benzamide
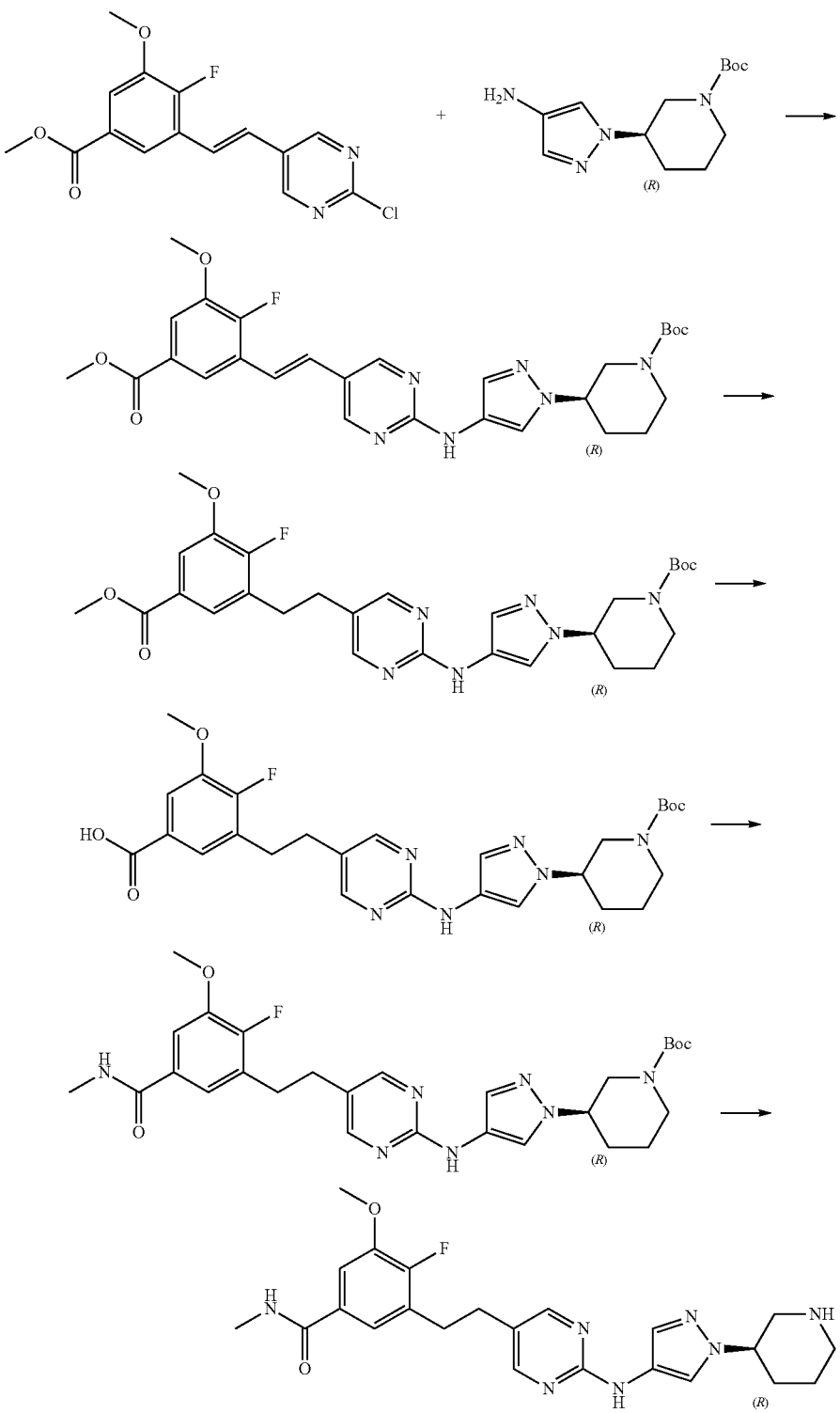

(A) (R)-tert-butyl 3-(4-((5-(2-fluoro-3-methoxy-5-(methylcarbamoyl)phenethyl) pyrimidin-2-yl)amino)-1H-pyrazol-1-yl)piperidine-1-carboxylate The title compound was prepared according to the procedures of Example 11 using the corresponding intermediates and reagents.

(B)(R)-4-fluoro-3-methoxy-N-methyl-5-(2-(2-((1-(piperidin-3-yl)-1H-pyrazol-4-yl)amino)pyrimidin-5-yl)ethyl)benzamide A mixture of (R)-tert-butyl 3-(4-((5-(2-fluoro-3-methoxy-5-(methylcarbamoyl) phenethyl)py-rimidin-2-yl)amino)-1H-pyrazol-1-yl)piperidine-1-carboxylate (160 mg, 0.29 mmol) in MeOH (2 mL) was treated with 6 drops of conc. hydrochloric acid. The mixture was concentrated in vacuo (40° C. water bath) and the residue was taken in aq. NaHCO$_3$ (5 mL) and extracted with DCM (2*10 mL). The organic layers were combined and concentrated in vacuo. The residue was purified via ISCO (eluted with MeOH in H$_2$O 0-100%) to afford the title compound (87.0 mg, 66.4% yield). MS (m/z): 454.0 (M+H)+. $^1$H NMR (400 MHz, CD$_3$OD) δ 8.12 (s, 2H), 7.93 (s, 1H), 7.52 (s, 1H), 7.39 (dd, J=7.8 Hz, 2.2 Hz, 1H), 7.26 (dd, J=6.0 Hz, 2.1 Hz, 1H), 4.17-4.10 (m, 1H), 3.87 (s, 3H), 3.25-3.18 (m, 1H), 2.95-2.90 (m, 3H), 2.87 (s, 3H), 2.83-2.78 (m, 3H), 2.62-2.57 (m, 1H), 2.17-2.16 (m, 1H), 1.95-1.88 (m, 1H), 1.84-1.79 (m, 1H), 1.64-1.59 (m, 1H).

The following compounds were prepared according to the procedures of Compound 180 using the corresponding intermediates and reagents under appropriate conditions that could be recognized by one skilled in the art.

| Compound | Structure | LC-MS (m/z) (M + H)+ | $^1$H NMR |
|---|---|---|---|
| 181 | 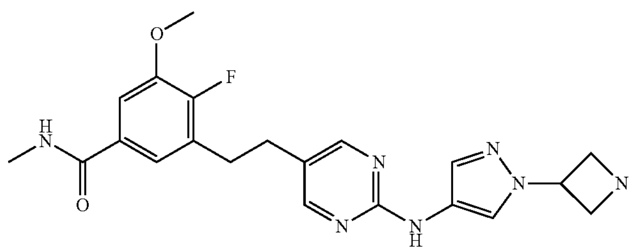 [SMILES: CNC(=O)c1cc(CCc2cnc(Nc3cnn(C4CNC4)c3)nc2)c(F)c(OC)c1] | 426.1 | $^1$H NMR (400 MHz, CD$_3$OD) δ 8.13 (s, 2H), 8.06 (s, 1H), 7.58 (s, 1H), 7.39 (dd, J = 7.7 Hz, 2.1 Hz, 1H), 7.26 (dd, J = 5.9 Hz, 2.0 Hz, 1H), 5.28-5.08 (m, 1H), 4.10-3.99 (m, 2H), 3.92-3.87 (m, 2H), 3.87 (s, 3H), 2.93 (t, J = 7.4 Hz, 2H), 2.87 (s, 3H), 2.80 (t, J = 7.4 Hz, 2H). |
| 182 | 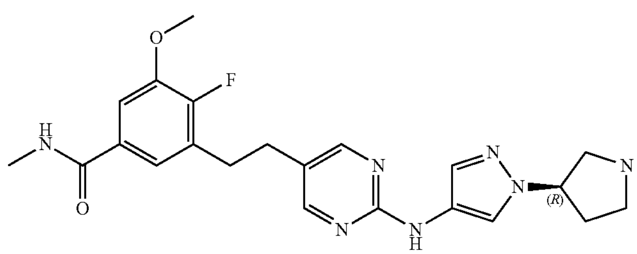 | 439.9 | $^1$H NMR (400 MHz, CD$_3$OD) δ 8.13 (s, 2H), 7.96 (s, 1H), 7.54 (s, 1H), 7.40 (dd, J = 7.8 Hz, 2.1 Hz, 1H), 7.27 (dd, J = 6.0 Hz, 2.1 Hz, 1H), 3.88 (s, 3H), 3.24-3.09 (m, 4H), 2.99-2.95 (m, 1H), 2.95 (t, J = 7.4 Hz, 2H) 2.89 (s, 3H), 2.81 (t, J = 7.4 Hz, 2H), 2.36-2.26 (m, 1H), 2.22-2.11 (m, 1H). |
| 183 | 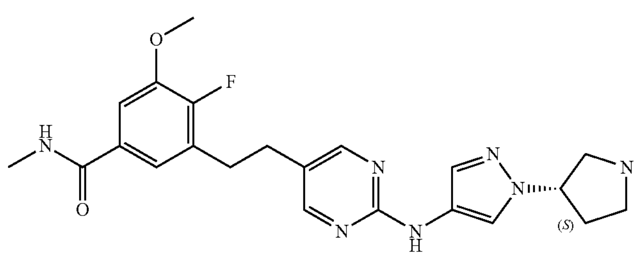 | 439.9 | $^1$H NMR (400 MHz, CD$_3$OD) δ 8.12 (s, 2H), 7.95 (s, 1H), 7.53 (s, 1H), 7.39 (dd, J = 7.8 Hz, 2.1 Hz, 1H), 7.26 (dd, J = 6.0 Hz, 2.1 Hz, 1H), 3.87 (s, 3H), 3.25-3.11 (m, 4H), 3.00-2.95 (m, 1H), 2.93 (t, J = 7.4 Hz, 2H), 2.88 (s, 3H), 2.80 (t, J = 7.4 Hz, 2H), 2.35-2.25 (m, 1H), 2.21-2.10 (m, 1H). |
| 184 | 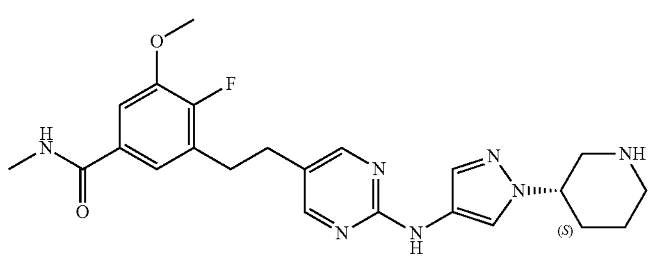 | 454.0 | $^1$H NMR (400 MHz, CD$_3$OD) δ 8.12 (s, 2H), 7.93 (s, 1H), 7.52 (s, 1H), 7.39 (dd, J = 7.6 Hz, 2.0 Hz, 1H), 7.26 (dd, J = 7.6 Hz, 2.0 Hz, 1H), 4.19-4.12 (m, 1H), 3.87 (s, 3H), 3.25-3.20 (m, 1H), 2.93-2.91 (m, 3H), 2.87 (s, 3H), 2.82-2.80 (m, 3H), 2.61-2.58 (m, 1H), 2.18-2.16 (m, 1H), 2.00-1.90 (m, 1H), 1.90-1.79 (m, 1H), 1.65-1.59 (m, 1H). |

| Compound | Structure | LC-MS (m/z) (M + H)+ | 1H NMR |
|---|---|---|---|
| 185 | 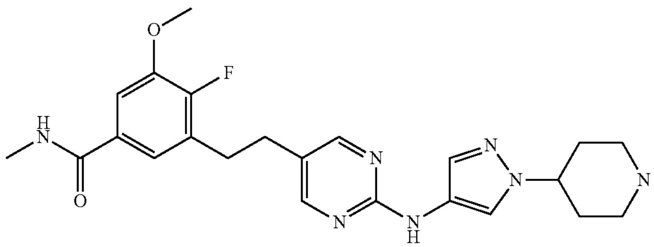 [SMILES: CNC(=O)c1cc(CCc2cnc(Nc3cnn(C4CCNCC4)c3)nc2)c(F)c(OC)c1] | 454.0 | 1H NMR (400 MHz, CD3OD) δ 8.12 (s, 2H), 7.93 (s, 1H), 7.52 (s, 1H), 7.39 (d, J = 6.4 Hz, 1H), 7.26 (d, J = 4.1 Hz, 1H), 4.26-4.12 (m, 1H), 3.87 (s, 3H), 3.18-3.09 (m, 2H), 2.92 (t, J = 7.2 Hz, 2H), 2.87 (s, 3H), 2.79 (t, J = 7.4 Hz, 2H), 2.75-2.64 (m, 2H), 2.11-1.99 (m, 2H), 1.94-1.80 (m, 2H). |

Example 18: Synthesis of Compounds 186-199

Compound 186

(R)-4-fluoro-3-methoxy-N-methyl-5-(2-(2-((1-(1-methylpiperidin-3-yl)-1H-pyrazol-4-yl)amino)pyrimidin-5-yl)ethyl)benzamide

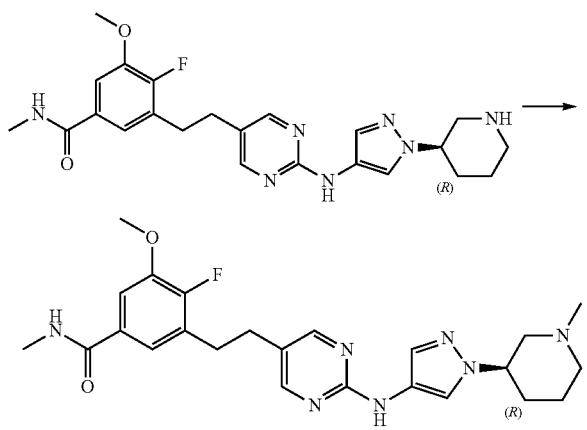

(A) (R)-4-fluoro-3-methoxy-N-methyl-5-(2-(2-((1-(1-methylpiperidin-3-yl)-1H-pyrazol-4-yl)amino)pyrimidin-5-yl)ethyl)benzamide To a mixture of (R)-4-fluoro-3-methoxy-N-methyl-5-(2-(2-((1-(piperidin-3-yl)-1H-pyrazol-4-yl)amino)pyrimidin-5-yl)ethyl)benzamide (37.0 mg, 0.082 mmol) and formaldehyde (37%, 0.01 mL) in THF (5 mL) was added sodium triacetoxyborohydride (52 mg, 0.25 mmol) in portions under ice-water bath cooling. The mixture was then stirred at room temperature for 2 h. The resulting mixture was concentrated in vacuo. The residue was taken in aq. Na2CO3 (10 mL) and extracted with DCM (2*10 mL). The organic layers were combined and concentrated in vacuo. The residue was purified via PTLC (DCM/MeOH=7:1) to afford the title compound as a yellow solid (31.2 mg, 81.8% yield). MS (m/z): 468.0 (M+H)+. 1H NMR (400 MHz, CD3OD) δ 8.13 (s, 2H), 8.00 (s, 1H), 7.55 (s, 1H), 7.40 (dd, J=7.8 Hz, 2.2 Hz, 1H), 7.27 (dd, J=5.9 Hz, 2.1 Hz, 1H), 4.47-4.36 (m, 1H), 3.87 (s, 3H), 3.36-3.33 (m, 1H), 3.25-3.20 (m, 1H), 3.20-3.10 (m, 1H), 3.07-3.00 (m, 1H), 2.94 (t, J=7.3 Hz, 2H), 2.88 (s, 3H), 2.81 (t, J=7.3 Hz, 2H), 2.55 (s, 3H), 2.17-2.06 (m, 1H), 2.00-1.87 (m, 2H), 1.83-1.74 (m, 1H).

The following compounds were prepared according to the procedures of Compound 186 using the corresponding intermediates and reagents under appropriate conditions that could be recognized by one skilled in the art.

| Compound | Structure | LC-MS (m/z) (M + H)+ | 1H NMR |
|---|---|---|---|
| 187 | 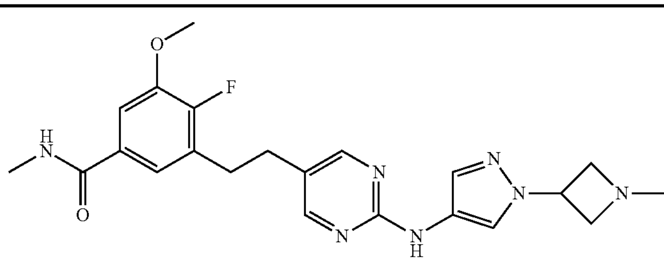 | 440.1 | 1H NMR (400 MHz, CD3OD) δ 8.13 (s, 2H), 8.03 (s, 1H), 7.58 (s, 1H), 7.39 (dd, J = 7.8 Hz, 2.0 Hz, 1H), 7.26 (dd, J = 5.9 Hz, 2.0 Hz, 1H), 4.95-4.89 (m, 1H), 3.87 (s, 3H), 3.84-3.78 (m, 2H), 3.59-3.50 (m, 2H), 2.92 (t, J = 7.3 Hz, 2H), 2.87 (s, 3H), 2.80 (t, J = 7.4 Hz, 2H), 2.43 (s, 3H). |
| 188 | 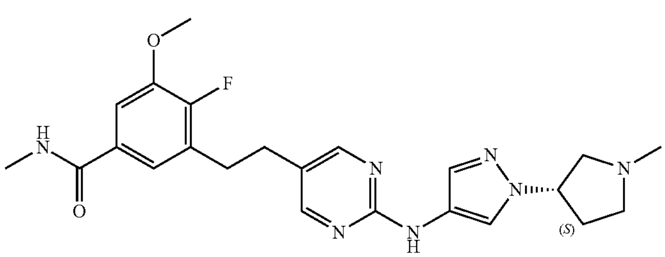 | 454.0 | 1H NMR (400 MHz, CD3OD) δ 8.14 (s, 2H), 8.01 (s, 1H), 7.55 (s, 1H), 7.41 (dd, J = 7.8 Hz, 2.1 Hz, 1H), 7.28 (dd, J = 6.0 Hz, 2.1 Hz, 1H), 4.90-4.89 (m, 1H), 3.89 (s, 3H), 3.11-3.04 (m, 1H), 2.95 (t, J = 7.4 Hz, 2H), 2.92-2.86 (m, 5H), 2.82 (t, J = 7.3 Hz, 2H), 2.77-2.71 (m, 1H), 2.52-2.45 (m, 1H), 2.44 (s, 3H), 2.27-2.16 (m, 1H). |

| Compound | Structure | LC-MS (m/z) (M + H)+ | 1H NMR |
|---|---|---|---|
| 189 | 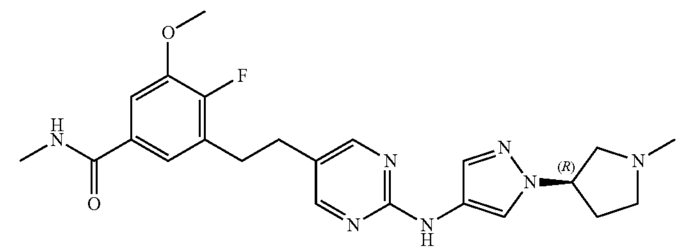 | 454.0 | 1H NMR (400 MHz, CD3OD) δ 8.14 (s, 2H), 8.01 (s, 1H), 7.54 (s, 1H), 7.41 (dd, J = 7.8 Hz, 2.2 Hz, 1H), 7.27 (dd, J = 6.0 Hz, 2.1 Hz, 1H), 4.90-4.87 (m, 1H), 3.89 (s, 3H), 3.09-3.03 (m, 1H), 2.95 (t, J = 7.4 Hz, 2H), 2.92-2.85 (m, 5H), 2.82 (t, J = 7.4 Hz, 2H), 2.76-2.69 (m, 1H), 2.52-2.44 (m, 1H), 2.43 (s, 3H), 2.25-2.15 (m, 1H). |
| 190 | 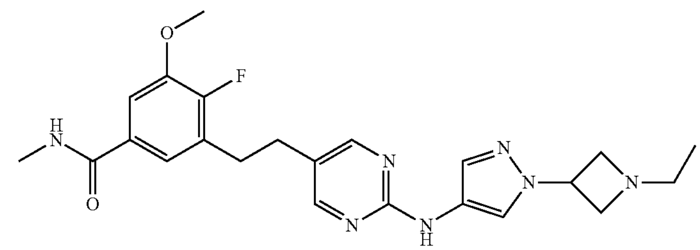 [SMILES: CCN1CC(n2cc(Nc3ncc(CCc4cc(C(=O)NC)cc(OC)c4F)cn3)cn2)C1] | 454.2 | 1H NMR (400 MHz, CD3OD) δ 8.13 (s, 2H), 8.03 (s, 1H), 7.58 (s, 1H), 7.39 (dd, J = 7.8 Hz, 2.1 Hz, 1H), 7.26 (dd, J = 5.9 Hz, 2.1 Hz, 1H), 4.98-4.90 (m, 1H), 3.86 (s, 3H), 3.82-3.75 (m, 2H), 3.52-3.45 (m, 2H), 2.92 (t, J = 7.4 Hz, 2H), 2.87 (s, 3H), 2.79 (t, J = 7.4 Hz, 2H), 2.63 (q, J = 7.2 Hz, 2H), 1.01 (t, J = 7.2 Hz, 3H). |
| 191 | 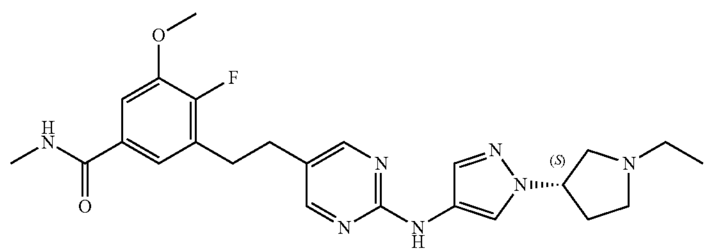 | 468.0 | 1H NMR (400 MHz, CD3OD) δ 8.15 (s, 2H), 8.04 (s, 1H), 7.57 (s, 1H), 7.42 (dd, J = 7.8 Hz, 2.1 Hz, 1H), 7.29 (dd, J = 7.8 Hz, 2.1 Hz, 1H), 5.01-4.98 (m, 1H), 3.89 (s, 3H), 3.49-3.48 (m, 2H), 3.36-3.35 (m, 2H), 3.15-3.12 (m, 2H), 2.96 (t, J = 7.2 Hz, 2H), 2.90 (s, 3H), 2.83 (t, J = 7.2 Hz, 2H), 2.54-2.45 (m, 1H), 2.31-2.19 (m, 1H), 1.23 (t, J = 7.0 Hz, 3H). |
| 192 | 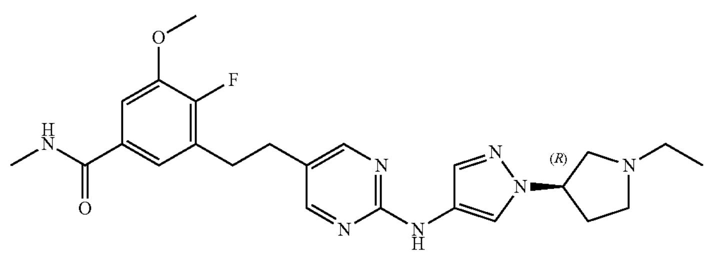 | 468.0 | 1H NMR (400 MHz, CD3OD) δ 8.15 (s, 2H), 8.06 (s, 1H), 7.60 (s, 1H), 7.42 (dd, J = 7.7 Hz, 2.1 Hz, 1H), 7.30 (dd, J = 7.7 Hz, 2.1 Hz, 1H), 5.15-5.08 (m, 1H), 3.89 (s, 3H), 3.56-3.42 (m, 2H), 3.40-3.33 (m, 2H), 3.12-3.04 (m, 2H), 2.96 (t, J = 7.3 Hz, 2H), 2.90 (s, 3H), 2.84 (d, J = 7.5 Hz, 2H), 2.64-2.54 (m, 1H), 2.36-2.27 (m, 1H), 1.30 (t, J = 7.4 Hz, 3H). |
| 193 | 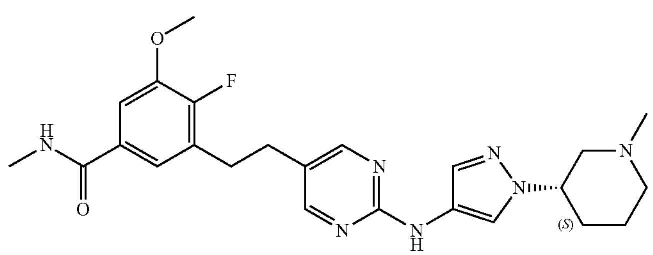 | 468.0 | 1H NMR (400 MHz, CD3OD) δ 8.13 (s, 2H), 8.02 (s, 1H), 7.57 (s, 1H), 7.40 (dd, J = 7.8 Hz, 2.1 Hz, 1H), 7.27 (dd, J = 6.0 Hz, 2.2 Hz, 1H), 4.54-4.48 (m, 1H), 3.87 (s, 3H), 3.48-3.42 (m, 1H), 3.35-3.33 (m, 2H), 3.21-3.16 (m, 1H), 2.94 (t, J = 7.4 Hz, 2H), 2.88 (s, 3H), 2.81 (t, J = 7.4 Hz, 2H), 2.74 (s, 3H), 2.16-2.06 (m, 1H), 2.04-1.92 (m, 2H), 1.87-1.75 (m, 1H). |
| 194 | 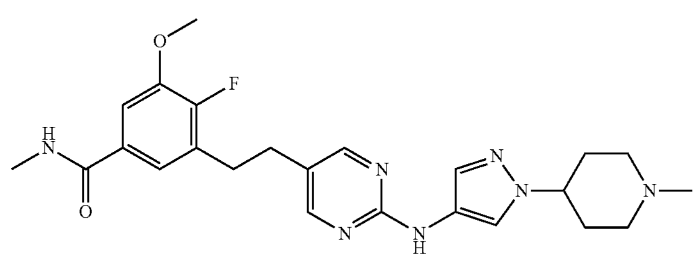 | 468.1 | 1H NMR (400 MHz, CD3OD) δ 8.12 (s, 2H), 7.93 (s, 1H), 7.52 (s, 1H), 7.39 (d, J = 6.9 Hz, 1H), 7.26 (d, J = 4.3 Hz, 1H), 4.15-4.03 (m, 1H), 3.87 (s, 3H), 3.01-2.90 (m, 4H), 2.87 (s, 3H), 2.83-2.72 (m, 2H), 2.30 (s, 3H), 2.25-2.15 (m, 2H), 2.12-1.98 (m, 4H). |

-continued

| Com-pound | Structure | LC-MS (m/z) (M + H)+ | 1H NMR |
|---|---|---|---|
| 195 | 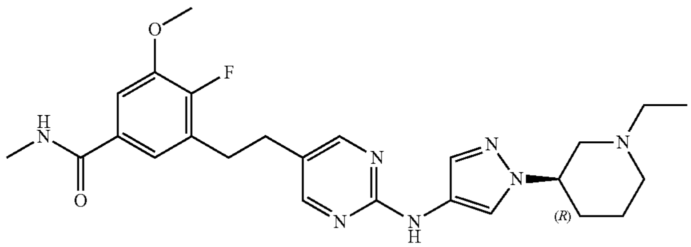 | 482.0 | 1H NMR (400 MHz, CD3OD) δ 8.13 (s, 2H), 8.02 (s, 1H), 7.56 (s, 1H), 7.40 (dd, J = 7.7 Hz, 2.1 Hz, 1H), 7.26 (dd, J = 6.0 Hz, 2.1 Hz, 1H), 4.55-4.51 (m, 1H), 3.87 (s, 3H), 3.47-3.36 (m, 2H), 3.35-3.32 (m, 2H), 3.25-3.20 (m, 1H), 3.20-3.12 (m, 1H), 2.94 (t, J = 7.4 Hz, 2H), 2.88 (s, 3H), 2.81 (t, J = 7.4 Hz, 2H), 2.21-2.08 (m, 1H), 2.07-1.93 (m, 2H), 1.89-1.80 (m, 1H), 1.33-1.21 (m, 3H). |
| 196 | 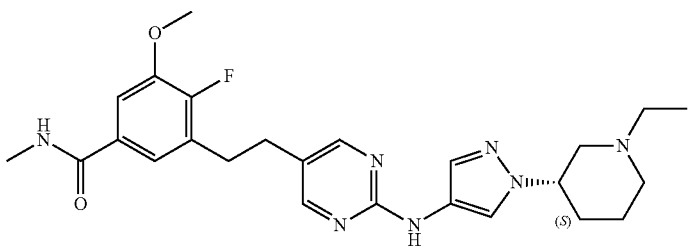 | 482.0 | 1H NMR (400 MHz, CD3OD) δ 8.13 (s, 2H), 8.03 (s, 1H), 7.57 (s, 1H), 7.40 (dd, J = 7.8 Hz, 2.1 Hz, 1H), 7.27 (dd, J = 5.9 Hz, 2.1 Hz, 1H), 4.53-4.52 (m, 1H), 3.87 (s, 3H), 3.48-3.43 (m, 1H), 3.35-3.33 (m, 2H), 3.23-3.20 (m, 1H), 3.05-2.94 (m, 4H), 2.88 (s, 3H), 2.81 (t, J = 7.4 Hz, 2H), 2.17-2.10 (m, 1H), 2.06-1.90 (m, 2H), 1.89-1.80 (m, 1H), 1.27 (t, J = 8.0 Hz, 3H). |
| 197 | 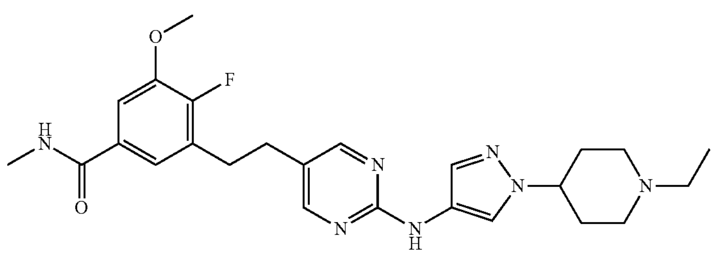 [SMILES: CCN1CCC(n2cc(Nc3ncc(CCc4cc(C(=O)NC)cc(OC)c4F)cn3)cn2)CC1] | 482.2 | 1H NMR (400 MHz, CD3OD) δ 8.12 (s, 2H), 7.93 (s, 1H), 7.52 (s, 1H), 7.39 (dd, J = 7.7 Hz, 1.7 Hz, 1H), 7.26 (dd, J = 5.8 Hz, 1.7 Hz, 1H), 4.18-4.04 (m, 1H), 3.87 (s, 3H), 3.12-3.01 (m, 2H), 2.93 (t, J = 7.2 Hz, 2H), 2.87 (s, 3H), 2.80 (t, J = 7.4 Hz, 2H), 2.47 (q, J = 7.2 Hz, 2H), 2.20-1.97 (m, 6H), 1.11 (t, J = 7.2 Hz, 3H). |
| 198 | 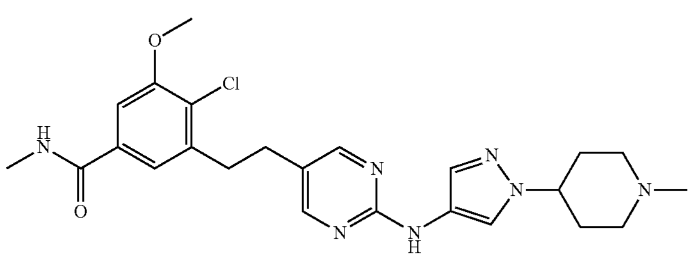 | 484.0 | 1H NMR (400 MHz, CD3OD) δ 8.14 (s, 2H), 7.95 (s, 1H), 7.53 (s, 1H), 7.36 (d, J = 2.0 Hz, 1H), 7.30 (d, J = 2.0 Hz, 1H), 4.15-4.06 (m, 1H), 3.92 (s, 3H), 3.05 (t, J = 7.6 Hz, 2H), 3.01-2.95 (m, 2H), 2.89 (s, 3H), 2.82 (t, J = 7.6 Hz, 2H), 2.31 (s, 3H), 2.26-2.17 (m, 2H), 2.11-2.01 (m, 4H). |
| 199 | 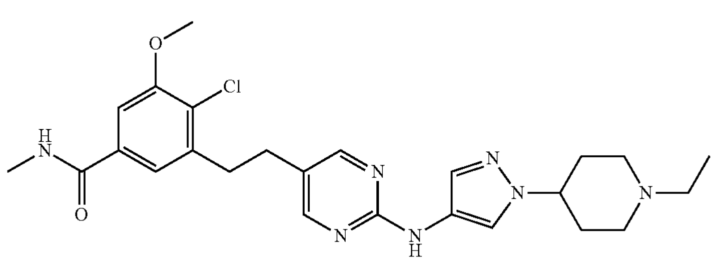 [SMILES: CCN1CCC(n2cc(Nc3ncc(CCc4cc(C(=O)NC)cc(OC)c4Cl)cn3)cn2)CC1] | 498.0 | 1H NMR (400 MHz, CD3OD) δ 8.15 (s, 2H), 8.01 (s, 1H), 7.57 (s, 1H), 7.37 (s, 1H), 7.30 (s, 1H), 4.51-4.39 (m, 1H), 3.92 (s, 3H), 3.67-3.57 (m, 2H), 3.23-3.08 (m, 4H), 3.05 (t, J = 7.5 Hz, 2H), 2.89 (s, 3H), 2.83 (t, J = 7.6 Hz, 2H), 2.37-2.26 (m, 4H), 1.35 (t, J = 7.3 Hz, 3H). |

Example 19: Synthesis of Compound 200

Compound 200
4-cyano-3-(2-(2-((1-ethyl-1H-pyrazol-4-yl)amino)pyrimidin-5-yl)ethyl)-5-methoxy-N-methylbenzamide

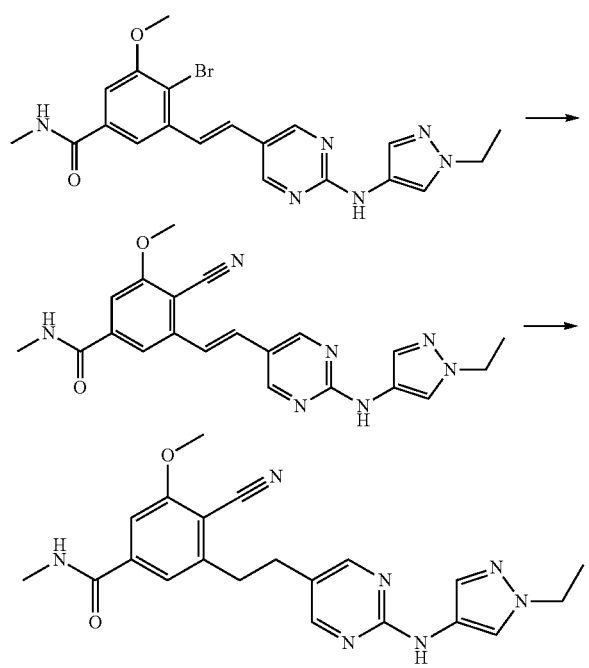

(A) (E)-4-cyano-3-(2-(2-((1-ethyl-1H-pyrazol-4-yl)amino)pyrimidin-5-yl)vinyl)-5-methoxy-N-methylbenzamide A mixture of (E)-4-bromo-3-(2-(2-((1-ethyl-1H-pyrazol-4-yl)amino)pyrimidin-5-yl) vinyl)-5-methoxy-N-methylbenzamide (0.060 g, 0.13 mmol), zinc cyanide (0.030 g, 0.26 mmol) and Pd(PPh$_3$)$_4$ (0.015 g, 0.013 mmol) in DMF (5 mL) was heated at 100° C. for 30 min under microwave. Then the mixture was purified via ISCO (eluted with MeOH in H$_2$O 0~100%) directly to afford the title compound as a white solid (0.045 g, 85.0% yield). MS (m/z): 404.1 (M+H)$^+$.

(B) 4-cyano-3-(2-(2-((1-ethyl-1H-pyrazol-4-yl)amino)pyrimidin-5-yl)ethyl)-5-methoxy-N-methylbenzamide To a solution of (E)-4-cyano-3-(2-(2-((1-ethyl-1H-pyrazol-4-yl)amino)pyrimidin-5-yl) vinyl)-5-methoxy-N-methylbenzamide (0.045 g, 0.11 mmol) in MeOH (10 mL) was added Pd/C (10%, 0.012 g) and the resulting mixture was stirred at 40° C. for 16 h under hydrogen atmosphere. The catalyst was filtered off through celite and the filtrate was concentrated. The residue was purified via PTLC (DCM/MeOH) to afford the title compound as a yellow solid (0.023 g, 50.9% yield). MS (m/z): 406.1 (M+H)$^+$. $^1$H NMR (400 MHz, CD$_3$OD) δ 8.15 (s, 2H), 7.91 (s, 1H), 7.51 (s, 1H), 7.40 (s, 1H), 7.37 (s, 1H), 4.12 (q, J=6.6 Hz, 2H), 3.97 (s, 3H), 3.08 (t, J=7.1 Hz, 2H), 2.91 (s, 3H), 2.89-2.83 (m, 2H), 1.43 (t, J=6.6 Hz, 3H).

Example 20: Synthesis of Compounds 201-205

Compound 201
3-(((2-((1-ethyl-1H-pyrazol-4-yl)amino)pyrimidin-5-yl)oxy)methyl)-4-fluoro-5-methoxy-N-methylbenzamide

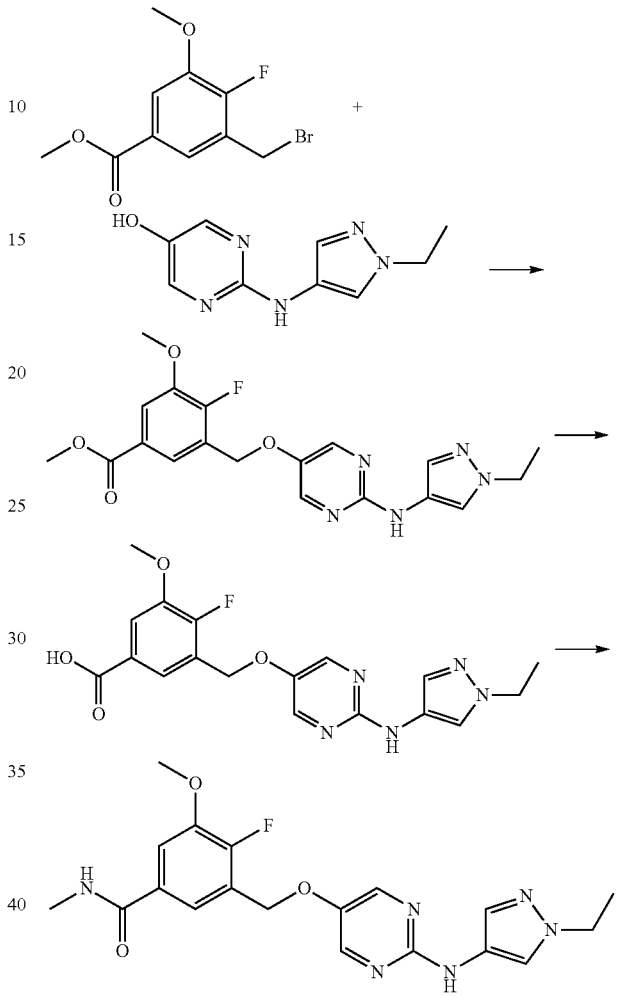

(A) Methyl 3-(((2-((1-ethyl-1H-pyrazol-4-yl)amino)pyrimidin-5-yl)oxy) methyl)-4-fluoro-5-methoxybenzoate To a solution of 2-((1-ethyl-1H-pyrazol-4-yl)amino)pyrimidin-5-ol (150 mg, 0.73 mmol) and methyl 3-(bromomethyl)-4-fluoro-5-methoxybenzoate (203 mg, 0.73 mmol) in DMF (10 mL) were added K$_2$CO$_3$ (203 mg, 1.47 mmol) and Bu$_4$NI (54 mg, 0.15 mmol). Then the mixture was stirred overnight at 60° C. After cooled to room temperature, the mixture was partitioned between EA and water and the organic layer was washed with water and brine, dried over anhydrous sodium sulfate and concentrated. The residue was purified via ISCO (eluted with EA in PE 0~100%) to afford the title compound as a yellow solid (160 mg, 54.5% of yield). MS (m/z): 402.1 (M+H)$^+$.

(B) 3-(((2-((1-ethyl-1H-pyrazol-4-yl)amino)pyrimidin-5-yl)oxy)methyl)-4-fluoro-5-methoxy-N-methylbenzamide To a solution of methyl 3-(((2-((1-ethyl-1H-pyrazol-4-yl)amino)pyrimidin-5-yl)oxy) methyl)-4-fluoro-5-methoxybenzoate (160 mg, 0.40 mmol) in MeOH (20 mL) was added aqueous NaOH solution (2 N, 5 mL, 10 mmol). Then the mixture was stirred at room temperature for overnight. The volatiles were removed under reduced pressure and the residue was adjusted to pH<2 with conc HCl and concentrated to give a brown solid which was suspended in DMF (10 mL). Then methanamine hydrochloride (32 mg, 0.48 mmol), HATU (228 mg, 0.60 mmol) and DIPEA (155 mg, 1.20 mmol) were added. The resulting mixture was stirred for 2 h at room temperature and then partitioned between EA and water. The organic layer was washed with water and brine, dried over anhydrous sodium sulfate and concentrated. The residue was purified via ISCO (eluted with MeOH in DCM 0-10%) to afford the title compound as a yellow solid (94.3 mg, 59.1% of yield). MS (m/z): 401.1 (M+H)$^+$. $^1$H NMR (400 MHz, CD$_3$OD) δ 8.22 (s, 2H), 7.92 (s, 1H), 7.58 (s, 1H), 7.56 (s, 1H), 7.51 (s, 1H), 5.16 (s, 2H), 4.12 (q, J=7.3 Hz, 2H), 3.94 (s, 3H), 2.91 (s, 3H), 1.43 (t, J=7.3 Hz, 3H).

The following compounds were prepared according to the procedures of Compound 201 using the corresponding intermediates and reagents under appropriate conditions that could be recognized by one skilled in the art.

Example 21: Synthesis of Compounds 206-303

Compound 206
4-chloro-3-(((2-((4-((3S,5R)-3,5-dimethylpiperazin-1-yl)phenyl)amino)pyrimidin-5-yl)oxy)methyl)-5-methoxy-N-methylbenzamide

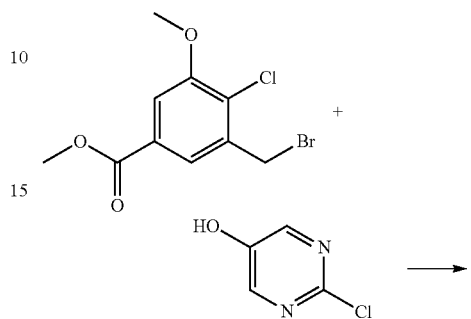

| Compound | Structure | LC-MS (m/z) (M + H)$^+$ | $^1$H NMR |
|---|---|---|---|
| 202 | 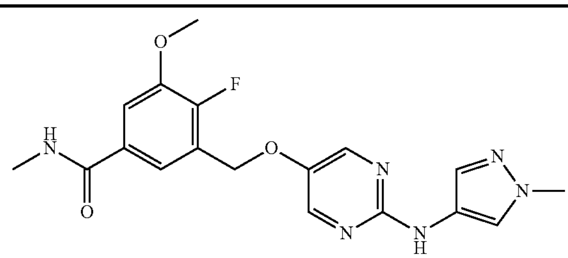 | 387.1 | $^1$H NMR (400 MHz, CD$_3$OD) δ 8.22 (s, 2H), 7.89 (s, 1H), 7.57 (s, 1H), 7.56 (s, 1H), 7.50 (s, 1H), 5.16 (s, 2H), 3.94 (s, 3H), 3.84 (s, 3H), 2.91 (s, 3H). |
| 203 | 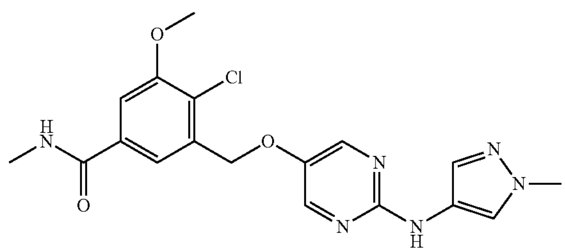 | 403.1 | $^1$H NMR (400 MHz, CD$_3$OD) δ 8.23 (s, 2H), 7.89 (s, 1H), 7.64 (d, J = 1.8 Hz, 1H), 7.51 (d, J = 1.9 Hz, 1H), 7.50 (s, 1H), 5.20 (s, 2H), 3.97 (s, 3H), 3.84 (s, 3H), 2.92 (s, 3H). |
| 204 | 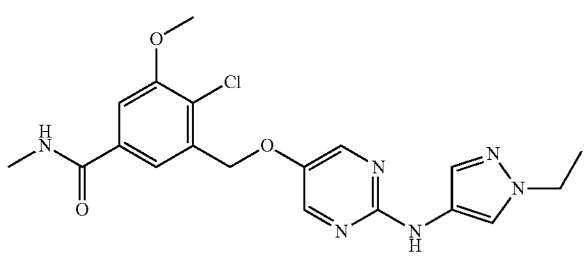 [SMILES: CCn1cc(Nc2ncc(OCc3cc(C(=O)NC)cc(OC)c3Cl)cn2)cn1] | 416.9 | $^1$H NMR (400 MHz, CD$_3$OD) δ 8.22 (s, 2H), 7.92 (s, 1H), 7.64 (s, 1H), 7.51 (s, 2H), 5.20 (s, 2H), 4.11 (q, J = 7.2 Hz, 2H), 3.96 (s, 3H), 2.91 (s, 3H), 1.42 (t, J = 7.3 Hz, 3H). |
| 205 | 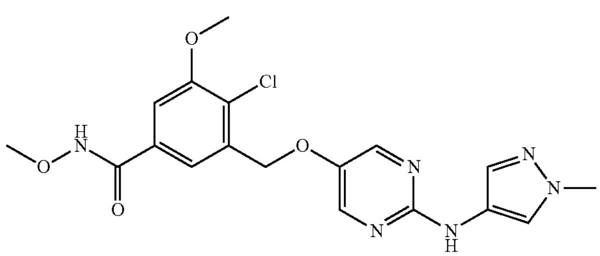 | 419.1 | $^1$H NMR (400 MHz, DMSO-d6) δ 11.99 (s, 1H), 9.27 (s, 1H), 8.37 (s, 2H), 7.90 (s, 1H), 7.67 (d, J = 1.6 Hz, 1H), 7.55 (d, J = 1.6 Hz, 1H), 7.49 (s, 1H), 5.27 (s, 2H), 4.00 (s, 3H), 3.85 (s, 3H), 3.79 (s, 3H). |

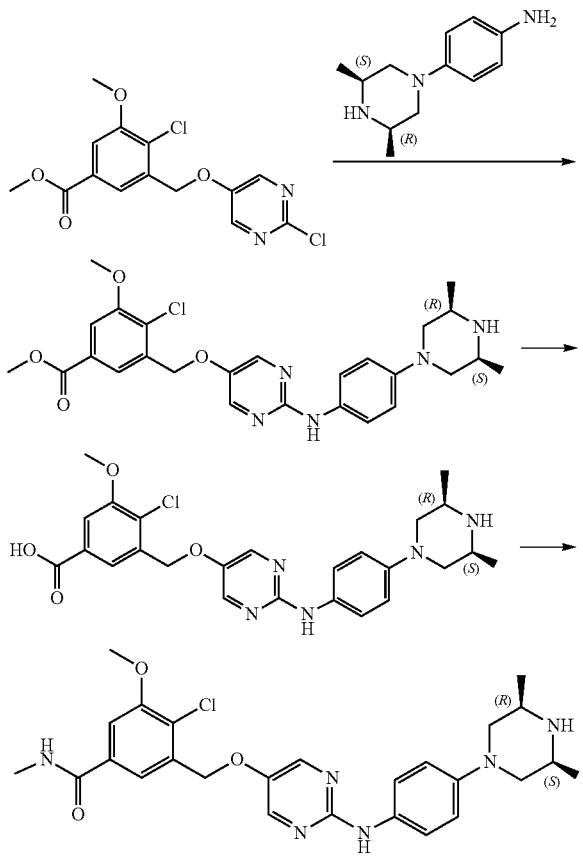

(A) Methyl 4-chloro-3-(((2-chloropyrimidin-5-yl)oxy)methyl)-5-methoxybenzoate

A mixture of 3-(bromomethyl)-4-chloro-5-methoxybenzoate (600 mg, 2.04 mmol), 2-chloropyrimidin-5-ol (320 mg, 2.45 mmol), Bu$_4$NI (151 mg, 0.408 mmol) and K$_2$CO$_3$ (564 mg, 4.08 mmol) in DMF (15 mL) was stirred at 60° C. for 2 h. The resulting mixture was partitioned between water (100 mL) and DCM (100 mL). Then the organic layer was concentrated to afford the title compound as a yellow solid (700 mg, quantative yield). MS (m/z): 343.0 (M+H)$^+$.

(B) Methyl 4-chloro-3-(((2-((4-((3S,5R)-3,5-dimethylpiperazin-1-yl) phenyl)amino)pyrimidin-5-yl)oxy)methyl)-5-methoxybenzoate A mixture of methyl 4-chloro-3-(((2-chloropyrimidin-5-yl)oxy)methyl)-5-methoxybenzoate (500 mg, 1.460 mmol), 4-((3S,5R)-3,5-dimethylpiperazin-1-yl) aniline (359 mg, 1.750 mmol), Palladium(II) acetate (33 mg, 0.146 mmol), Xantphos (169 mg, 0.292 mmol) and Cs$_2$CO$_3$ (1.43 g, 4.38 mmol) in 1,4-dioxane (10 mL) was stirred at 80° C. for overnight. The resulting mixture was concentrated and the residue was partitioned between water (50 mL) and EA (50 mL). The aqueous layer was extracted with EA (2*50 mL). The combined organic layers were concentrated and the residue was purified via ISCO (eluted with MeOH in H$_2$O 0~100%) to afford the title compound as a brown solid (480 mg, 64.3% yield). MS (m/z): 511.9 (M+H)$^+$.

(C) 4-chloro-3-(((2-((4-((3S,5R)-3,5-dimethylpiperazin-1-yl)phenyl)amino)pyrimidin-5-yl)oxy)methyl)-5-methoxybenzoic acid A mixture of methyl 4-chloro-3-(((2-((4-((3S,5R)-3,5-dimethylpiperazin-1-yl) phenyl)amino)pyrimidin-5-yl)oxy)methyl)-5-methoxybenzoate (288 mg, 0.562 mmol) and a solution of 30% sodium hydroxide (3 mL, 22.5 mmol) in MeOH (10 mL) was stirred at 50° C. for 2 h. The resulting mixture was cooled to ambient temperature, adjusted to pH=7 with 2N HCl, concentrated to afford the title compound as a white solid (280 mg, quantitative yield). MS (m/z): 497.9 (M+H)$^+$.

(D) 4-chloro-3-(((2-((4-((3S,5R)-3,5-dimethylpiperazin-1-yl)phenyl)amino)pyrimidin-5-yl)oxy)methyl)-5-methoxy-N-methylbenzamide A mixture of 4-chloro-3-(((2-((4-((3S,5R)-3,5-dimethylpiperazin-1-yl) phenyl)amino)pyrimidin-5-yl)oxy)methyl)-5-methoxybenzoic acid (280 mg, 0.562 mmol), methylamine hydrochloride (75 mg, 1.124 mmol), HATU (641 mg, 1.686 mmol) and DIPEA (217 mg, 1.686 mmol) in DMF (10 mL) was stirred at ambient temperature for 1 h. The resulting mixture was concentrated, purified via ISCO (eluted with MeOH in H$_2$O 0~100%) to afford the title compound as a yellow solid (184 mg, 64.0% yield). MS (m/z): 510.9 (M+H)$^+$. $^1$H NMR (400 MHz, CD$_3$OD) δ 8.21 (s, 2H), 7.65 (d, J=1.9 Hz, 1H), 7.52 (d, J=1.9 Hz, 1H), 7.47 (d, J=9.0 Hz, 2H), 6.94 (d, J=9.0 Hz, 2H), 5.22 (s, 2H), 3.97 (s, 3H), 3.48-3.45 (m, 2H), 3.06-2.99 (m, 2H), 2.92 (s, 3H), 2.28-2.23 (m, 2H), 1.16 (d, J=6.4 Hz, 6H).

The following compounds were prepared according to the procedures of Compound 206 using the corresponding intermediates and reagents under appropriate conditions that could be recognized by one skilled in the art.

| Compound | Structure | LC-MS (m/z) (M+H)$^+$ | $^1$H NMR |
|---|---|---|---|
| 207 | 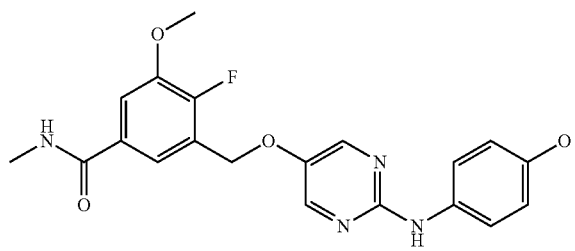 [SMILES: CNC(=O)c1cc(COc2cnc(Nc3ccc(O)cc3)nc2)c(F)c(OC)c1] | 398.9 | $^1$H NMR (400 MHz, DMSO-d6) δ 9.00 (s, 1H), 8.89 (s, 1H), 8.45 (s, 1H), 8.24 (s, 2H), 7.64-7.52 (m, 2H), 7.39 (d, J = 8.5 Hz, 2H), 6.63 (d, J = 8.6 Hz, 2H), 5.15 (s, 2H), 3.87 (s, 3H), 2.75 (d, J = 3.9 Hz, 3H). |

-continued

| Compound | Structure | LC-MS (m/z) (M+H)+ | 1H NMR |
|---|---|---|---|
| 208 | 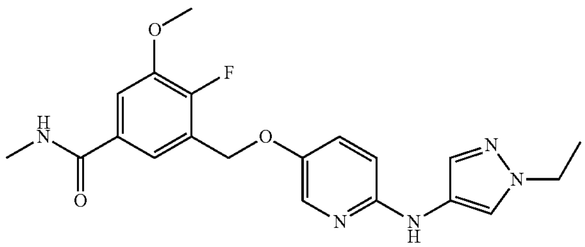 [SMILES: CCn1cc(Nc2ccc(OCc3cc(C(=O)NC)cc(OC)c3F)cn2)cn1] | 400.2 | 1H NMR (400 MHz, CD3OD) δ 7.93-7.74 (m, 2H), 7.65-7.50 (m, 2H), 7.42 (s, 1H), 7.33-7.20 (m, 1H), 6.68-6.54 (m, 1H), 5.09 (s, 2H), 4.22-4.04 (m, 2H), 3.92 (s, 3H), 2.90 (s, 3H), 1.58-1.29 (m, 3H). |
| 209 | 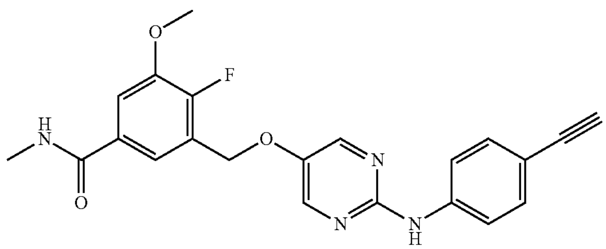 [SMILES: C#Cc1ccc(Nc2ncc(OCc3cc(C(=O)NC)cc(OC)c3F)cn2)cc1] | 406.9 | 1H NMR (400 MHz, DMSO-d6) δ 9.66 (s, 1H), 8.46 (s, 1H), 8.37 (s, 2H), 7.71 (d, J = 8.7 Hz, 2H), 7.62-7.56 (m, 2H), 7.33 (d, J = 8.6 Hz, 2H), 5.20 (s, 2H), 3.92 (s, 1H), 3.88 (s, 3H), 2.76 (d, J = 4.5 Hz, 3H). |
| 210 | 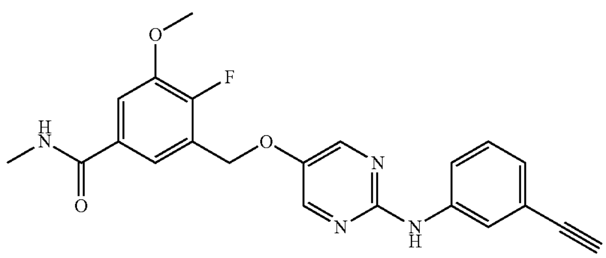 [SMILES: C#Cc1cccc(Nc2ncc(OCc3cc(C(=O)NC)cc(OC)c3F)cn2)c1] | 406.9 | 1H NMR (400 MHz, DMSO-d6) δ 9.55 (s, 1H), 8.46 (d, J = 4.1 Hz, 1H), 8.41 (s, 2H), 7.92 (s, 1H), 7.71 (d, J = 7.8 Hz, 1H), 7.63 (s, 1H), 7.61 (s, 1H), 7.25 (t, J = 7.9 Hz, 1H), 7.00 (d, J = 7.7 Hz, 1H), 5.23 (s, 2H), 4.07 (s, 1H), 3.91 (s, 3H), 2.79 (d, J = 4.5 Hz, 3H). |
| 211 | 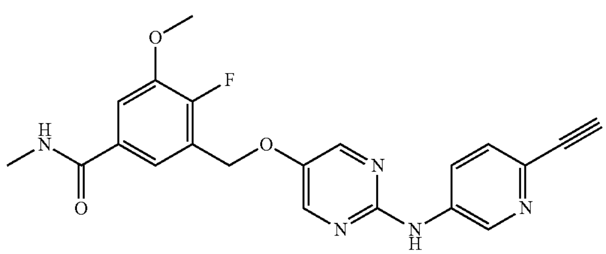 [SMILES: C#Cc1ccc(Nc2ncc(OCc3cc(C(=O)NC)cc(OC)c3F)cn2)cn1] | 408.1 | 1H NMR (400 MHz, CDCl3) δ 8.66 (s, 1H), 8.29 (d, J = 5.9 Hz, 1H), 8.23 (s, 2H), 7.51-7.44 (m, 3H), 7.38 (s, 1H), 6.28 (s, 1H), 5.15 (s, 2H), 3.94 (s, 3H), 3.13 (s, 1H), 3.00 (d, J = 4.6 Hz, 3H). |
| 212 | 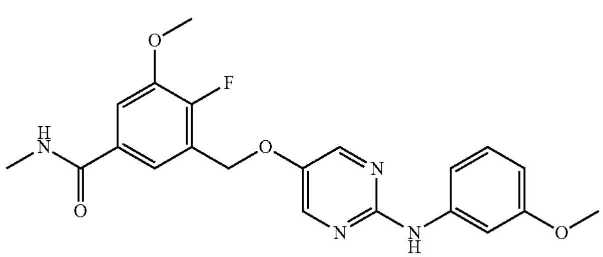 | 413.3 | 1H NMR (400 MHz, CDCl3OD) δ 8.25 (s, 1H), 7.56-7.54 (m, 2H), 7.36 (d, J = 2.4 Hz, 1H), 7.15-7.07 (m, 2H), 6.52-6.49 (m, 1H), 5.17 (s, 2H), 3.93 (s, 3H), 3.76 (s, 3H), 2.89 (s, 3H). |
| 213 | 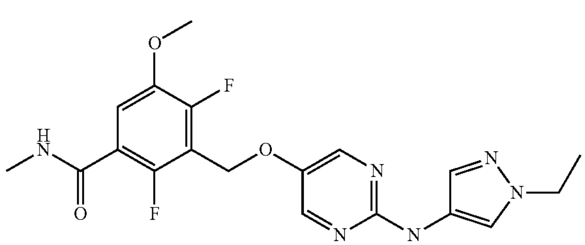 [SMILES: CCn1cc(Nc2ncc(OCc3c(F)c(OC)cc(C(=O)NC)c3F)cn2)cn1] | 419.4 | 1H NMR (400 MHz, CD3OD) δ 8.19 (s, 2H), 7.90 (s, 1H), 7.51 (s, 1H), 7.47 (dd, J = 9.4 Hz, 6.8 Hz, 1H), 5.17 (s, 2H), 4.11 (q, J = 7.3 Hz, 2H), 3.89 (s, 3H), 2.91 (s, 3H), 1.42 (t, J = 7.3 Hz, 3H). |

-continued

| Compound | Structure | LC-MS (m/z) (M + H)+ | 1H NMR |
|---|---|---|---|
| 214 | 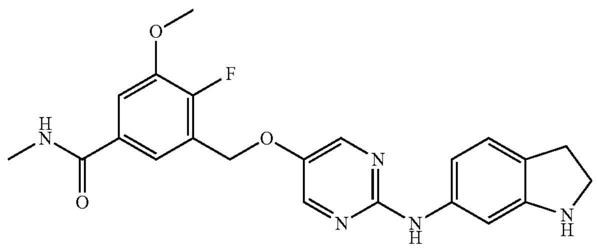 [SMILES: CNC(=O)c1cc(COc2cnc(Nc3ccc4c(c3)NCC4)nc2)c(F)c(OC)c1] | 424.1 | 1H NMR (400 MHz, CD3OD) δ 8.20 (s, 2H), 7.58-7.53 (m, 2H), 7.13-7.08 (m, 1H), 7.00-6.93 (m, 1H), 6.83 (dd, J = 7.9 Hz, 2.0 Hz, 1H), 5.17 (s, 2H), 3.93 (s, 3H), 3.46 (t, J = 8.3 Hz, 2H), 2.95-2.90 (m, 5H). |
| 215 | 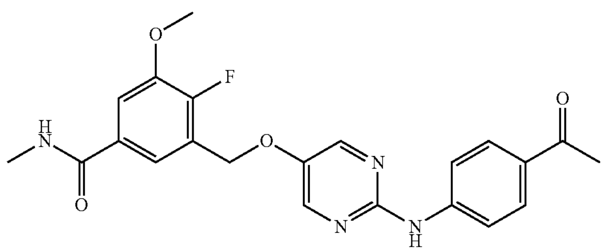 [SMILES: CNC(=O)c1cc(COc2cnc(Nc3ccc(C(C)=O)cc3)nc2)c(F)c(OC)c1] | 425.1 | 1H NMR (400 MHz, CD3OD) δ 8.34 (s, 2H), 7.92 (d, J = 8.8 Hz, 2H), 7.81 (d, J = 8.7 Hz, 2H), 7.59 (s, 1H), 7.58 (s, 1H), 5.23 (s, 2H), 3.94 (s, 3H), 2.91 (s, 3H), 2.54 (s, 3H). |
| 216 | 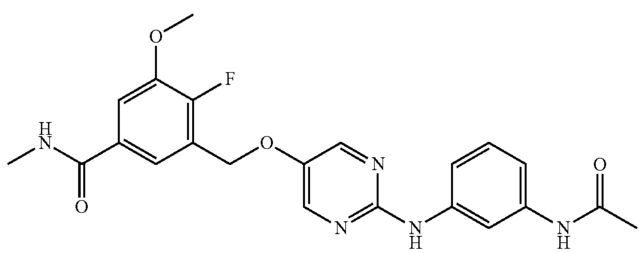 [SMILES: CNC(=O)c1cc(COc2cnc(Nc3cccc(NC(C)=O)c3)nc2)c(F)c(OC)c1] | 439.1 | 1H NMR (400 MHz, DMSO-d6) δ 9.77 (s, 1H), 9.34 (s, 1H), 8.48-8.40 (m, 1H), 8.31 (s, 2H), 7.84 (s, 1H), 7.59 (s, 1H), 7.58 (s, 1H), 7.30 (d, J = 8.0 Hz, 1H), 7.17 (d, J = 8.0 Hz, 1H), 7.10 (t, J = 8.0 Hz, 1H), 5.19 (s, 2H), 3.88 (s, 3H), 2.76 (d, J = 4.5 Hz, 3H), 1.99 (s, 3H). |
| 217 | 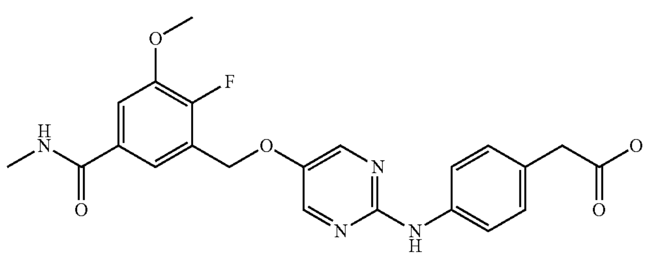 [SMILES: CNC(=O)c1cc(COc2cnc(Nc3ccc(CC(=O)O)cc3)nc2)c(F)c(OC)c1] | 441.2 | 1H NMR (400 MHz, DMSO-d6) δ 9.31 (s, 1H), 8.51-8.45 (m, 1H), 8.34 (s, 2H), 7.64-7.60 (m, 2H), 7.58 (d, J = 8.4 Hz, 2H), 7.11 (d, J = 8.4 Hz, 2H), 5.20 (s, 2H), 3.91 (s, 3H), 3.34 (s, 2H), 2.76 (d, J = 4.3 Hz, 3H). |
| 218 | 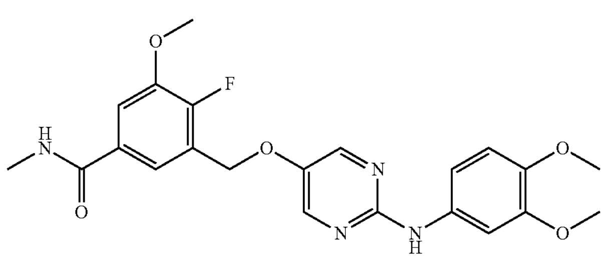 | 443.3 | 1H NMR (400 MHz, CD3OD) δ 8.20 (s, 2H), 7.56-7.54 (m, 2H), 7.32 (d, J = 2.5 Hz, 1H), 7.08 (dd, J = 8.7 Hz, 2.5 Hz, 1H), 6.85 (d, J = 8.7 Hz, 1H), 5.16 (s, 2H), 3.92 (s, 3H), 3.80 (s, 3H), 3.78 (s, 3H), 2.89 (s, 3H). |
| 219 | 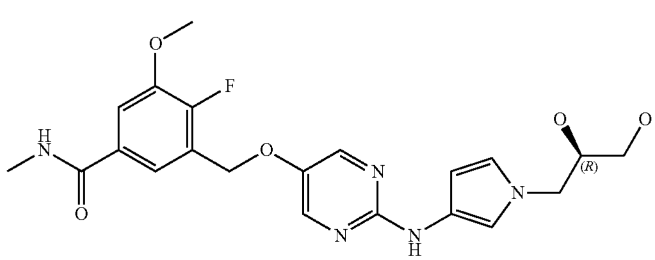 | 447.1 | 1H NMR (400 MHz, CD3OD) δ 8.22 (s, 2H), 7.96 (s, 1H), 7.58 (s, 1H), 7.57-7.56 (m, 2H), 5.18 (s, 2H), 4.27-4.23 (m, 1H), 4.10-4.06 (m, 1H), 4.01-3.96 (m, 1H), 3.95 (s, 3H), 3.52-3.50 (m, 2H), 2.92 (s, 3H). |

| Compound | Structure | LC-MS (m/z) (M + H)+ | 1H NMR |
|---|---|---|---|
| 220 | 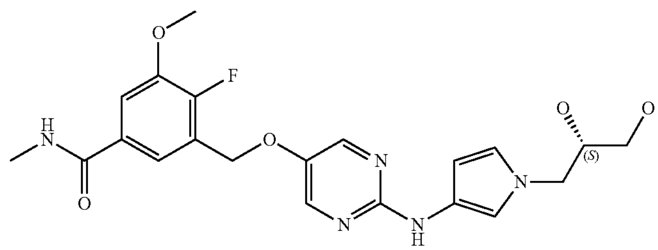 | 447.1 | 1H NMR (400 MHz, CD3OD) δ 8.19 (s, 2H), 7.93 (s, 1H), 7.56 (s, 1H), 7.54-7.53 (m, 2H), 5.15 (s, 2H), 4.24-4.21 (m, 1H), 4.06-4.04 (m, 1H), 3.96-3.94 (m, 1H), 3.92 (s, 3H), 3.49-3.47 (m, 2H), 2.89 (s, 3H). |
| 221 | 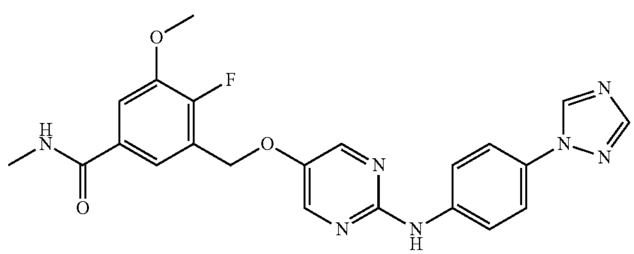 [SMILES: CNC(=O)c1cc(COc2cnc(Nc3ccc(-n4cncn4)cc3)nc2)c(F)c(OC)c1] | 449.8 | 1H NMR (400 MHz, DMSO-d6) δ 9.66 (s, 1H), 9.09 (s, 1H), 8.45 (s, 1H), 8.39 (s, 2H), 8.14 (s, 1H), 7.86 (d, J = 8.6 Hz, 2H), 7.69 (d, J = 8.5 Hz, 2H), 7.61 (d, J = 6.6 Hz, 2H), 5.21 (s, 2H), 3.89 (s, 3H), 2.77 (s, 3H). |
| 222 | 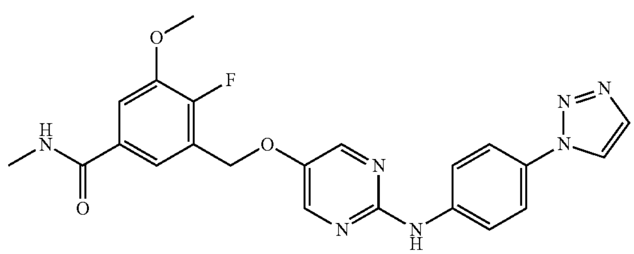 [SMILES: CNC(=O)c1cc(COc2cnc(Nc3ccc(-n4ccnn4)cc3)nc2)c(F)c(OC)c1] | 449.9 | 1H NMR (400 MHz, DMSO-d6) δ 9.72 (s, 1H), 8.64 (s, 1H), 8.44 (s, 1H), 8.40 (s, 2H), 7.92-7.90 (m, 1H), 7.90-7.87 (m, 2H), 7.76-7.70 (m, 2H), 7.60 (d, J = 7.0 Hz, 2H), 5.22 (s, 2H), 3.89 (s, 3H), 2.77 (d, J = 4.5 Hz, 3H). |
| 223 | 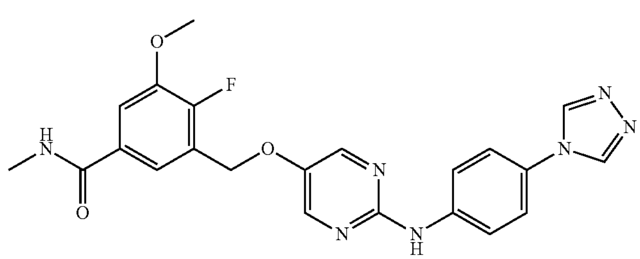 [SMILES: CNC(=O)c1cc(COc2cnc(Nc3ccc(-n4cnnc4)cc3)nc2)c(F)c(OC)c1] | 450.2 | 1H NMR (400 MHz, DMSO-d6) δ 9.69 (s, 1H), 8.98 (s, 2H), 8.47 (s, 1H), 8.41 (s, 2H), 7.91-7.84 (m, 2H), 7.63 (d, J = 6.9 Hz, 2H), 7.59-7.52 (m, 2H), 5.24 (s, 2H), 3.91 (s, 3H), 2.79 (d, J = 4.5 Hz, 3H). |
| 224 | 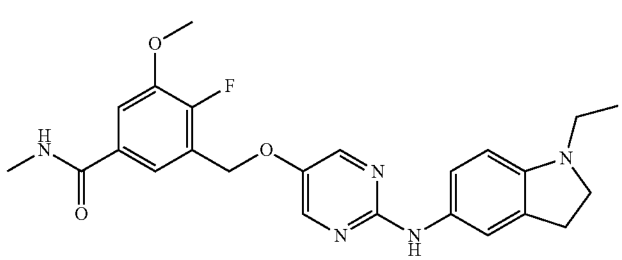 [SMILES: CCN1CCc2cc(Nc3ncc(OCc4cc(C(=O)NC)cc(OC)c4F)cn3)ccc21] | 452.1 | 1H NMR (400 MHz, CD3OD) δ 8.15 (s, 2H), 7.56 (d, J = 6.9 Hz, 2H), 7.28 (s, 1H), 7.18-7.10 (m, 1H), 6.54-6.46 (m, 1H), 5.15 (s, 2H), 3.93 (s, 3H), 3.28-3.19 (m, 2H), 3.15-3.04 (m, 2H), 2.93-2.87 (m, 5H), 1.18 (t, J = 7.2 Hz, 3H). |

| Compound | Structure | LC-MS (m/z) (M+H)+ | 1H NMR |
|---|---|---|---|
| 225 | 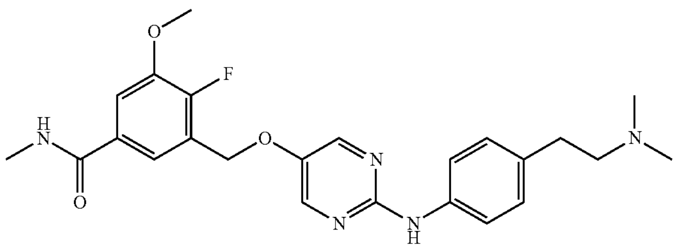 | 454.2 | 1H NMR (400 MHz, CD3OD) δ 8.29 (s, 2H), 7.64-7.60 (m, 2H), 7.60-7.58 (m, 2H), 7.19-7.17 (m, 2H), 5.24 (s, 2H), 4.00 (s, 3H), 2.98 (s, 3H), 2.83-2.81 (m, 2H), 2.64-2.60 (m, 2H), 2.37 (s, 6H). |
| 226 | 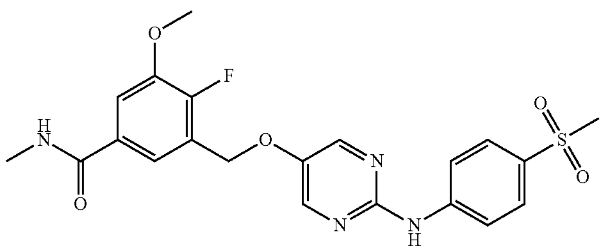 | 461.2 | 1H NMR (400 MHz, CDCl3) δ 8.28 (s, 2H), 7.87 (d, J = 8.9 Hz, 2H), 7.79 (d, J = 9.0 Hz, 2H), 7.50 (dd, J = 8.0 Hz, 2.0 Hz, 1H), 7.38 (dd, J = 5.5 Hz, 2.0 Hz, 1H), 7.32 (s, 1H), 6.16-6.03 (m, 1H), 5.18 (s, 2H), 3.96 (s, 3H), 3.04 (s, 3H), 3.02 (d, J = 4.9 Hz, 3H). |
| 227 | 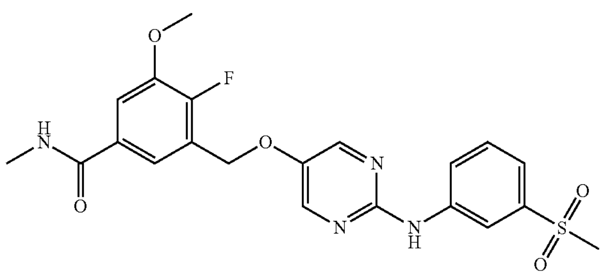 | 461.2 | 1H NMR (400 MHz, DMSO-d6) δ 9.86 (s, 1H), 8.46 (d, J = 4.0 Hz, 1H), 8.44 (s, 2H), 8.40 (t, J = 1.8 Hz, 1H), 8.04-7.93 (m, 1H), 7.64 (s, 1H), 7.62 (s, 1H), 7.53 (t, J = 8.0 Hz, 1H), 7.48-7.40 (m, 1H), 5.25 (s, 2H), 3.91 (s, 3H), 3.17 (s, 3H), 2.79 (d, J = 4.4 Hz, 3H). |
| 228 | 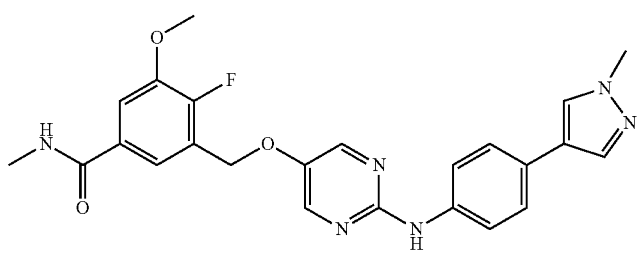 [SMILES: CNC(=O)c1cc(COc2cnc(Nc3ccc(-c4cnn(C)c4)cc3)nc2)c(F)c(OC)c1] | 463.2 | 1H NMR (400 MHz, DMSO-d6) δ 9.37 (s, 1H), 8.44 (d, J = 4.2 Hz, 1H), 8.34 (s, 2H), 7.96 (s, 1H), 7.72 (s, 1H), 7.66 (d, J = 8.7 Hz, 2H), 7.60 (d, J = 6.9 Hz, 2H), 7.40 (d, J = 8.7 Hz, 2H), 5.19 (s, 2H), 3.88 (s, 3H), 3.82 (s, 3H), 2.77 (d, J = 4.5 Hz, 3H). |
| 230 | 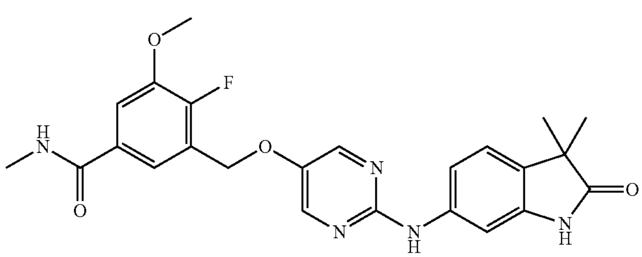 [SMILES: CNC(=O)c1cc(COc2cnc(Nc3ccc4c(c3)NC(=O)C4(C)C)nc2)c(F)c(OC)c1] | 466.1 | 1H NMR (400 MHz, DMSO-d6) δ 10.16 (s, 1H), 9.34 (s, 1H), 8.42 (br, 1H), 8.31 (s, 2H), 7.59 (d, J = 6.9 Hz, 2H), 7.39 (d, J = 1.9 Hz, 1H), 7.16 (dd, J = 8.1 Hz, 1.9 Hz, 1H), 7.06 (d, J = 8.1 Hz, 1H), 5.19 (s, 2H), 3.87 (s, 3H), 2.76 (d, J = 4.5 Hz, 3H), 1.18 (s, 6H). |
| 231 | 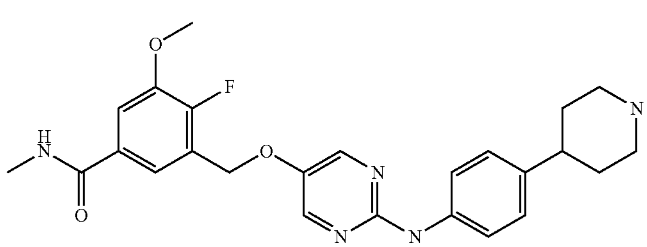 [SMILES: CNC(=O)c1cc(COc2cnc(Nc3ccc(C4CCNCC4)cc3)nc2)c(F)c(OC)c1] | 466.1 | 1H NMR (400 MHz, CD3OD) δ 8.13 (s, 2H), 7.51-7.45 (m, 2H), 7.45-7.38 (m, 2H), 7.07-7.02 (m, 2H), 5.08 (s, 2H), 3.84 (s, 3H), 3.08-3.02 (m, 2H), 2.82 (s, 3H), 2.68-2.61 (m, 2H), 2.57-2.48 (m, 1H), 1.75-1.69 (m, 2H), 1.61-1.50 (m, 2H). |

-continued

| Compound | Structure | LC-MS (m/z) (M+H)+ | 1H NMR |
|---|---|---|---|
| 232 | 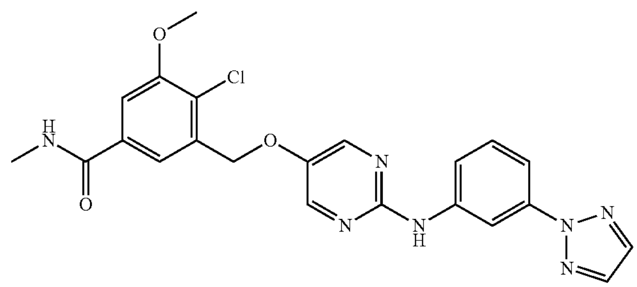 [SMILES: CNC(=O)c1cc(COc2cnc(Nc3cccc(-n4nccn4)c3)nc2)c(Cl)c(OC)c1] | 465.8 | 1H NMR (400 MHz, DMSO-d6) δ 9.74 (s, 1H), 8.60-8.58 (m, 1H), 8.52 (d, J = 4.3 Hz, 1H), 8.42 (s, 2H), 8.06 (s, 2H), 7.68-7.65 (m, 2H), 7.55 (d, J = 1.8 Hz, 1H), 7.53-7.51 (m, 1H), 7.41-7.37 (m, 1H), 5.24 (s, 2H), 3.92 (s, 3H), 2.77 (d, J = 4.5 Hz, 3H). |
| 233 | 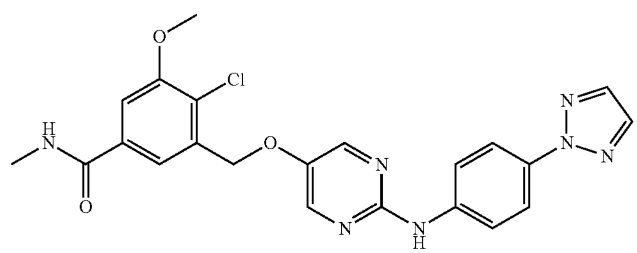 [SMILES: CNC(=O)c1cc(COc2cnc(Nc3ccc(-n4nccn4)cc3)nc2)c(Cl)c(OC)c1] | 466.1 | 1H NMR (400 MHz, DMSO-d6) δ 9.70 (s, 1H), 8.52 (d, J = 4.1 Hz, 1H), 8.39 (s, 2H), 8.00 (s, 2H), 7.88-7.86 (m, 4H), 7.66 (s, 1H), 7.55 (s, 1H), 5.24 (s, 2H), 3.92 (s, 3H), 2.77 (d, J = 4.4 Hz, 3H). |
| 234 | 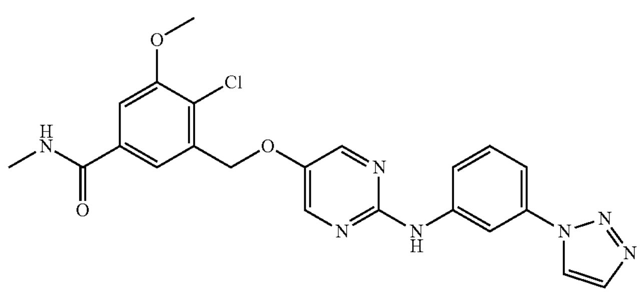 [SMILES: CNC(=O)c1cc(COc2cnc(Nc3cccc(-n4ccnn4)c3)nc2)c(Cl)c(OC)c1] | 466.1 | 1H NMR (400 MHz, DMSO-d6) δ 9.75 (s, 1H), 8.67 (s, 1H), 8.52 (d, J = 4.5 Hz, 1H), 8.42-8.38 (m, 3H), 7.92 (s, 1H), 7.74-7.70 (m, 1H), 7.65 (d, J = 1.9 Hz, 1H), 7.54 (d, J = 1.8 Hz, 1H), 7.43 (t, J = 8.1 Hz, 1H), 7.35-7.29 (m, 1H), 5.23 (s, 2H), 3.91 (s, 3H), 2.77 (d, J = 4.5 Hz, 3H). |
| 235 | 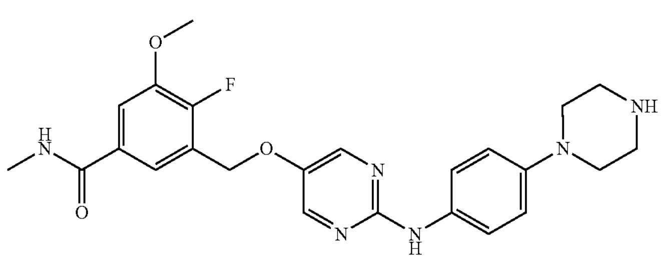 [SMILES: CNC(=O)c1cc(COc2cnc(Nc3ccc(N4CCNCC4)cc3)nc2)c(F)c(OC)c1] | 466.9 | 1H NMR (400 MHz, CD3OD) δ 8.19 (s, 2H), 7.58-7.54 (m, 2H), 7.46 (d, J = 8.2 Hz, 2H), 6.93 (d, J = 8.3 Hz, 2H), 5.16 (s, 2H), 3.93 (s, 3H), 3.09-3.03 (m, 4H), 3.01-2.94 (m, 4H), 2.90 (s, 3H). |
| 236 | 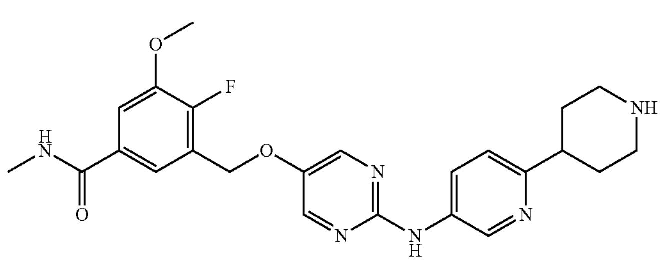 [SMILES: CNC(=O)c1cc(COc2cnc(Nc3ccc(C4CCNCC4)nc3)nc2)c(F)c(OC)c1] | 467.2 | 1H NMR (400 MHz, CD3OD) δ 8.74-8.70 (m, 1H), 8.28 (s, 2H), 8.16-8.11 (m, 1H), 7.59-7.55 (m, 2H), 7.22 (d, J = 8.7 Hz, 1H), 5.20 (s, 2H), 3.94 (s, 3H), 3.19-3.11 (m, 2H), 2.91 (s, 3H), 2.84-2.69 (m, 3H), 1.92-1.85 (m, 2H), 1.76-1.64 (m, 2H). |

| Compound | Structure | LC-MS (m/z) (M + H)+ | 1H NMR |
|---|---|---|---|
| 237 | 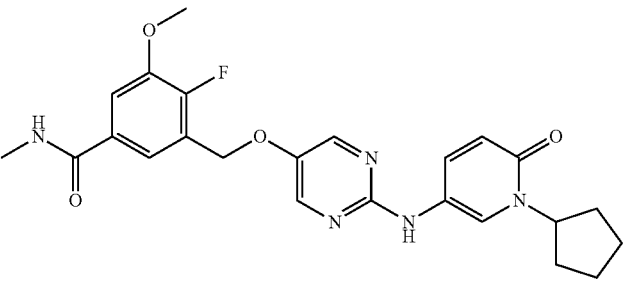 [SMILES: CNC(=O)c1cc(COc2cnc(Nc3ccc(=O)n(C4CCCC4)c3)nc2)c(F)c(OC)c1] | 468.2 | 1H NMR (400 MHz, DMSO-d6) δ 8.94 (s, 1H), 8.49-8.41 (m, 1H), 8.27 (s, 2H), 8.06 (d, J = 2.5 Hz, 1H), 7.61-7.56 (m, 2H), 7.50 (dd, J = 9.6 Hz, 2.7 Hz, 1H), 6.33 (d, J = 9.6 Hz, 1H), 5.16 (s, 2H), 5.10 (m, 1H), 3.87 (s, 3H), 2.76 (d, J = 4.4 Hz, 3H), 2.07-1.93 (m, 2H), 1.87-1.74 (m, 2H), 1.67-1.56 (m, 4H). |
| 238 | 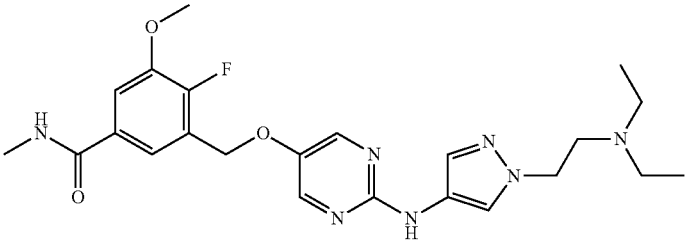 [SMILES: CCN(CC)CCn1cc(Nc2ncc(OCc3cc(C(=O)NC)cc(OC)c3F)cn2)cn1] | 472.0 | 1H NMR (400 MHz, CD3OD) δ 8.22 (s, 2H), 7.96 (s, 1H), 7.57-7.55 (m, 2H), 7.53 (s, 1H), 5.16 (s, 2H), 4.17 (t, J = 7.0 Hz, 2H), 3.94 (s, 3H), 2.94-2.86 (m, 5H), 2.57 (q, J = 7.2 Hz, 4H), 1.03 (t, J = 7.2 Hz, 6H). |
| 239 | 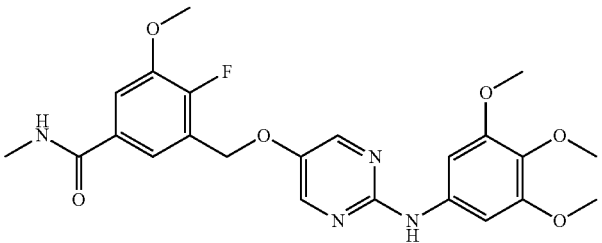 | 473.2 | 1H NMR (400 MHz, CD3OD) δ 8.25 (s, 2H), 7.59-7.52 (m, 2H), 7.04 (s, 2H), 5.18 (s, 2H), 3.93 (s, 3H), 3.81 (s, 6H), 3.70 (s, 3H), 2.90 (s, 3H). |
| 240 | 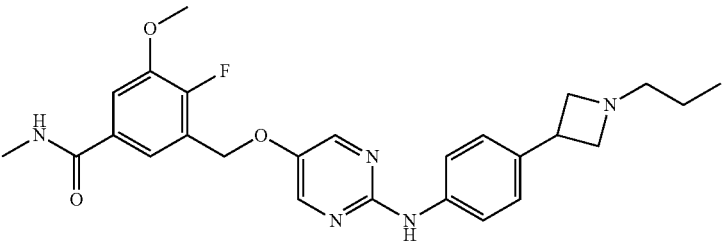 [SMILES: CCCN1CC(c2ccc(Nc3ncc(OCc4cc(C(=O)NC)cc(OC)c4F)cn3)cc2)C1] | 480.1 | 1H NMR (400 MHz, DMSO-d6) δ 7.91 (s, 2H), 7.67 (dd, J = 8.4 Hz, 1.9 Hz, 1H), 7.60 (dd, J = 6.3 Hz, 1.9 Hz, 1H), 7.36 (d, J = 8.5 Hz, 2H), 6.97 (d, J = 8.5 Hz, 2H), 4.97 (s, 2H), 3.85 (s, 3H), 3.55 (t, J = 7.3 Hz, 2H), 3.45-3.20 (m, 1H), 2.92 (t, J = 7.2 Hz, 2H), 2.72 (s, 3H), 2.35 (t, J = 7.2 Hz, 2H), 1.40-1.20 (m, 2H), 0.87 (t, J = 7.4 Hz, 3H). |
| 241 | 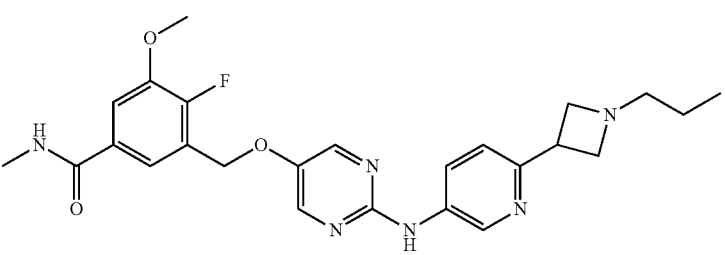 [SMILES: CCCN1CC(c2ccc(Nc3ncc(OCc4cc(C(=O)NC)cc(OC)c4F)cn3)cn2)C1] | 481.1 | 1H NMR (400 MHz, CD3OD) δ 8.76 (d, J = 2.6 Hz, 1H), 8.29 (s, 2H), 8.16 (dd, J = 8.6 Hz, 2.6 Hz, 1H), 7.58-7.55 (m, 2H), 7.27 (d, J = 8.6 Hz, 1H), 5.20 (s, 2H), 3.94 (s, 3H), 3.84 (s, 1H), 3.78-3.75 (m, 1H), 3.75-3.71 (m, 1H), 3.34-3.31 (m, 2H), 2.91 (s, 3H), 2.50 (t, J = 7.6 Hz, 2H), 1.45-1.38 (m, 2H), 0.92 (t, J = 7.5 Hz, 3H). |

| Compound | Structure | LC-MS (m/z) (M + H)+ | 1H NMR |
|---|---|---|---|
| 242 | 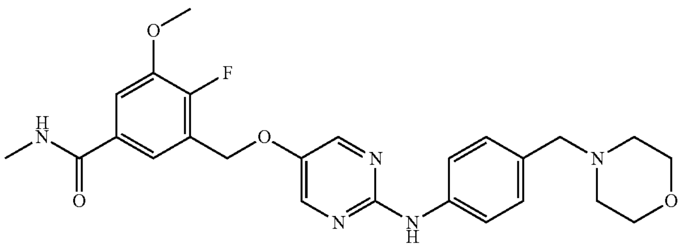 [SMILES: CNC(=O)c1cc(COc2cnc(Nc3ccc(CN4CCOCC4)cc3)nc2)c(F)c(OC)c1] | 481.9 | 1H NMR (400 MHz, DMSO-d6) δ 9.33 (s, 1H), 8.44 (d, J = 4.6 Hz, 1H), 8.32 (s, 2H), 7.62-7.57 (m, 4H), 7.15 (s, 1H), 7.13 (s, 1H), 5.18 (s, 2H), 3.88 (s, 3H), 3.55-3.50 (m, 4H), 3.35 (s, 2H), 2.76 (d, J = 4.5 Hz, 3H), 2.31-2.28 (m, 4H). |
| 243 | 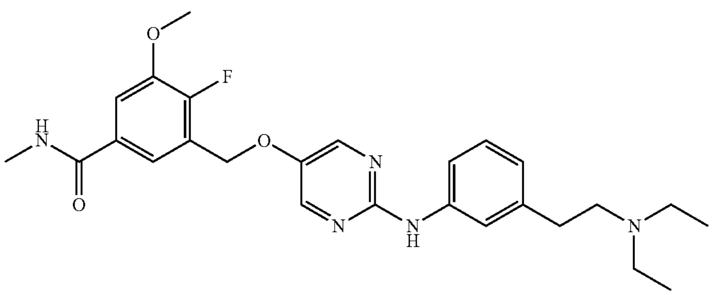 [SMILES: CCN(CC)CCc1cccc(Nc2ncc(OCc3cc(C(=O)NC)cc(OC)c3F)cn2)c1] | 482.3 | 1H NMR (400 MHz, CDCl3) δ 8.19 (s, 2H), 7.49 (dd, J = 7.9 Hz, 2.0 Hz, 1H), 7.41 (d, J = 6.7 Hz, 2H), 7.35 (dd, J = 5.5 Hz, 2.0 Hz, 1H), 7.21 (dd, J = 8.7 Hz, 7.6 Hz, 1H), 6.99 (s, 1H), 6.84 (d, J = 7.6 Hz, 1H), 6.23-6.12 (m, 1H), 5.12 (s, 2H), 3.93 (s, 3H), 2.99 (d, J = 4.8 Hz, 3H), 2.76-2.62 (m, 8H), 1.10 (t, J = 7.2 Hz, 6H). |
| 244 | 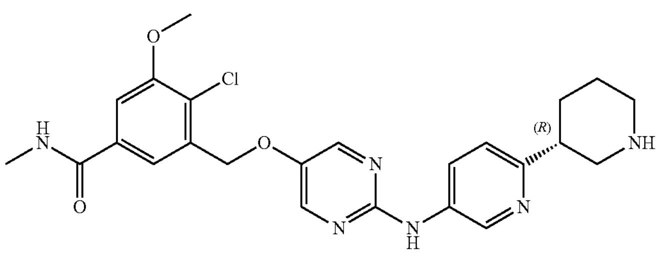 | 482.8 | 1H NMR (400 MHz, CD3OD) δ 8.71 (d, J = 2.6 Hz, 1H), 8.29 (s, 2H), 8.12 (dd, J = 8.6 Hz, 2.7 Hz, 1H), 7.64 (d, J = 2.0 Hz, 1H), 7.51 (d, J = 2.0 Hz, 1H), 7.20 (d, J = 8.6 Hz, 1H), 5.24 (s, 2H), 3.96 (s, 3H), 3.16-3.11 (m, 1H), 3.07-3.01 (m, 1H), 2.91 (s, 3H), 2.85-2.81 (m, 1H), 2.80-2.71 (m, 1H), 2.66-2.60 (m, 1H), 2.02-1.99 (m, 1H), 1.83-1.59 (m, 3H). |
| 245 | 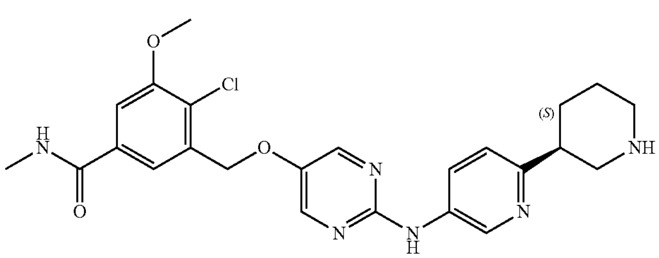 | 482.8 | 1H NMR (400 MHz, CD3OD) δ 8.69 (d, J = 2.6 Hz, 1H), 8.27 (s, 2H), 8.10 (dd, J = 8.4 Hz, 2.6 Hz, 1H), 7.62 (d, J = 1.9 Hz, 1H), 7.50 (d, J = 1.9 Hz, 1H), 7.19 (d, J = 8.4 Hz, 1H), 5.23 (s, 2H), 3.95 (s, 3H), 3.11-3.09 (m, 1H), 3.02-2.99 (m, 1H), 2.89 (s, 3H), 2.81-2.76 (m, 1H), 2.72-2.66 (m, 1H), 2.61-2.56 (m, 1H), 2.02-1.97 (m, 2H), 1.78-1.71 (m, 1H), 1.62-1.55 (m, 1H). |
| 246 | 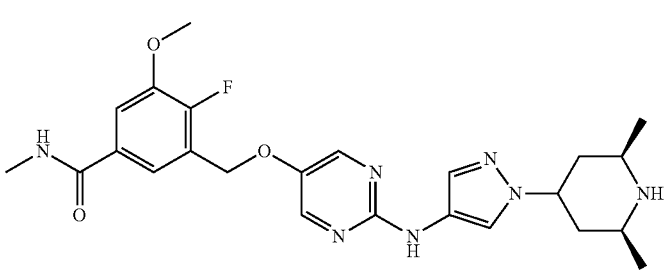 | 483.9 | 1H NMR (400 MHz, CD3OD) δ 8.20 (s, 2H), 8.00 (s, 1H), 7.57-7.53 (m, 3H), 5.16 (s, 2H), 3.93 (s, 3H), 3.91-3.85 (m, 1H), 3.64-3.56 (m, 1H), 3.39-3.36 (m, 1H), 2.90 (s, 3H), 2.32-2.22 (m, 2H), 2.21-2.09 (m, 2H), 1.48 (d, J = 7.2 Hz, 3H), 1.34 (d, J = 6.8 Hz, 3H). |

| Compound | Structure | LC-MS (m/z) (M+H)+ | 1H NMR |
|---|---|---|---|
| 247 | 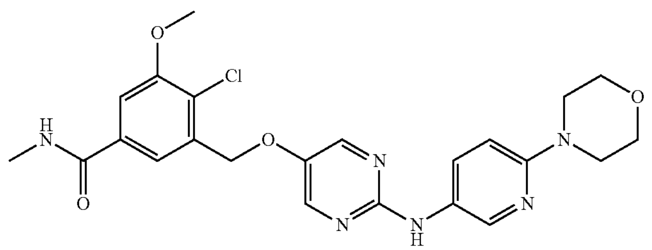 [SMILES: CNC(=O)c1cc(COc2cnc(Nc3ccc(N4CCOCC4)nc3)nc2)c(Cl)c(OC)c1] | 484.8 | 1H NMR (400 MHz, DMSO-d6) δ 9.14 (s, 1H), 8.56-8.53 (m, 1H), 8.41 (d, J = 2.7 Hz, 1H), 8.31 (s, 2H), 7.87 (dd, J = 9.1 Hz, 2.8 Hz, 1H), 7.68 (d, J = 1.9 Hz, 1H), 7.58 (d, J = 1.9 Hz, 1H), 6.80 (d, J = 9.1 Hz, 1H), 5.21 (s, 2H), 3.94 (s, 3H), 3.72-3.68 (m, 4H), 3.40-3.21 (m, 4H), 2.80 (d, J = 4.6 Hz, 3H). |
| 248 | 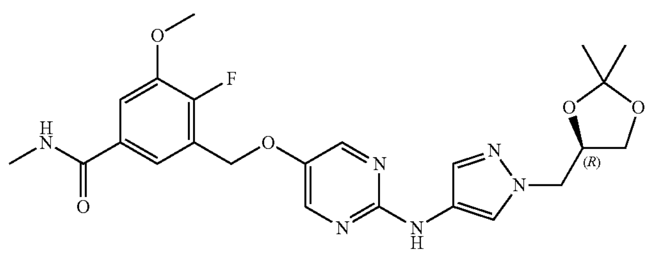 | 487.2 | 1H NMR (400 MHz, CD3OD) δ 8.28 (s, 2H), 8.04 (s, 1H), 7.64 (s, 1H), 7.62 (s, 1H), 7.61 (s, 1H), 5.23 (s, 2H), 4.50-4.47 (m, 1H), 4.28 (t, J = 5.2 Hz, 2H), 4.13-4.08 (m, 1H), 4.00 (s, 3H), 3.83-3.75 (m, 1H), 2.97 (s, 3H), 1.42 (s, 3H), 1.37 (s, 3H). |
| 249 | 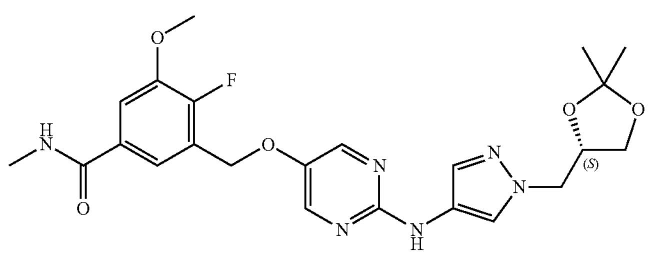 | 487.2 | 1H NMR (400 MHz, CD3OD) δ 8.21 (s, 2H), 7.97 (s, 1H), 7.56 (s, 1H), 7.54 (s, 1H), 7.53 (s, 1H), 5.15 (s, 2H), 4.44-4.37 (m, 1H), 4.20 (t, J = 5.3 Hz, 2H), 4.05-4.01 (m, 1H), 3.92 (s, 3H), 3.73-3.69 (m, 1H), 2.89 (s, 3H), 1.34 (s, 3H), 1.30 (s, 3H). |
| 250 | 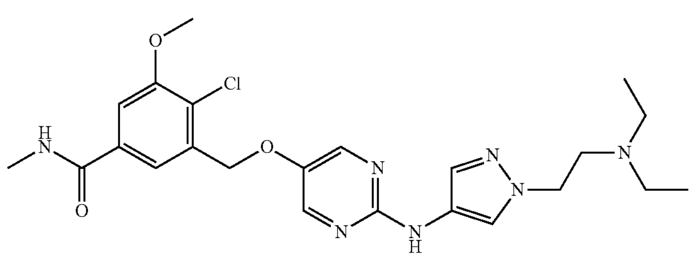 [SMILES: CCN(CC)CCn1cc(Nc2ncc(OCc3cc(C(=O)NC)cc(OC)c3Cl)cn2)cn1] | 487.9 | 1H NMR (400 MHz, CD3OD) δ 8.22 (s, 2H), 7.96 (s, 1H), 7.63 (s, 1H), 7.53 (s, 1H), 7.50 (s, 1H), 5.19 (s, 2H), 4.17 (t, J = 7.0 Hz, 2H), 3.94 (s, 3H), 2.93-2.84 (m, 5H), 2.57 (q, J = 7.2 Hz, 4H), 1.03 (t, J = 7.2 Hz, 6H). |
| 251 | 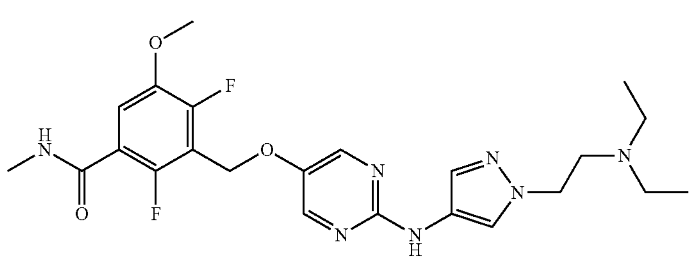 [SMILES: CCN(CC)CCn1cc(Nc2ncc(OCc3c(F)c(OC)cc(C(=O)NC)c3F)cn2)cn1] | 490.3 | 1H NMR (400 MHz, CD3OD) δ 8.19 (s, 2H), 7.95 (d, J = 0.6 Hz, 1H), 7.53 (d, J = 0.6 Hz, 1H), 7.47 (dd, J = 9.4 Hz, 6.8 Hz, 1H), 5.17 (s, 2H), 4.21-4.15 (m, 2H), 3.89 (s, 3H), 2.94-2.88 (m, 2H), 2.91 (s, 3H), 2.59 (q, J = 7.2 Hz, 4H), 1.03 (t, J = 7.2 Hz, 6H). |
| 252 | 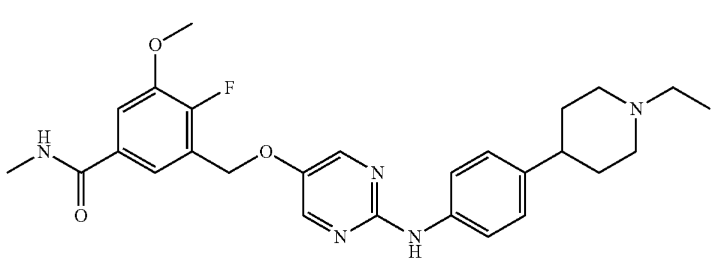 [SMILES: CCN1CCC(c2ccc(Nc3ncc(OCc4cc(C(=O)NC)cc(OC)c4F)cn3)cc2)CC1] | 494.1 | 1H NMR (400 MHz, CDCl3) δ 8.18 (s, 2H), 7.52-7.45 (m, 3H), 7.35 (dd, J = 5.4 Hz, 1.8 Hz, 1H), 7.22-7.15 (m, 2H), 5.12 (s, 2H), 3.94 (s, 3H), 3.11-3.03 (m, 2H), 2.99 (s, 3H), 2.51-2.41 (m, 3H), 2.04-1.98 (m, 2H), 1.84-1.75 (m, 4H), 1.12 (t, J = 7.2 Hz, 3H). |

-continued

| Compound | Structure | LC-MS (m/z) (M + H)+ | 1H NMR |
|---|---|---|---|
| 253 | 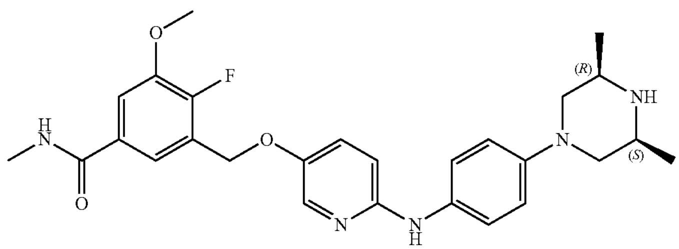 | 494.3 | 1H NMR (400 MHz, CD3OD) δ 7.81 (d, J = 2.9 Hz, 1H), 7.61-7.51 (m, 2H), 7.38-7.20 (m, 3H), 6.93 (d, J = 8.7 Hz, 2H), 6.73 (d, J = 9.0 Hz, 1H), 5.11 (s, 2H), 3.93 (s, 3H), 3.47-3.39 (m, 2H), 3.05-2.96 (m, 2H), 2.90 (s, 3H), 2.23 (t, J = 11.0 Hz, 2H), 1.13 (d, J = 6.4 Hz, 6H). |
| 254 | 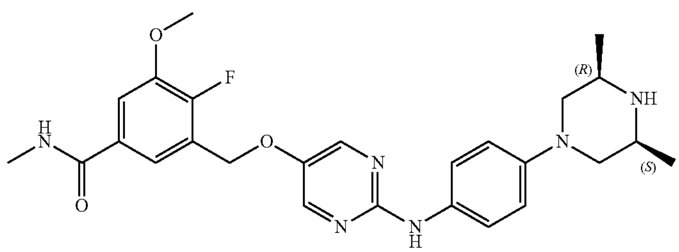 | 494.9 | 1H NMR (400 MHz, CD3OD) δ 8.20 (s, 2H), 7.59-7.55 (m, 2H), 7.47 (d, J = 8.9 Hz, 2H), 6.94 (d, J = 8.9 Hz, 2H), 5.17 (s, 2H), 3.94 (s, 3H), 3.44-3.42 (m, 2H), 3.00-2.98 (m, 2H), 2.91 (s, 3H), 2.26-2.20 (m, 2H), 1.14 (d, J = 6.4 Hz, 6H). |
| 255 | 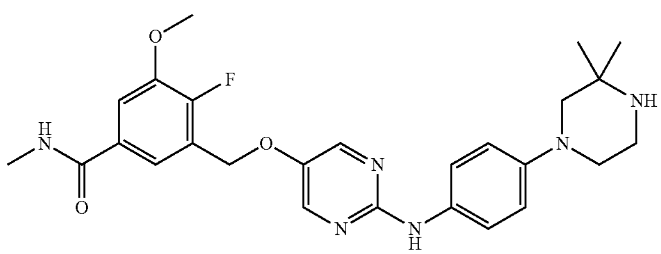 [SMILES: CNC(=O)c1cc(COc2cnc(Nc3ccc(N4CCNC(C)(C)C4)cc3)nc2)c(F)c(OC)c1] | 495.0 | 1H NMR (400 MHz, CD3OD) δ 8.18 (s, 2H), 7.58-7.54 (m, 2H), 7.43 (d, J = 8.1 Hz, 2H), 6.88 (d, J = 8.3 Hz, 2H), 5.16 (s, 2H), 3.93 (s, 3H), 3.01-2.97 (m, 4H), 2.90 (s, 3H), 2.82-2.81 (m, 2H), 1.22 (s, 6H). |
| 256 | 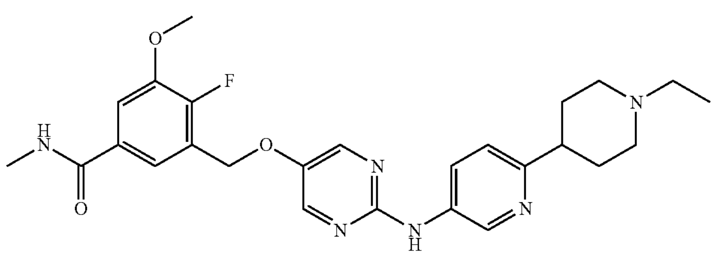 [SMILES: CCN1CCC(c2ccc(Nc3ncc(OCc4cc(C(=O)NC)cc(OC)c4F)cn3)cn2)CC1] | 495.2 | 1H NMR (400 MHz, CD3OD) δ 8.72 (d, J = 2.6 Hz, 1H), 8.28 (s, 2H), 8.14 (dd, J = 8.6 Hz, 2.6 Hz, 1H), 7.60-7.54 (m, 2H), 7.23 (d, J = 8.6 Hz, 1H), 5.20 (s, 2H), 3.94 (s, 3H), 3.14-3.06 (m, 2H), 2.91 (s, 3H), 2.73-2.64 (m, 1H), 2.48 (q, J = 7.2 H, 2H), 2.15-2.08 (m, 2H), 1.97-1.91 (m, 2H), 1.86-1.76 (m, 2H), 1.13 (t, J = 7.2 Hz, 3H). |
| 257 | 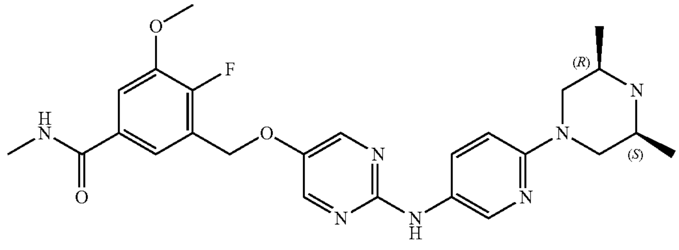 | 495.9 | 1H NMR (400 MHz, CD3OD) δ 8.24 (d, J = 2.6 Hz, 1H), 8.12 (s, 2H), 7.76 (dd, J = 9.1 Hz, 2.7 Hz, 1H), 7.51-7.46 (m, 2H), 6.72 (d, J = 9.0 Hz, 1H), 5.09 (s, 2H), 3.92 (dd, J = 12.5 Hz, 2.4 Hz, 2H), 3.85 (s, 3H), 2.86-2.78 (m, 2H), 2.83 (s, 3H), 2.31-2.20 (m, 2H), 1.06 (d, J = 6.4 Hz, 6H). |

-continued

| Compound | Structure | LC-MS (m/z) (M + H)+ | 1H NMR |
|---|---|---|---|
| 258 | 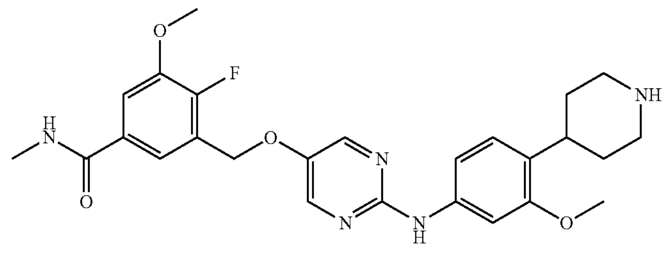 [SMILES: CNC(=O)c1cc(COc2cnc(Nc3ccc(C4CCNCC4)c(OC)c3)nc2)c(F)c(OC)c1] | 496.2 | 1H NMR (400 MHz, CDCl3) δ 8.18 (s, 2H), 7.48 (d, J = 7.4 Hz, 1H), 7.34 (d, J = 4.6 Hz, 1H), 7.10-7.06 (m, 1H), 7.01-6.99 (m, 1H), 6.95 (s, 1H), 6.13 (s, 1H), 5.13 (s, 2H), 3.93 (s, 3H), 3.84 (s, 3H), 3.75-3.73 (m, 2H), 3.17-3.14 (m, 1H), 3.01-2.98 (m, 4H), 2.78-2.72 (m, 1H), 2.25 (s, 1H), 1.84-1.81 (m, 2H), 1.79-1.69 (m, 2H). |
| 259 | 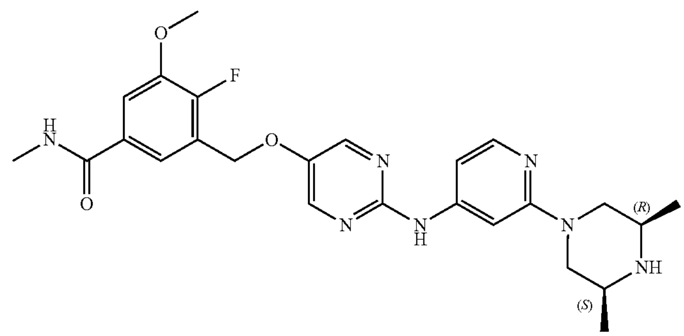 | 496.3 | 1H NMR (400 MHz, CD3OD) δ 8.33 (s, 2H), 7.85 (d, J = 5.9 Hz, 1H), 7.58-7.54 (m, 2H), 7.24 (d, J = 1.3 Hz, 1H), 7.00 (dd, J = 5.9 Hz, 1.8 Hz, 1H), 5.21 (s, 2H), 4.05-3.97 (m, 2H), 3.93 (s, 3H), 2.92-2.84 (m, 5H), 2.43-2.33 (m, 2H), 1.14 (d, J = 6.4 Hz, 6H). |
| 260 | 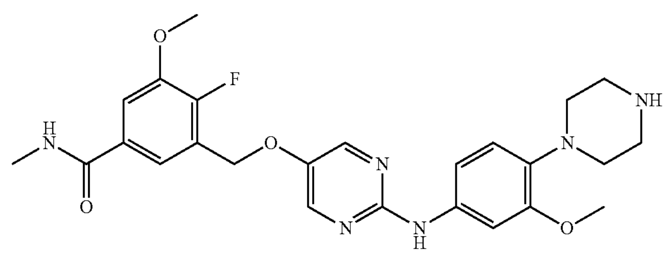 [SMILES: CNC(=O)c1cc(COc2cnc(Nc3ccc(N4CCNCC4)c(OC)c3)nc2)c(F)c(OC)c1] | 497.2 | 1H NMR (400 MHz, CD3OD) δ 8.22 (s, 2H), 7.62-7.49 (m, 2H), 7.37 (d, J = 2.4 Hz, 1H), 7.11 (dd, J = 8.6 Hz, 2.4 Hz, 1H), 6.88 (d, J = 8.6 Hz, 1H), 5.16 (s, 2H), 3.92 (s, 3H), 3.85 (s, 3H), 3.00-2.92 (m, 8H), 2.89 (s, 3H). |
| 261 | 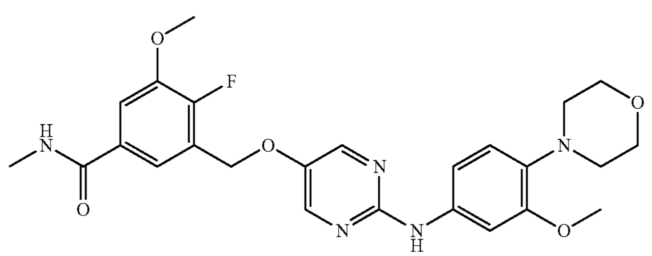 [SMILES: CNC(=O)c1cc(COc2cnc(Nc3ccc(N4CCOCC4)c(OC)c3)nc2)c(F)c(OC)c1] | 498.2 | 1H NMR (400 MHz, CD3OD) δ 8.22 (s, 2H), 7.58-7.51 (m, 2H), 7.37 (d, J = 2.2 Hz, 1H), 7.11 (dd, J = 8.6 Hz, 2.2 Hz, 1H), 6.88 (d, J = 8.6 Hz, 1H), 5.17 (s, 2H), 3.92 (s, 3H), 3.85 (s, 3H), 3.82-3.78 (m, 4H), 2.99-2.95 (m, 4H), 2.89 (s, 3H). |
| 262 | 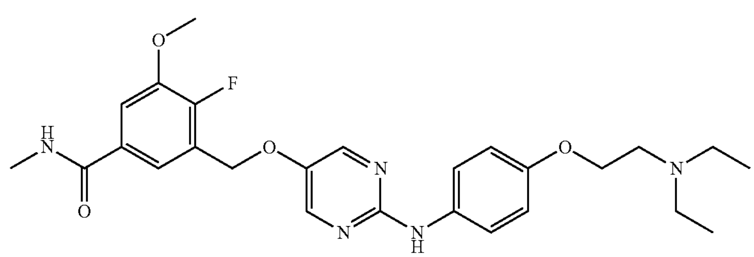 [SMILES: CCN(CC)CCOc1ccc(Nc2ncc(OCc3cc(C(=O)NC)cc(OC)c3F)cn2)cc1] | 498.2 | 1H NMR (400 MHz, CD3OD) δ 8.13 (s, 2H), 7.51 (s, 1H), 7.49 (s, 1H), 7.39 (d, J = 8.8 Hz, 2H), 6.80 (d, J = 8.8 Hz, 2H), 5.10 (s, 2H), 4.00 (t, J = 5.7 Hz, 2H), 3.87 (s, 3H), 2.84 (s, 3H), 2.81 (t, J = 5.8 Hz, 2H), 2.60 (q, J = 7.1 Hz, 4H), 1.02 (t, J = 7.2 Hz, 6H). |

| Compound | Structure | LC-MS (m/z) (M + H)+ | 1H NMR |
|---|---|---|---|
| 263 | 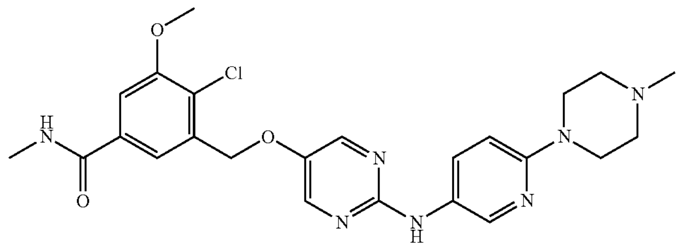 | 497.8 | 1H NMR (400 MHz, DMSO-d6) δ 9.09 (s, 1H), 8.54 (s, 1H), 8.37 (d, J = 2.8 Hz, 1H), 8.30 (s, 2H), 7.83 (dd, J = 9.1 Hz, 2.8 Hz, 1H), 7.67 (d, J = 1.9 Hz, 1H), 7.57 (d, J = 1.8 Hz, 1H), 6.78 (d, J = 9.2 Hz, 1H), 5.21 (s, 2H), 3.94 (s, 3H), 3.39-3.36 (m, 4H), 2.80 (d, J = 4.5 Hz, 3H), 2.42-2.37 (m, 4H), 2.21 (s, 3H). |
| 264 | 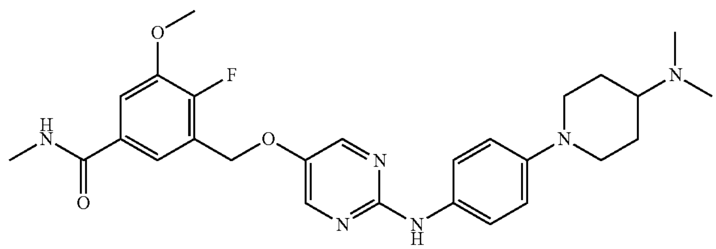 | 509.2 | 1H NMR (400 MHz, CD3OD) δ 8.18 (s, 2H), 7.56-7.54 (m, 2H), 7.45-7.43 (m, 2H), 6.95-6.92 (m, 2H), 5.15 (s, 2H), 3.92 (s, 3H), 3.64-3.60 (m, 2H), 2.90 (s, 3H), 2.67-2.61 (m, 2H), 2.32-228 (m, 7H), 1.97-1.94 (m, 2H), 1.64-1.62 (m, 2H). |
| 265 | 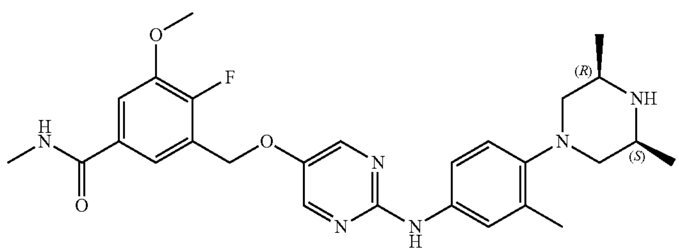 | 509.3 | 1H NMR (400 MHz, CD3OD) δ 8.20 (s, 2H), 7.56 (s, 1H), 7.55-7.53 (m, 1H), 7.44 (dd, J = 8.6 Hz, 2.5 Hz, 1H), 7.41 (d, J = 1.7 Hz, 1H), 6.99 (d, J = 8.6 Hz, 1H), 5.16 (s, 2H), 3.92 (s, 3H), 3.51-3.41 (m, 2H), 3.17-3.10 (m, 2H), 2.89 (s, 3H), 2.63 (t, J = 11.8 Hz, 2H), 2.27 (s, 3H), 1.31 (d, J = 6.8 Hz, 6H). |
| 266 | 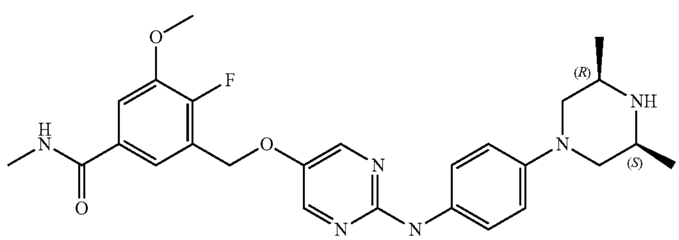 | 509.3 | 1H NMR (400 MHz, CD3OD) δ 8.18 (s, 2H), 7.59-7.53 (m, 2H), 7.45 (d, J = 9.0 Hz, 2H), 6.91 (d, J = 9.0 Hz, 2H), 5.14 (s, 2H), 3.92 (s, 3H), 3.46 (dd, J = 12.1 Hz, 2.3 Hz, 2H), 3.39 (q, J = 7.3 Hz, 2H), 3.04-2.94 (m, 2H), 2.22 (t, J = 11.1 Hz, 2H), 1.20 (t, J = 7.3 Hz, 3H), 1.13 (d, J = 6.4 Hz, 6H). |
| 267 | 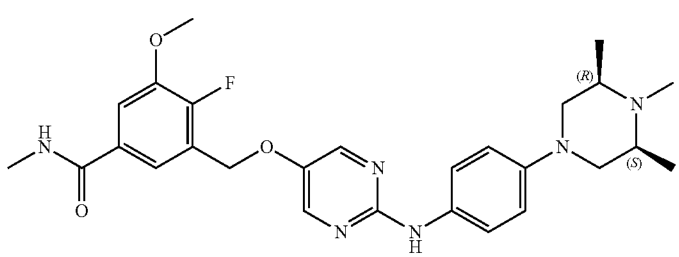 | 509.3 | 1H NMR (400 MHz, CD3OD) δ 8.18 (s, 2H), 7.56 (s, 1H), 7.54 (s, 1H), 7.49-7.40 (m, 2H), 6.94-6.87 (m, 2H), 5.15 (s, 2H), 3.92 (s, 3H), 3.41 (d, J = 10.5 Hz, 2H), 2.90 (s, 3H), 2.51-2.37 (m, 4H), 2.32 (s, 3H), 1.17 (d, J = 5.8 Hz, 6H). |
| 268 | 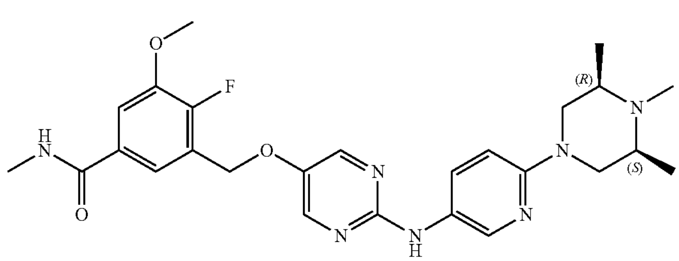 | 510.1 | 1H NMR (400 MHz, CD3OD) δ 8.53-8.32 (m, 2H), 8.21 (s, 2H), 7.92 (dd, J = 8.7 Hz, 2.1 Hz, 1H), 7.62-7.47 (m, 2H), 6.88 (d, J = 8.7 Hz, 1H), 5.17 (s, 2H), 4.28-4.18 (m, 2H), 3.93 (s, 3H), 3.14 (m, 2H), 2.94-2.83 (m, 5H), 2.76 (s, 3H), 1.39 (d, J = 6.3 Hz, 6H). |

| Compound | Structure | LC-MS (m/z) (M + H)+ | 1H NMR |
|---|---|---|---|
| 269 | 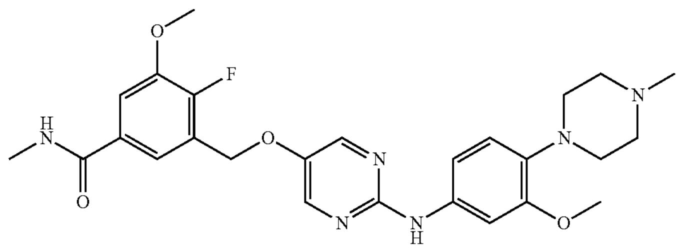 | 511.2 | 1H NMR (400 MHz, CD3OD) δ 8.22 (s, 2H), 7.56 (s, 1H), 7.54 (s, 1H), 7.37 (d, J = 2.2 Hz, 1H), 7.11 (dd, J = 8.6 Hz, 1.4 Hz, 1H), 6.88 (d, J = 8.6 Hz, 1H), 5.16 (s, 2H), 3.92 (s, 3H), 3.84 (s, 3H), 3.02-3.00 (m, 4H), 2.90 (s, Hz, 3H), 2.62-2.60 (m, 4H), 2.32 (s, 3H). |
| 270 | 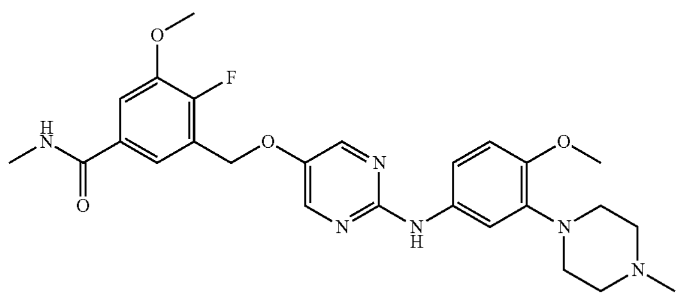 | 511.3 | 1H NMR (400 MHz, CD3OD) δ 8.17 (s, 2H), 7.58-7.49 (m, 2H), 7.27-7.18 (m, 2H), 6.87-6.79 (m, 1H), 5.13 (s, 2H), 3.91 (s, 3H), 3.80 (s, 3H), 3.15-2.96 (m, 4H), 2.89 (s, 3H), 2.68-2.51 (m, 4H), 2.32 (s, 3H). |
| 271 | 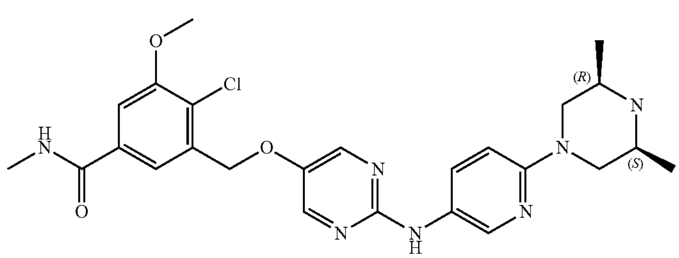 | 511.9 | 1H NMR (400 MHz, CD3OD) δ 8.32 (d, J = 2.7 Hz, 1H), 8.20 (s, 2H), 7.84 (dd, J = 9.0 Hz, 2.8 Hz, 1H), 7.63 (d, J = 1.9 Hz, 1H), 7.50 (d, J = 1.8 Hz, 1H), 6.80 (d, J = 9.1 Hz, 1H), 5.20 (s, 2H), 4.01 (dd, J = 12.7 Hz, 2.4 Hz, 2H), 3.95 (s, 3H), 2.96-2.91 (m, 2H), 2.90 (s, 3H), 2.40-2.32 (m, 2H), 1.15 (d, J = 6.4 Hz, 6H). |
| 272 | 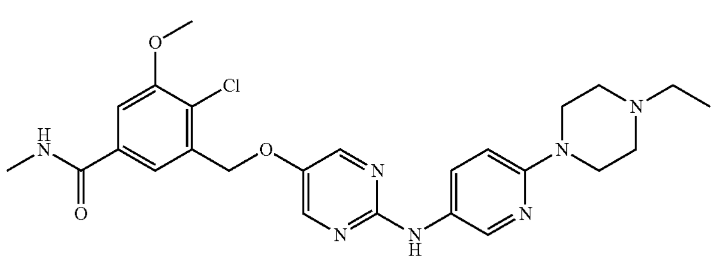 [SMILES: CCN1CCN(c2ccc(Nc3ncc(OCc4cc(C(=O)NC)cc(OC)c4Cl)cn3)cn2)CC1] | 511.9 | 1H NMR (400 MHz, CD3OD) δ 8.33 (d, J = 2.4 Hz, 1H), 8.21 (s, 2H), 7.85 (dd, J = 9.1 Hz, 2.8 Hz, 1H), 7.63 (d, J = 2.0 Hz, 1H), 7.50 (d, J = 2.0 Hz, 1H), 6.81 (d, J = 9.1 Hz, 1H), 5.21 (s, 2H), 3.96 (s, 3H), 3.48-3.43 (m, 4H), 2.91 (s, 3H), 2.65-2.50 (m, 4H), 2.48 (q, J = 7.2 Hz, 2H), 1.13 (t, J = 7.2 Hz, 3H). |
| 273 | 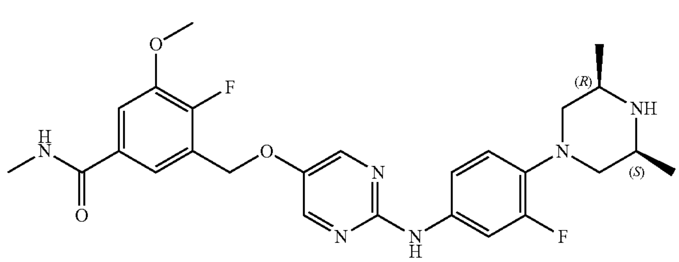 | 513.3 | 1H NMR (400 MHz, CD3OD) δ 8.25 (s, 2H), 7.70-7.65 (m, 1H), 7.58-7.53 (m, 2H), 7.26 (dd, J = 8.6 Hz, 1.4 Hz, 1H), 7.00 (t, J = 9.1 Hz, 1H), 5.18 (s, 2H), 3.93 (s, 3H), 3.58-3.51 (m, 2H), 3.46 (dd, J = 12.6 Hz, 1.4 Hz, 2H), 2.90 (s, 3H), 2.73 (t, J = 11.9 Hz, 2H), 1.35 (d, J = 6.8 Hz, 6H). |

-continued
| Compound | Structure | LC-MS (m/z) (M + H)+ | 1H NMR |
|---|---|---|---|
| 274 | 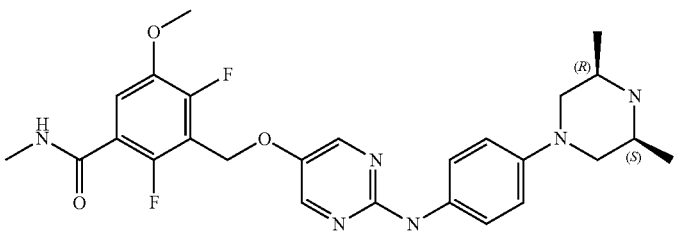 | 513.3 | 1H NMR (400 MHz, CD3OD) δ 8.17 (s, 2H), 7.53-7.47 (m, 1H), 7.45 (d, J = 8.9 Hz, 2H), 6.92 (d, J = 8.8 Hz, 2H), 5.17 (s, 2H), 3.89 (s, 3H), 3.49-3.41 (m, 2H), 3.06-2.96 (m, 2H), 2.91 (s, 3H), 2.24 (t, J = 11.1 Hz, 2H), 1.14 (d, J = 6.4 Hz, 6H). |
| 275 | 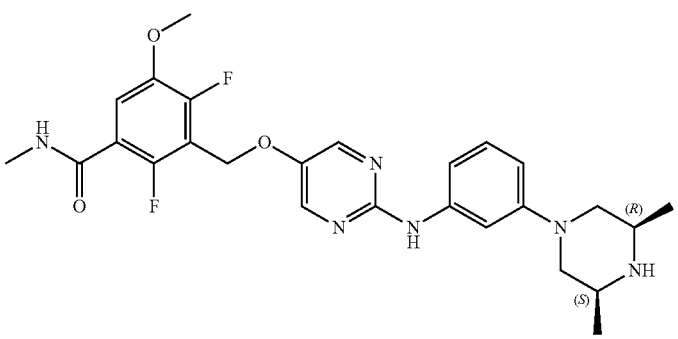 | 513.3 | 1H NMR (400 MHz, CD3OD) δ 8.23 (s, 2H), 7.48 (dd, J = 9.4 Hz, 6.9 Hz, 1H), 7.34-7.29 (m, 1H), 7.17-7.09 (m, 2H), 6.64-6.57 (m, 1H), 5.20 (s, 2H), 3.90 (s, 3H), 3.64-3.55 (m, 2H), 3.16-3.07 (m, 2H), 2.92 (s, 3H), 2.43-2.34 (m, 2H), 1.20 (d, J = 6.5 Hz, 6H). |
| 276 | 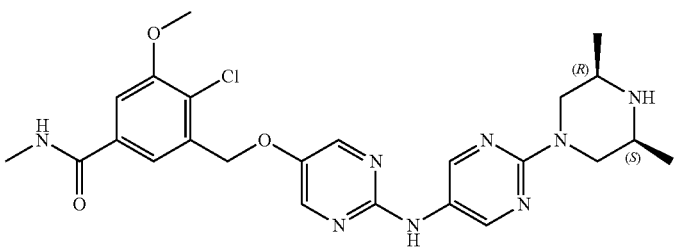 | 513.4 | 1H NMR (400 MHz, CD3OD) δ 8.55 (s, 2H), 8.20 (s, 2H), 7.62 (d, J = 2.0 Hz, 1H), 7.50 (d, J = 2.0 Hz, 1H), 5.20 (s, 2H), 4.54-4.49 (m, 2H), 3.95 (s, 3H), 2.91 (s, 3H), 2.85-2.76 (m, 2H), 2.47-2.39 (m, 2H), 1.12 (d, J = 6.4 Hz, 6H). |
| 277 | 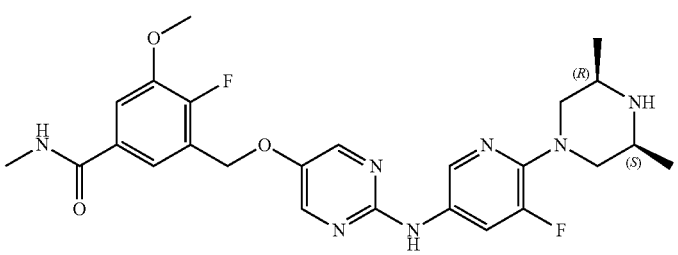 | 513.9 | 1H NMR (400 MHz, CD3OD) δ 8.25 (s, 2H), 8.16 (d, J = 2.2 Hz, 1H), 7.99 (dd, J = 14.8 Hz, 2.2 Hz, 1H), 7.61-7.48 (m, 2H), 5.18 (s, 2H), 3.93 (s, 3H), 3.71-3.63 (m, 2H), 3.04-2.94 (m 2H), 2.90 (s, 3H), 2.48-2.40 (m, 2H), 1.11 (d, J = 6.4 Hz, 6H). |
| 278 | 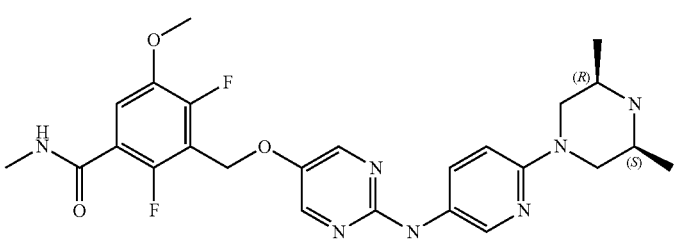 | 514.2 | 1H NMR (400 MHz, CD3OD) δ 8.30 (d, J = 2.7 Hz, 1H), 8.18 (s, 2H), 7.82 (dd, J = 9.1 Hz, 2.8 Hz, 1H), 7.48 (dd, J = 9.4 Hz, 6.8 Hz, 1H), 6.80 (d, J = 9.1 Hz, 1H), 5.18 (s, 2H), 4.02-3.96 (m, 2H), 3.90 (s, 3H), 2.92 (s, 3H), 2.91-2.84 (m, 2H), 2.39-2.30 (m, 2H), 1.14 (d, J = 6.4 Hz, 6H). |

-continued

| Compound | Structure | LC-MS (m/z) (M + H)+ | 1H NMR |
|---|---|---|---|
| 279 | 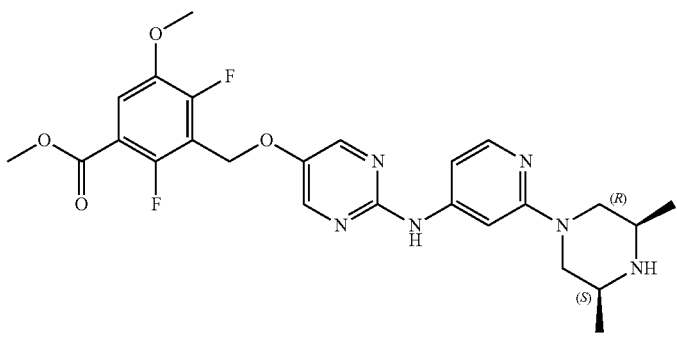 | 514.2 | 1H NMR (400 MHz, CD3OD) δ 8.40 (s, 2H), 7.90 (d, J = 6.3 Hz, 1H), 7.54 (s, 1H), 7.49 (dd, J = 9.3 Hz, 6.8 Hz, 1H), 7.18 (dd, J = 6.2 Hz, 1.2 Hz, 1H), 5.27 (s, 2H), 4.29 (dd, J = 14.0 Hz, 1.9 Hz, 2H), 3.91 (s, 3H), 3.49-3.40 (m, 2H), 2.99 (dd, J = 13.6 Hz, 11.7 Hz, 2H), 2.92 (s, 3H), 1.42 (d, J = 6.6 Hz, 6H). |
| 280 | 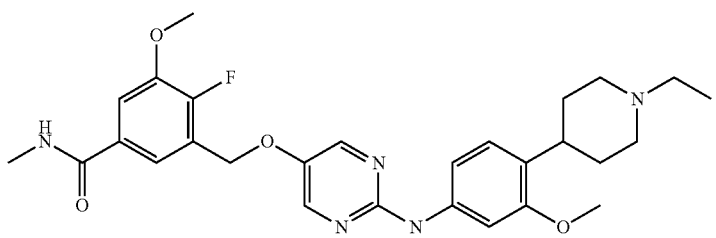 [SMILES: CCN1CCC(c2ccc(Nc3ncc(OCc4cc(C(=O)NC)cc(OC)c4F)cn3)cc2OC)CC1] | 524.2 | 1H NMR (400 MHz, CDCl3) δ 8.18 (s, 2H), 7.48 (d, J = 6.9 Hz, 1H), 7.33 (s, 1H), 7.12 (d, J = 7.2 Hz, 1H), 7.00 (d, J = 8.0 Hz, 1H), 6.93-6.92 (m, 1H), 6.08 (s, 1H), 5.11 (s, 2H), 3.93 (s, 3H), 3.82 (s, 3H), 3.05-3.03 (m, 2H), 2.99 (s, 3H), 2.89-2.87 (m, 1H), 2.45-2.42 (m, 2H), 2.05-2.00 (m, 2H), 1.74-1.72 (m, 4H), 1.09 (t, J = 6.9 Hz, 3H). |
| 281 | 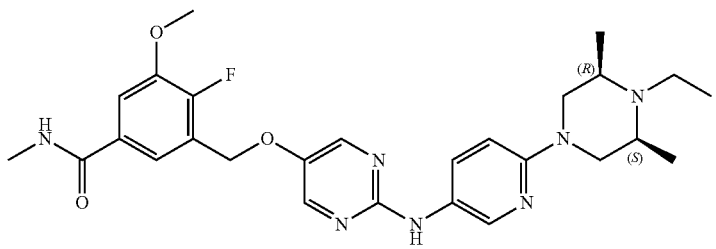 | 524.2 | 1H NMR (400 MHz, CD3OD) δ 8.32 (d, J = 2.8 Hz, 1H), 8.20 (s, 2H), 7.85 (dd, J = 9.2 Hz, 2.8 Hz, 1H), 7.58-7.54 (m, 2H), 6.80 (d, J = 9.2 Hz, 1H), 5.16 (s, 2H), 3.99-3.94 (mm, 2H), 3.93 (s, 3H), 2.99 (q, J = 7.2 Hz, 2H), 2.90 (s, 3H), 2.82-2.74 (m, 2H), 2.62-2.54 (m, 2H), 1.17 (d, J = 6.3 Hz, 6H), 0.96 (t, J = 7.2 Hz, 3H). |
| 282 | 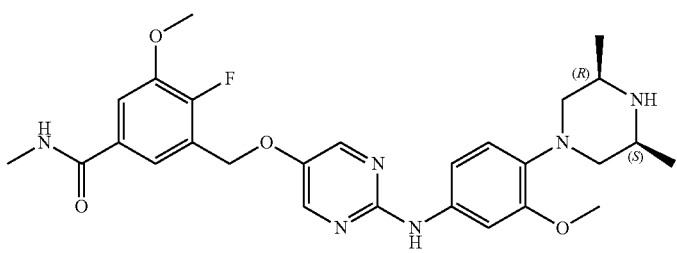 | 525.3 | 1H NMR (400 MHz, CD3OD) δ 8.22 (s, 2H), 7.58-7.55 (m, 1H), 7.54 (dd, J = 4.7 Hz, 2.2 Hz, 1H), 7.41 (d, J = 2.3 Hz, 1H), 7.14 (d, J = 8.6 Hz, 2.3 Hz, 1H), 6.89 (d, J = 8.6 Hz, 1H), 5.16 (s, 2H), 3.92 (s, 3H), 3.85 (s, 3H), 3.53-3.45 (m, 2H), 3.45-3.39 (m, 2H), 2.90 (s, 3H), 2.72-2.61 (m, 2H), 1.33 (d, J = 6.5 Hz, 6H). |
| 283 | 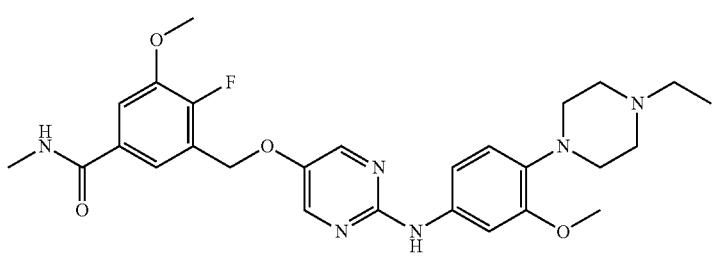 [SMILES: CCN1CCN(c2ccc(Nc3ncc(OCc4cc(C(=O)NC)cc(OC)c4F)cn3)cc2OC)CC1] | 525.3 | 1H NMR (400 MHz, CDCl3) δ 8.17 (s, 2H), 7.48 (dd, J = 7.9 Hz, 2.1 Hz, 1H), 7.33 (dd, J = 5.5 Hz, 2.1 Hz, 1H), 7.23 (d, J = 2.4 Hz, 1H), 7.00 (dd, J = 8.5 Hz, 2.4 Hz, 1H), 6.91-6.85 (m, 2H), 6.10 (s, 1H), 5.11 (s, 2H), 3.93 (s, 3H), 3.86 (s, 3H), 3.18-3.05 (m, 4H), 2.99 (d, J = 4.9 Hz, 3H), 2.82-2.66 (m, 4H), 2.58 (q, J = 7.1 Hz, 2H), 1.18 (t, J = 7.1 Hz, 3H). |

| Compound | Structure | LC-MS (m/z) (M+H)+ | 1H NMR |
|---|---|---|---|
| 284 | 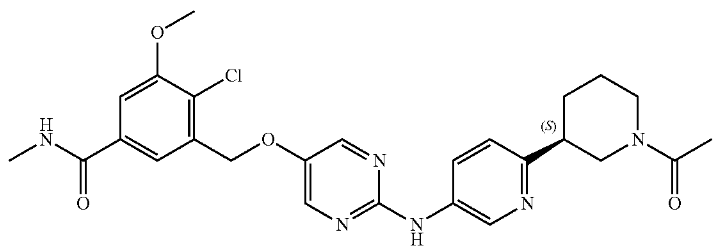 | 524.8 | 1H NMR (400 MHz, CD3OD) δ 8.75 (dd, J = 8.0 Hz, 2.6 Hz, 1H), 8.30 (s, 2H), 8.16 (dd, J = 8.8 Hz, 2.6 Hz, 1H), 7.65 (d, J = 1.7 Hz, 1H), 7.52 (d, J = 1.7 Hz, 1H), 7.30-7.24 (m, 1H), 5.25 (s, 2H), 4.02-3.96 (m, 1H), 3.97 (s, 3H), 3.38-3.30 (m, 1H), 3.27-3.16 (m, 1H), 2.92 (s, 3H), 2.89-2.65 (m, 2H), 2.13 (s, 3H), 2.13-2.00 (m, 1H), 1.90-1.79 (m, 2H), 168-1.50 (m, 1H). |
| 285 | 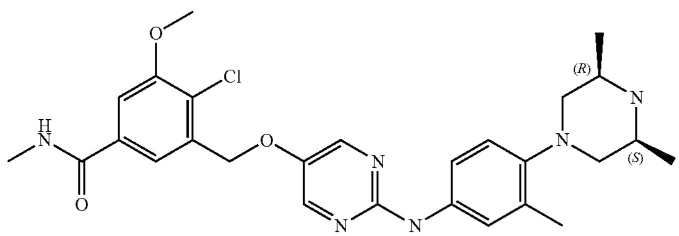 | 524.9 | 1H NMR (400 MHz, CD3OD) δ 8.21 (s, 2H), 7.63 (d, J = 2.0 Hz, 1H), 7.50 (d, J = 1.9 Hz, 1H), 7.39-7.35 (m, 2H), 6.94 (d, J = 8.6 Hz, 1H), 5.20 (s, 2H), 3.95 (s, 3H), 3.07-2.96 (m, 2H), 2.93-2.88 (m, 2H), 2.90 (s, 3H), 2.30-2.23 (m, 2H), 2.25 (s, 3H), 1.09 (d, J = 6.5 Hz, 6H). |
| 286 | 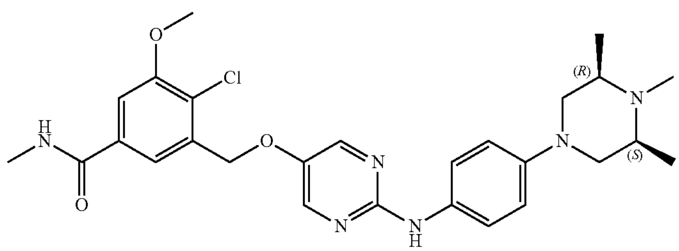 | 524.9 | 1H NMR (400 MHz, CD3OD) δ 8.20 (s, 2H), 7.63 (d, J = 2.0 Hz, 1H), 7.50 (d, J = 2.0 Hz, 1H), 7.48-7.43 (m, 2H), 6.94-6.89 (m, 2H), 5.20 (s, 2H), 3.96 (s, 3H), 3.45-3.40 (m, 2H), 2.91 (s, 3H), 2.51-2.42 (m, 4H), 2.33 (s, 3H), 1.17 (d, J = 5.9 Hz, 6H). |
| 287 | 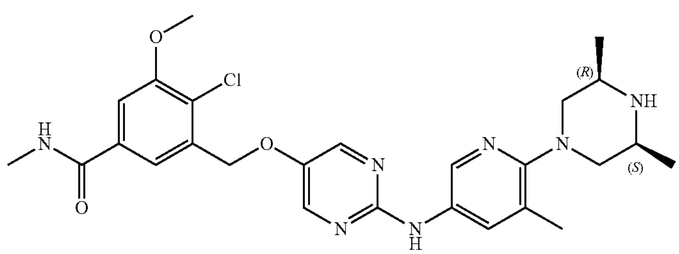 | 526.3 | 1H NMR (400 MHz, CD3OD) δ 8.35 (d, J = 2.7 Hz, 1H), 8.23 (s, 2H), 7.84 (d, J = 2.7 Hz, 1H), 7.63 (d, J = 1.8 Hz, 1H), 7.49 (d, J = 1.8 Hz, 1H), 5.20 (s, 2H), 3.95 (s, 3H), 3.20-3.13 (m, 2H), 3.04-2.97 (m, 2H), 2.91 (s, 3H), 2.44-2.38 (m, 2H), 2.26 (s, 3H), 1.10 (d, J = 6.4 Hz, 6H). |
| 288 | 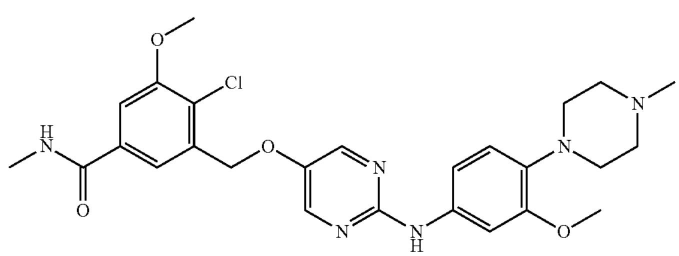 | 527.4 | 1H NMR (400 MHz, CD3OD) δ 8.22 (s, 2H), 7.63 (d, J = 1.9 Hz, 1H), 7.49 (d, J = 1.9 Hz, 1H), 7.37 (d, J = 2.3 Hz, 1H), 7.10 (dd, J = 8.6 Hz, 2.3 Hz, 1H), 6.88 (d, J = 8.6 Hz, 1H), 5.20 (s, 2H), 3.93 (s, 3H), 3.84 (s, 3H), 3.03-2.99 (m, 4H), 2.90 (s, 3H), 2.66-2.62 (m, 4H), 2.32 (s, 3H). |
| 289 | 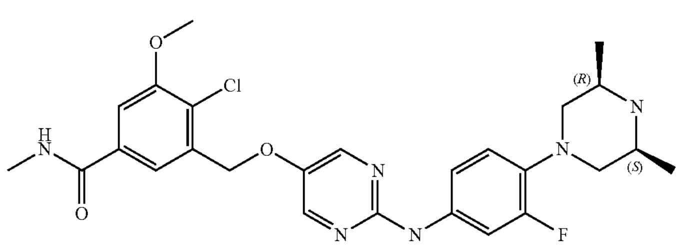 | 528.9 | 1H NMR (400 MHz, CD3OD) δ 8.25 (s, 2H), 7.64 (d, J = 1.7 Hz, 1H), 7.60 (dd, J = 15.1 Hz, 2.4 Hz, 1H), 7.51 (d, J = 1.7 Hz, 1H), 7.21 (dd, J = 8.7 Hz, 1.6 Hz, 1H), 6.93 (t, J = 9.2 Hz, 1H), 5.22 (s, 2H), 3.96 (s, 3H), 3.22-3.16 (m, 2H), 3.05-2.98 (m, 2H), 2.91 (s, 3H), 2.27 (t, J = 10.9 Hz, 2H), 1.10 (d, J = 6.4 Hz, 6H). |

| Compound | Structure | LC-MS (m/z) (M+H)+ | 1H NMR |
|---|---|---|---|
| 290 | 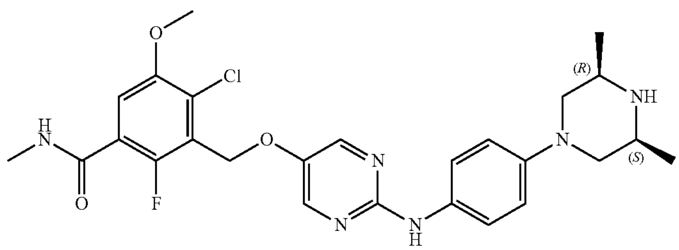 | 529.3 | 1H NMR (400 MHz, CD3OD) δ 8.18 (s, 2H), 7.47-7.43 (m, 2H), 7.43-7.41 (m, 1H), 6.95-6.89 (m, 2H), 5.25 (d, J = 2.3 Hz, 2H), 3.92 (s, 3H), 3.46-3.40 (m, 2H), 3.02-2.95 (m, 2H), 2.92 (s, 3H), 2.25-2.18 (m, 2H), 1.12 (d, J = 6.4 Hz, 6H). |
| 291 | 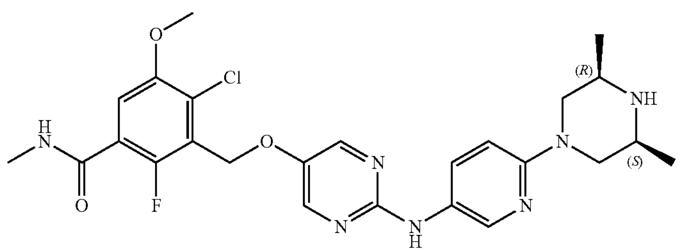 | 530.2 | 1H NMR (400 MHz, CD3OD) δ 8.30 (d, J = 2.5 Hz, 1H), 8.19 (s, 2H), 7.82 (dd, J = 9.1 Hz, 2.7 Hz, 1H), 7.43 (d, J = 6.3 Hz, 1H), 6.80 (d, J = 9.2 Hz, 1H), 5.26 (d, J = 2.2 Hz, 2H), 3.99 (dd, J = 12.6 Hz, 2.3 Hz, 2H), 3.92 (s, 3H), 2.92 (s, 3H), 2.92-2.85 (m, 2H), 2.38-2.32 (m, 2H), 1.14 (d, J = 6.4 Hz, 6H). |
| 292 | 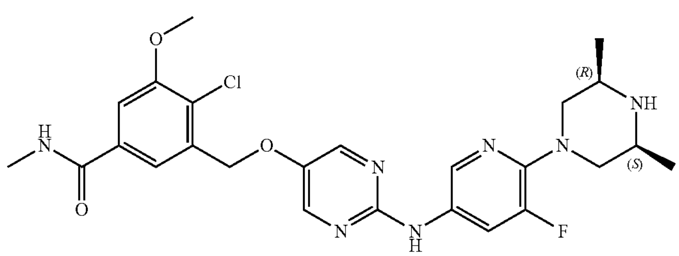 | 530.4 | 1H NMR (400 MHz, CD3OD) δ 8.26 (s, 2H), 8.19-8.14 (m, 1H), 8.03-7.94 (m, 1H), 7.63 (d, J = 1.4 Hz, 1H), 7.50 (d, J = 1.7 Hz, 1H), 5.22 (s, 2H), 3.95 (s, 3H), 3.73-3.64 (m, 2H), 3.03-2.94 (m, 2H), 2.91 (s, 3H), 2.47-2.41 (m, 2H), 1.11 (d, J = 6.4 Hz, 6H). |
| 293 | 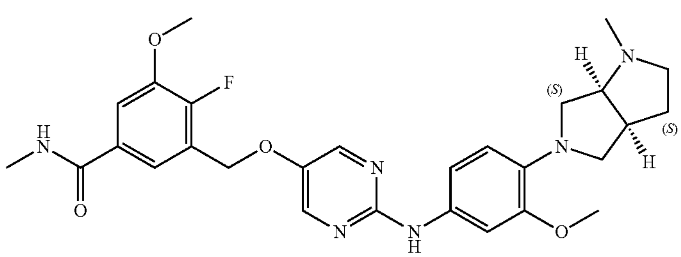 | 537.0 | 1H NMR (400 MHz, CD3OD) δ 8.18 (s, 2H), 7.57-7.51 (m, 2H), 7.27 (d, J = 2.3 Hz, 1H), 7.04 (dd, J = 8.5 Hz, 2.3 Hz, 1H), 6.72 (d, J = 8.5 Hz, 1H), 5.13 (s, 2H), 3.91 (s, 3H), 3.81 (s, 3H), 3.33-3.29 (m, 1H), 3.08-2.73 (m, 6H), 2.90 (s, 3H), 2.45-2.28 (m, 1H), 2.34 (s, 3H), 2.14-2.03 (m, 1H), 1.82-1.62 (m, 1H). |
| 294 | 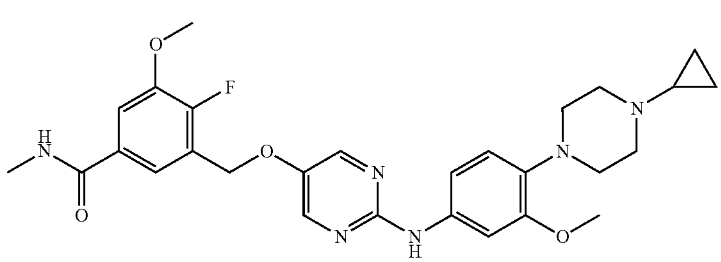 [SMILES: CNC(=O)c1cc(COc2cnc(Nc3ccc(N4CCN(C5CC5)CC4)c(OC)c3)nc2)c(F)c(OC)c1] | 537.2 | 1H NMR (400 MHz, CDCl3) δ 8.15 (s, 2H), 7.49-7.44 (m, 1H), 7.35-7.29 (m, 1H), 7.19 (d, J = 2.2 Hz, 1H), 6.99 (dd, J = 8.5 Hz, 1.8 Hz, 1H), 6.86 (d, J = 8.5 Hz, 1H), 5.08 (s, 2H), 3.91 (s, 3H), 3.85 (s, 3H), 3.11-2.87 (m, 8H), 2.79 (s, 3H), 1.70-1.63 (m, 1H), 0.47-0.39 (m, 4H). |

-continued

| Compound | Structure | LC-MS (m/z) (M + H)+ | 1H NMR |
|---|---|---|---|
| 295 | 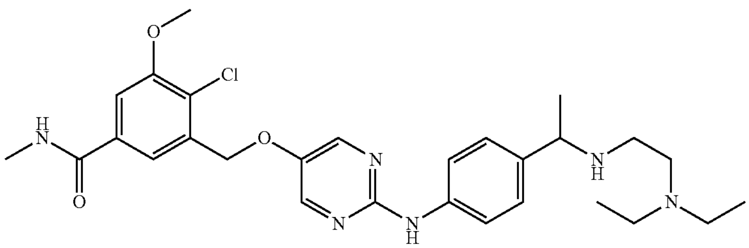 [SMILES: CCN(CC)CCNC(C)c1ccc(Nc2ncc(OCc3cc(C(=O)NC)cc(OC)c3Cl)cn2)cc1] | 540.9 | 1H NMR (400 MHz, CD3OD) δ 8.31 (s, 2H), 7.75 (s, 4H), 7.65 (s, 1H), 7.51 (s, 1H), 5.25 (s, 2H), 3.96 (s, 3H), 3.47 (t, J = 7.2 Hz, 2H), 2.91 (s, 3H), 2.69 (t, J = 7.2 Hz, 2H), 2.63 (q, J = 7.2 Hz, 4H), 1.08 (t, J = 7.1 Hz, 6H). |
| 296 | 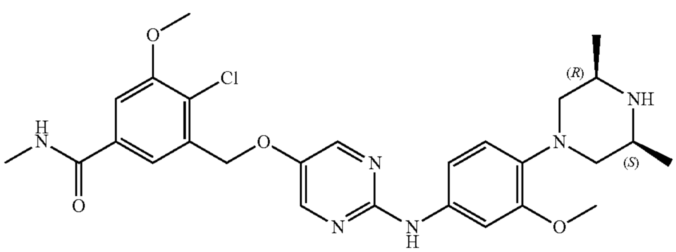 | 541.3 | 1H NMR (400 MHz, DMSO-d6) δ 9.17 (s, 1H), 8.54 (d, J = 4.4 Hz, 1H), 8.30 (s, 2H), 7.64 (d, J = 1.8 Hz, 1H), 7.54 (d, J = 1.9 Hz, 1H), 7.30 (d, J = 2.3 Hz, 1H), 7.20 (dd, J = 8.6 Hz, 2.3 Hz, 1H), 6.72 (d, J = 8.6 Hz, 1H), 5.19 (s, 2H), 3.90 (s, 3H), 3.71 (s, 3H), 3.07-3.05 (m, 2H), 2.84-2.82 (m, 2H), 2.76 (d, J = 4.6 Hz, 3H), 2.02-1.97 (m, 2H), 0.92 (d, J = 6.4 Hz, 3H). |
| 297 | 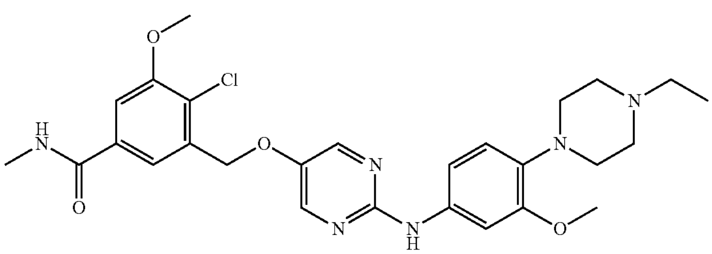 | 541.3 | 1H NMR (400 MHz, CD3OD) δ 8.23 (s, 2H), 7.63 (d, J = 2.0 Hz, 1H), 7.50 (d, J = 1.9 Hz, 1H), 7.38 (d, J = 2.4 Hz, 1H), 7.11 (dd, J = 8.6 Hz, 2.4 Hz, 1H), 6.89 (d, J = 8.6 Hz, 1H), 5.20 (s, 2H), 3.95 (s, 3H), 3.84 (s, 3H), 3.07-3.03 (m, 4H), 2.90 (s, 3H), 2.70-2.66 (m, 4H), 2.49 (q, J = 7.2 Hz, 2H), 1.12 (t, J = 7.2 Hz, 3H). |
| 298 | 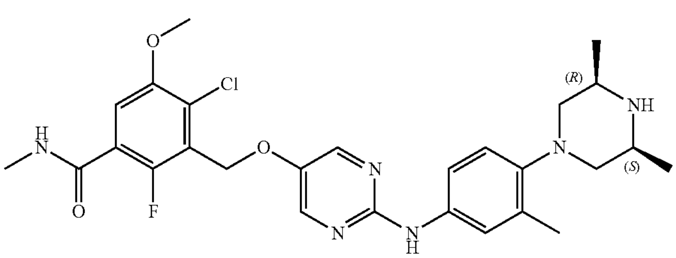 | 543.3 | 1H NMR (400 MHz, CD3OD) δ 8.12 (s, 2H), 7.35 (d, J = 6.3 Hz, 1H), 7.33-7.24 (m, 2H), 6.87 (d, J = 8.6 Hz, 1H), 5.18 (d, J = 1.8 Hz, 2H), 3.84 (s, 3H), 2.97-2.88 (m, 2H), 2.84 (s, 3H), 2.83-2.78 (m, 2H), 2.22-2.18 (m, 2H), 2.18 (s, 3H), 1.01 (d, J = 6.4 Hz, 6H). |
| 299 | 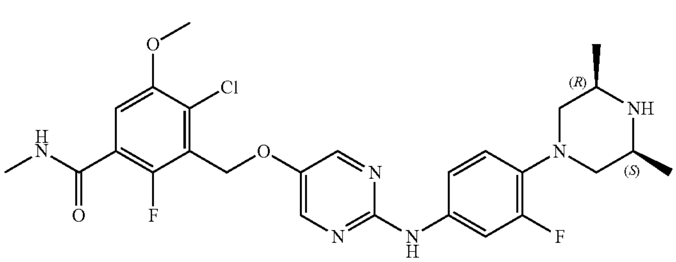 | 547.2 | 1H NMR (400 MHz, CD3OD) δ 8.24 (s, 2H), 7.66-7.52 (m, 1H), 7.43 (d, J = 6.2 Hz, 1H), 7.26-7.15 (m, 1H), 7.00-6.89 (m, 1H), 5.28 (s, 2H), 3.92 (s, 3H), 3.22-3.16 (m, 2H), 3.07-2.98 (m, 2H), 2.92 (s, 3H), 2.34-2.22 (m, 2H), 1.10 (d, J = 6.4 Hz, 6H). |

| Compound | Structure | LC-MS (m/z) (M + H)+ | 1H NMR |
|---|---|---|---|
| 301 | 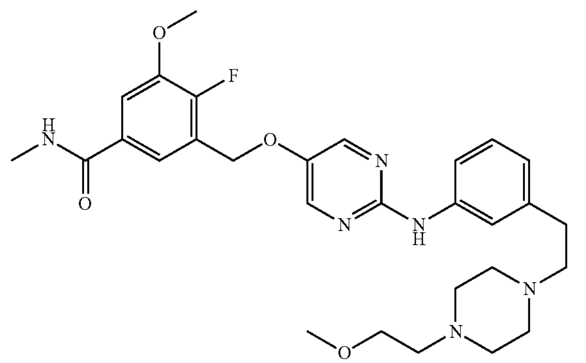 [SMILES: CNC(=O)c1cc(COc2cnc(Nc3cccc(CCN4CCN(CCOC)CC4)c3)nc2)c(F)c(OC)c1] | 553.3 | 1H NMR (400 MHz, CD3OD) δ 8.24 (s, 2H), 7.58-7.54 (m, 2H), 7.51 (t, J = 1.7 Hz, 1H), 7.48-7.42 (m, 1H), 7.17 (t, J = 7.8 Hz, 1H), 6.84-6.80 (m, 1H), 5.17 (s, 2H), 3.93 (s, 3H), 3.55 (t, J = 5.5 Hz, 2H), 3.33 (s, 3H), 2.90 (s, 3H), 2.83-2.77 (m, 2H), 2.74-2.65 (m, 12H). |
| 302 | 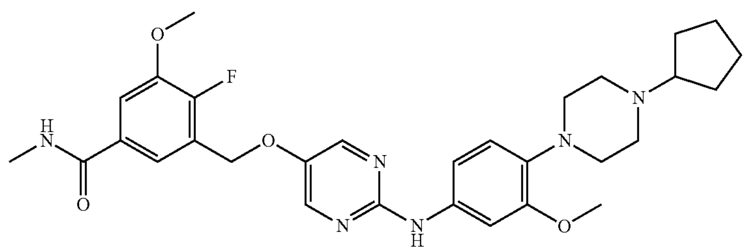 [SMILES: CNC(=O)c1cc(COc2cnc(Nc3ccc(N4CCN(C5CCCC5)CC4)c(OC)c3)nc2)c(F)c(OC)c1] | 565.1 | 1H NMR (400 MHz, CDCl3) δ 8.17 (s, 2H), 7.48 (dd, J = 7.9 Hz, 1.9 Hz, 1H), 7.33 (dd, J = 5.5 Hz, 1.7 Hz, 1H), 7.21-7.17 (m, 1H), 7.01 (dd, J = 8.5 Hz, 2.3 Hz, 1H), 6.91-6.86 (m, 2H), 6.12 (s, 1H), 5.11 (s, 2H), 3.93 (s, 3H), 3.86 (s, 3H), 3.13-3.02 (m, 4H), 2.99 (d, J = 4.7 Hz, 3H), 2.75-2.62 (m, 4H), 2.59-2.47 (m, 1H), 1.93-1.83 (m, 2H), 1.71-1.39 (m, 6H). |
| 303 | 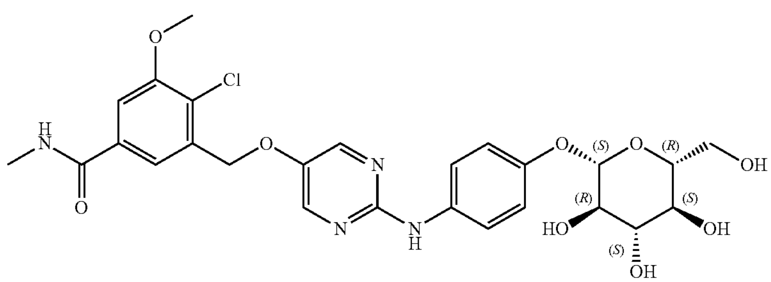 | 577.2 | 1H NMR (400 MHz, DMSO-d6) δ 9.24 (s, 1H), 8.56 (d, J = 4.4 Hz, 1H), 8.32 (s, 2H), 7.67 (d, J = 1.7 Hz, 1H), 7.58 (d, J = 9.3 Hz, 2H), 7.57 (s, 1H), 6.96 (d, J = 9.1 Hz, 2H), 5.22 (s, 2H), 4.74 (d, J = 7.4 Hz, 1H), 3.94 (s, 3H), 3.73-3.68 (m, 1H), 3.28-3.12 (m, 5H), 2.80 (d, J = 4.5 Hz, 3H). |

Example 22: Synthesis of Compounds 304-309

Compound 304
4-chloro-3-((2-((4-((3S,5R)-3,5-dimethylpiperazin-1-yl)phenyl)amino)pyrimidin-5-yl)ethynyl)-5-methoxy-N-methylbenzamide

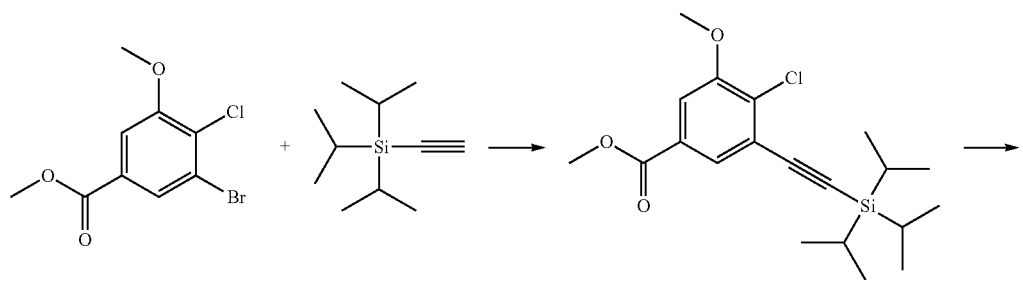

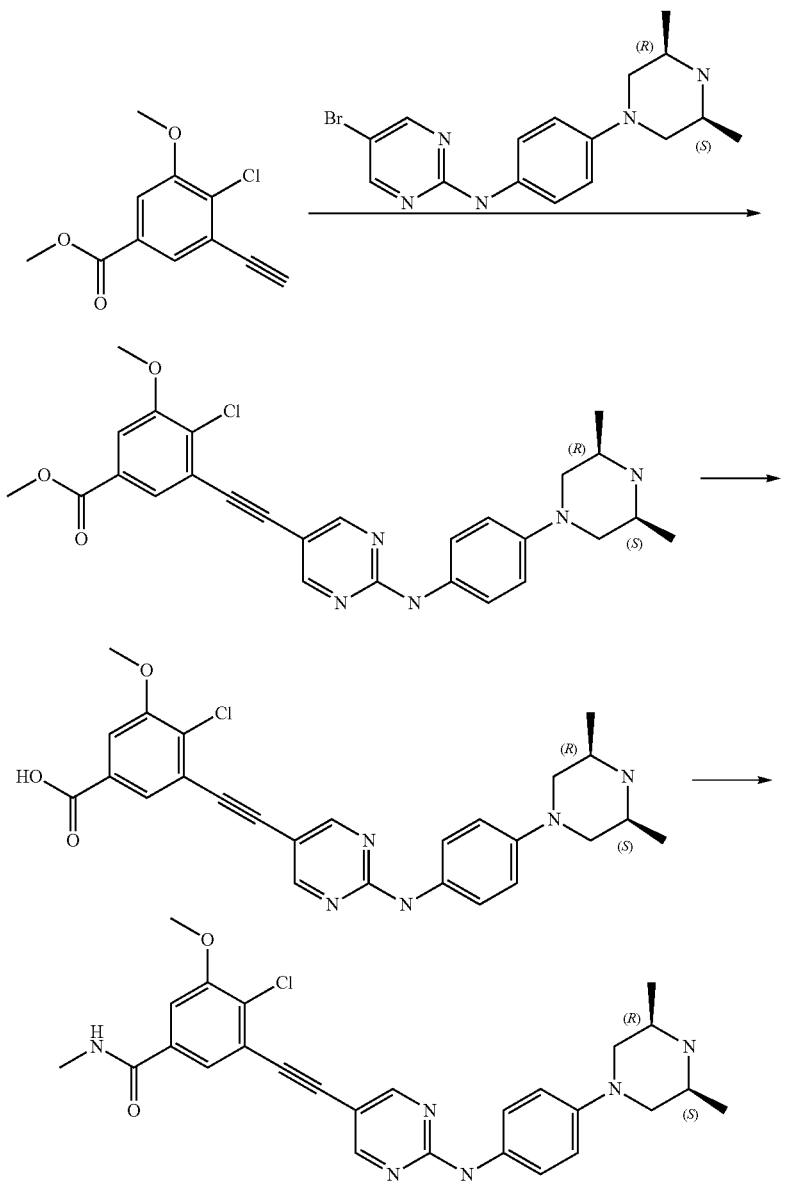

ⓔ indicates text missing or illegible when filed (A) Methyl 4-chloro-3-ethynyl-5-methoxybenzoate A mixture of methyl 3-bromo-4-chloro-5-methoxybenzoate (0.81 g, 2.90 mmol), ethynyltriisopropylsilane (0.6 g, 3.29 mmol), CuI (0.055 g, 0.29 mmol), PdCl$_2$(PPh$_3$)$_2$ (0.202 g, 0.29 mmol) and triethylamine (0.6 g, 5.93 mmol) in THF (20 mL) was stirred at 60° C. for 16 h under nitrogen atmosphere. The resulting mixture was partitioned between water (100 mL) and EA (100 mL). The organic layer was then dried over anhydrous Na$_2$SO$_4$ and concentrated under reduced pressure. The residue was dissolved in tetrabutylammonium fluoride THF solution (1 M, 10 mL) and the resulting mixture was stirred at ambient temperature for 4 h. The volatiles were removed under reduced pressure and the residue was purified via ISCO (eluted with MeOH in H$_2$O 0~100%) to afford the title compound as a yellow solid (0.25 g, 38.4% yield). MS (m/z): 225.0 (M+H)$^+$.

(B) Methyl 4-chloro-3-((2-((4-((3S,5R)-3,5-dimethylpiperazin-1-yl)phenyl)amino)pyrimidin-5-yl)ethynyl)-5-methoxybenzoate A mixture of methyl 4-chloro-3-ethynyl-5-methoxybenzoate (0.052 g, 0.231 mmol), 5-bromo-N-(4-((3R,5S)-3,5-dimethylpiperazin-1-yl)phenyl)pyrimidin-2-amine (0.160 g, 0.442 mmol), CuI (0.005 g, 0.026 mmol) and PdCl$_2$(PPh$_3$)$_2$ (0.018 g, 0.026 mmol) in THF (8 mL) was stirred at 60° C. for 3 h under nitrogen atmosphere. The volatiles were removed under reduced pressure and the residue was purified via ISCO (eluted with MeOH in H$_2$O 0~100%) to afford the title compound as a yellow solid (0.045 g, 38.4% yield). MS (m/z): 506.3 (M+H)$^+$.

(C) 4-chloro-3-((2-((4-((3S,5R)-3,5-dimethylpiperazin-1-yl)phenyl)amino)pyrimidin-5-yl)ethynyl)-5-methoxy-N-methylbenzamide A mixture of methyl 4-chloro-3-((2-((4-((3S,5R)-3,5-dimethylpiperazin-1-yl)phenyl)amino)pyrimidin-5-yl)ethynyl)-5-methoxybenzoate (0.045 g, 0.089 mmol) and a solution of sodium hydroxide (0.043 g in 1 mL water, 1.075 mmol) in MeOH (2 mL) and THF (3 mL) was stirred at ambient temperature for 2 h. Then the reaction mixture was purified via ISCO (eluted with MeOH in H$_2$O 0~100%) directly to afford the acid as a white solid (0.031 g, 70.9% yield). MS (m/z): 492.3 (M+H)$^+$. A mixture of the intermediate acid (0.031 g, 0.063 mmol), methylamine hydrochloride (0.012 g, 0.179 mmol), HATU (0.080 g, 0.210 mmol) and DIPEA (0.040 g, 0.310 mmol) in DMF (5 mL) was stirred at ambient temperature for 30 min. Then the reaction mixture was purified via ISCO (eluted with MeOH in H$_2$O 0~100%) directly to afford the title compound as a yellow solid (0.011 g, 34.6% yield). MS (m/z): 505.3 (M+H)$^+$. $^1$H NMR (400 MHz, CDCl$_3$) δ 8.53 (s, 2H), 7.53-7.38 (m, 4H), 7.16 (s, 1H), 6.93 (d, J=8.4 Hz, 2H), 6.15 (s, 1H), 3.97 (s, 3H), 3.55-3.38 (m, 2H), 3.13-3.03 (m, 2H), 3.02 (d, J=4.6 Hz, 3H), 2.37-2.20 (m, 2H), 1.14 (d, J=5.8 Hz, 6H).

The following compounds were prepared according to the procedures of Compound 304 using the corresponding intermediates and reagents under appropriate conditions that could be recognized by one skilled in the art.

| Compound | Structure | LC-MS (m/z) (M + H)$^+$ | $^1$H NMR |
|---|---|---|---|
| 305 | 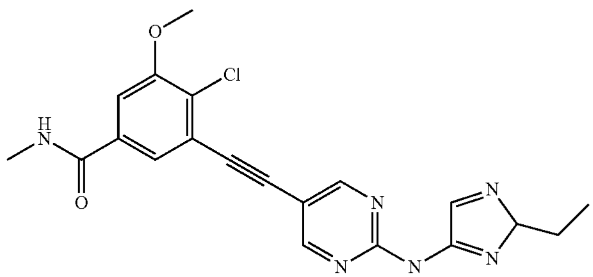 [SMILES: CCC1N=CC(Nc2ncc(C#Cc3cc(C(=O)NC)cc(OC)c3Cl)cn2)=N1] | 411.2 | $^1$H NMR (400 MHz, CD$_3$OD) δ 8.55 (s, 2H), 8.00 (s, 1H), 7.63 (d, J = 1.7 Hz, 1H), 7.60 (s, 1H), 7.50 (d, J = 1.7 Hz, 1H), 4.16 (q, J = 7.2 Hz, 2H), 3.97 (s, 3H), 2.93 (s, 3H), 1.47 (t, J = 7.2 Hz, 3H). |
| 306 | 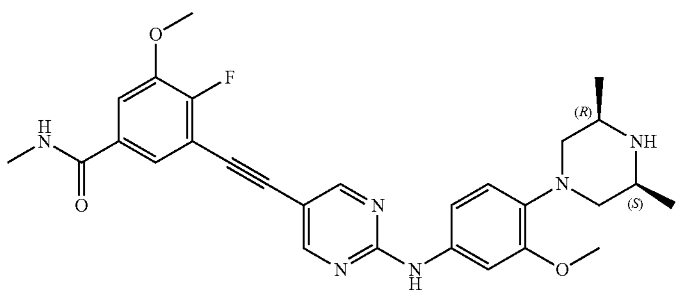 | 519.2 | $^1$H NMR (400 MHz, CD$_3$OD) δ 8.53 (s, 2H), 7.55 (d, J = 6.6 Hz, 2H), 7.41 (d, J = 2.3 Hz, 1H), 7.19 (dd, J = 8.6 Hz, 2.3 Hz, 1H), 6.90 (d, J = 8.6 Hz, 1H), 3.93 (s, 3H), 3.86 (s, 3H), 3.27-3.22 (m, 2H), 3.11-3.01 (m, 2H), 2.90 (s, 3H), 2.25-2.17 (m, 2H), 1.10 (d, J = 6.4 Hz, 6H). |
| 307 | 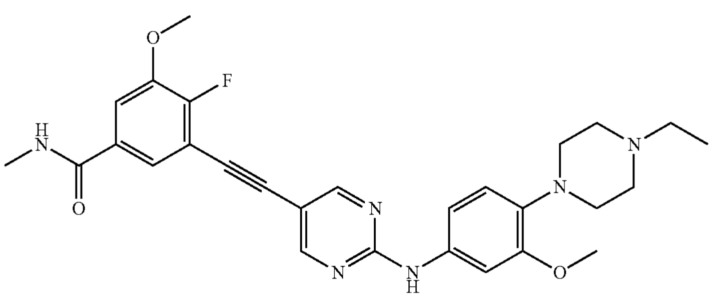 [SMILES: CCN1CCN(c2ccc(Nc3ncc(C#Cc4cc(C(=O)NC)cc(OC)c4F)cn3)cc2OC)CC1] | 519.4 | $^1$H NMR (400 MHz, CD$_3$OD) δ 8.51 (s, 2H), 7.54 (d, J = 6.6 Hz, 2H), 7.40 (d, J = 2.4 Hz, 1H), 7.17 (dd, J = 8.6 Hz, 2.4 Hz, 1H), 6.92 (d, J = 8.6 Hz, 1H), 3.93 (s, 3H), 3.86 (s, 3H), 3.10-2.99 (m, 4H), 2.90 (s, 3H), 2.72-2.58 (m, 4H), 2.49 (q, J = 7.2 Hz, 2H), 1.12 (t, J = 7.2 Hz, 3H). |
| 308 | 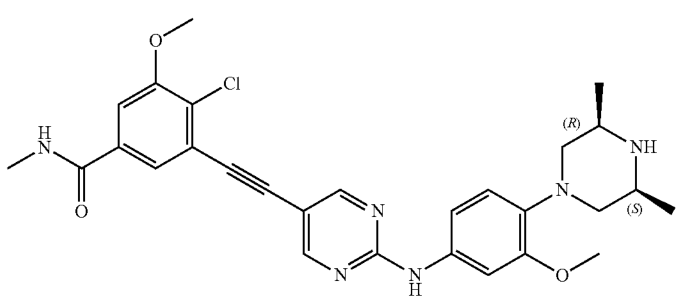 | 535.2 | $^1$H NMR (400 MHz, CD$_3$OD) δ 8.51 (s, 2H), 7.59 (d, J = 1.9 Hz, 1H), 7.46 (d, J = 1.9 Hz, 1H), 7.40 (d, J = 2.3 Hz, 1H), 7.18 (dd, J = 8.6 Hz, 2.3 Hz, 1H), 6.89 (d, J = 8.6 Hz, 1H), 3.94 (s, 3H), 3.86 (s, 3H), 3.26-3.21 (m, 2H), 3.09-2.98 (m, 2H), 2.90 (s, 3H), 2.20-2.16 (m, 2H), 1.08 (d, J = 6.4 Hz, 6H). |

| Compound | Structure | LC-MS (m/z) (M + H)+ | 1H NMR |
|---|---|---|---|
| 309 | 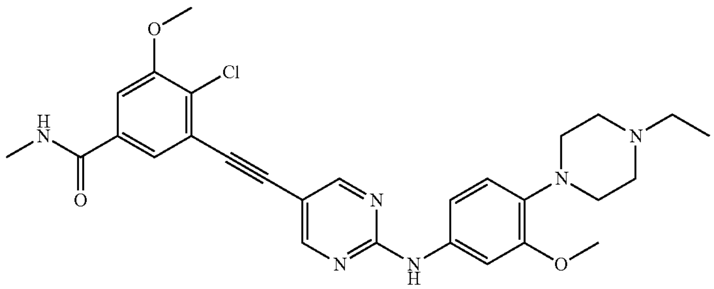 [SMILES: CCN1CCN(c2ccc(Nc3ncc(C#Cc4cc(C(=O)NC)cc(OC)c4Cl)cn3)cc2OC)CC1] | 535.6 | 1H NMR (400 MHz, CD3OD) δ 8.54 (s, 2H), 7.62 (d, J = 1.9 Hz, 1H), 7.49 (d, J = 1.9 Hz, 1H), 7.43 (d, J = 2.3 Hz, 1H), 7.19 (dd, J = 8.6 Hz, 2.4 Hz, 1H), 6.94 (d, J = 8.6 Hz, 1H), 3.96 (s, 3H), 3.87 (s, 3H), 3.10-3.06 (m, 4H), 2.91 (s, 3H), 2.70-2.66 (m, 4H), 2.51 (q, J = 7.4 Hz, 2H), 1.14 (t, J = 7.3 Hz, 3H). |

Example 23: Transcreener Kinase Assay of FGFR1

1. Materials and Reagents:
   Transcreenen™ KINASE Assay kit: Bellbrook Labs., 3003-10K;
   Recombinant human FGFR1: Invitrogen, PV3146;
   Poly E4Y (substrate): Sigma, P0275; 5 mg/mL, dissolved in MilliQ water;
   Assay buffer: 67 mM HEPES, 0.013% Triton X-100, 27 mM $MgCl_2$, 0.67 mM $MnCl_2$, 1.25 mM DTT, pH 7.4;
   10 mM ATP: Invitrogen, PV3227;
   500 mM EDTA: Invitrogen, 15575-038;
   96 well black Greiner plate: Greiner, 675076.
2. Prepare Solution
   Test compounds were solved in DMSO and were diluted with assay buffer to 5 folds of final concentration keeping the DMSO concentration at 5%. Further dilution are needed to make final concentrations are at 1, 0.33, 0.11, 0.037, 0.012, 0.004, 0.0014, 0.0005 μM; (the final concentration of DMSO is 1%).
   Enzyme/Substrate stock Preparation: Recombinant human FGFR1 and Poly E4Y are both diluted in assay buffer. The final concentration is 0.4 ng/μL for FGFR1 and 62.5 ng/μL for Poly E4Y. The mixture is being kept in ice before use;
   ATP Diluents Preparation: 10 mM ATP is diluted in assay buffer, the final concentration is 25 μM;
   ADP Diluents Preparation: dilute ADP (500 μM) in assay buffer, the final concentration is 25 μM;
   Prepare ATP standard curve stock as following:

| Column | ADP diluents (μL) | ATP diluents (μL) |
|---|---|---|
| 1 | 50 | 0 |
| 2 | 25 | 25 |
| 3 | 10 | 40 |
| 4 | 5 | 45 |
| 5 | 5 | 95 |
| 6 | 5 | 195 |
| 7 | 5 | 495 |
| 8 | 4 | 496 |
| 9 | 3 | 497 |
| 10 | 2 | 498 |
| 11 | 1 | 499 |
| 12 | 1 | 999 |

3. Enzymatic Reaction
   In a 96-well plate, add 5 μL of diluted solution of test compound or control solution. (positive control: 5 μL of 5% DMSO; negative control: 5 μL of 500 mM EDTA) into desired wells respectively;
   Add 10 μL of Enzyme/Substrate stock into each well;
   Add 10 μL of ATP Diluents to initiate the enzyme reaction and vortex the plate immediately on a plate shaker;
   For the wells to make standard curve, add 5 μL of 5% DMSO, 10 μL of assay buffer and 10 μL of ATP standard curve stock.
   Incubate the plate for 45 min at 28° C. on a plate shaker in a low speed.
4. Stoping Reaction and Detecting ADP
   Detection Mix Preparation: The mixture is made by dilution with MilliQ water; as following: ADP Alexa633 tracer (1:100), ADP antibody (1:158), and stop & detect buffer (1:10);
   Tracer Only control Preparation: The mixture is made by dilution with MilliQ water; as following: ADP Alexa633 tracer (1:100), and stop & detect buffer (1:10)
   No Tracer control Preparation: stop & detect buffer is diluted with MilliQ water; by 10 fold.
   Add 25 μL of detection mix, Tracer Only control and No Tracer control into corresponding wells, respectively;
   Incubate at 28° C. for 1 h, on a plate shaker in a low speed;
   Measure florescence polarization (mP) on TECAN F500. Excitation wavelength: 610 nm, Emission wavelength: 670 nm.
5. Data Analysis $$\text{Inhibition}(\%) = 100 - \frac{[ADP] \text{ in Compound well}}{[ADP] \text{ in Positive control well}} \times 100$$

Note:
   [ADP] in Compound well represents the ADP concentration in test compound well.
   [ADP] in Positive control well represents the ADP concentration in 5% DMSO well
   Conversion of mP value to ADP concentration is calculated based on the formula which determined by standard curve. And mP value is measured by following the instruction provided by BellBrook Labs. (www.bellbrooklabs.com).
6. $IC_{50}$: determined with add-in software for Microsoft Excel, XLfit™ (version 2.0) from ID Business Solutions (Guildford, UK).

Example 24: Transcreener Kinase Assay of FGFR2

1. Materials and Reagents
   Transcreenen™ KINASE Assay kit: Bellbrook Labs., 3003-10K;

Recombinant human FGFR2: Invitrogen, PV3368;
Poly E4Y (substrate): Sigma, P0275; 5 mg/mL, dissolved in MilliQ water;
Assay buffer: 67 mM HEPES, 0.013% Triton X-100, 27 mM $MgCl_2$, 0.67 mM $MnCl_2$, 1.25 mM DTT, PH 7.4;
10 mM ATP: Invitrogen, PV3227;
500 mM EDTA: Invitrogen, 15575-038;
96 well black Greiner plate: Greiner, 675076.

2. Prepare Solution

Test compounds were solved in DMSO and were diluted with assay buffer to 5 folds of final concentration keeping the DMSO concentration at 5%. Further dilution are needed to make final concentrations are at 1, 0.33, 0.11, 0.037, 0.012, 0.004, 0.0014, 0.0005 µM; (the final concentration of DMSO is 1%).

Enzyme/Substrate stock Preparation: Recombinant human FGFR2 and Poly E4Y are both diluted in assay buffer. The final concentration is 0.3 ng/µL for FGFR2 and 62.5 ng/µL for Poly E4Y. The mixture is being kept in ice before use;

Prepare ATP Diluents, 10 mM ATP is diluted in assay buffer, the final concentration is 25 µM;

Prepare ADP Diluents: diluted ADP (500 µM) in assay buffer, the final concentration is 25 µM;

Prepare ATP standard curve stock as following:

| Column | ADP diluents (µL) | ATP diluents (µL) |
|---|---|---|
| 1 | 50 | 0 |
| 2 | 25 | 25 |
| 3 | 10 | 40 |
| 4 | 5 | 45 |
| 5 | 5 | 95 |
| 6 | 5 | 195 |
| 7 | 5 | 495 |
| 8 | 4 | 496 |
| 9 | 3 | 497 |
| 10 | 2 | 498 |
| 11 | 1 | 499 |
| 12 | 1 | 999 |

3. Enzymatic Reaction

In a 96-well plate, add 5 µL of deluted solution of test compound or control solution. (positive control: 5 µL of 5% DMSO; negative control: 5 µL of 500 mM EDTA) into desired wells respectively;

Add 10 µL of Enzyme/Substrate stock into each well;

Add 10 µL of ATP Diluents to initiate the enzyme reaction and vortex the plate immediately on a plate shaker;

For the wells to make standard curve, add 5 µL of 5% DMSO, 10 µL of assay buffer and 10 µL of ATP standard curve stock.

Incubate the plate for 45 min at 28° C. on a plate shaker in a low speed.

4. Stoping Reaction and Detecting ADP

Detection Mix Preparation: The mixture is made by dilution with MilliQ water; as following: ADP Alexa633 tracer (1:100), ADP antibody (1:158), and stop & detect buffer (1:10);

Tracer Only control Preparation: The mixture is made by dilution with MilliQ water; as following: ADP Alexa633 tracer (1:100), and stop & detect buffer (1:10);

No Tracer control Preparation: stop & detect buffer is diluted with MilliQ water; by 10 fold.

Add 25 µL of detection mix, Tracer Only control and No Tracer control into corresponding wells, respectively;

Incubate at 28° C. for 1 h, on a plate shaker in a low speed;

Measure florescence polarization (mP) on TECAN F500. Excitation wavelength: 610 nm, Emission wavelength: 670 nm.

5. Data Analysis $$\text{Inhibition}(\%) = 100 - \frac{[ADP] \text{ in Compound well}}{[ADP] \text{ in Positive control well}} \times 100$$

Note:

[ADP] in Compound well represents the ADP concentration in test compound well.

[ADP] in Positive control well represents the ADP concentration in 5% DMSO well

Conversion of mP value to ADP concentration is calculated based on the formula which determined by standard curve. And mP value is measured by following the instruction provided by BellBrook Labs. (www.bellbrooklabs.com).

6. $IC_{50}$: determined with add-in software for Microsoft Excel, XLfit™ (version 2.0) from ID Business Solutions (Guildford, UK).

Example 25: Z-Lyte Kinase Assay of FGFR3

1. Materials and Reagents:

| | Vender | Cat Number |
|---|---|---|
| Z-lyte assay kit-TYR4 | Invitrogen | PV3193 |
| Z-LYTE Tyr 4 Peptide | Invitrogen | PV1279 |
| Z-LYTE Tyr 4 Phospho-peptide | Invitrogen | PV3280 |
| 5X Kinase Buffer | Invitrogen | PV3189 |
| 10 mM ATP | Invitrogen | PV3227 |
| Development Reagent B | Invitrogen | PV3298 |
| Development Buffer | Invitrogen | P3127 |
| Stop Reagent | Invitrogen | P3094 |
| FGFR3 kinase | Invitrogen | PV3145 |
| 384-well plate(black) | Corning | 3575 |
| Victor3 | PerkinElmer ™ | |

2. Reaction Steps:

Plate Map

| 1 | Ref cpd Cons (µM) | Cpd 1 Cons (µM) | Cpd 2 Cons (µM) | Cpd N Cons (µM) |
|---|---|---|---|---|
| C1 | 1.00E+00 | 1.00E+00 | 1.00E+00 | 1.00E+00 |
|    | 1.00E+00 | 1.00E+00 | 1.00E+00 | 1.00E+00 |
|    | 3.33E-01 | 3.33E-01 | 3.33E-01 | 3.33E-01 |
|    | 3.33E-01 | 3.33E-01 | 3.33E-01 | 3.33E-01 |
| C2 | 1.11E-01 | 1.11E-01 | 1.11E-01 | 1.11E-01 |
|    | 1.11E-01 | 1.11E-01 | 1.11E-01 | 1.11E-01 |
|    | 3.70E-02 | 3.70E-02 | 3.70E-02 | 3.70E-07 |
|    | 3.70E-02 | 3.70E-02 | 3.70E-02 | 3.70E-02 |
| C3 | 1.23E-02 | 1.23E-02 | 1.23E-02 | 1.23E-02 |
|    | 1.23E-02 | 1.23E-02 | 1.23E-02 | 1.23E-02 |
|    | 4.12E-03 | 4.12E-03 | 4.12E-03 | 4.12E-03 |
|    | 4.12E-03 | 4.12E-03 | 4.12E-03 | 4.12E-03 |
|    | 1.37E-03 | 1.37E-03 | 1.37E-03 | 1.37E-03 |
|    | 1.37E-03 | 1.37E-03 | 1.37E-03 | 1.37E-03 |
|    | 4.57E-04 | 4.57E-04 | 4.57E-04 | 4.57E-04 |
|    | 4.57E-04 | 4.57E-04 | 4.57E-04 | 4.57E-04 |

3. Solution Preparation 1) 1.33× Kinase Buffer: Dilute 5× Kinase Buffer to 1.33× with $ddH_2O$.

2) 4× Test Compounds: Serially dilute the test compounds to 4 folds of the concentrations desired, keeping the DMSO concentration at 8%. The final concentrations are 1, 0.33, 0.11, 0.037, 0.012, 0.004, 0.0014, 0.00046 μM, and the final concentration of DMSO is 2%.

3) Kinase/Peptide Mixture (P/K solution): Prepare Kinase/Peptide Mixture by diluting the kinase to 0.7 μg/ml and the Z-LYTE™ Tyr 4 peptide to 4 μM in 1.33× Kinase Buffer. Mix gently by pipetting.

4) Phospho-peptide Solution (PP solution): Add 0.4 μl of Z-LYTE™ Tyr 4 Phospho-peptide to 99.6 μl of 1.33× Kinase Buffer.

5) ATP Solution: Prepare ATP Solution by diluting the 10 mM of ATP in 1.33× Kinase Buffer to 300 uM.

6) Development Solution: Dilute Development Reagent B with Development Buffer as 1:128.

4. Reaction

1) Kinase reaction (10 μl of Volume)
   In a 384-well plate, add 2.5 μl of 4× test Cpds to each well except C1, C2, C3 wells.
   Add 2.5 μl of 8% DMSO to C1, C2, C3 wells.
   Put the plate on ice.
   Add 5 μl of P/K mixture to each test Cpd wells and C1,C2 wells.
   Add 5 μl of PP Solution to C3 well.
   Add 2.5 μl of 1.33× kinase buffer to C1 and C3 wells.
   Add 2.5 μl of 4× ATP Solution to each test Cpd wells and C2 well, respectively. Shake the plate for 30 Sec and centrifuge (1500 rpm, 1 min).
   Seal the plate to protect from the light and incubate the plate for 1 hour at RT (25-30° C.).

2) Development reaction
   Add 5 μl of the Development solution to all wells.
   Shake the plate for 30 Sec and centrifuge (1500 rpm, 1 min).
   Seal the plate to protect from the light and incubate the plate for 1 hour at RT (25-30° C.).

3) Stop and Read
   Add 5 μl of the Stop reagent to all wells.
   Shake the plate for 30 Sec and centrifuge (1500 rpm, 1 min).
   Measure the value of Coumarin (Ex400 nm, Em445 nm) and fluorescein (Ex400 nm, Em520 nm), respectively.

5. Data Analysis

Emission Ratio($ER$)=Coumarin Emission (445 nm)/Fluorescein Emission (520 nm)

% Phosphorylation=$1-[ER \times C3_{520nm}-C3_{445nm}]/[(C1_{445nm}-C3_{445nm})+ER \times (C3_{520nm}-C1_{520nm})]$ Inhibition rate ($IR$)=$1-\% Pho_{test\ Cpd}/\% Pho_{C2}$ 6. $IC_{50}$ Value: determined with add-in software for Microsoft Excel, XLfit™ (version 2.0) from ID Business Solutions (Guildford, UK)

Example 26: Cellular Proliferation Assay

1. Cell Line
   KG-1 (ATCC Accession No. CCL-246),
   SNU-16 (ATCC Accession No. CRL-5974),
   RT-112 (ECACC Accession No. 85061106)

2. Assay Protocol
   FGFR related cancer cell proliferation is measured in 96-well plates using Cell Counting Kit-8 (Dojindo CK04-13).
   Seed 30000 cells/well of KG1, 5000 cells/well of SNU16, and 1000 cells/well of RT112 in a volume of 100 μL/well in growth media.
   After 24 hours, dilute the test compound to 10, 3.3, 1.1, 0.37, 0.12, 0.04, 0.013, 0.004 μM, keeping the DMSO concentration at 5%.
   Add 10 μL of 8-point compound series to the wells of culturing cells.
   Incubate at 37° C. and 5% CO2 for 72 hours
   Add 10 μL/well of CCkit8 and incubate at 37° C. and 5% CO2 for an hour
   Detect the optical density of each well at 450 nm on Labsystems Multiskan K3.

3. Data Analysis $$\text{Inhibition}(\%) = 100 - \frac{OD_{compound\ well} - OD_{control\ well}}{OD_{cell\ well} - OD_{control\ well}} \times 100$$

Note:
$OD_{compound\ well}$ represents the optical density of cells treated with compound.
$OD_{cell\ well}$ represents the optical density of cells without compounds treatment.(only 0.5% DMSO)
$OD_{control\ well}$ represents the optical density of culture media background
$IC_{50}$: determined with add-in software for Microsoft Excel, XLfit™ (version 2.0) from ID Business Solutions (Guildford, UK).

Bioassay Results:

| Example No. | FGFR1 (FP) IC50 (uM) | FGFR2 (FP) IC50 (uM) | FGFR3 (Z-lyte) IC50 (uM) | KG1 IC50 (uM) | SNU-16 IC50 (uM) | RT-112 IC50 (uM) |
|---|---|---|---|---|---|---|
| 1 | 0.024 | 0.019 | 0.028 | 0.049 | 0.095 | 0.612 |
| 2 | 0.017 | 0.010 | 0.017 | 0.017 | 0.031 | 0.019 |
| 3 | 0.028 | 0.028 | 0.188 | 0.072 | 0.134 | 0.370 |
| 4 | 0.201 | 0.233 | 0.795 | | | |
| 5 | 0.013 | 0.012 | 0.047 | 0.024 | 0.056 | |
| 7 | 0.143 | 0.169 | 0.590 | | | |
| 8 | 0.006 | 0.005 | 0.014 | 0.011 | 0.014 | 0.019 |
| 9 | 0.038 | 0.028 | 0.064 | 0.098 | 0.044 | |
| 10 | 0.025 | 0.005 | 0.008 | 0.018 | 0.022 | 0.029 |
| 11 | 0.018 | 0.009 | 0.007 | 0.040 | 0.028 | 0.034 |
| 12 | 0.098 | 0.025 | 0.128 | | 0.266 | |
| 13 | 0.029 | 0.010 | 0.007 | | 0.021 | 0.059 |
| 14 | 0.003 | 0.004 | 0.004 | 0.009 | 0.007 | |
| 15 | 0.012 | 0.008 | 0.016 | 0.013 | 0.017 | |
| 16 | 0.004 | 0.006 | 0.009 | 0.009 | 0.012 | |
| 17 | 0.012 | 0.006 | 0.008 | 0.077 | 0.003 | |
| 18 | 0.005 | 0.005 | 0.011 | 0.019 | 0.022 | |
| 19 | 0.043 | 0.034 | 0.128 | | | |
| 20 | 0.009 | 0.006 | 0.014 | 0.040 | 0.016 | 0.052 |
| 21 | 0.009 | 0.005 | 0.020 | 0.028 | 0.026 | 0.084 |
| 22 | 0.047 | 0.027 | 0.094 | 0.122 | 0.151 | |
| 23 | 0.009 | 0.006 | 0.013 | 0.029 | 0.018 | |
| 24 | 0.015 | 0.008 | 0.030 | 0.039 | 0.023 | 0.218 |
| 25 | 0.020 | 0.012 | 0.027 | 0.048 | 0.029 | 0.093 |
| 26 | 0.256 | 0.042 | 0.021 | 0.340 | 0.293 | 0.402 |
| 27 | 0.360 | 0.245 | 0.347 | | | |
| 28 | 0.003 | 0.002 | 0.007 | 0.005 | 0.005 | |
| 29 | 0.029 | 0.010 | 0.040 | 0.055 | 0.068 | 0.241 |
| 30 | 0.042 | 0.023 | 0.287 | 0.178 | 0.236 | 0.491 |
| 31 | 0.018 | 0.006 | 0.005 | 0.057 | 0.030 | 0.104 |
| 32 | 0.022 | 0.007 | 0.017 | 0.047 | 0.019 | 0.135 |
| 33 | 0.033 | 0.013 | 0.046 | 0.132 | 0.058 | 0.308 |
| 34 | 0.030 | 0.009 | 0.083 | 0.189 | 0.157 | 0.455 |
| 35 | 0.021 | 0.010 | 0.031 | 0.052 | 0.029 | 0.160 |
| 36 | 0.010 | 0.007 | 0.016 | 0.046 | 0.044 | |
| 37 | 0.008 | 0.003 | 0.020 | 0.028 | 0.030 | 0.086 |
| 38 | 0.043 | 0.041 | 0.043 | 0.049 | 0.071 | 0.342 |
| 39 | 0.012 | 0.010 | 0.039 | 0.031 | 0.048 | |
| 40 | 0.004 | 0.006 | 0.009 | 0.038 | 0.024 | |
| 41 | 0.002 | 0.004 | 0.008 | 0.011 | 0.015 | |

-continued

| Example No. | FGFR1 (FP) IC50 (uM) | FGFR2 (FP) IC50 (uM) | FGFR3 (Z-lyte) IC50 (uM) | KG1 IC50 (uM) | SNU-16 IC50 (uM) | RT-112 IC50 (uM) |
|---|---|---|---|---|---|---|
| 42 | 0.016 | 0.010 | 0.048 | 0.069 | 0.033 | |
| 43 | 0.005 | 0.004 | 0.009 | 0.009 | 0.015 | 0.051 |
| 44 | 0.014 | 0.007 | 0.010 | 0.388 | 0.034 | |
| 45 | 0.132 | 0.034 | 0.061 | 0.059 | 0.113 | |
| 46 | 0.006 | 0.006 | 0.008 | 0.063 | 0.074 | |
| 47 | 0.005 | 0.005 | 0.015 | 0.011 | 0.016 | |
| 48 | 0.006 | 0.005 | 0.008 | 0.075 | 0.018 | 0.062 |
| 49 | 0.014 | 0.015 | 0.029 | 0.045 | 0.132 | 0.352 |
| 50 | 0.103 | 0.113 | 0.175 | 0.387 | 0.581 | |
| 51 | 0.001 | 0.002 | 0.005 | 0.004 | 0.005 | |
| 52 | 0.005 | 0.004 | 0.008 | 0.014 | 0.019 | 0.049 |
| 53 | 0.006 | 0.003 | 0.006 | 0.018 | 0.010 | 0.031 |
| 54 | 0.002 | 0.003 | 0.002 | 0.003 | 0.004 | 0.016 |
| 55 | 0.004 | 0.004 | 0.009 | 0.007 | 0.017 | |
| 56 | 0.008 | 0.009 | 0.014 | 0.016 | 0.032 | |
| 57 | 0.325 | 0.123 | 0.509 | | | |
| 58 | 0.019 | 0.008 | 0.011 | 0.805 | 0.070 | 0.560 |
| 59 | 0.003 | 0.002 | 0.002 | 0.002 | 0.004 | |
| 60 | 0.016 | 0.007 | 0.023 | 0.051 | 0.046 | 0.137 |
| 61 | 0.054 | 0.017 | 0.062 | 0.400 | 0.158 | |
| 62 | 0.195 | 0.027 | 0.243 | 0.427 | 0.419 | 0.895 |
| 63 | 0.020 | 0.009 | 0.033 | 0.046 | 0.049 | 0.152 |
| 64 | 0.048 | 0.028 | 0.112 | 0.203 | 0.055 | 0.296 |
| 65 | 0.018 | 0.007 | 0.025 | 0.194 | 0.055 | 0.201 |
| 66 | 0.037 | 0.027 | 0.044 | 0.089 | 0.071 | 0.263 |
| 67 | 0.031 | 0.013 | 0.025 | | | |
| 68 | 0.042 | 0.020 | 0.042 | 0.268 | 0.085 | 0.337 |
| 69 | 0.027 | 0.016 | 0.022 | | | |
| 70 | 0.126 | 0.053 | 0.591 | 0.398 | 0.708 | 0.101 |
| 71 | 0.058 | 0.024 | 0.038 | 0.195 | 0.094 | 0.554 |
| 72 | 0.034 | 0.011 | 0.040 | | | |
| 73 | 0.009 | 0.008 | 0.025 | 0.070 | 0.065 | 0.493 |
| 74 | 0.041 | 0.033 | 0.061 | 0.123 | 0.094 | |
| 75 | 0.005 | 0.004 | 0.008 | 0.043 | 0.016 | 0.067 |
| 76 | 0.005 | 0.003 | 0.004 | 0.011 | 0.012 | |
| 77 | 0.044 | 0.018 | 0.031 | | | |
| 78 | 0.006 | 0.006 | 0.006 | 0.013 | 0.014 | 0.034 |
| 79 | 0.012 | 0.010 | 0.014 | 0.009 | 0.019 | 0.142 |
| 80 | 0.010 | 0.011 | 0.013 | 0.013 | 0.018 | 0.044 |
| 81 | 0.017 | 0.013 | 0.026 | 0.026 | 0.059 | 0.133 |
| 82 | 0.019 | 0.010 | 0.022 | 0.048 | 0.046 | 0.334 |
| 83 | 0.009 | 0.005 | 0.014 | 0.024 | 0.059 | 0.495 |
| 84 | 0.024 | 0.016 | 0.019 | 0.033 | 0.039 | 0.024 |
| 85 | 0.015 | 0.008 | 0.033 | 0.067 | 0.017 | 0.021 |
| 86 | 0.008 | 0.005 | 0.011 | 0.016 | 0.025 | 0.010 |
| 87 | 0.015 | 0.006 | 0.006 | 0.031 | 0.033 | 0.062 |
| 88 | 0.012 | 0.005 | 0.003 | 0.030 | 0.024 | 0.050 |
| 89 | 0.015 | 0.009 | 0.035 | 0.053 | 0.055 | 0.201 |
| 90 | 0.015 | 0.016 | 0.152 | 0.071 | 0.149 | 0.626 |
| 91 | 0.019 | 0.007 | 0.016 | 0.248 | 0.239 | 0.122 |
| 92 | 0.008 | 0.008 | 0.010 | 0.090 | 0.032 | 0.087 |
| 93 | 0.019 | 0.012 | 0.038 | 0.056 | 0.029 | 0.088 |
| 94 | 0.015 | 0.009 | 0.017 | 0.030 | 0.093 | 0.026 |
| 95 | 0.017 | 0.010 | 0.010 | 0.042 | 0.016 | 0.012 |
| 96 | 0.010 | 0.010 | 0.036 | 0.025 | 0.050 | 0.084 |
| 97 | 0.015 | 0.007 | 0.016 | 0.177 | 0.059 | 0.240 |
| 98 | 0.012 | 0.005 | 0.009 | 0.370 | 0.016 | 0.021 |
| 99 | 0.015 | 0.006 | 0.009 | 0.214 | 0.013 | 0.027 |
| 100 | 0.010 | 0.004 | 0.004 | 0.461 | 0.018 | 0.012 |
| 101 | 0.012 | 0.008 | 0.008 | 0.130 | 0.029 | 0.046 |
| 102 | 0.011 | 0.005 | 0.007 | 0.031 | 0.009 | 0.026 |
| 103 | 0.020 | 0.016 | 0.017 | 0.032 | 0.019 | 0.064 |
| 104 | 0.164 | 0.040 | 0.198 | 0.255 | 0.238 | 0.831 |
| 105 | 0.018 | 0.009 | 0.011 | | | |
| 106 | 0.034 | 0.012 | 0.033 | 0.044 | 0.033 | 0.072 |
| 107 | 0.161 | 0.053 | 0.213 | 0.344 | 0.170 | 0.287 |
| 108 | 0.063 | 0.044 | 0.119 | | | |
| 109 | 0.011 | 0.006 | 0.012 | 0.026 | 0.022 | 0.159 |
| 110 | 0.032 | 0.015 | 0.026 | 0.048 | 0.024 | 0.225 |
| 111 | 0.014 | 0.007 | 0.012 | 0.030 | 0.017 | 0.110 |
| 112 | 0.012 | 0.005 | 0.013 | 0.021 | 0.024 | 0.094 |
| 113 | 0.008 | 0.004 | 0.015 | 0.022 | 0.042 | 0.257 |
| 114 | 0.012 | 0.007 | 0.018 | 0.033 | 0.055 | 0.461 |
| 115 | 0.032 | 0.021 | 0.047 | 0.138 | 0.139 | 0.659 |
| 116 | 0.015 | 0.009 | 0.044 | 0.053 | 0.038 | 0.142 |
| 117 | 0.031 | 0.011 | 0.030 | 0.201 | 0.048 | 0.428 |
| 118 | 0.010 | 0.007 | 0.035 | 0.040 | 0.033 | |
| 119 | 0.010 | 0.007 | 0.014 | 0.028 | 0.026 | 0.090 |
| 120 | 0.005 | 0.003 | 0.010 | 0.110 | 0.112 | 0.562 |
| 121 | 0.068 | 0.014 | 0.024 | 0.095 | 0.046 | 0.197 |
| 122 | 0.107 | 0.033 | 0.061 | 0.162 | 0.127 | 0.570 |
| 123 | 0.009 | 0.007 | 0.008 | 0.018 | 0.017 | 0.036 |
| 124 | 0.379 | 0.275 | 0.311 | | | |
| 125 | 0.048 | 0.018 | 0.146 | | | |
| 126 | 0.012 | 0.005 | 0.014 | 0.071 | 0.088 | 0.591 |
| 127 | 0.014 | 0.006 | 0.011 | 0.012 | 0.019 | 0.053 |
| 128 | 0.027 | 0.010 | 0.028 | 0.020 | 0.045 | 0.019 |
| 129 | 0.028 | 0.005 | 0.013 | 0.031 | 0.026 | 0.188 |
| 130 | 0.023 | 0.012 | 0.034 | 0.026 | 0.029 | 0.220 |
| 131 | 0.011 | 0.006 | 0.019 | 0.022 | 0.027 | 0.124 |
| 132 | 0.015 | 0.007 | 0.017 | 0.032 | 0.031 | 0.165 |
| 133 | 0.009 | 0.006 | 0.015 | 0.007 | 0.018 | 0.065 |
| 134 | 0.038 | 0.013 | 0.021 | | | |
| 135 | 0.014 | 0.006 | 0.009 | 0.020 | 0.013 | 0.067 |
| 136 | 0.010 | 0.007 | 0.013 | 0.029 | 0.018 | 0.166 |
| 137 | 0.009 | 0.005 | 0.013 | 0.026 | 0.018 | 0.135 |
| 138 | 0.028 | 0.019 | 0.020 | 0.030 | 0.029 | 0.750 |
| 139 | 0.015 | 0.008 | 0.017 | 0.045 | 0.018 | 0.112 |
| 140 | 0.009 | 0.005 | 0.009 | 0.022 | 0.020 | 0.066 |
| 141 | 0.020 | 0.010 | 0.014 | 0.047 | 0.015 | 0.112 |
| 142 | 0.031 | 0.012 | 0.049 | 0.064 | 0.043 | 0.127 |
| 143 | 0.008 | 0.005 | 0.010 | 0.028 | 0.032 | 0.048 |
| 144 | 0.012 | 0.006 | 0.006 | 0.020 | 0.010 | 0.059 |
| 145 | 0.019 | 0.008 | 0.011 | 0.037 | 0.013 | 0.131 |
| 146 | 0.020 | 0.008 | 0.016 | 0.345 | 0.051 | 0.713 |
| 147 | 0.071 | 0.008 | 0.024 | 0.033 | 0.034 | 0.084 |
| 148 | 0.022 | 0.019 | 0.022 | 0.368 | 0.046 | 0.230 |
| 149 | 0.023 | 0.011 | 0.018 | 0.092 | 0.025 | 0.037 |
| 150 | 0.012 | 0.006 | 0.007 | 0.319 | 0.029 | 0.086 |
| 151 | 0.009 | 0.007 | 0.008 | 0.617 | 0.032 | 0.202 |
| 152 | 0.012 | 0.006 | 0.008 | 0.064 | 0.022 | 0.146 |
| 156 | 0.014 | 0.006 | 0.006 | 0.218 | 0.009 | 0.013 |
| 157 | 0.007 | 0.005 | 0.006 | | | |
| 158 | 0.014 | 0.007 | 0.006 | 0.016 | 0.007 | 0.029 |
| 159 | 0.023 | 0.011 | 0.010 | 0.026 | 0.006 | 0.021 |
| 162 | 0.038 | 0.016 | 0.060 | 0.152 | 0.062 | 0.438 |
| 163 | 0.011 | 0.005 | 0.017 | 0.015 | 0.017 | 0.112 |
| 164 | 0.020 | 0.011 | 0.028 | 0.060 | 0.028 | 0.208 |
| 165 | 0.041 | 0.007 | 0.203 | 0.803 | 0.100 | 0.991 |
| 166 | 0.013 | 0.006 | 0.016 | | | |
| 167 | 0.037 | 0.013 | 0.032 | 0.154 | 0.052 | 0.260 |
| 168 | 0.006 | 0.002 | 0.004 | 0.002 | 0.004 | 0.004 |
| 169 | 0.020 | 0.010 | 0.019 | 0.048 | 0.048 | 0.254 |
| 170 | 0.006 | 0.005 | 0.009 | 0.051 | 0.014 | 0.020 |
| 171 | 0.012 | 0.008 | 0.011 | 0.008 | 0.016 | 0.043 |
| 172 | 0.007 | 0.006 | 0.006 | 0.013 | 0.004 | 0.012 |
| 173 | 0.009 | 0.006 | 0.006 | 0.091 | 0.020 | 0.034 |
| 174 | 0.010 | 0.011 | 0.017 | | | |
| 175 | 0.012 | 0.008 | 0.006 | 0.011 | 0.012 | 0.030 |
| 176 | 0.010 | 0.005 | 0.009 | 0.060 | 0.017 | 0.021 |
| 177 | 0.006 | 0.005 | 0.006 | 0.011 | 0.002 | 0.011 |
| 178 | 0.009 | 0.005 | 0.008 | 0.018 | 0.007 | 0.015 |
| 179 | 0.008 | 0.008 | 0.006 | | | |
| 180 | 0.008 | 0.006 | 0.008 | 0.290 | 0.075 | 0.759 |
| 181 | 0.015 | 0.010 | 0.016 | | | |
| 182 | 0.017 | 0.009 | 0.012 | | | |
| 183 | 0.017 | 0.010 | 0.014 | | | |
| 184 | 0.007 | 0.006 | 0.008 | 0.201 | 0.060 | 0.584 |
| 185 | 0.008 | 0.008 | 0.008 | | | |
| 186 | 0.011 | 0.007 | 0.007 | 0.056 | 0.023 | 0.106 |
| 187 | 0.020 | 0.013 | 0.015 | 0.069 | 0.057 | 0.592 |
| 188 | 0.016 | 0.011 | 0.015 | 0.032 | 0.016 | 0.414 |
| 189 | 0.015 | 0.014 | 0.015 | 0.017 | 0.018 | 0.539 |
| 190 | 0.018 | 0.010 | 0.015 | 0.062 | 0.048 | 0.382 |
| 191 | 0.099 | 0.087 | 0.132 | | | |
| 192 | 0.043 | 0.041 | 0.050 | 0.128 | 0.048 | 0.655 |
| 193 | 0.009 | 0.006 | 0.006 | 0.022 | 0.014 | 0.064 |
| 194 | 0.008 | 0.007 | 0.028 | 0.041 | 0.020 | 0.135 |

| Example No. | FGFR1 (FP) IC50 (uM) | FGFR2 (FP) IC50 (uM) | FGFR3 (Z-lyte) IC50 (uM) | KG1 IC50 (uM) | SNU-16 IC50 (uM) | RT-112 IC50 (uM) |
|---|---|---|---|---|---|---|
| 195 | 0.010 | 0.006 | 0.005 | 0.040 | 0.017 | 0.065 |
| 196 | 0.009 | 0.006 | 0.008 | 0.023 | 0.014 | 0.057 |
| 197 | 0.007 | 0.007 | 0.008 | 0.066 | 0.017 | 0.100 |
| 198 | 0.006 | 0.005 | 0.009 | 0.025 | 0.019 | 0.086 |
| 199 | 0.014 | 0.015 | 0.018 | 0.072 | 0.027 | 0.186 |
| 200 | 0.069 | 0.056 | 0.091 | 0.284 | 0.202 | 0.952 |
| 201 | 0.019 | 0.005 | 0.009 | 0.026 | 0.008 | 0.035 |
| 202 | 0.027 | 0.009 | 0.010 | | | |
| 203 | 0.007 | 0.005 | 0.007 | 0.009 | 0.008 | 0.014 |
| 204 | 0.009 | 0.007 | 0.009 | 0.005 | 0.010 | 0.053 |
| 205 | 0.005 | 0.003 | 0.004 | 0.002 | 0.002 | 0.005 |
| 206 | 0.005 | 0.004 | 0.005 | 0.010 | 0.007 | 0.007 |
| 207 | 0.018 | 0.009 | 0.021 | 0.084 | 0.053 | 0.163 |
| 208 | 0.271 | 0.132 | 0.227 | | | |
| 209 | 0.119 | 0.027 | 0.690 | | | |
| 210 | 0.024 | 0.013 | 0.177 | 0.166 | 0.115 | 0.305 |
| 211 | 0.040 | 0.016 | 0.042 | 0.103 | 0.155 | 0.078 |
| 212 | 0.026 | 0.016 | 0.080 | 0.059 | 0.014 | 0.057 |
| 213 | 0.011 | 0.008 | 0.014 | 0.011 | 0.023 | 0.037 |
| 214 | 0.067 | 0.025 | 0.019 | 0.006 | 0.027 | 0.090 |
| 215 | 0.044 | 0.020 | 0.065 | 0.026 | 0.072 | 0.127 |
| 216 | 0.010 | 0.007 | 0.011 | 0.024 | 0.020 | 0.132 |
| 217 | 0.045 | 0.016 | 0.029 | | | |
| 218 | 0.025 | 0.012 | 0.021 | 0.027 | 0.007 | 0.044 |
| 219 | 0.014 | 0.010 | 0.008 | | | |
| 220 | 0.017 | 0.010 | 0.008 | | | |
| 221 | 0.034 | 0.011 | 0.037 | 0.035 | 0.027 | 0.072 |
| 222 | 0.039 | 0.012 | 0.040 | 0.052 | 0.034 | 0.083 |
| 223 | 0.029 | 0.018 | 0.020 | 0.102 | 0.051 | 0.729 |
| 224 | 0.065 | 0.027 | 0.056 | 0.063 | 0.056 | 0.234 |
| 225 | 0.026 | 0.015 | 0.011 | 0.007 | 0.014 | 0.021 |
| 226 | 0.030 | 0.010 | 0.027 | 0.035 | 0.032 | 0.285 |
| 227 | 0.023 | 0.008 | 0.025 | 0.035 | 0.020 | 0.085 |
| 228 | 0.029 | 0.018 | 0.120 | 0.094 | 0.097 | 0.270 |
| 230 | 0.101 | 0.032 | 0.045 | 0.076 | 0.014 | 0.026 |
| 231 | 0.016 | 0.016 | 0.011 | 0.058 | 0.008 | 0.009 |
| 232 | 0.017 | 0.009 | 0.228 | 0.070 | 0.060 | 0.107 |
| 233 | 0.098 | 0.031 | 0.310 | 0.058 | 0.063 | 0.121 |
| 234 | 0.006 | 0.004 | 0.030 | 0.014 | 0.015 | 0.035 |
| 235 | 0.008 | 0.005 | 0.010 | 0.020 | 0.006 | 0.012 |
| 236 | 0.028 | 0.014 | 0.009 | | | |
| 237 | 0.066 | 0.027 | 0.029 | 0.079 | 0.042 | 0.134 |
| 238 | 0.023 | 0.020 | 0.013 | 0.038 | 0.028 | 0.023 |
| 240 | 0.034 | 0.023 | 0.023 | 0.023 | 0.039 | 0.056 |
| 241 | 0.031 | 0.021 | 0.019 | 0.162 | 0.031 | 0.112 |
| 242 | 0.018 | 0.010 | 0.013 | 0.010 | 0.014 | 0.032 |
| 243 | 0.020 | 0.009 | 0.009 | 0.069 | 0.006 | 0.015 |
| 244 | 0.010 | 0.010 | 0.013 | 0.362 | 0.115 | 0.585 |
| 245 | 0.016 | 0.017 | 0.018 | 0.533 | 0.136 | 0.581 |
| 246 | 0.015 | 0.006 | 0.007 | | | |
| 247 | 0.034 | 0.016 | 0.023 | 0.042 | 0.028 | 0.057 |
| 248 | 0.016 | 0.011 | 0.014 | 0.006 | 0.009 | 0.021 |
| 249 | 0.038 | 0.014 | 0.015 | 0.027 | 0.010 | 0.030 |
| 250 | 0.012 | 0.009 | 0.007 | 0.037 | 0.016 | 0.017 |
| 251 | 0.025 | 0.023 | 0.024 | 0.031 | 0.041 | 0.087 |
| 252 | 0.021 | 0.022 | 0.016 | 0.028 | 0.008 | 0.006 |
| 253 | 0.181 | 0.068 | 0.334 | | | |
| 254 | 0.012 | 0.006 | 0.008 | 0.008 | 0.002 | 0.014 |
| 255 | 0.008 | 0.005 | 0.011 | 0.062 | 0.017 | 0.021 |
| 256 | 0.100 | 0.040 | 0.039 | 0.202 | 0.022 | 0.057 |
| 257 | 0.029 | 0.012 | 0.019 | 0.103 | 0.019 | 0.066 |
| 258 | 0.028 | 0.015 | 0.017 | | | |
| 259 | 0.024 | 0.014 | 0.013 | 0.220 | 0.039 | 0.141 |
| 261 | 0.026 | 0.013 | 0.018 | 0.019 | 0.007 | 0.013 |
| 262 | 0.043 | 0.020 | 0.021 | 0.037 | 0.029 | 0.133 |
| 263 | 0.005 | 0.005 | 0.006 | 0.007 | 0.014 | 0.028 |
| 264 | 0.010 | 0.005 | 0.006 | 0.007 | 0.008 | 0.008 |
| 265 | 0.014 | 0.014 | 0.020 | 0.060 | 0.031 | 0.027 |
| 266 | 0.036 | 0.025 | 0.028 | 0.068 | 0.037 | 0.097 |
| 267 | 0.006 | 0.006 | 0.008 | 0.028 | 0.017 | 0.033 |
| 268 | 0.021 | 0.016 | 0.020 | 0.017 | 0.018 | 0.047 |
| 269 | 0.010 | 0.007 | 0.005 | 0.006 | 0.006 | 0.005 |
| 270 | 0.018 | 0.009 | 0.008 | 0.052 | 0.010 | 0.023 |
| 271 | 0.008 | 0.007 | 0.009 | 0.026 | 0.008 | 0.025 |
| 272 | 0.010 | 0.009 | 0.008 | 0.018 | 0.015 | 0.031 |
| 273 | 0.012 | 0.006 | 0.012 | 0.025 | 0.016 | 0.025 |
| 274 | 0.013 | 0.007 | 0.008 | 0.020 | 0.018 | 0.041 |
| 275 | 0.014 | 0.009 | 0.014 | 0.046 | 0.018 | 0.062 |
| 276 | 0.020 | 0.023 | 0.021 | 0.083 | 0.021 | 0.140 |
| 277 | 0.020 | 0.014 | 0.018 | 0.057 | 0.036 | 0.109 |
| 278 | 0.023 | 0.014 | 0.020 | 0.034 | 0.027 | 0.065 |
| 279 | 0.044 | 0.023 | 0.034 | 0.134 | 0.037 | 0.080 |
| 280 | 0.027 | 0.018 | 0.016 | 0.191 | 0.007 | 0.029 |
| 281 | 0.019 | 0.014 | 0.019 | 0.009 | 0.014 | 0.037 |
| 282 | 0.018 | 0.009 | 0.007 | 0.046 | 0.005 | 0.005 |
| 283 | 0.012 | 0.005 | 0.004 | 0.008 | 0.003 | 0.008 |
| 284 | 0.039 | 0.024 | 0.043 | 0.071 | 0.033 | 0.072 |
| 285 | 0.007 | 0.006 | 0.007 | 0.013 | 0.008 | 0.016 |
| 286 | 0.007 | 0.006 | 0.009 | 0.008 | 0.016 | 0.043 |
| 287 | 0.011 | 0.008 | 0.008 | 0.054 | 0.014 | 0.035 |
| 288 | 0.006 | 0.004 | 0.004 | 0.002 | 0.002 | 0.003 |
| 289 | 0.010 | 0.004 | 0.010 | | | |
| 290 | 0.010 | 0.007 | 0.011 | 0.006 | 0.011 | 0.012 |
| 291 | 0.017 | 0.018 | 0.017 | 0.015 | 0.017 | 0.027 |
| 292 | 0.013 | 0.011 | 0.014 | 0.046 | 0.017 | 0.070 |
| 293 | 0.018 | 0.008 | 0.011 | | | |
| 294 | 0.014 | 0.006 | 0.005 | | | |
| 295 | 0.013 | 0.013 | 0.019 | 0.040 | 0.104 | 0.337 |
| 298 | 0.009 | 0.008 | 0.013 | 0.008 | 0.014 | 0.015 |
| 299 | 0.006 | 0.006 | 0.008 | 0.007 | 0.011 | 0.015 |
| 301 | 0.009 | 0.006 | 0.010 | 0.024 | 0.011 | 0.037 |
| 302 | 0.012 | 0.007 | 0.009 | | | |
| 303 | 0.011 | 0.007 | 0.007 | 0.040 | 0.023 | 0.064 |
| 304 | 0.022 | 0.008 | 0.027 | | | |
| 306 | 0.029 | 0.012 | 0.026 | 0.100 | 0.023 | 0.016 |
| 307 | 0.019 | 0.017 | 0.021 | 0.005 | 0.0010 | 0.005 |

What is claimed is:

1. A compound of formula (I):

(I)

and/or a pharmaceutically acceptable salt thereof,
wherein
X is $CH_2$, Y is selected from $CH_2$, O, and $S(O)_2$; or X and Y together with the bond there-between form —CH=CH— or —C≡C—;
G is N or CH;
$R^1$ is aryl or heteroaryl, each of which is optionally substituted with one or more substituents independently selected from halo, $-NR^6R^7$, $-OR^8$, $-S(O)_n R^9$, $-(CH_2)_r-C(O)R^{10}$, $-CN$, $-C(O)NR^6R^7$, $-NR^6C(O)R^{10}$, $-NR^6S(O)_n R^9$, $-NR^6S(O)_n NR^{11}R^{12}$, $-NR^6C(O)OR^8$, $-NR^6C(O)NR^{11}R^{12}$, $-NO_2$, $-S(O)_n NR^6R^7$, oxo, optionally substituted alkyl, $-(CH_2)_p$-optionally substituted cycloalkyl, $-(CH_2)_m$-optionally substituted heterocyclyl, $-(CH_2)_q$-optionally substituted heteroaryl, optionally substituted alkenyl, and optionally substituted alkynyl;

R² is independently chosen from optionally substituted $C_1$-$C_6$ alkyl, optionally substituted $C_1$-$C_6$ alkoxy, and optionally substituted $C_3$-$C_8$ cycloalkyl;

R³, R⁴ are independently chosen from hydrogen, halogen, —CN, and optionally substituted $C_1$-$C_6$ alkyl, R⁵ is $C_1$-$C_6$ alkyl, or R³ and R⁵ together with the O atom to which R⁵ is attached and the bond there-between form a 5- or 6-membered oxy-containing heterocyclic ring;

n is 1 or 2;

m, p, q and r are independently chosen from 0, 1, 2, 3, 4, 5, and 6;

R⁶, R⁷, R⁸, R⁹, R¹⁰, R¹¹ and R¹² are independently selected from hydrogen, alkyl, cycloalkyl, aryl, heteroaryl, and heterocyclyl, each of which except for hydrogen, is optionally substituted with one or more substituents independently selected from halo, hydroxyl, mercapto, oxo, alkyl, cycloalkyl, heterocyclyl, optionally substituted amino, and optionally substituted amide, wherein each optionally substituted group above for which the substituent(s) is (are) not specifically designated, is unsubstituted or independently substituted with one or more substituents independently chosen from $C_1$-$C_6$ alkyl, $C_2$-$C_6$ alkenyl, $C_2$-$C_6$ alkynyl, cycloalkyl, aryl, heterocyclyl, heteroaryl, aryl-$C_1$-$C_6$ alkyl-, heteroaryl-$C_1$-$C_6$ alkyl-, $C_1$-$C_6$ haloalkyl-, —O$C_1$-$C_6$ alkyl, —O$C_2$-$C_6$ alkenyl, —O$C_1$-$C_6$ alkylphenyl, —$C_1$-$C_6$ alkyl-OH, —$C_1$-$C_6$ alkyl-SH, —$C_1$-$C_6$ alkyl-O—$C_1$-$C_6$ alkyl, —O$C_1$-$C_6$ haloalkyl, halo, —OH, mercapto, —NH₂, —$C_1$-$C_6$ alkyl-NH₂, H₂, —N($C_1$-$C_6$ alkyl)₂, —NH($C_1$-$C_6$ alkyl), —N($C_1$-$C_6$ alkyl)($C_1$-$C_6$ alkylphenyl), —NH($C_1$-$C_6$ alkylphenyl), cyano, nitro, oxo, —C(O)—OH, —C(O)O$C_1$-$C_6$ alkyl, —CON($C_1$-$C_6$ alkyl)₂, —CONH($C_1$-$C_6$ alkyl), —CONH₂, —NHC(O)($C_1$-$C_6$ alkyl), —NHC(O)(phenyl), —N($C_1$-$C_6$ alkyl)C(O)($C_1$-$C_6$ alkyl), —N($C_1$-$C_6$ alkyl)C(O)(phenyl), —C(O)$C_1$-$C_6$ alkyl, —C(O)$C_1$-$C_6$ alkylphenyl, —C(O)$C_1$-$C_6$ haloalkyl, —OC(O)$C_1$-$C_6$ alkyl, —S(O)₂—$C_1$-$C_6$ alkyl, —S(O)—$C_1$-$C_6$ alkyl, —S(O)₂-phenyl, —S(O)₂—$C_1$-$C_6$ haloalkyl, —S(O)₂NH₂, —S(O)₂NH($C_1$-$C_6$ alkyl), —S(O)₂NH(phenyl), —NHS(O)₂($C_1$-$C_6$ alkyl), —NHS(O)₂(phenyl), and —NHS(O)₂($C_1$-$C_6$ haloalkyl).

2. The compound of formula (I) according to claim 1, and/or a pharmaceutically acceptable salt thereof, wherein each optionally substituted group for which the substituent(s) is (are) not specifically designated is unsubstituted or independently substituted with one or more substituents independently chosen from hydroxyl, mercapto, halo, $C_1$-$C_6$ alkyl, $C_2$-$C_6$ alkenyl, $C_2$-$C_6$ alkynyl, —O$C_1$—C alkyl, —NH₂, —N($C_1$-$C_6$ alkyl)₂, —NH($C_1$-$C_6$ alkyl), cyano, nitro, oxo, —S(O)₂—$C_1$-$C_6$ alkyl, —S(O)—$C_1$-$C_6$ alkyl, —S(O)₂—$C_1$-$C_6$ haloalkyl, —C(O)—OH, —$C_1$-$C_6$ alkyl-OH, —$C_1$-$C_6$ alkyl-SH, and heterocyclyl.

3. The compound of formula (I) according to claim 1 or 2, and/or a pharmaceutically acceptable salt thereof, wherein R¹ is aryl or heteroaryl, each of which is optionally substituted by one or more substituents independently selected from:

(1) halo;
(2) oxo;
(3) optionally substituted alkyl;
(4) —(CH₂)$_m$-optionally substituted heterocyclyl;
(5) —(CH₂)$_p$-optionally substituted cycloalkyl;
(6) —(CH₂)$_q$-optionally substituted heteroaryl;
(7) —S(O)$_n$R⁹;
(8) —(CH₂)$_r$—C(O)R¹⁰;
(9) optionally substituted alkenyl;
(10) optionally substituted alkynyl; and
(11) —OR⁸;

wherein n is 1 or 2; m, p, q and r are independently chosen from 0, 1, 2, 3, 4, 5, and 6; R⁸, R⁹ and R¹⁰ are independently selected from hydrogen, alkyl, and heterocyclyl, each of which except for hydrogen, is optionally substituted with one or more substituents independently selected from alkyl, oxo, and heterocyclyl;

wherein "optionally substituted alkyl", "optionally substituted heterocyclyl", "optionally substituted cycloalkyl", "optionally substituted heteroaryl", "optionally substituted alkenyl" and "optionally substituted alkynyl" in R¹ above are unsubstituted or independently substituted with one or more substituents independently chosen from hydroxyl, mercapto, halo, $C_1$-$C_6$ alkyl, $C_2$-$C_6$ alkenyl, $C_2$-$C_6$ alkynyl, —O$C_1$-$C_6$ alkyl, —NH₂, —N($C_1$-$C_6$ alkyl)₂, —NH($C_1$-$C_6$ alkyl), cyano, nitro, oxo, —S(O)₂—$C_{1-6}$ alkyl, —S(O)—$C_1$-$C_6$ alkyl, —S(O)₂—$C_1$-$C_6$ haloalkyl, —C(O)—OH, —$C_1$-$C_6$ alkyl-OH, —$C_1$-$C_6$ alkyl-SH, and heterocyclyl.

4. The compound of formula (I) according to claim 3, and/or a pharmaceutically acceptable salt thereof, wherein R¹ is aryl or heteroaryl, each of which is optionally substituted with one or more substituents independently selected from:

(1) halo;
(2) oxo;
(3) alkyl optionally substituted with one or more substituents independently selected from hydroxyl, mercapto, halo, —O$C_1$-$C_6$ alkyl, —NH₂, —N($C_1$-$C_6$ alkyl)₂, —NH($C_1$-$C_6$ alkyl), cyano, nitro, —S(O)₂—$C_1$-$C_6$ alkyl, —S(O)—$C_1$-$C_6$ alkyl, and —C(O)—OH;
(4) —(CH₂)$_m$-heterocyclyl optionally substituted with one or more substituents independently selected from $C_1$-$C_6$ alkyl, —$C_1$-$C_6$ alkyl-OH, —$C_1$-$C_6$ alkyl-SH and oxo, wherein m is 0, 1, 2, 3, 4, 5 or 6;
(5) —(CH₂)$_p$-unsubstituted cycloalkyl, wherein p is 0, 1, 2, 3, 4, 5 or 6;
(6) —(CH₂)$_q$-heteroaryl optionally substituted with one or more substituents independently selected from $C_1$-$C_6$ alkyl, wherein q is 0, 1, 2, 3, 4, 5 or 6;
(7) —S(O)$_n$R⁹, wherein R⁹ is $C_1$-$C_6$ alkyl, and n is 1 or 2;
(8) —(CH₂)$_r$—C(O)R¹⁰, wherein R¹⁰ is heterocyclyl optionally substituted with one or more substituents independently selected from $C_1$-$C_6$ alkyl and oxo, wherein r is 0, 1, 2, 3, 4, 5 or 6;
(9) unsubstituted $C_2$-$C_6$ alkenyl;
(10) unsubstituted $C_2$-$C_6$ alkynyl; and
(11) —OR⁸, wherein R⁸ is selected from hydrogen and alkyl optionally substituted with one or more substituents independently selected from heterocyclyl.

5. The compound of formula (I) according to claim 1, and/or a pharmaceutically acceptable salt thereof, wherein R¹ is aryl or heteroaryl, each of which is optionally substituted with one or more substituents independently selected from:

(1) halo;
(2) —NR⁶R⁷, wherein R⁶ and R⁷ are independently selected from hydrogen and $C_1$-$C_6$ alkyl optionally substituted with amino which is optionally substituted with $C_1$-$C_6$ alkyl;
(3) —OR⁸, wherein R⁸ is selected from hydrogen and $C_1$-$C_6$ alkyl optionally substituted with one or more substituents independently selected from: heterocyclyl optionally substituted with —OH or mercapto, and amino optionally substituted with $C_1$-$C_6$ alkyl, (4) —S(O)$_n$R$^9$, wherein R$^9$ is $C_1$-$C_6$ alkyl, and n is 1 or 2;

(5) —(CH$_2$)$_r$—C(O)R$^{10}$, wherein R$^{10}$ is $C_1$-$C_6$ alkyl, or heterocyclyl optionally substituted with one or more substituents independently selected from $C_1$-$C_6$ alkyl and oxo, wherein r is 0, 1, 2, 3, 4, 5 or 6;

(6) —CN;

(7) —C(O)NR$^6$R$^7$, wherein R$^6$ and R$^7$ are independently selected from hydrogen and $C_1$-$C_6$ alkyl optionally substituted with amino which is optionally substituted with $C_1$-$C_6$ alkyl;

(8) —NR$^6$C(O)R$^{10}$, wherein R$^6$ is H, and R$^{10}$ is $C_1$-$C_6$ alkyl;

(9) oxo;

(10) alkyl optionally substituted with one or more substituents independently selected from hydroxyl, mercapto, halo, —O$C_1$-$C_6$ alkyl, —NH$_2$, —N($C_1$-$C_6$ alkyl)$_2$, —NH($C_1$-$C_6$ alkyl), cyano, nitro, —S(O)$_2$—$C_{1-6}$ alkyl, —S(O)—$C_1$-$C_6$ alkyl, —C(O)—OH;

(11) —(CH$_2$)$_p$-unsubstituted cycloalkyl, wherein p is 0, 1, 2, 3, 4, 5 or 6;

(12) —(CH$_2$)$_m$-heterocyclyl optionally substituted with one or more substituents independently selected from $C_1$-$C_6$ alkyl, $C_3$-$C_8$ cycloalkyl, —$C_1$-$C_6$ alkyl-OH, —$C_1$-$C_6$ alkyl-SH, —$C_1$-$C_6$ alkyl-O—$C_1$-$C_6$ alkyl, —NH$_2$, —N($C_1$-$C_6$alkyl)$_2$, —NH($C_1$-$C_6$alkyl), oxo, —C(O)$C_{1-6}$ alkyl, wherein m is 0, 1, 2, 3, 4, 5 or 6;

(13) —(CH$_2$)$_q$-heteroaryl optionally substituted with one or more substituents independently selected from $C_1$-$C_6$ alkyl, wherein q is 0, 1, 2, 3, 4, 5 or 6;

(14) unsubstituted $C_2$-$C_6$ alkenyl; and

(15) unsubstituted $C_2$-$C_6$ alkynyl.

6. The compound of formula (I) according to claim 5, and/or a pharmaceutically acceptable salt thereof, wherein R$^1$ is a radical of the ring or ring system chosen from

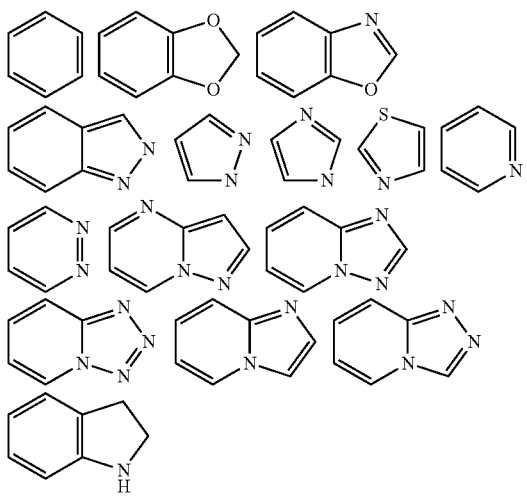

each of which is optionally substituted as defined in claim 5.

7. The compound of formula (I) according to claim 5, and/or a pharmaceutically acceptable salt thereof, wherein R$^1$ is chosen from

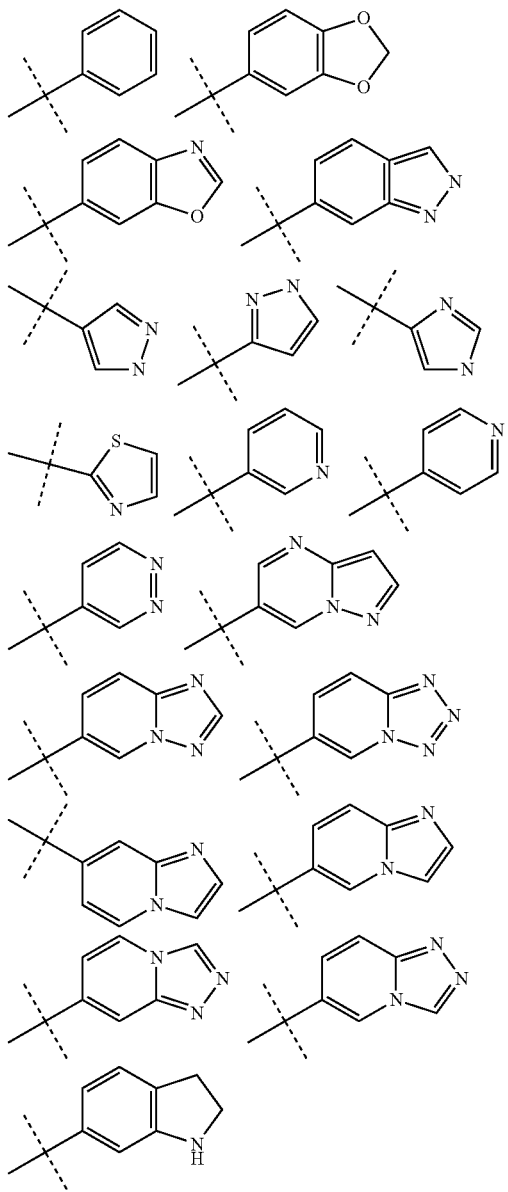

each of which is optionally substituted as defined in claim 5.

8. The compound of formula (I) according to claim 1, and/or a pharmaceutically acceptable salt thereof, wherein R$^8$ is hydrogen, or $C_1$-$C_6$ alkyl optionally substituted with heterocyclyl.

9. The compound of formula (I) according to claim 1, and/or a pharmaceutically acceptable salt thereof, wherein R$^{10}$ is heterocyclyl optionally substituted with one or more substituents independently selected from $C_1$-$C_6$ alkyl and oxo.

10. The compound of formula (I) according to claim 1, and/or a pharmaceutically acceptable salt thereof, wherein R$^1$ is aryl optionally substituted by one or more substituents independently selected from: (1) halo; (2) alkyl optionally substituted with —C(O)—OH; (3) —(CH$_2$)$_m$-heterocyclyl optionally substituted with one or more substituents independently selected from $C_1$-$C_6$ alkyl, —$C_1$-$C_6$ alkyl-OH, —$C_1$-$C_6$ alkyl-SH and oxo, wherein m is 0, 1, 2, 3, 4, 5 or 6; (4) —(CH$_2$)$_q$-heteroaryl optionally substituted with one or more substituents independently selected from $C_1$-$C_6$ alkyl, wherein q is 0; (5) —$(CH_2)_r$—$C(O)R^{10}$, wherein $R^{10}$ is heterocyclyl optionally substituted with one or more substituents independently selected from $C_1$-$C_6$ alkyl and oxo, wherein r is 0; (6) unsubstituted $C_2$-$C_6$ alkenyl; (7) unsubstituted $C_2$-$C_6$ alkynyl; and (8) —$OR^8$, wherein $R^8$ is selected from hydrogen, and alkyl optionally substituted with one or more substituents independently selected from heterocyclyl.

11. The compound of formula (I) according to claim 1, and/or a pharmaceutically acceptable salt thereof, wherein $R^1$ is phenyl substituted by piperazinyl, which is optionally substituted by one or more $C_1$-$C_6$ alkyl or $C_3$-$C_8$ cycloalkyl.

12. The compound of formula (I) according to claim 11, wherein $R^1$ is phenyl substituted by piperazinyl, which is optionally substituted by one or more $C_1$-$C_6$ alkyl.

13. The compound of formula (I) according to claim 1, and/or a pharmaceutically acceptable salt thereof, wherein $R^1$ is pyrazolyl, which is optionally substituted with one or more substituents selected from:
(1) alkyl optionally substituted with one or more substituents independently selected from hydroxyl, mercapto, halo, —$OC_1$-$C_6$ alkyl, —$NH_2$, —$N(C_1$-$C_6$ alkyl)$_2$, —$NH(C_1$-$C_6$ alkyl), —$S(O)_2$—$C_1$-$C_6$ alkyl, and —$S(O)$—$C_1$-$C_6$ alkyl;
(2) —$(CH_2)_m$-heterocyclyl optionally substituted with one or more substituents independently selected from $C_1$-$C_6$ alkyl, wherein m is 0, 1, 2, 3, 4, 5 or 6;
(3) —$(CH_2)_p$-unsubstituted cycloalkyl, wherein p is 0, 1, 2, 3, 4, 5 or 6;
(4) —$(CH_2)_q$-heteroaryl optionally substituted with one or more substituents independently selected from $C_1$-$C_6$ alkyl, wherein q is 0, 1, 2, 3, 4, 5 or 6;
(5) —$S(O)_nR^9$, wherein $R^9$ is $C_1$-$C_6$ alkyl, and n is 1 or 2; and
(6) —$(CH_2)_r$—$C(O)R^{10}$, wherein $R^{10}$ is heterocyclyl optionally substituted with one or more substituents independently selected from $C_1$-$C_6$ alkyl and oxo, wherein r is 0, 1, 2, 3, 4, 5 or 6.

14. The compound of formula (I) according to claim 1, and/or a pharmaceutically acceptable salt thereof, wherein $R^2$ is chosen from $C_1$-$C_6$ alkyl, $C_1$-$C_6$ alkoxy optionally substituted with hydroxyl, and $C_3$-$C_8$ cycloalkyl.

15. The compound of formula (I) according to claim 14, and/or a pharmaceutically acceptable salt thereof, wherein $R^2$ is methyl, ethyl, methoxy, ethoxy substituted with hydroxyl, isopropoxy or cyclopropyl.

16. The compound of formula (I) according to claim 1, and/or a pharmaceutically acceptable salt thereof, wherein $R^3$, $R^4$ are independently chosen from hydrogen, halogen, —CN, and unsubstituted $C_1$-$C_6$ alkyl, $R^5$ is $C_1$-$C_6$ alkyl, or $R^3$ and $R^5$ together with the O atom to which $R^5$ is attached and the bond there-between form a 5- or 6-membered oxy-containing heterocyclic ring.

17. The compound of formula (I) according to claim 1, and/or a pharmaceutically acceptable salt thereof, wherein $R^4$ is hydrogen, and $R^3$ and $R^5$ together with the O atom to which $R^5$ is attached and the bond there-between form a furan or dihydrofuran ring.

18. A compound selected from:

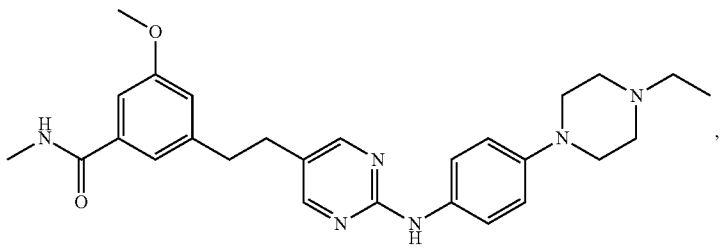

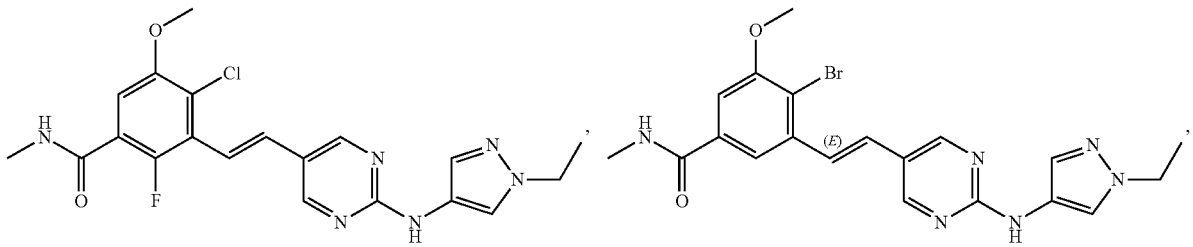

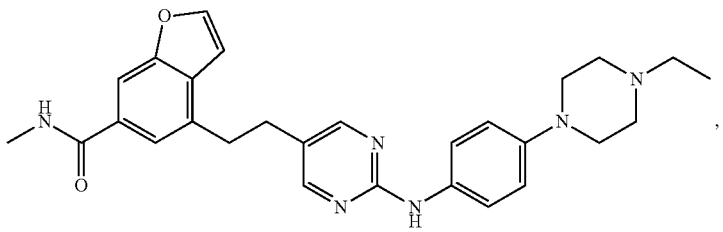

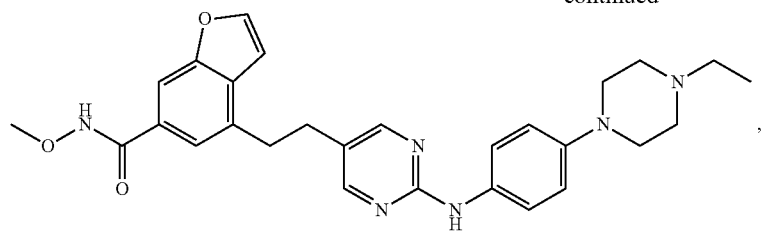,
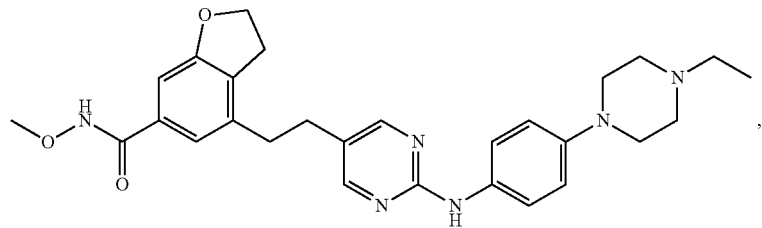,
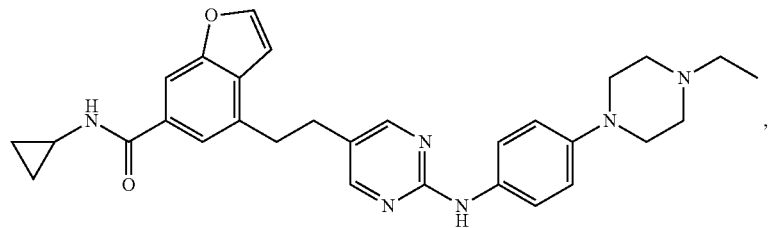,
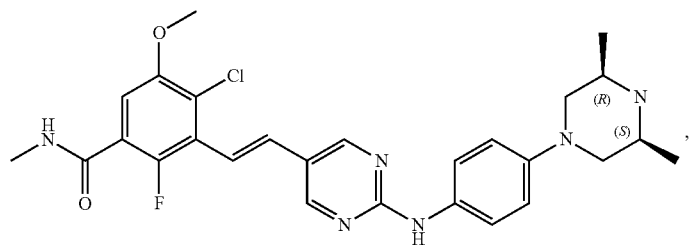,
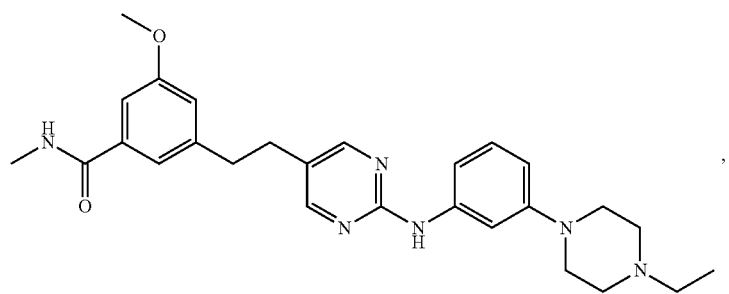,
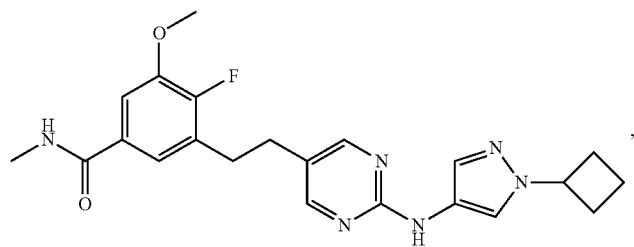,
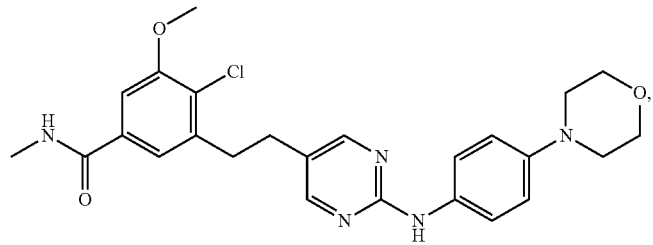, -continued
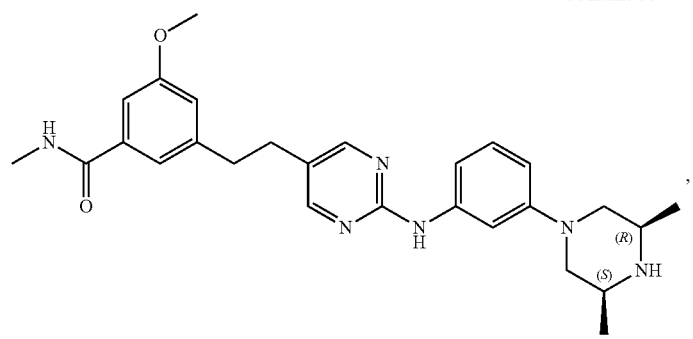
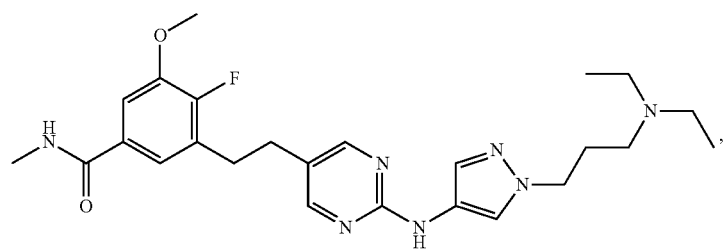
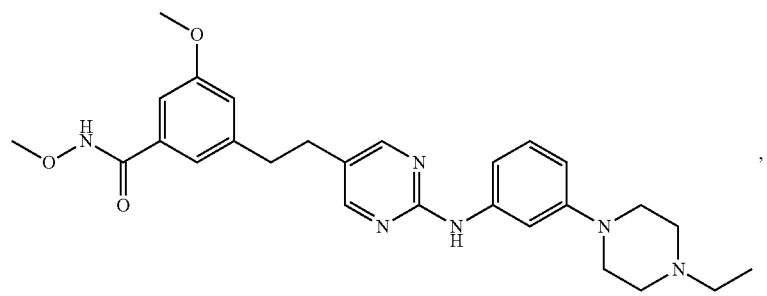
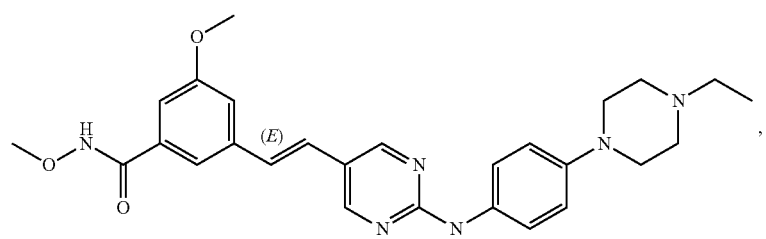
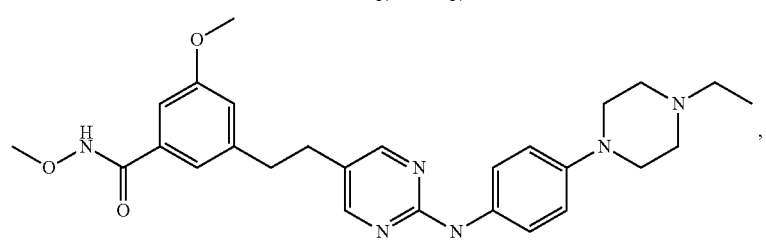
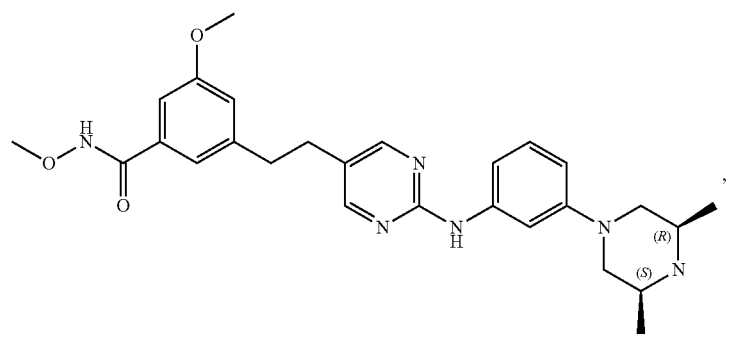

-continued
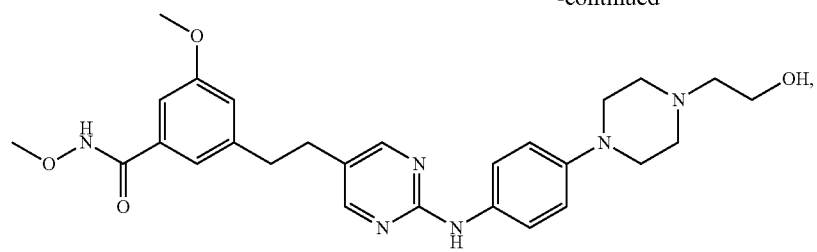
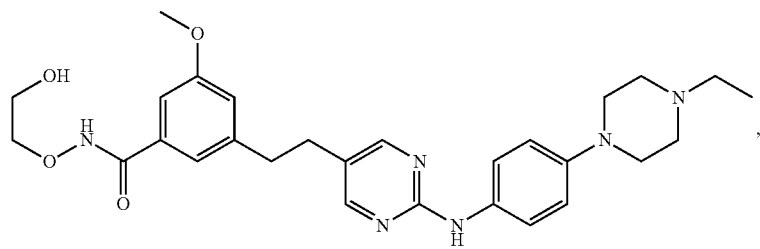
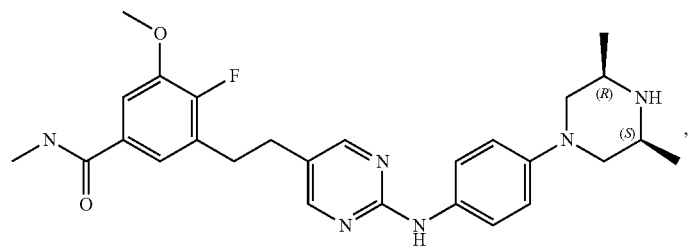
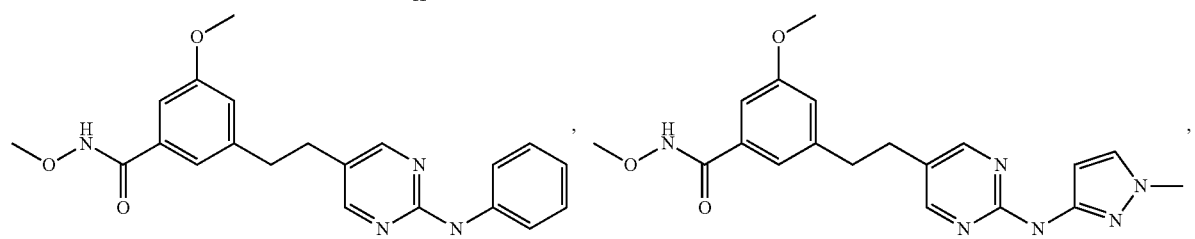
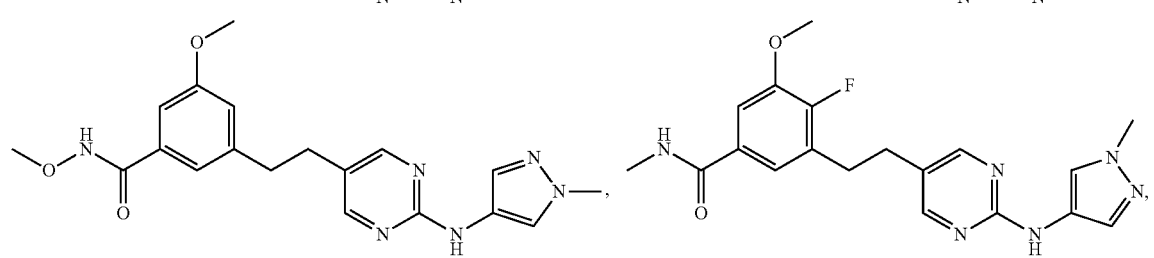
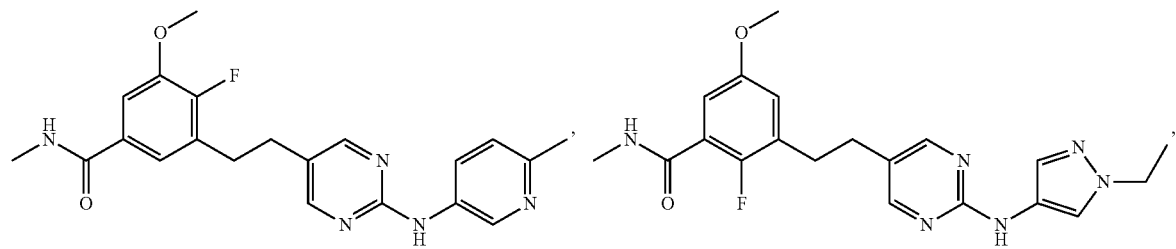
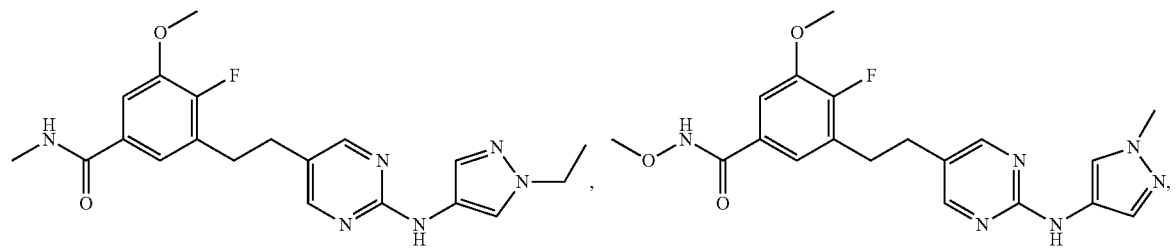

-continued
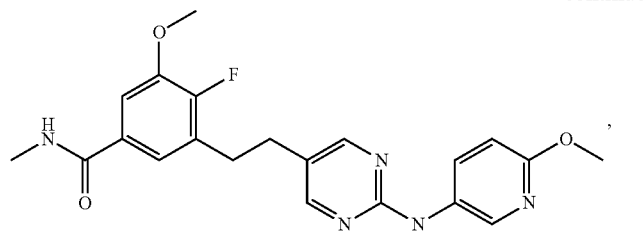
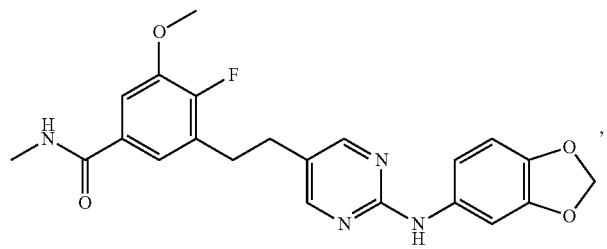
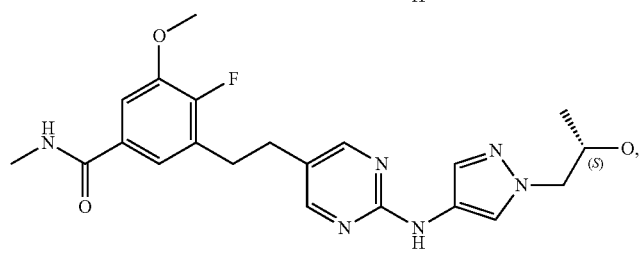
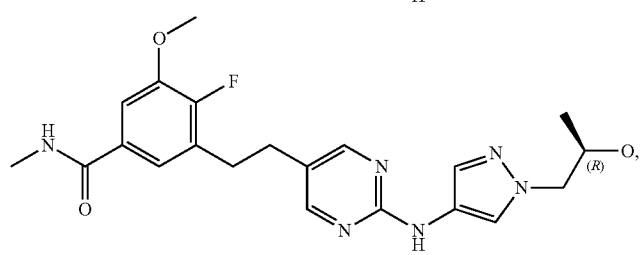
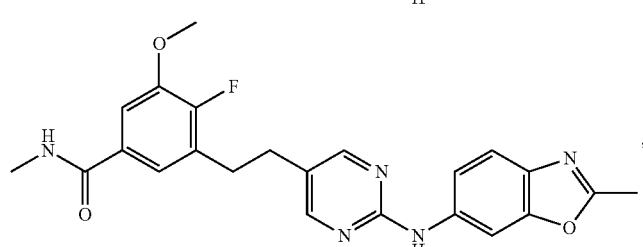
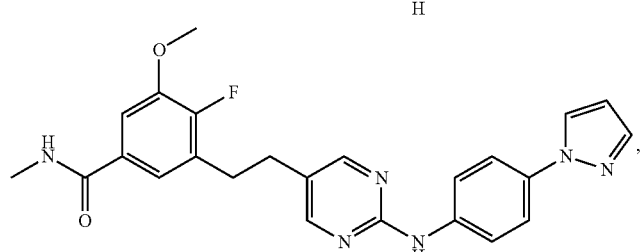
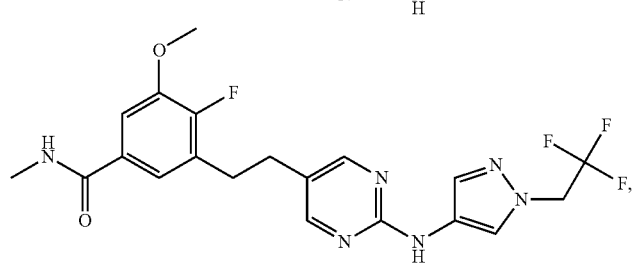

-continued
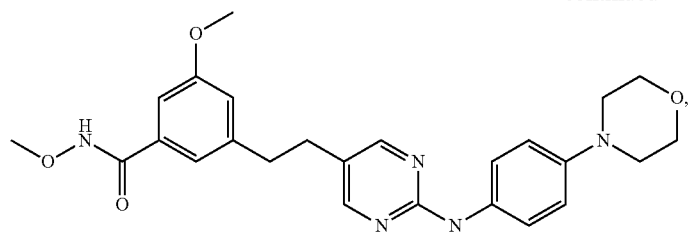
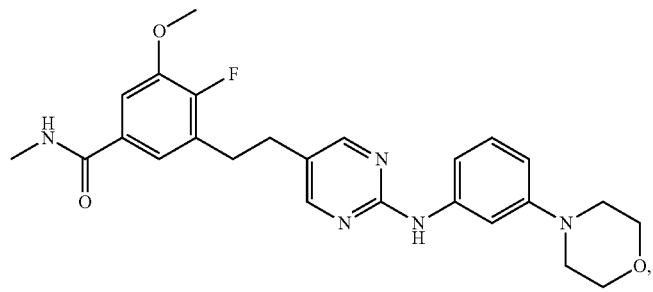
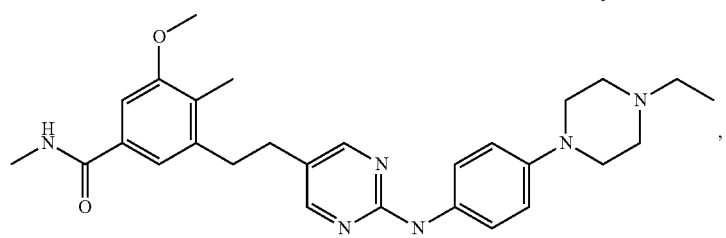
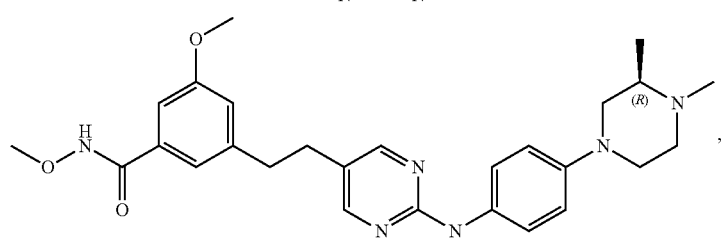
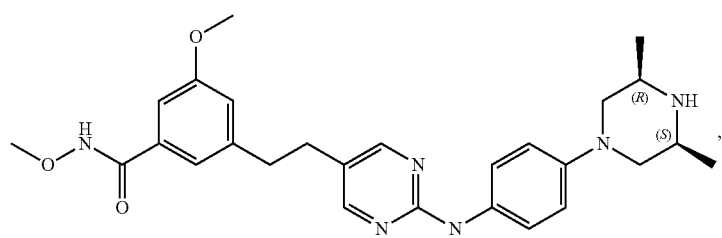
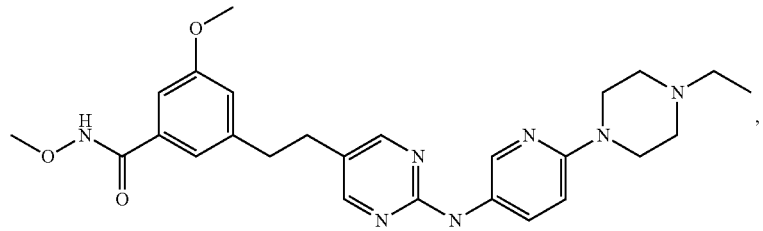
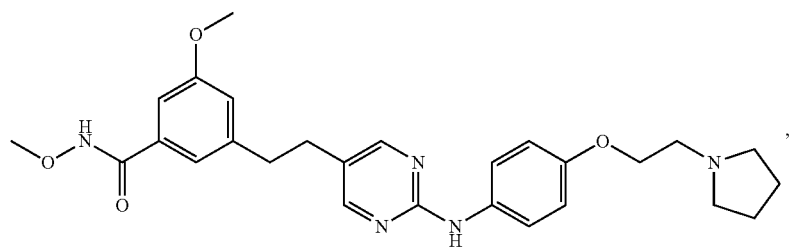

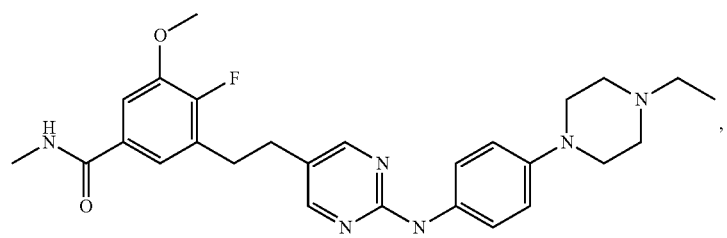,
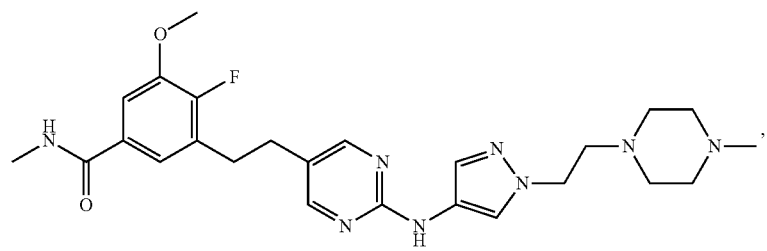,
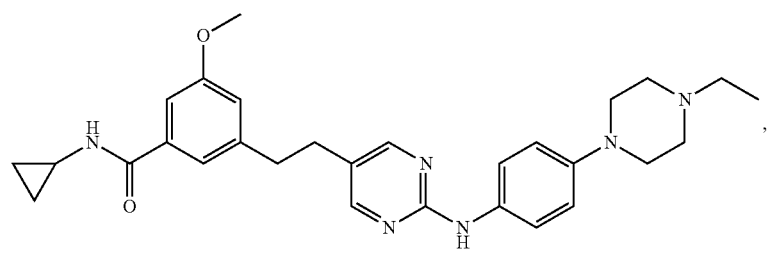,
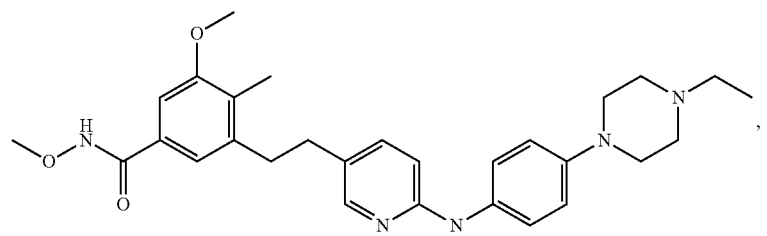,
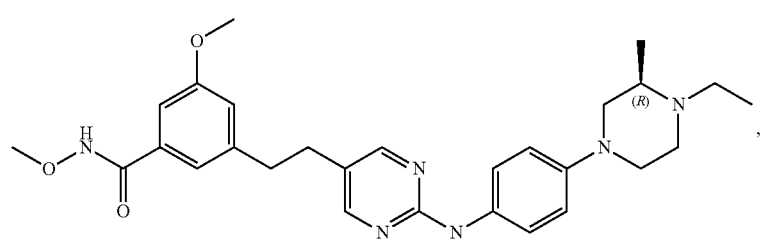,
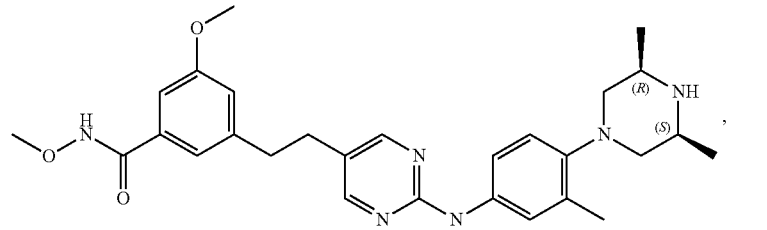,
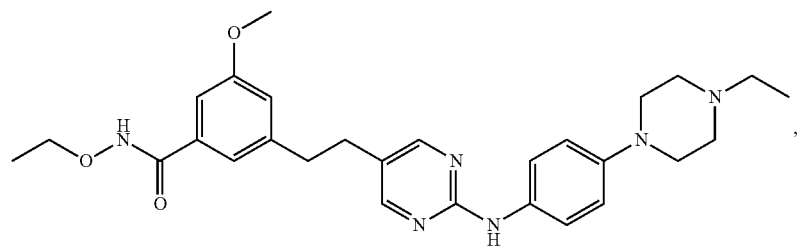, -continued
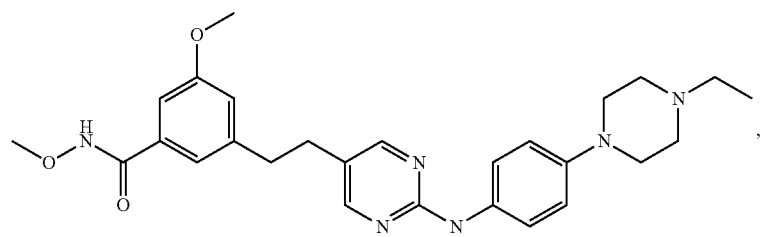
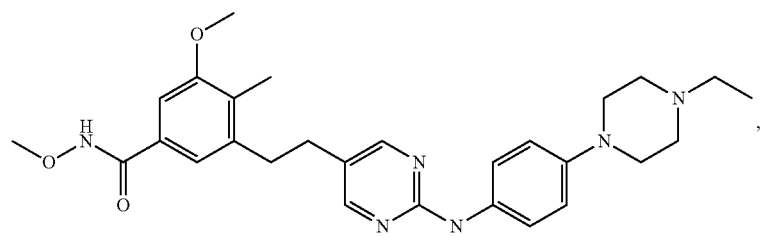
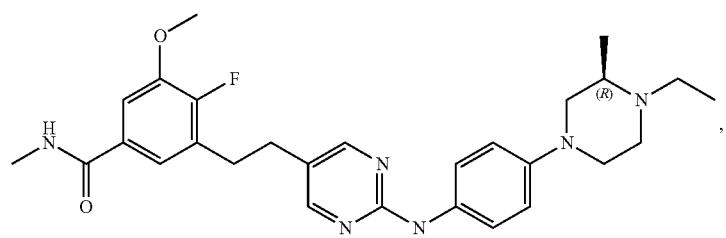
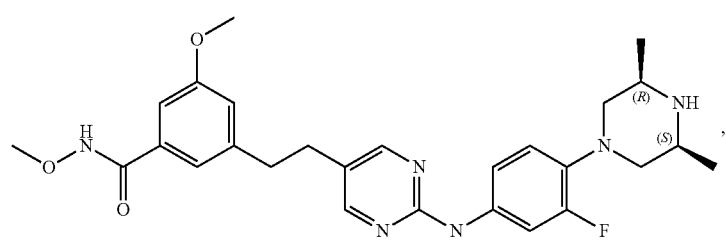
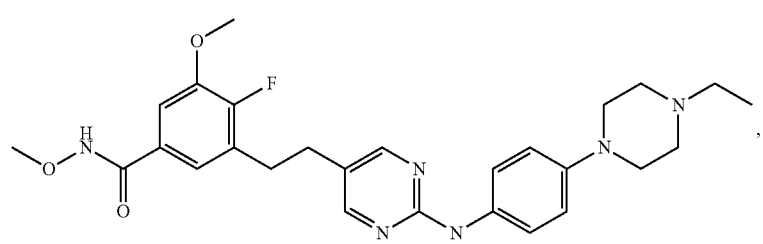
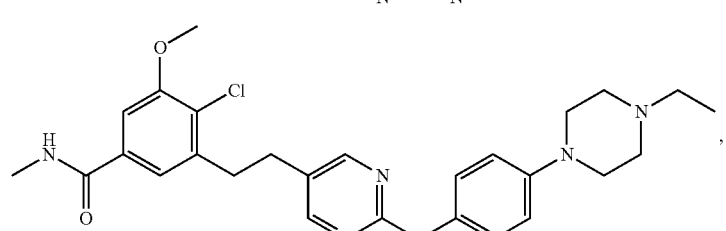
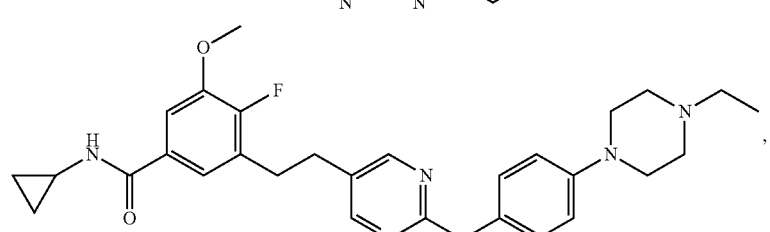

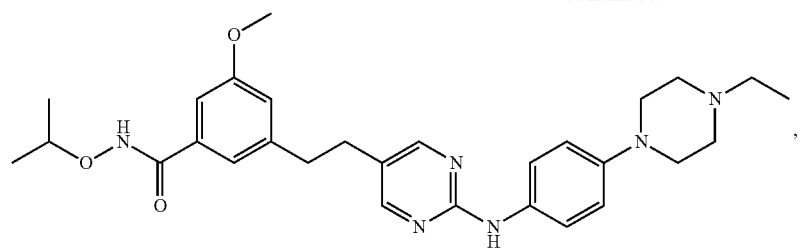
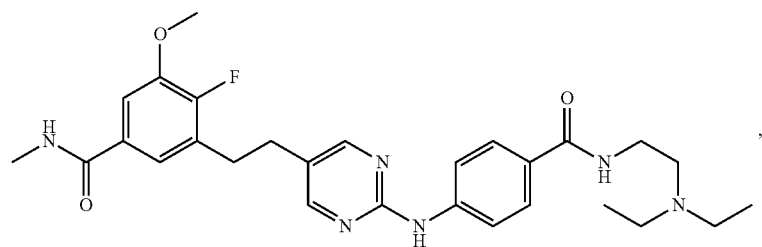
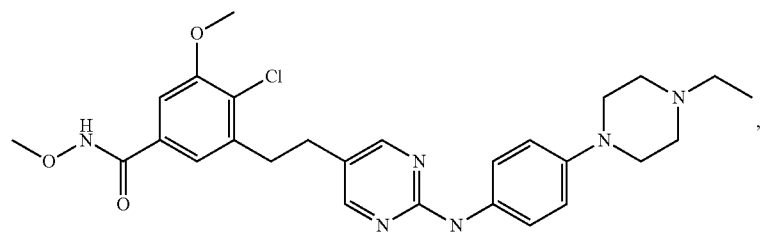
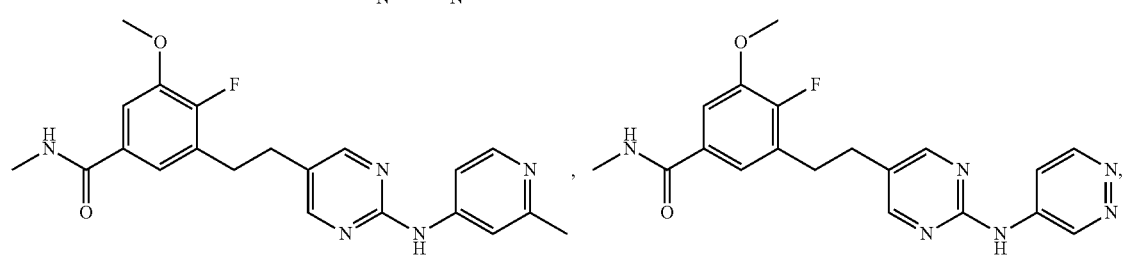
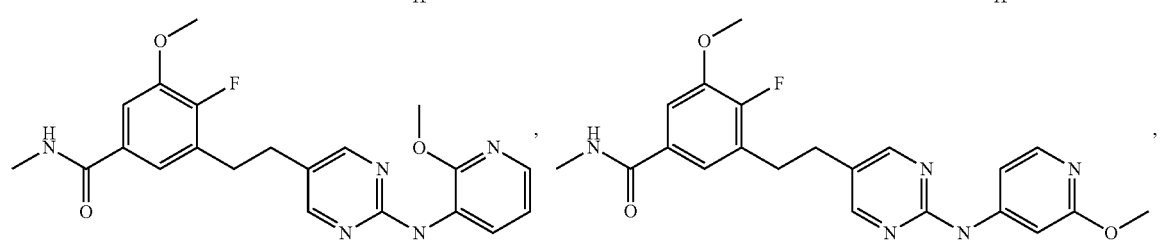
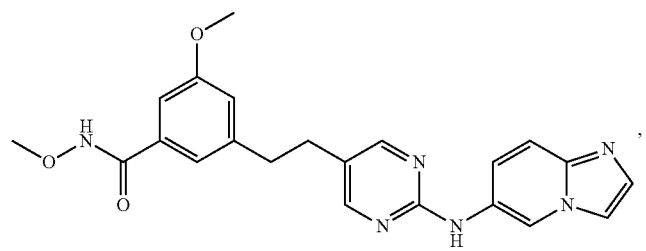
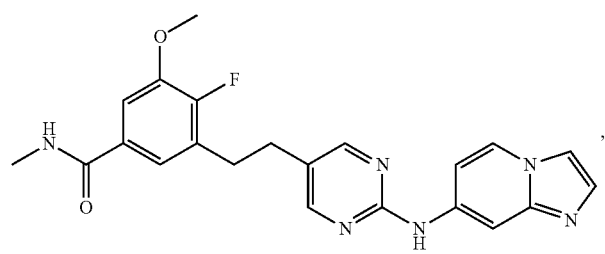

-continued
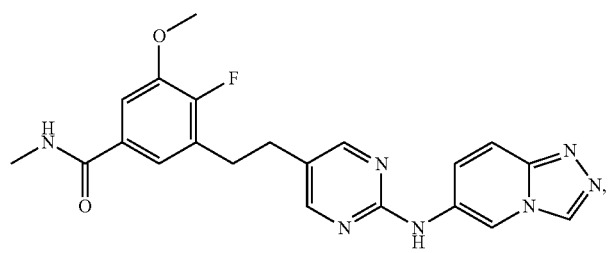
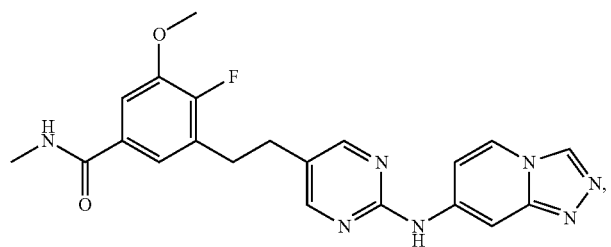
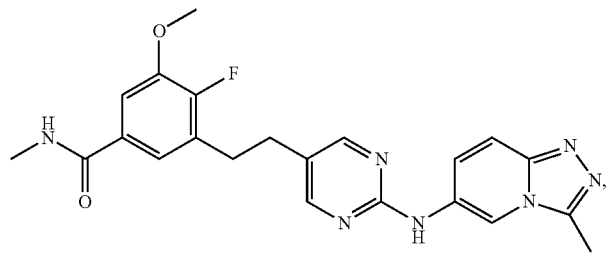
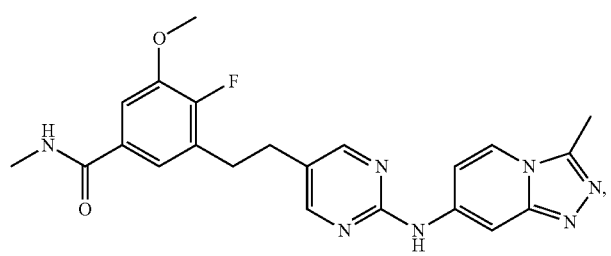
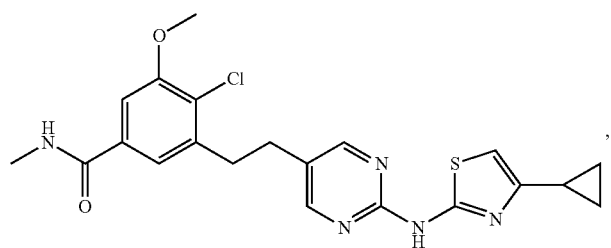
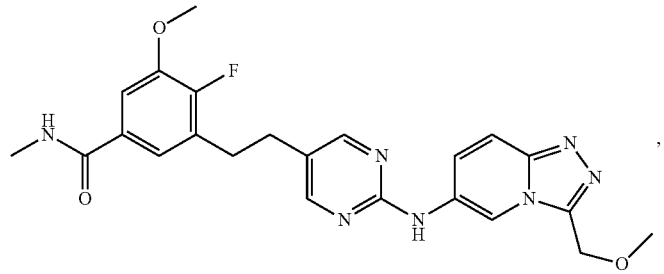

-continued
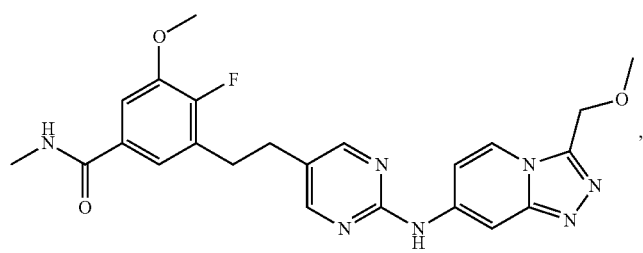
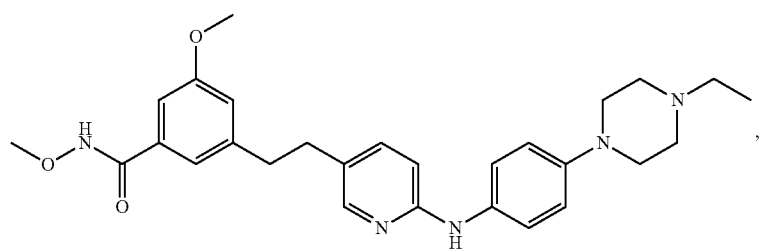
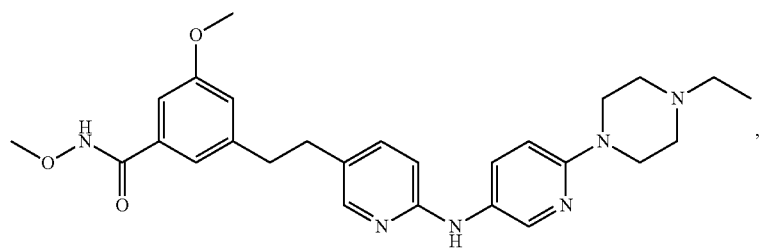
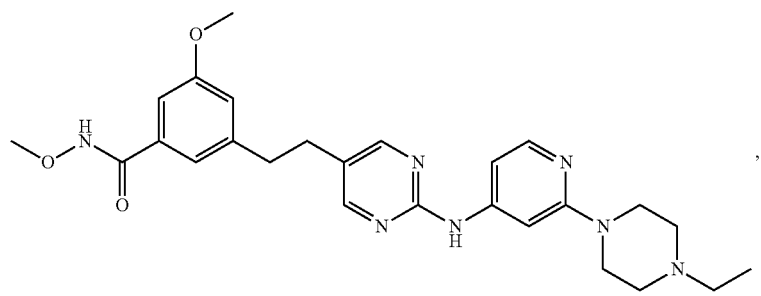
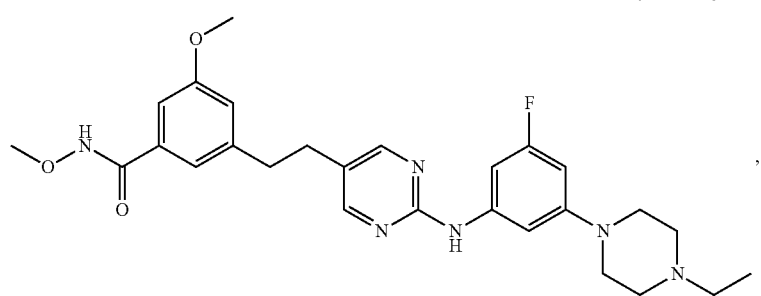
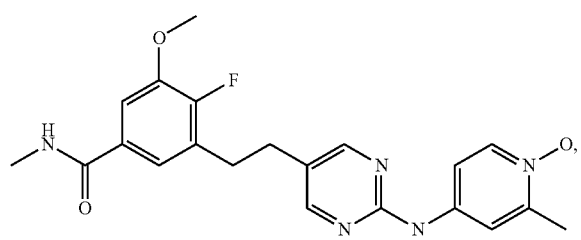

-continued
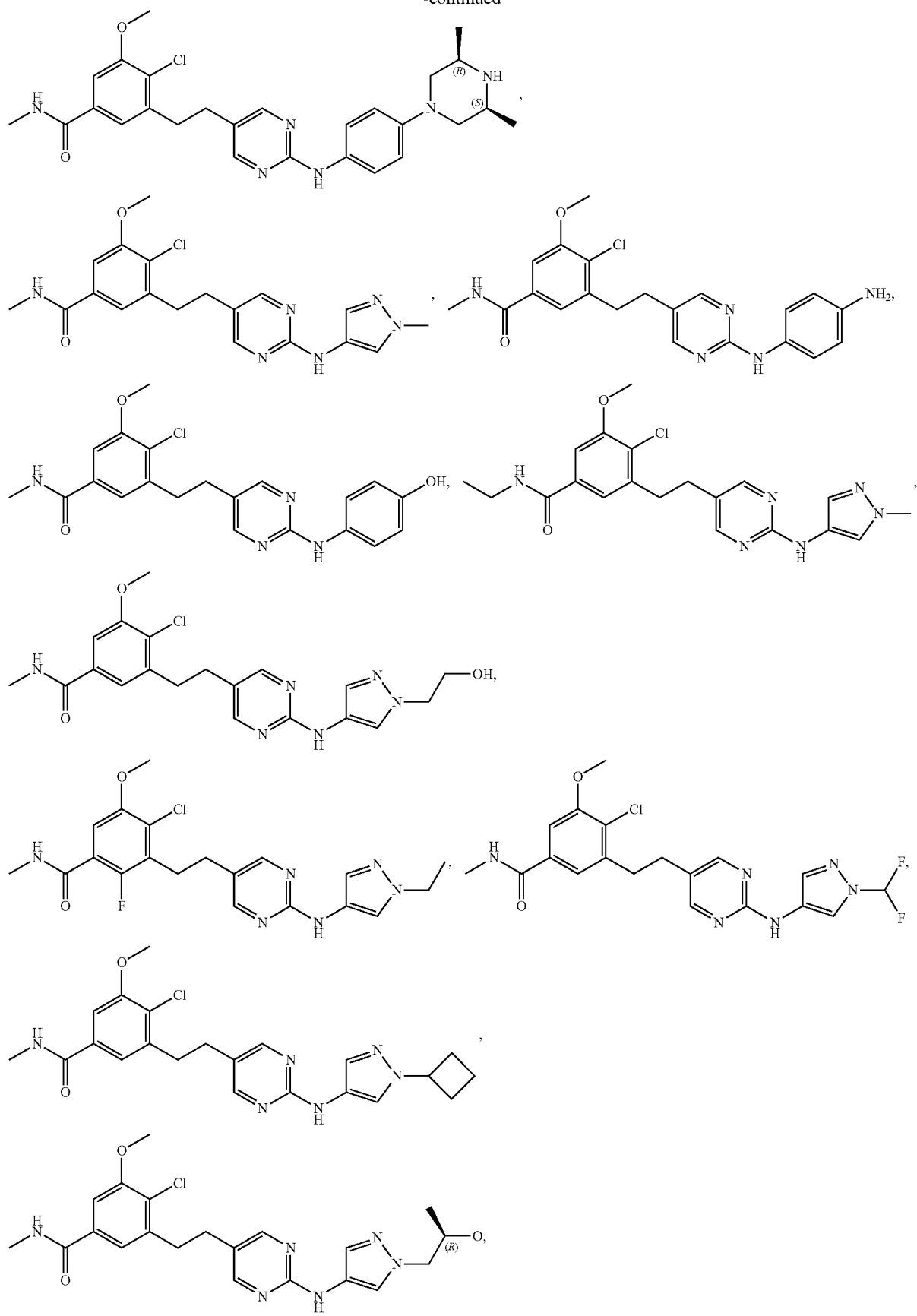

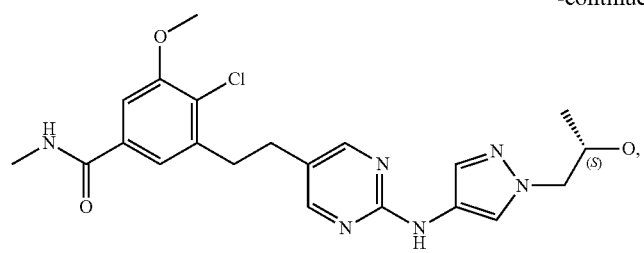,
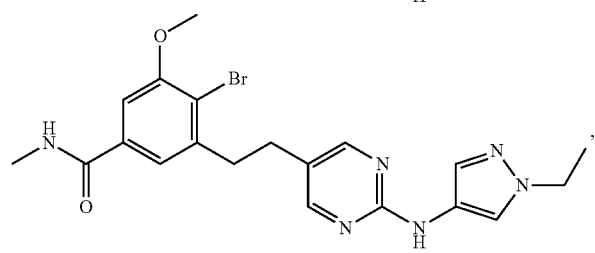,
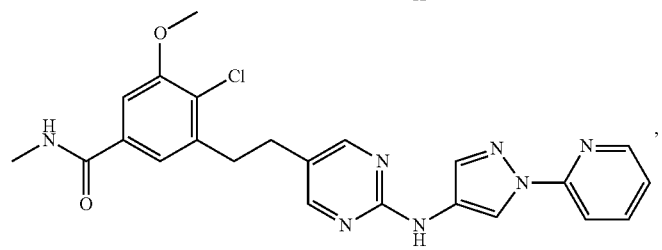,
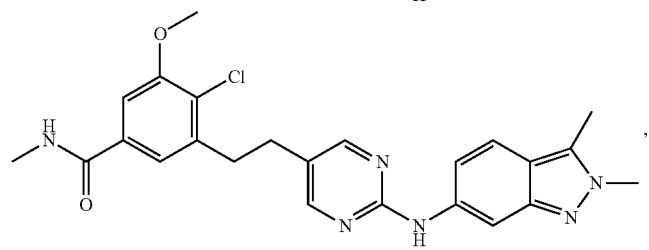,
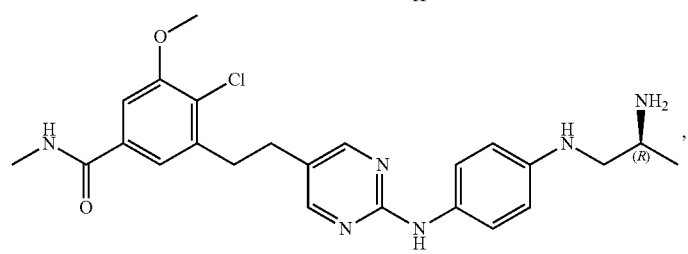,
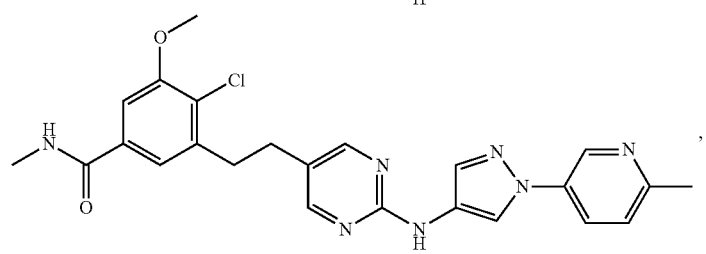,
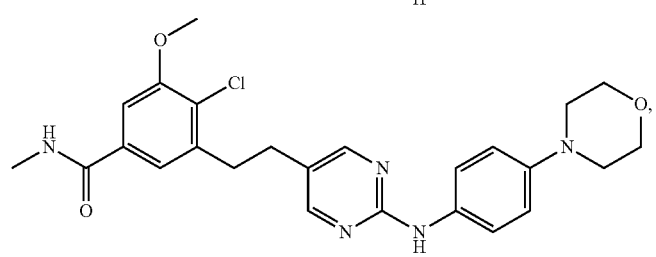, -continued
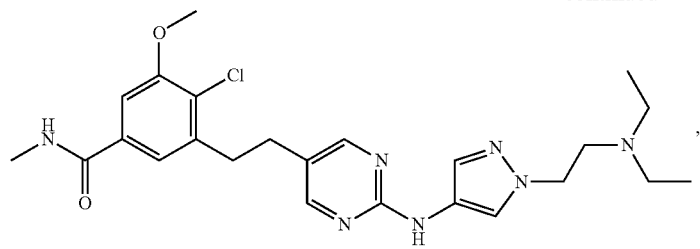
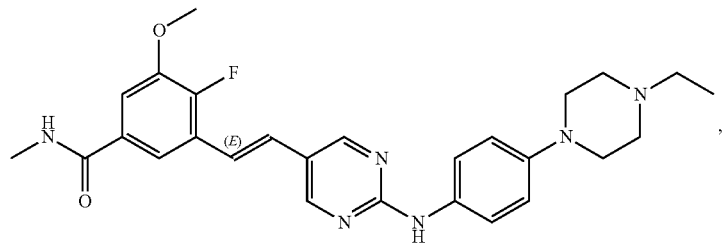
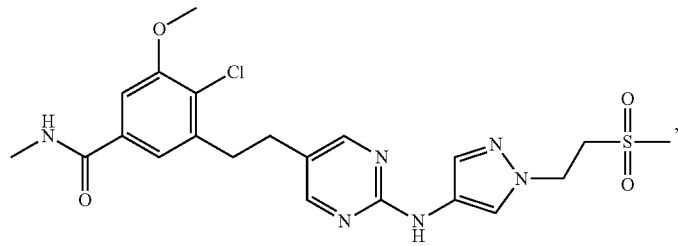
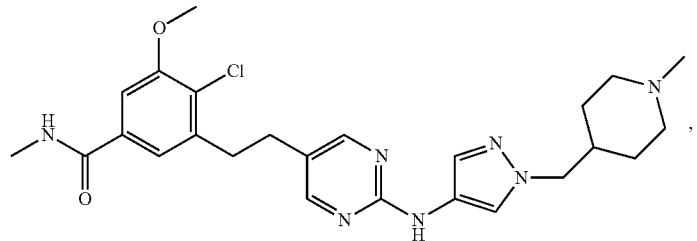
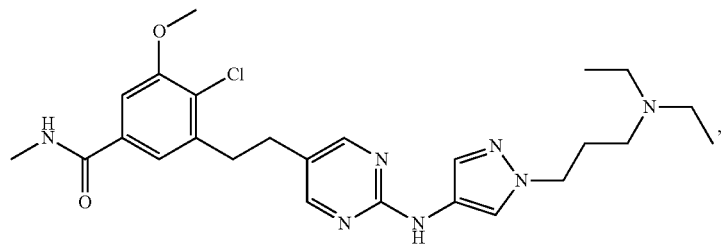
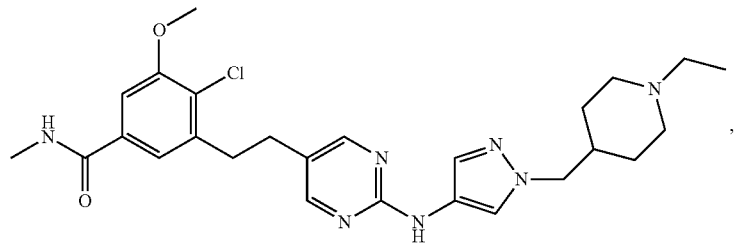
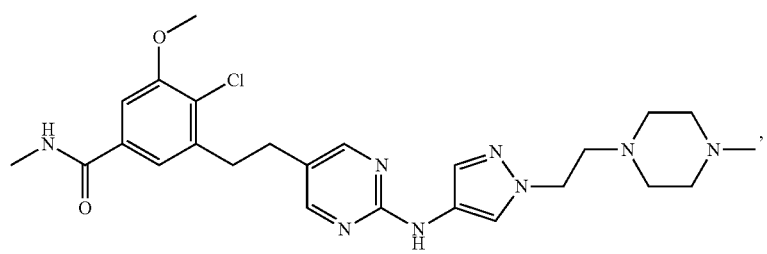

-continued
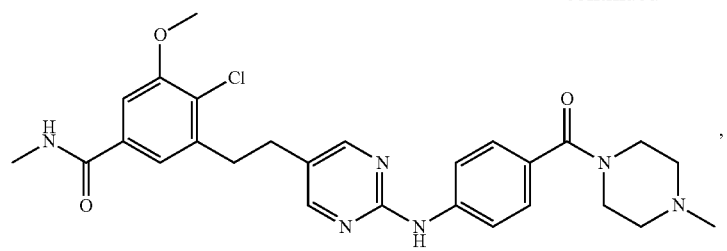,
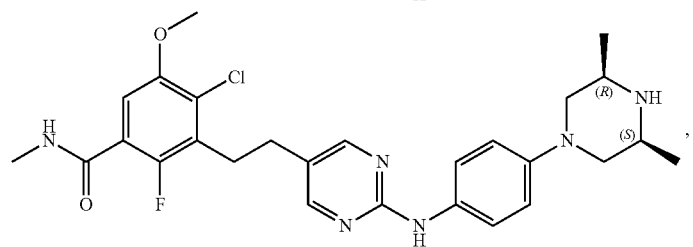,
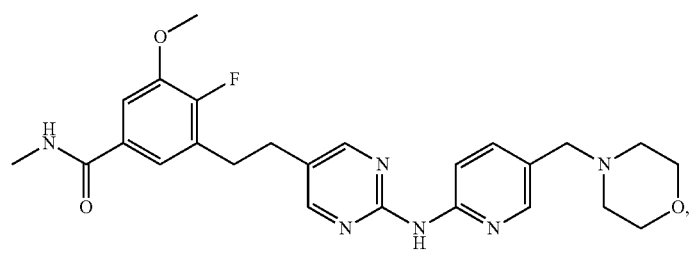,
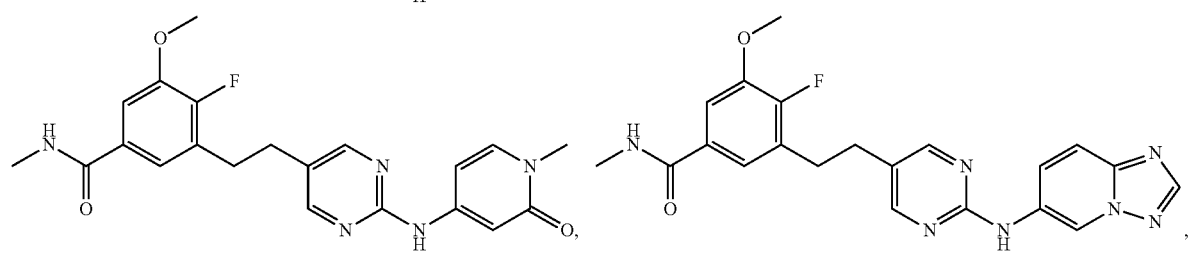,
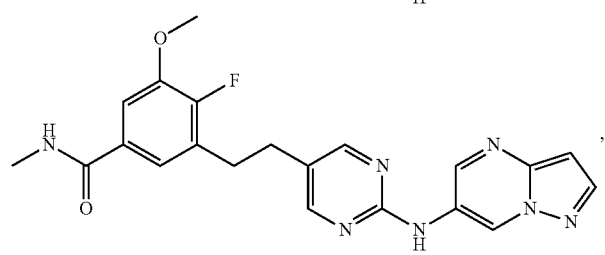,
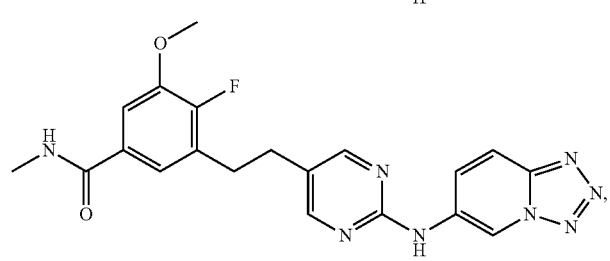,
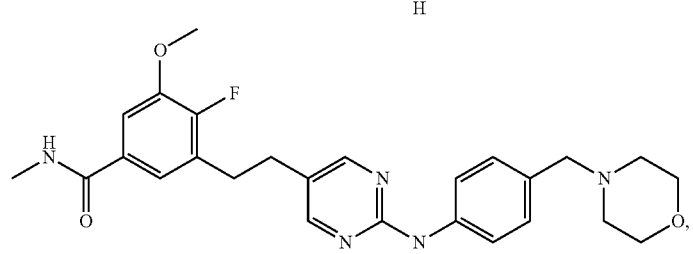,

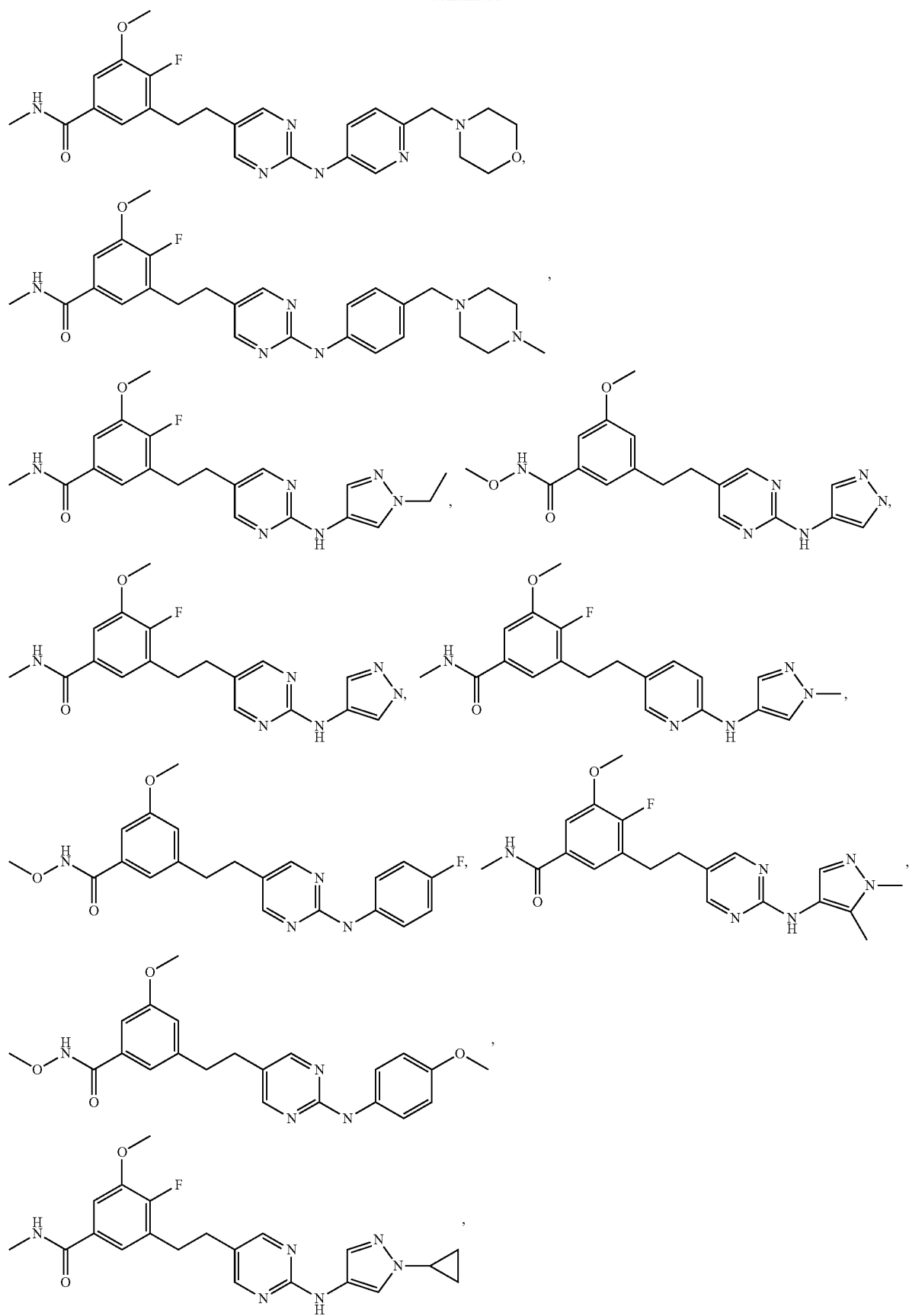

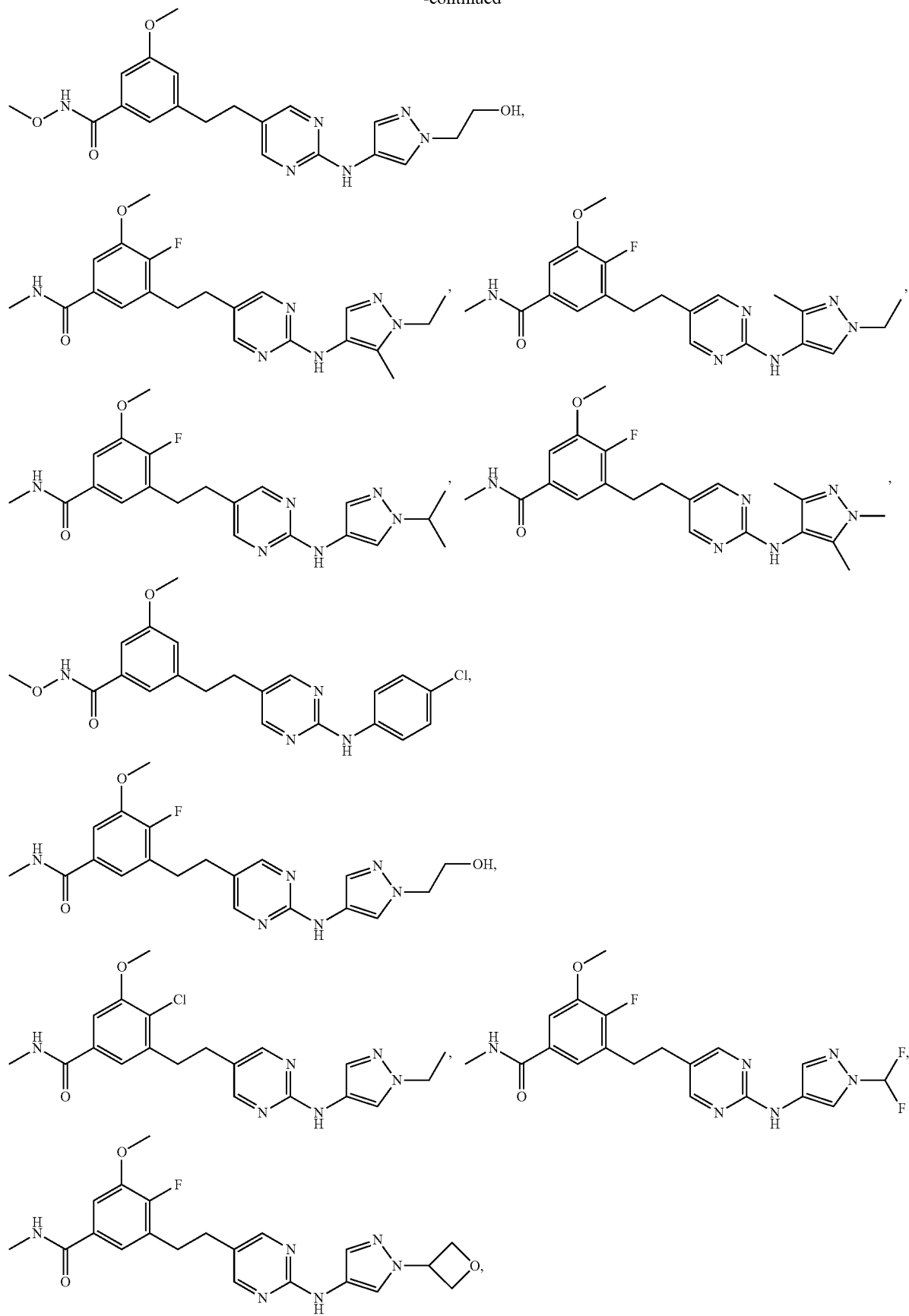

-continued
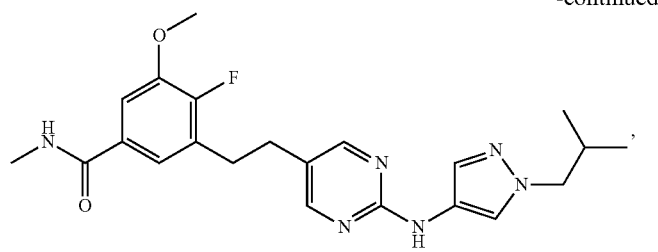
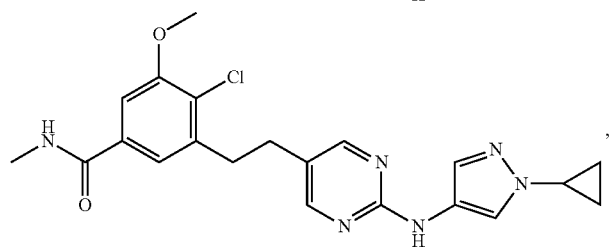
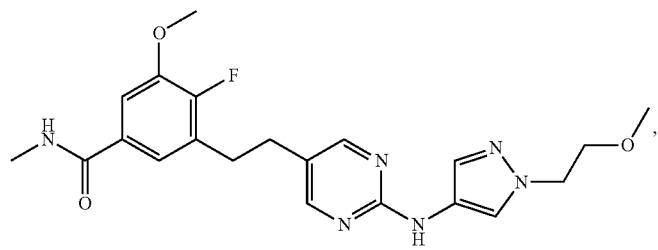
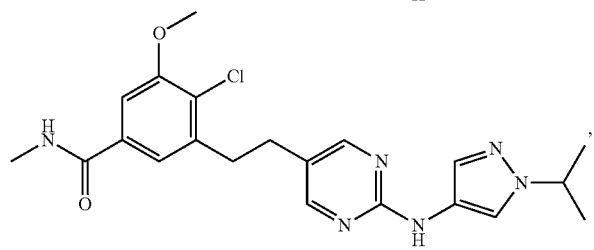
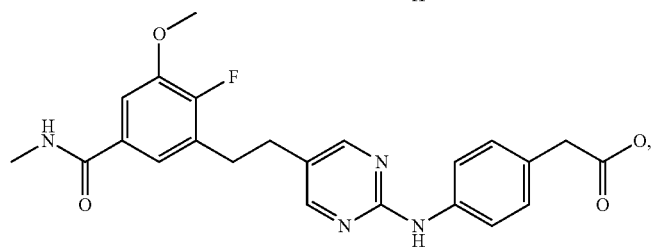
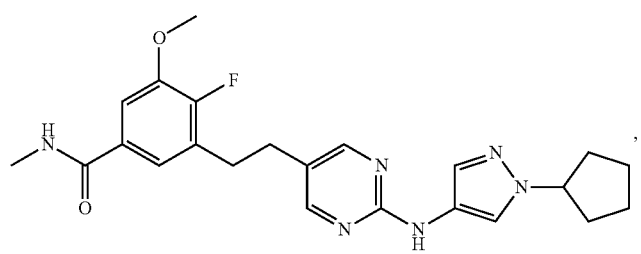
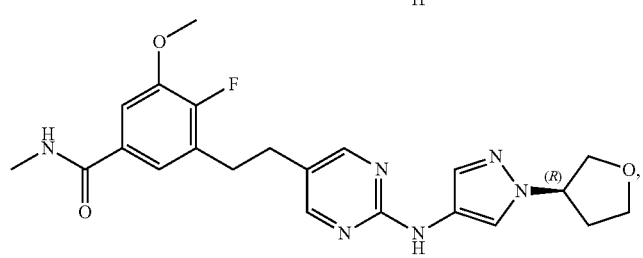

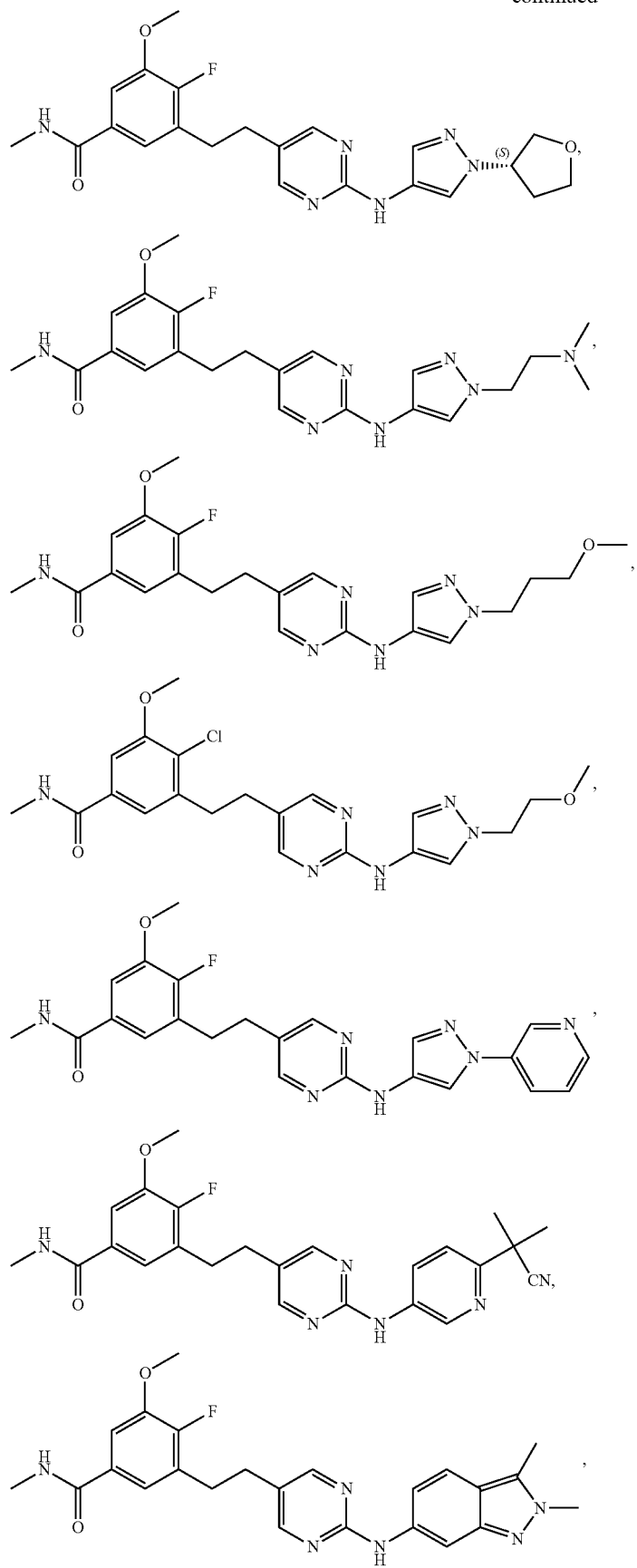

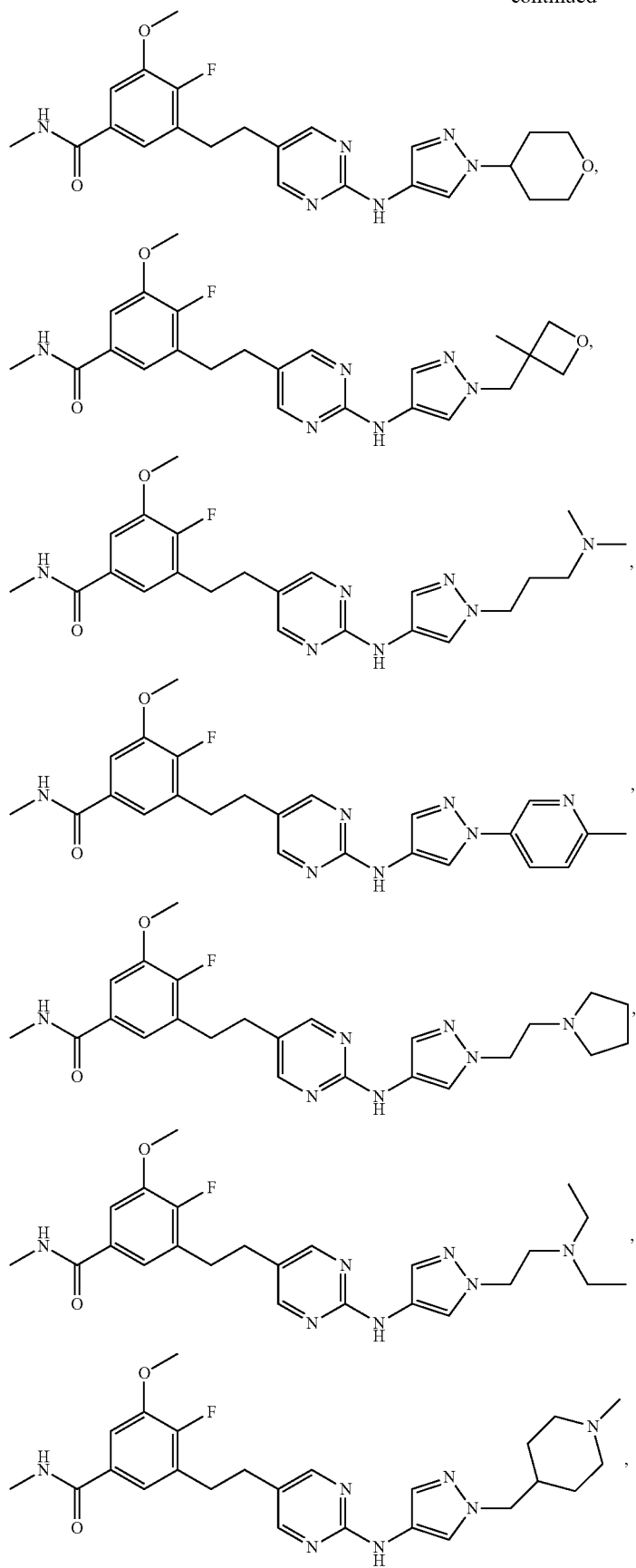

-continued
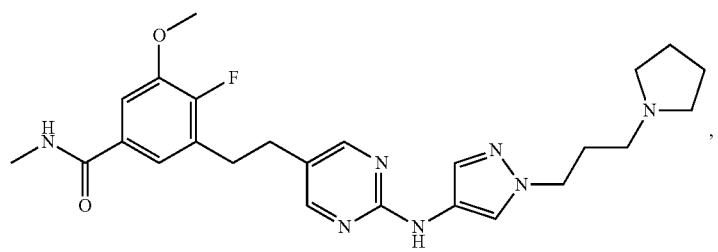
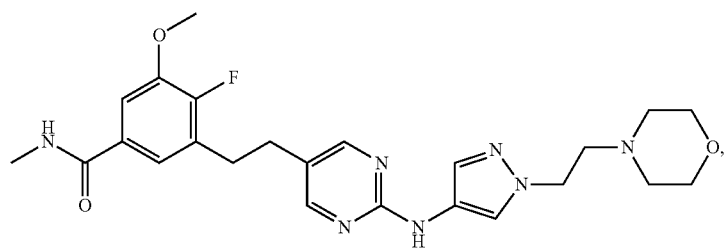
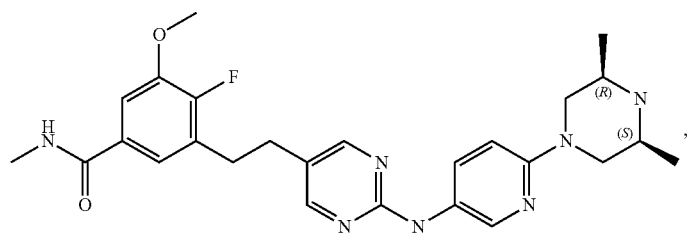
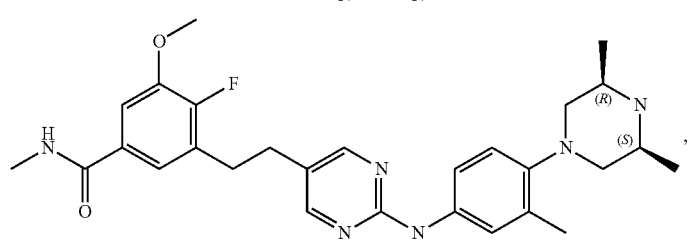
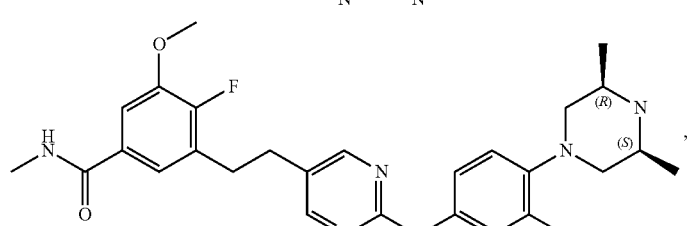
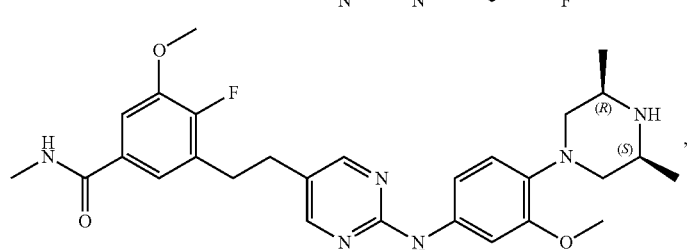
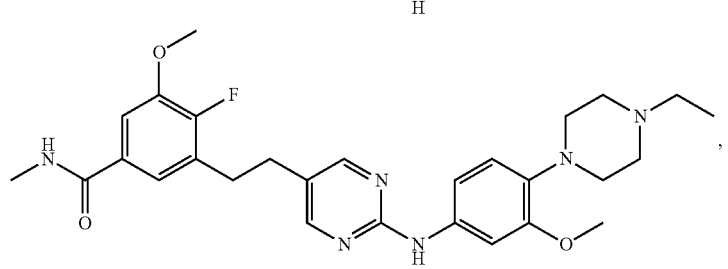

-continued
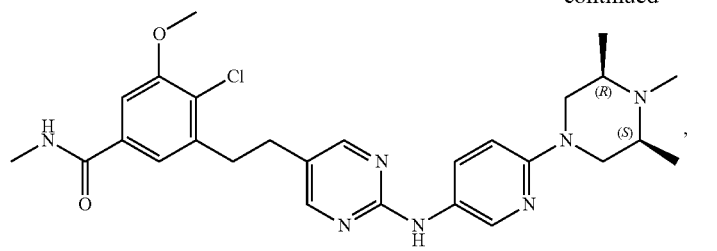,
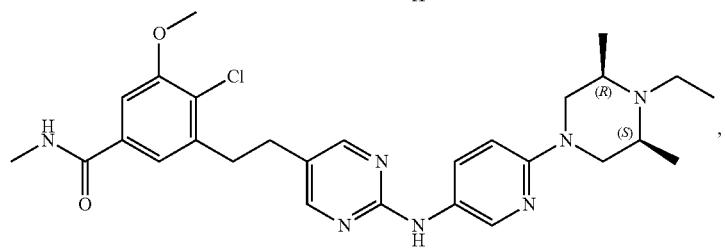,
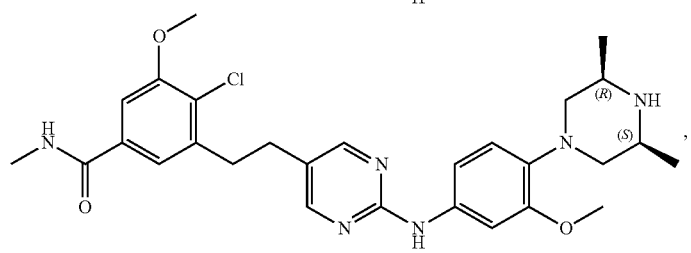,
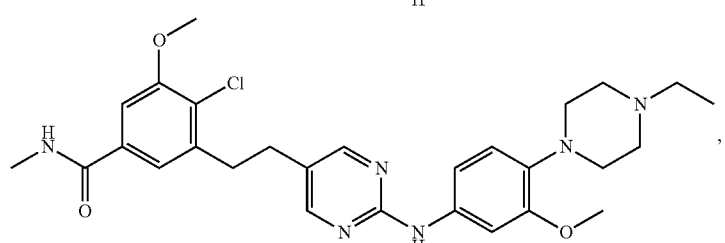,
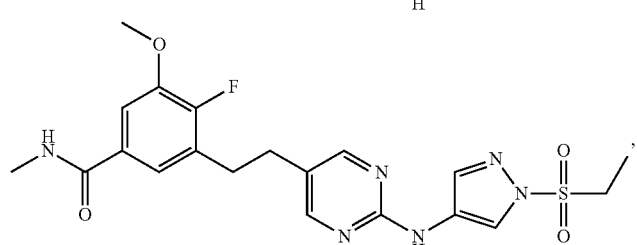,
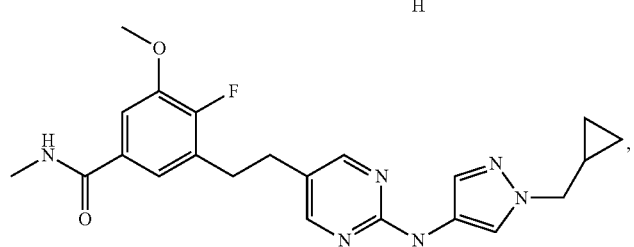,
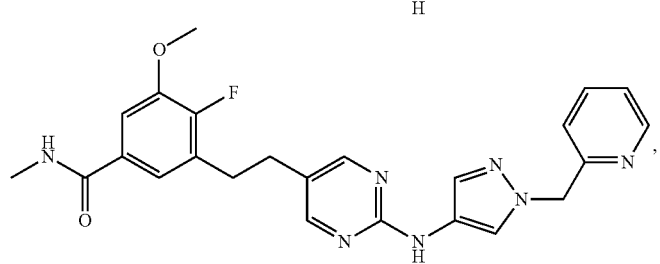,

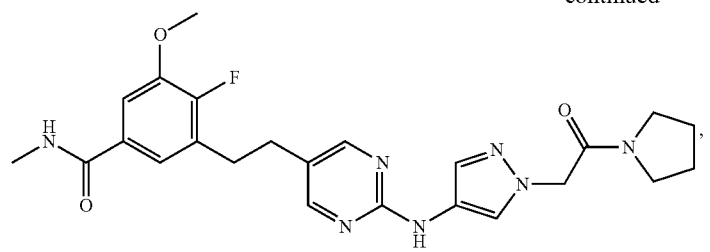
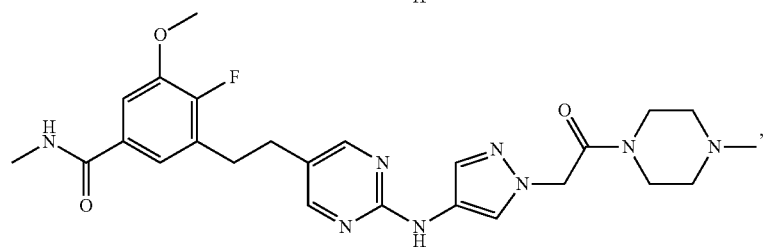
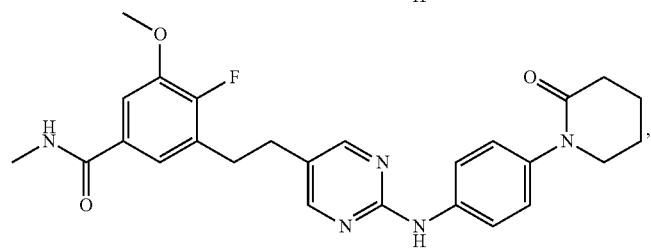
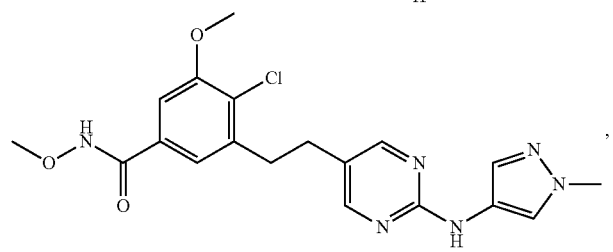
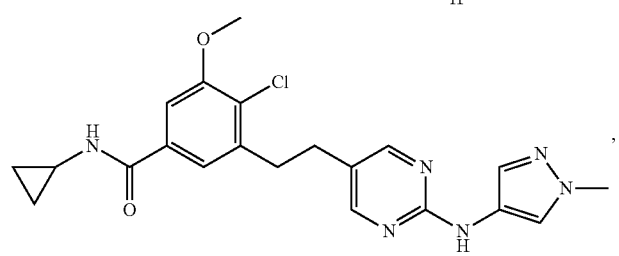
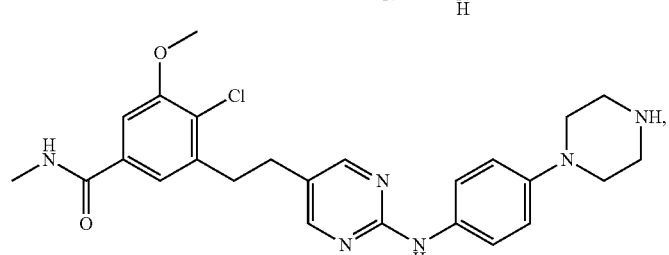
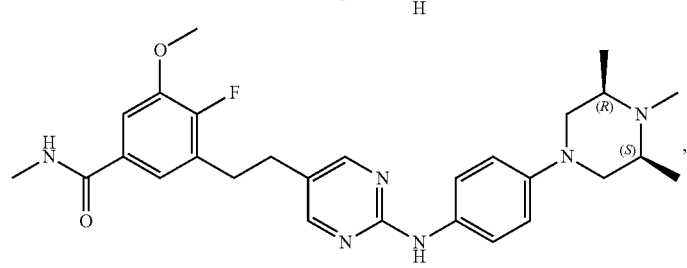

-continued
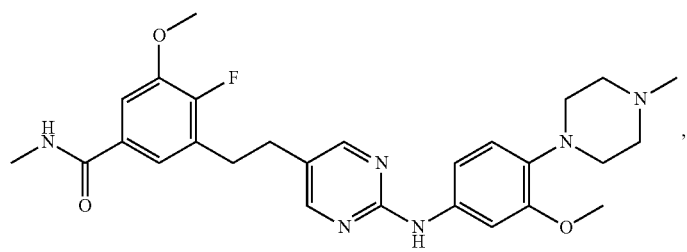
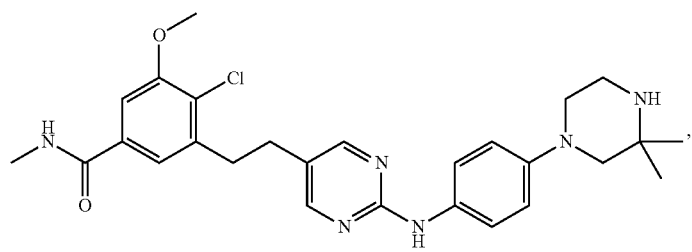
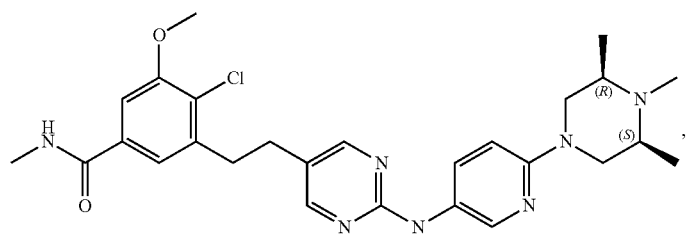
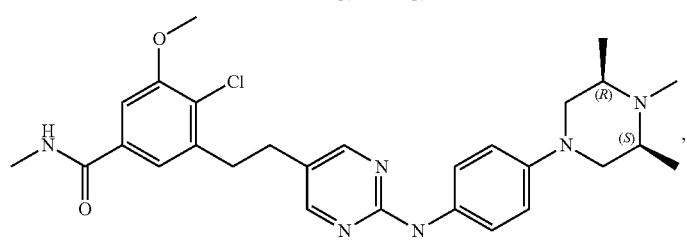
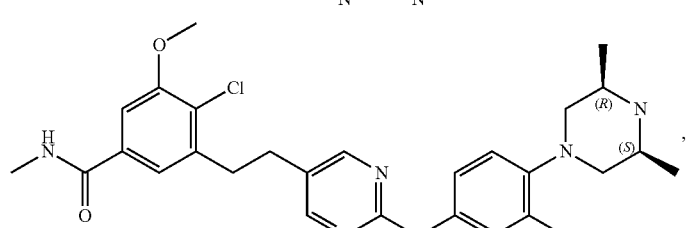
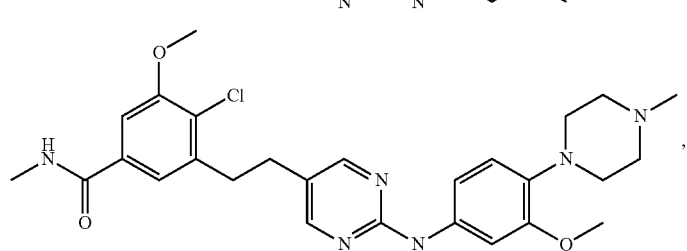
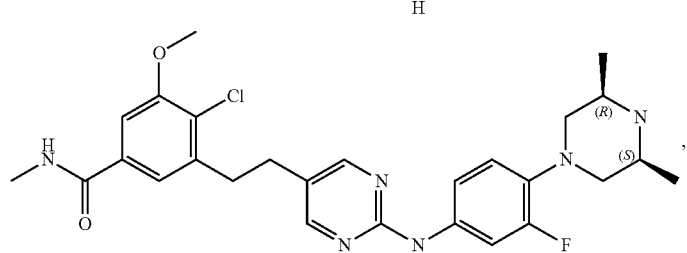

-continued
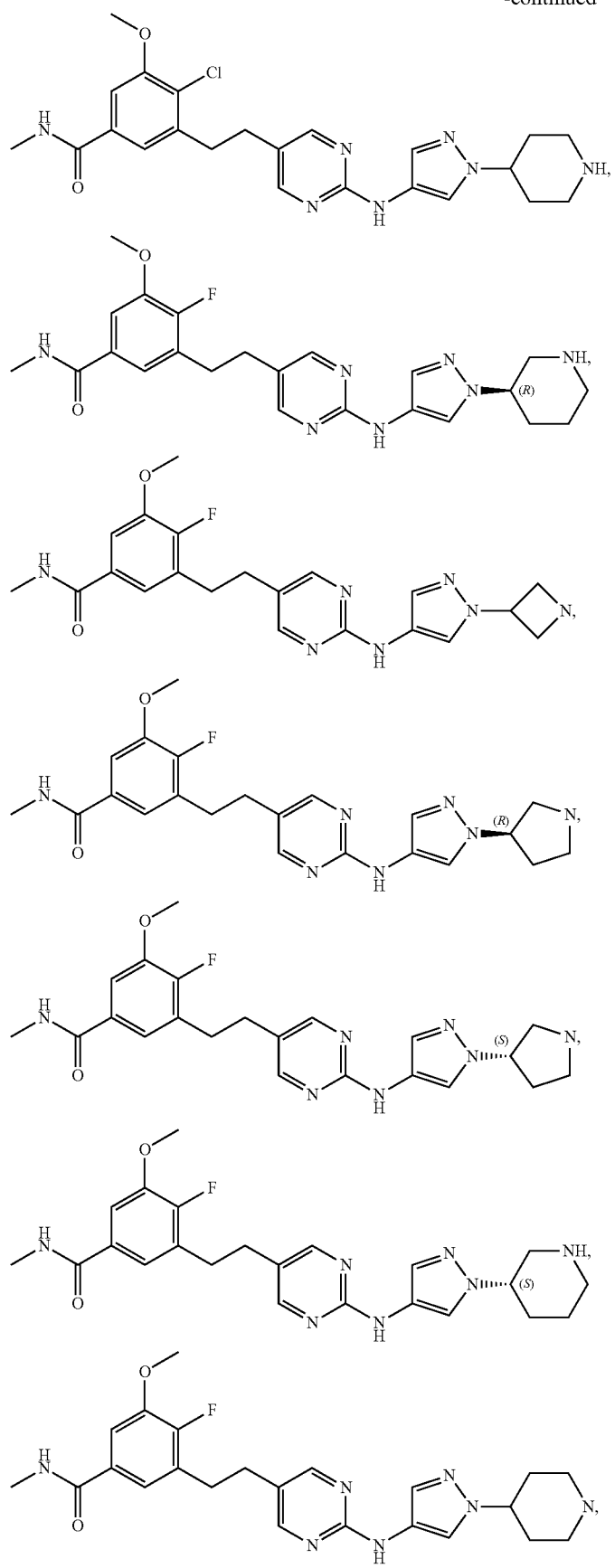

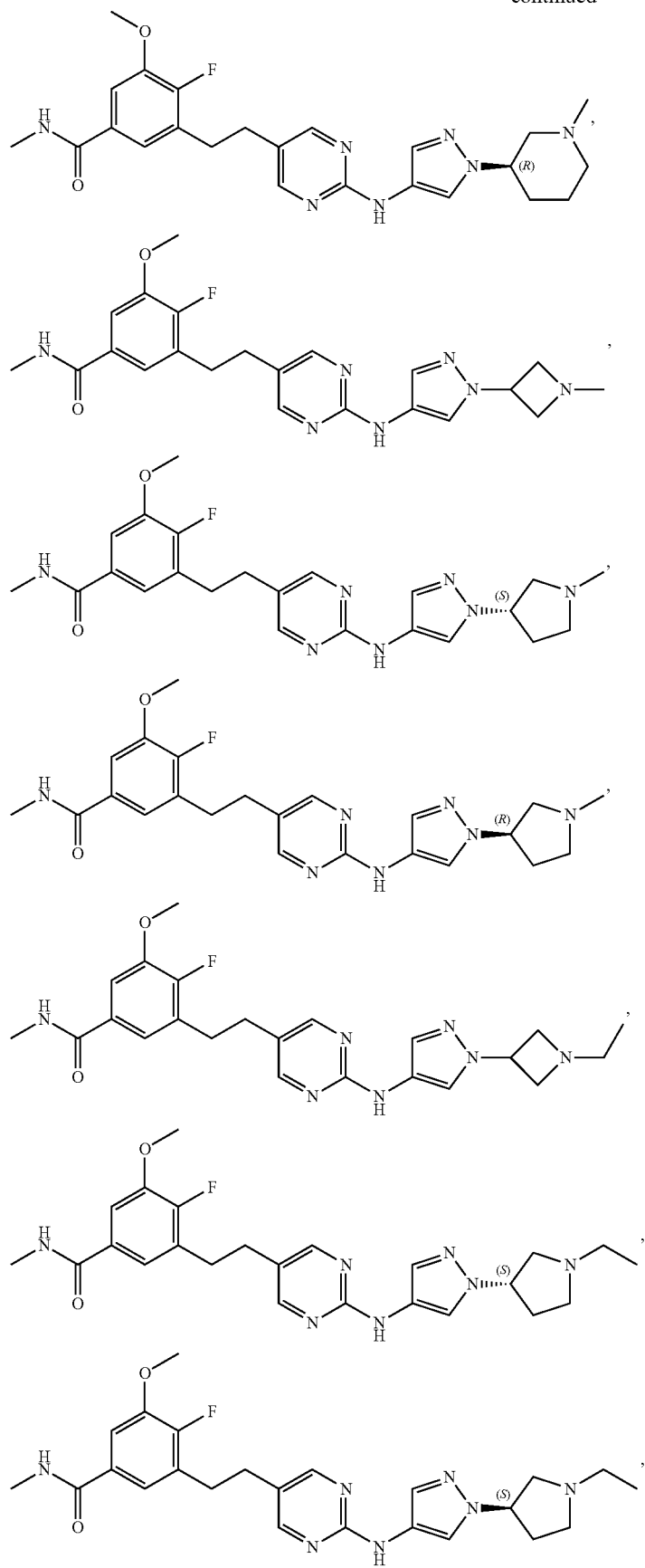

-continued
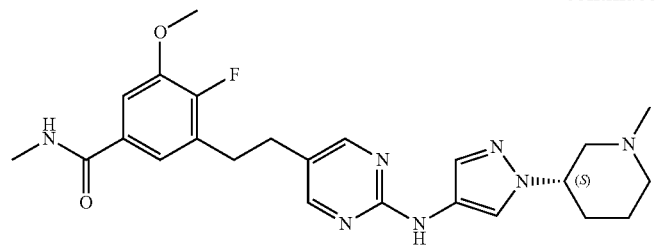
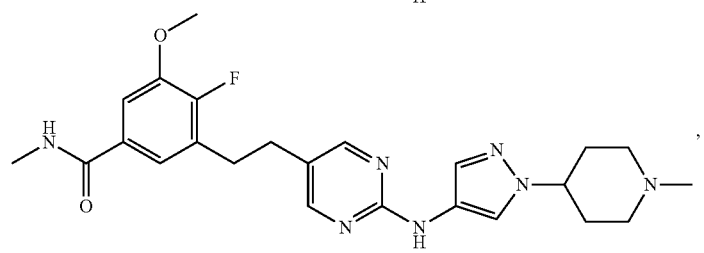
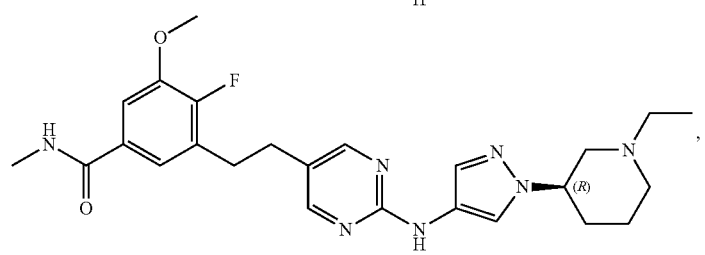
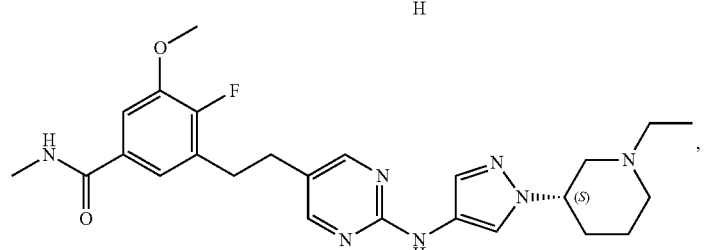
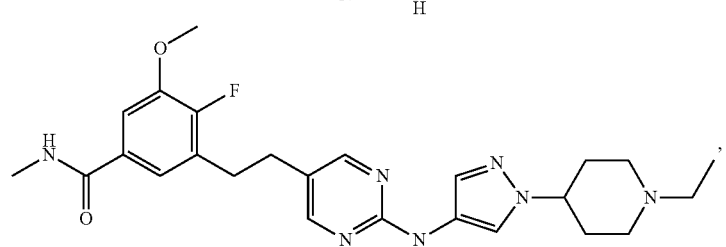
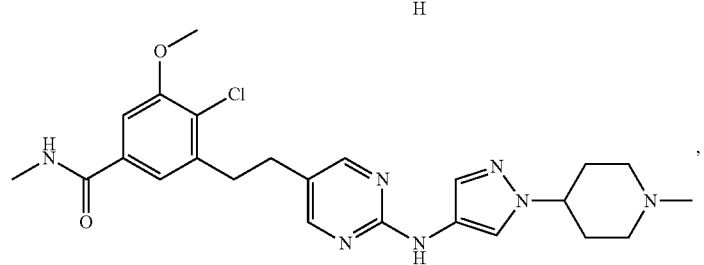
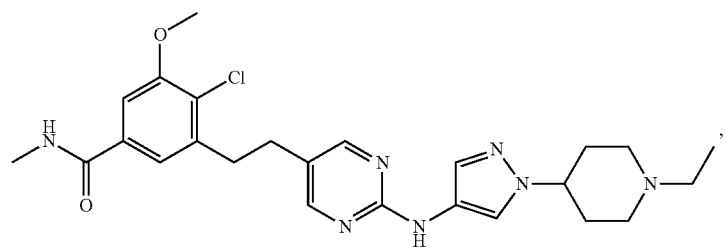

-continued
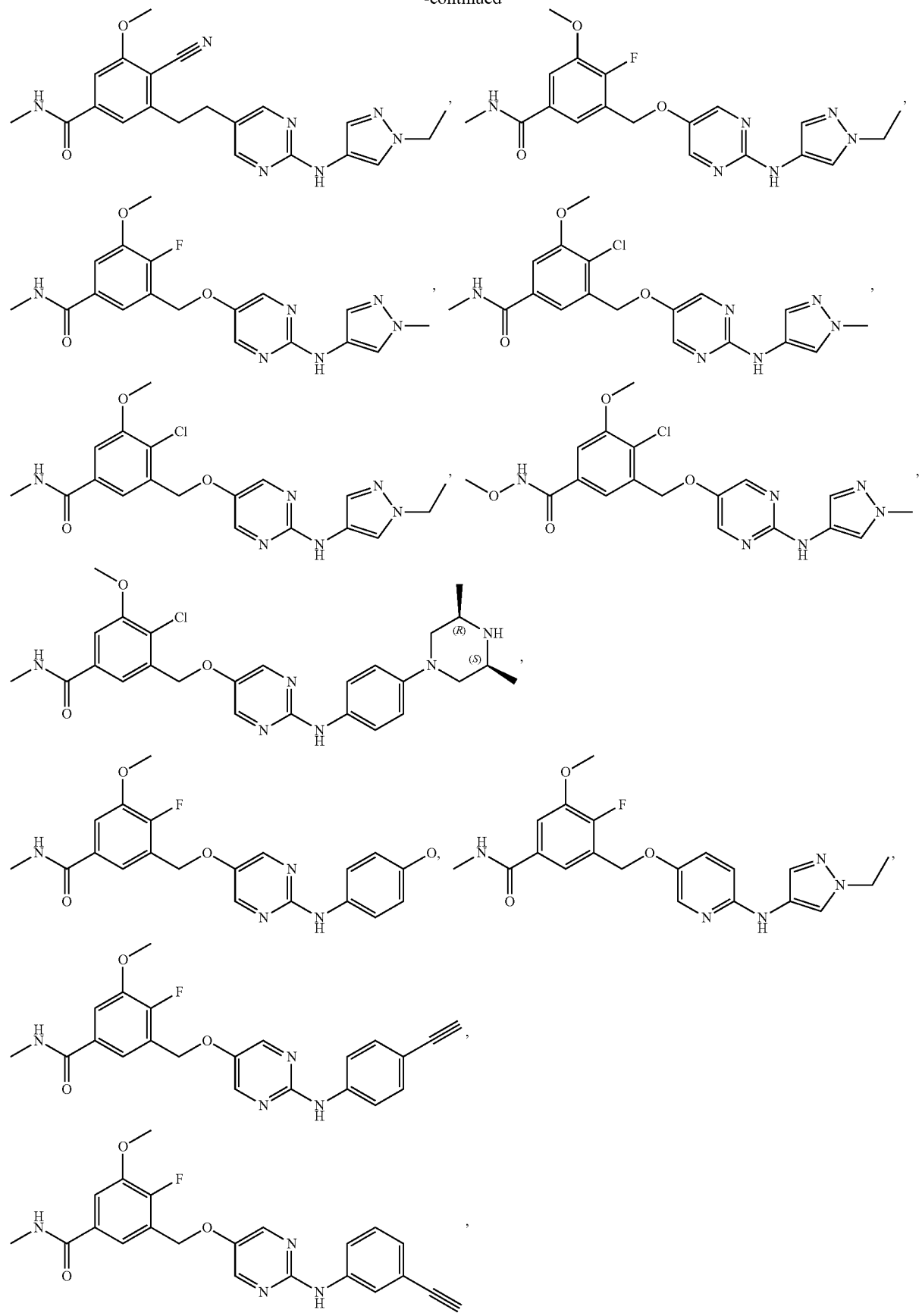

-continued
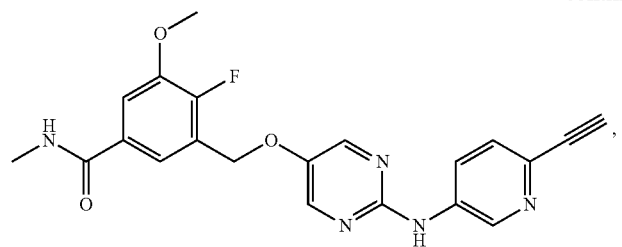
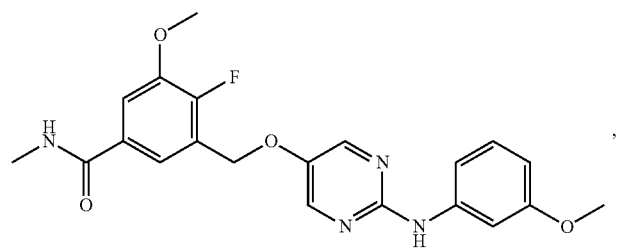
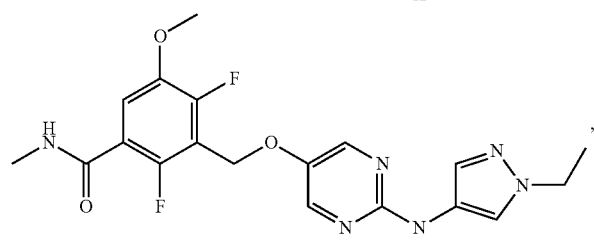
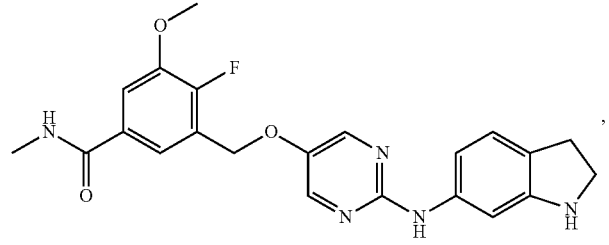
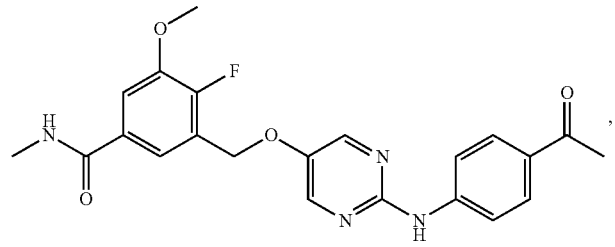
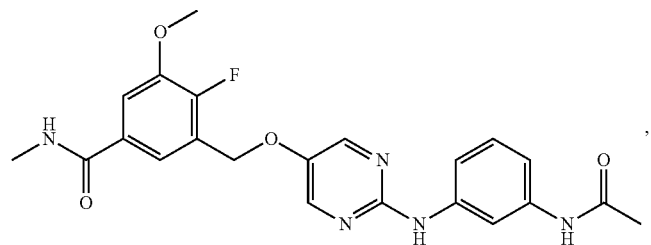
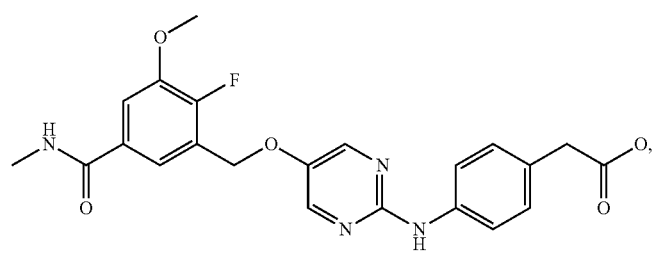

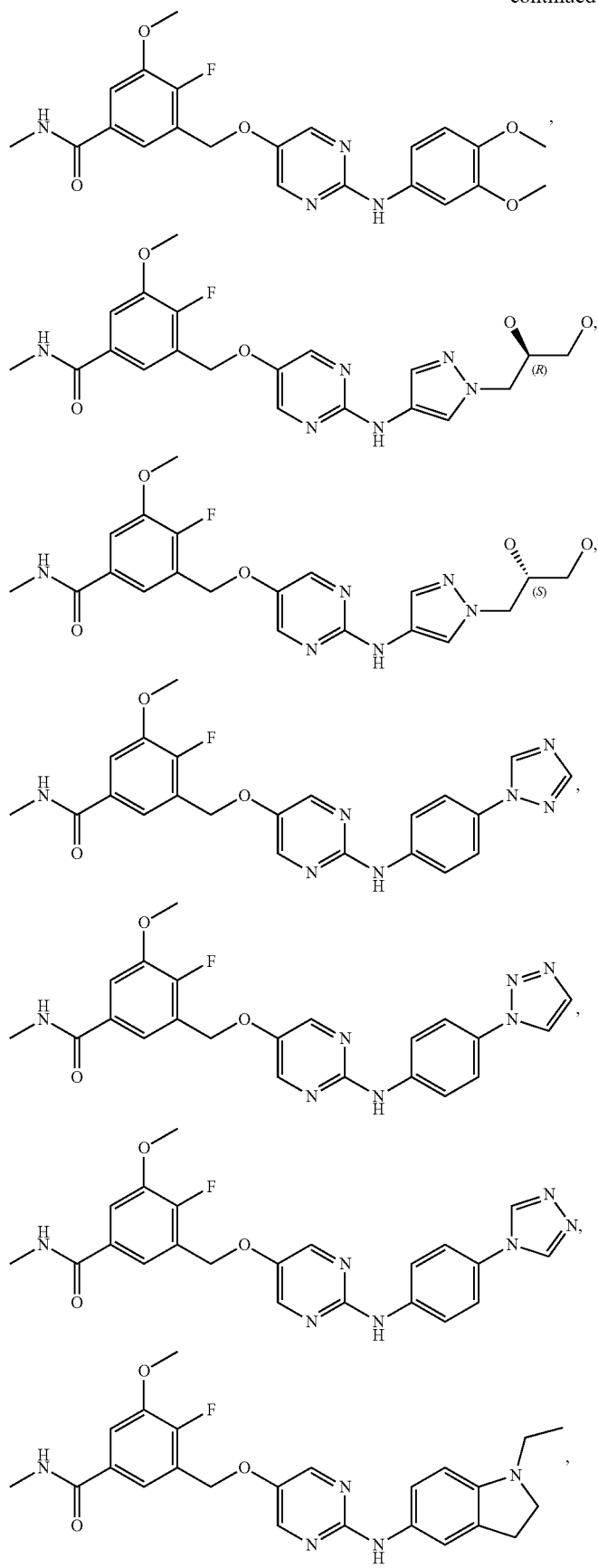

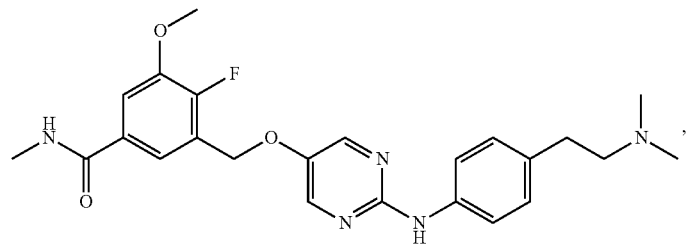
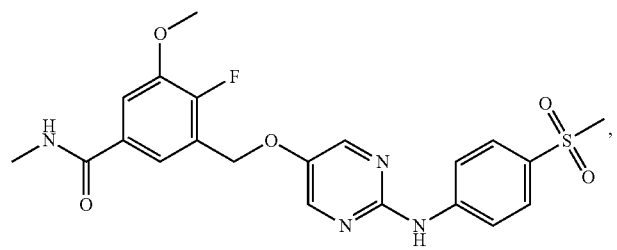
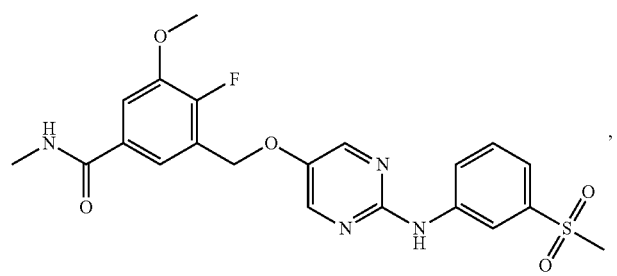
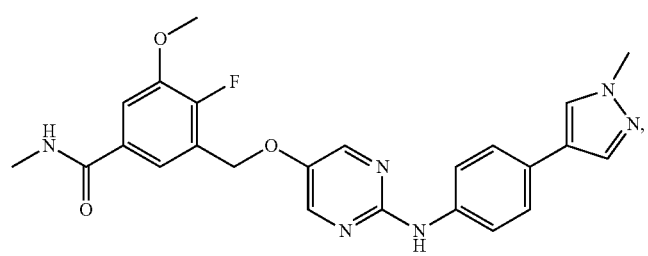
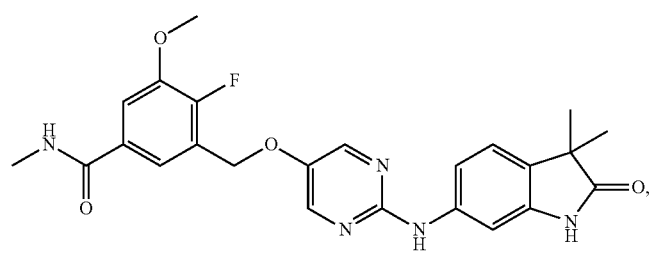
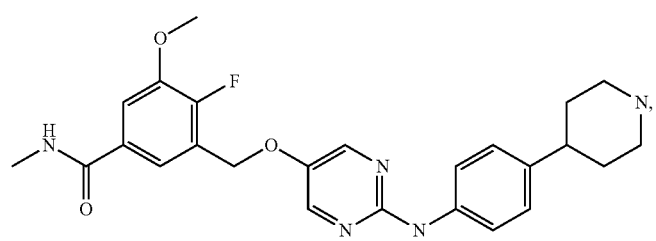

-continued
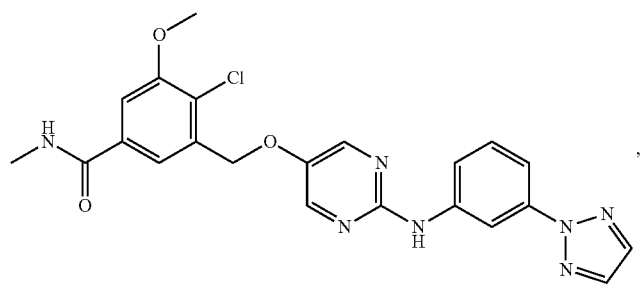
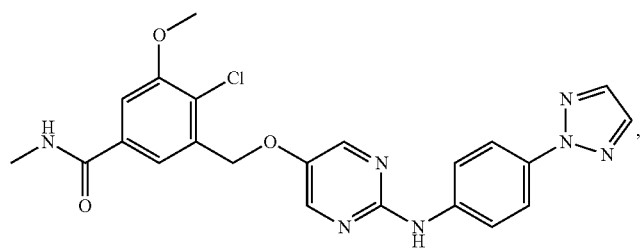
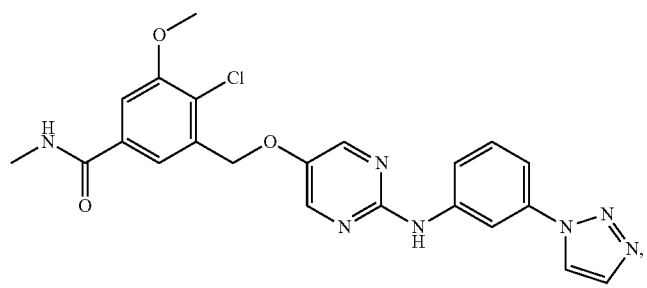
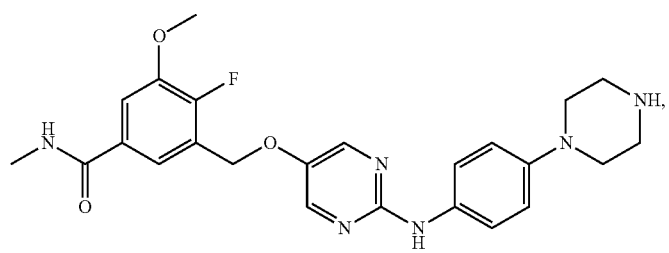
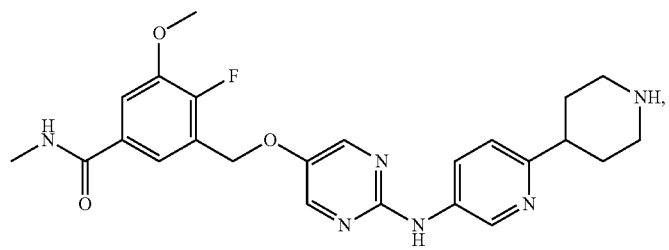
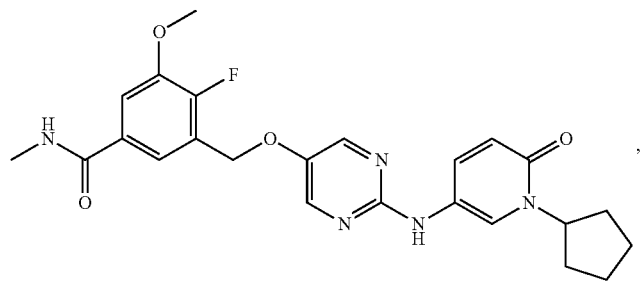

-continued
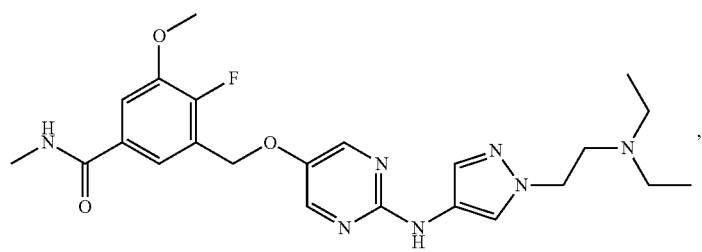
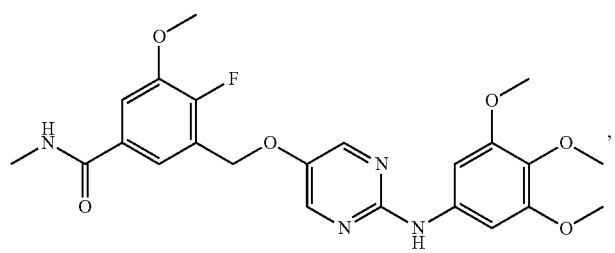
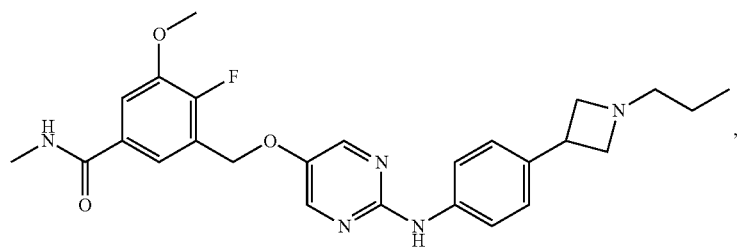
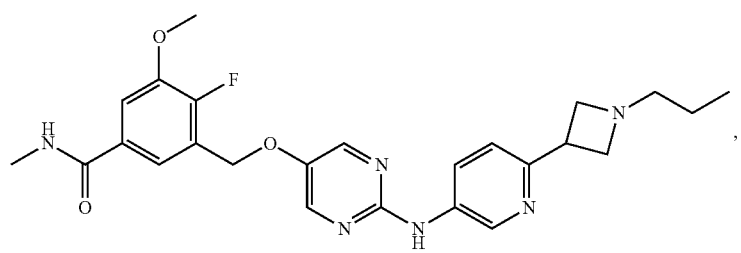
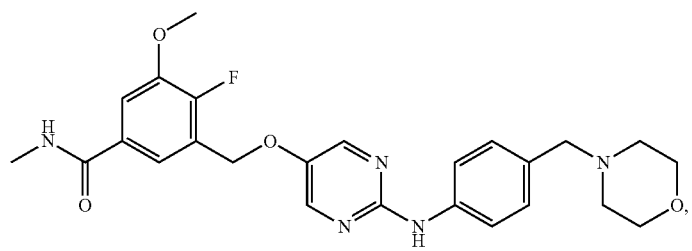
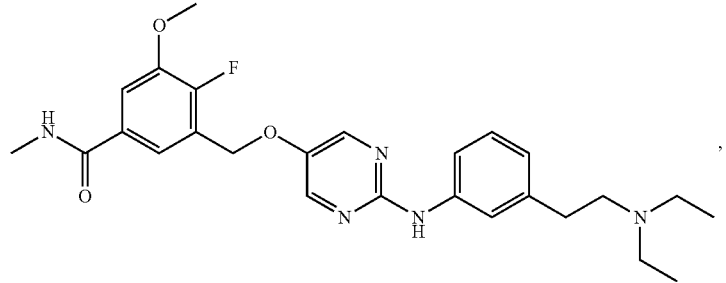

-continued
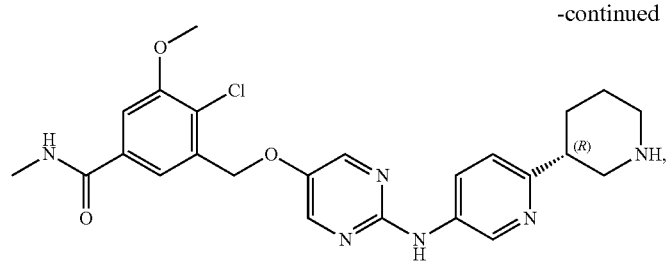
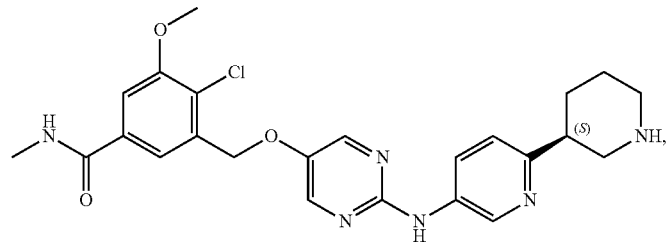
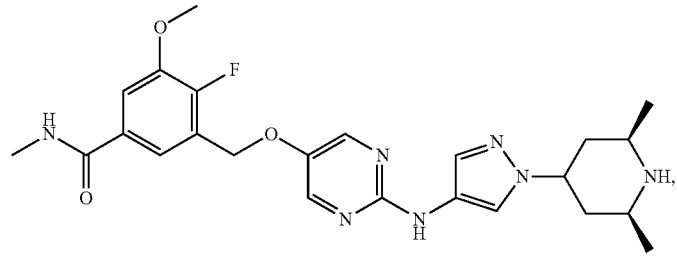
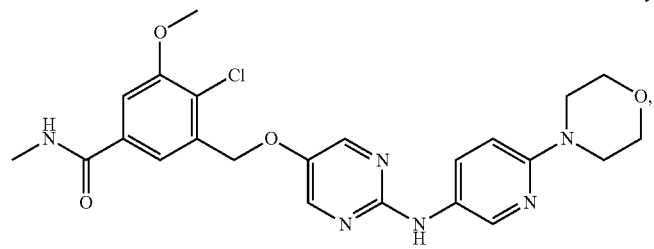
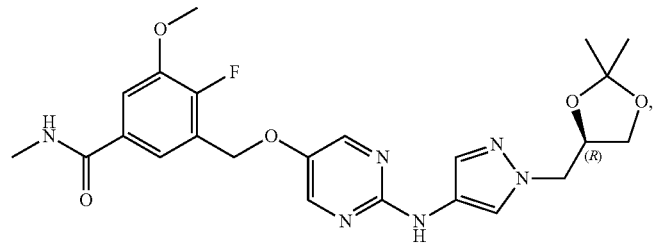
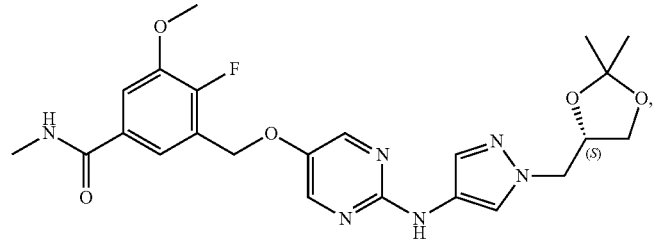
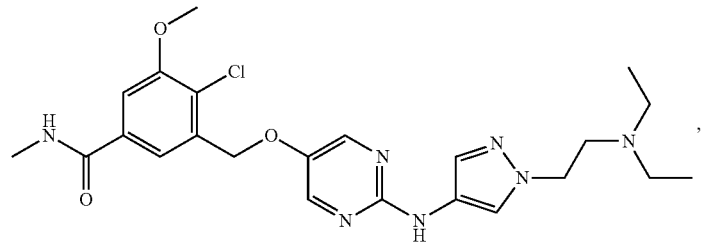

-continued
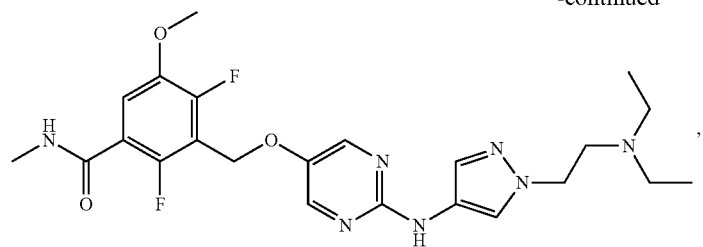
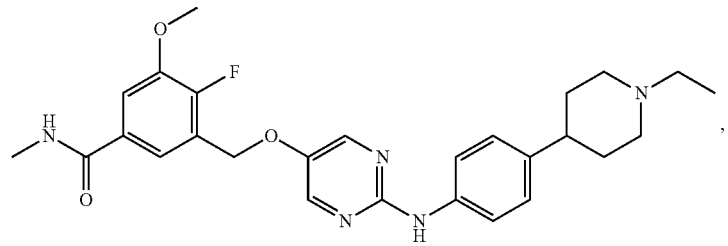
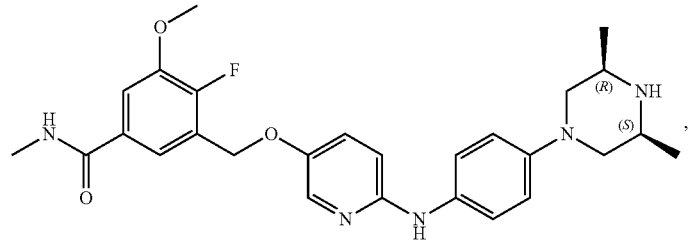
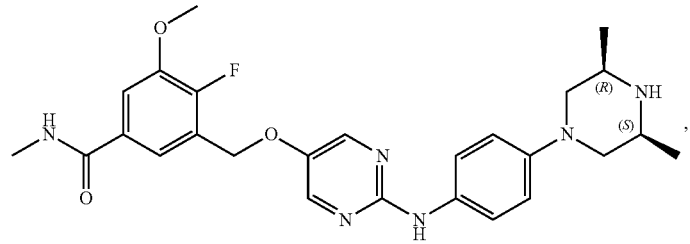
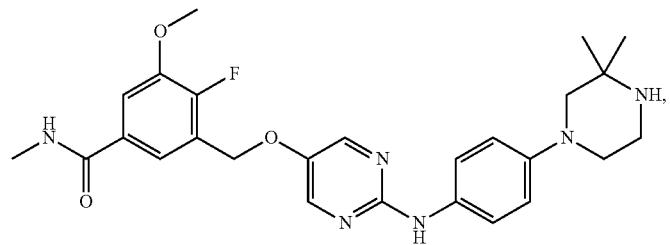
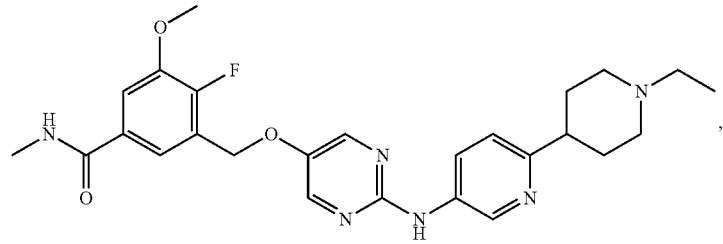
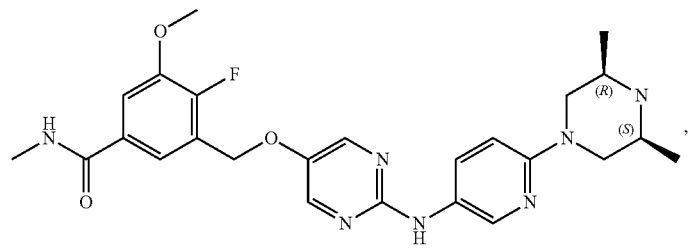

-continued
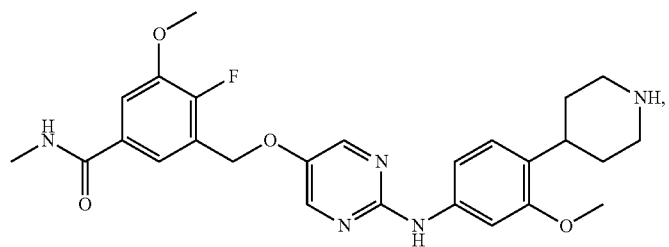
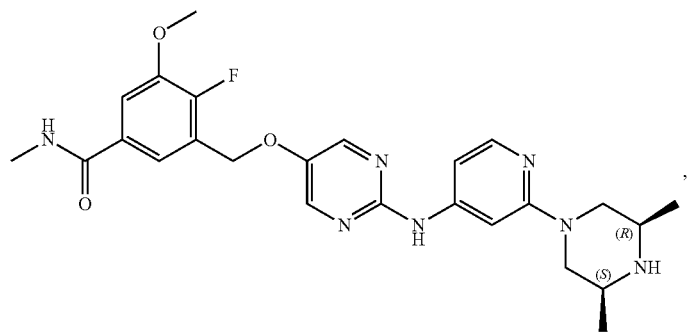
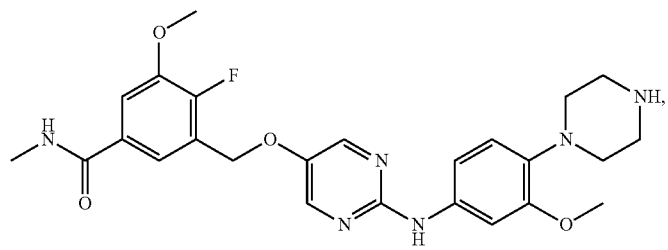
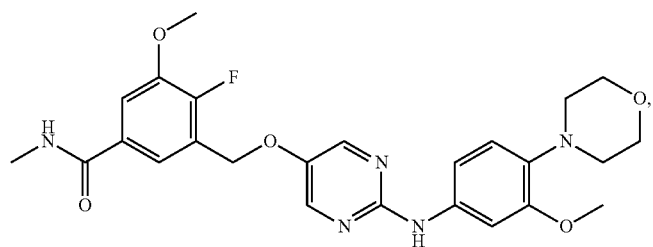
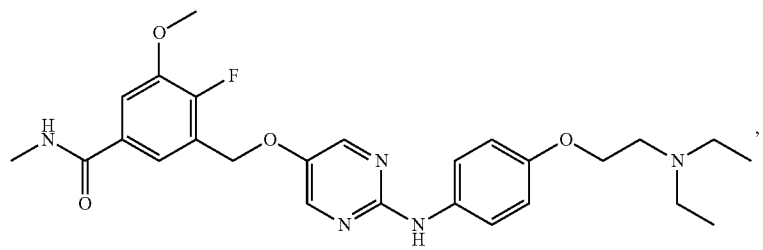
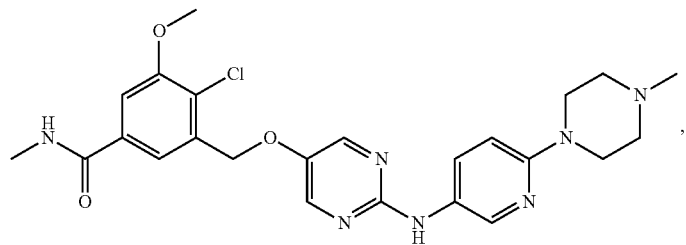

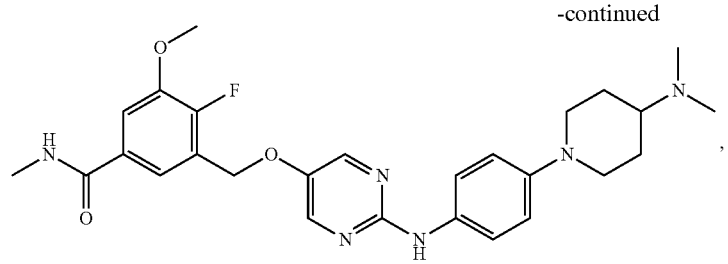,
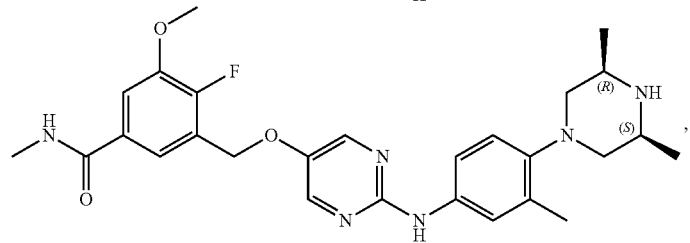,
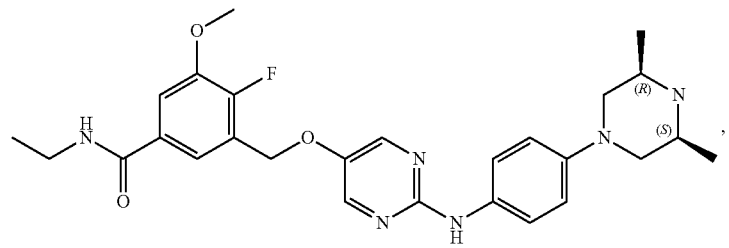,
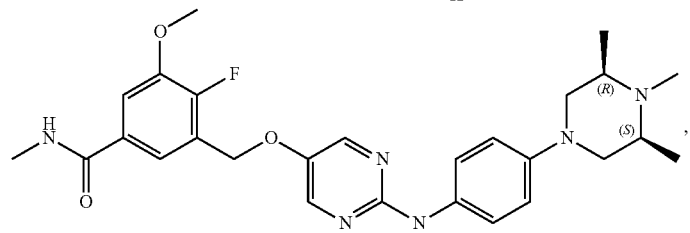,
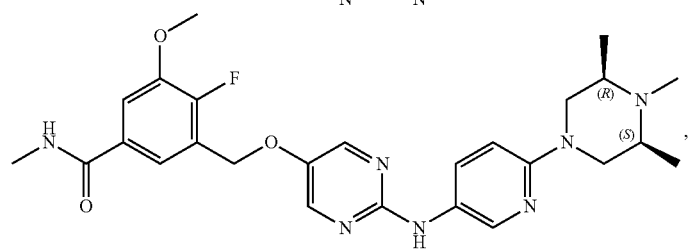,
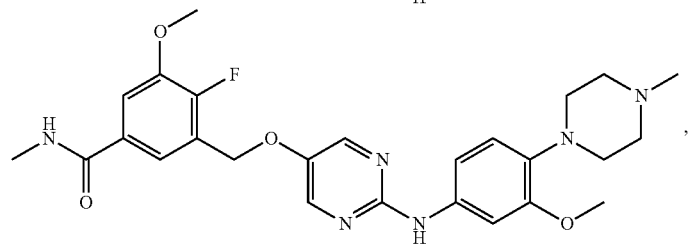,
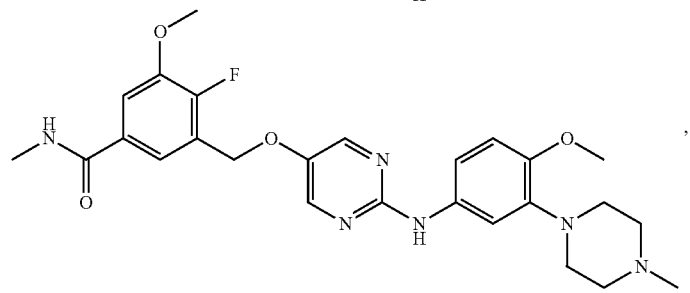, -continued
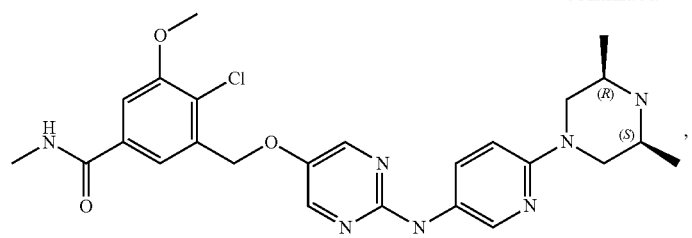,
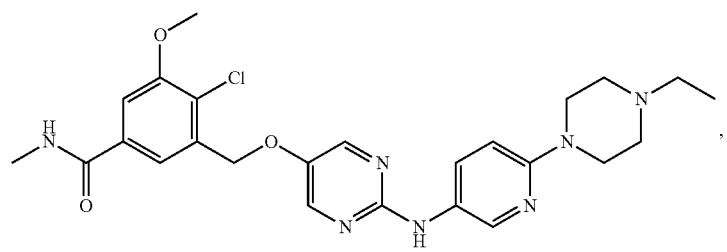,
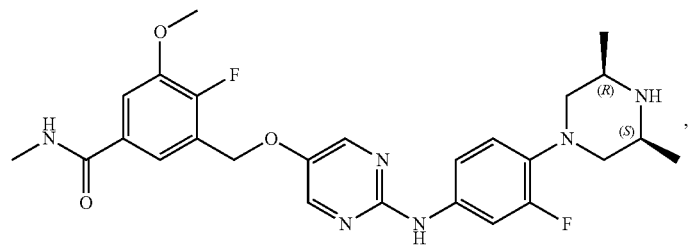,
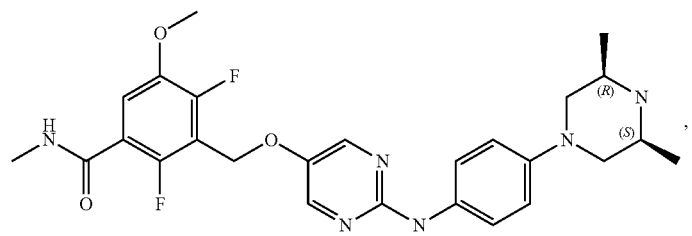,
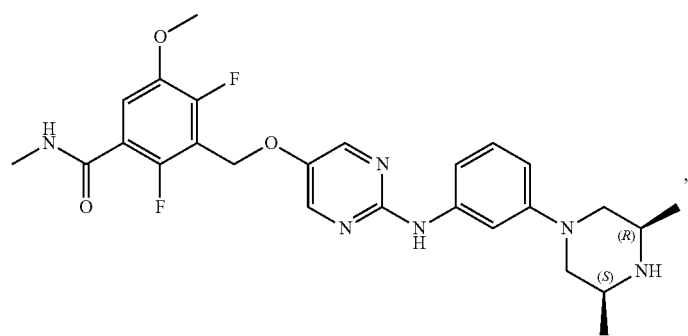,
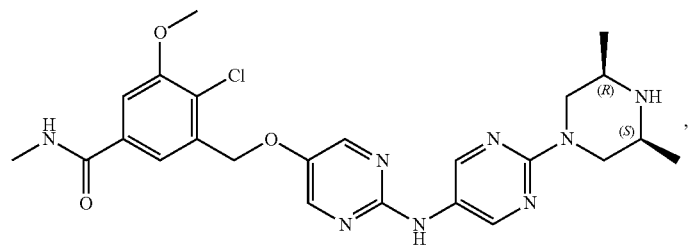, -continued
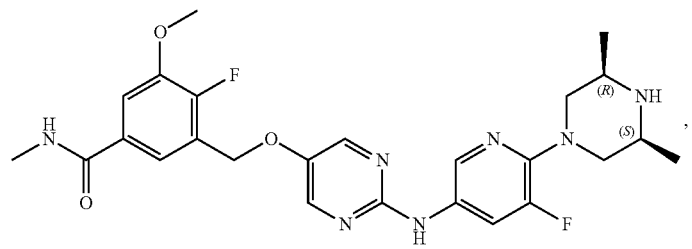
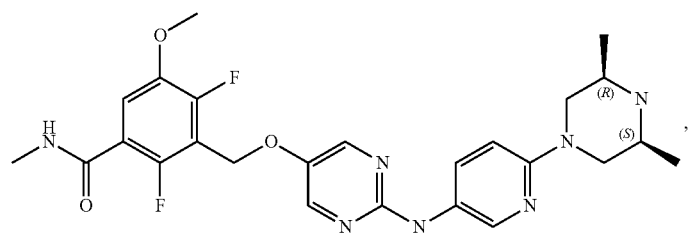
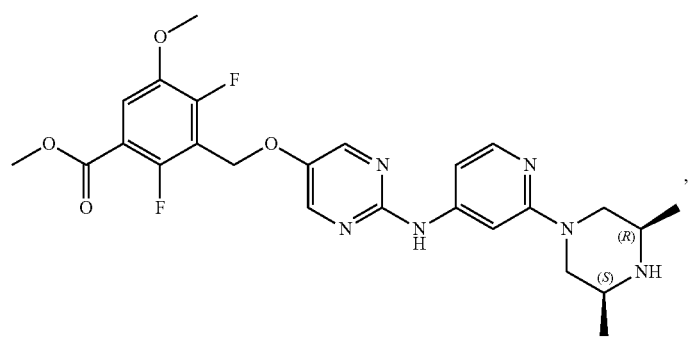
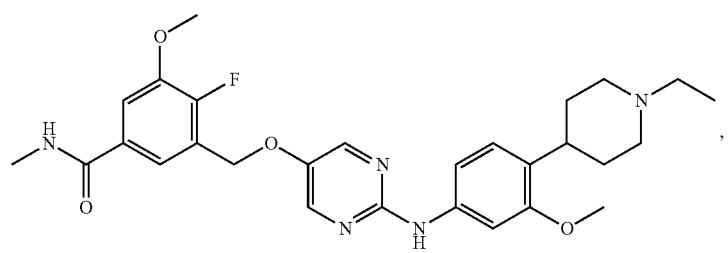
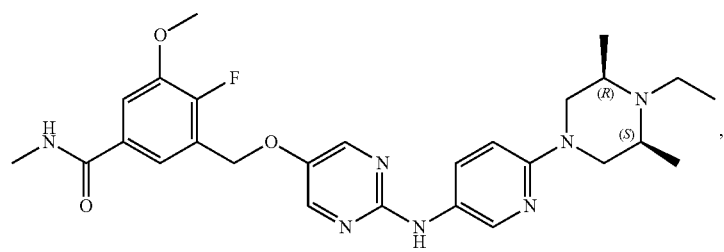
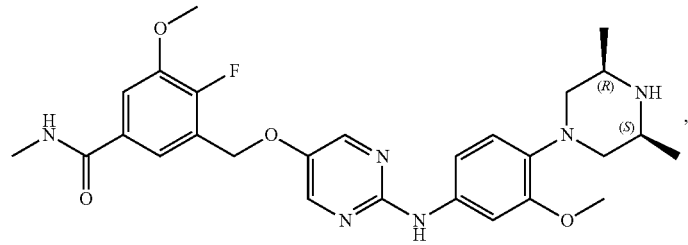

-continued
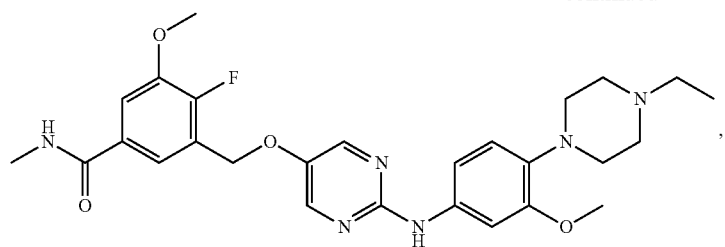
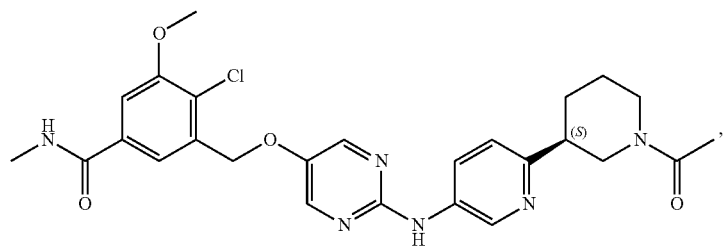
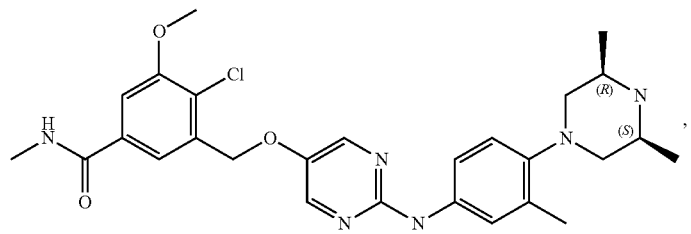
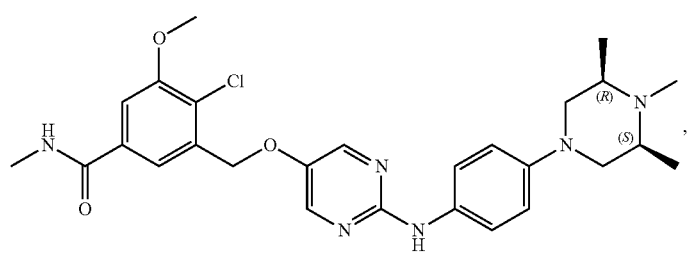
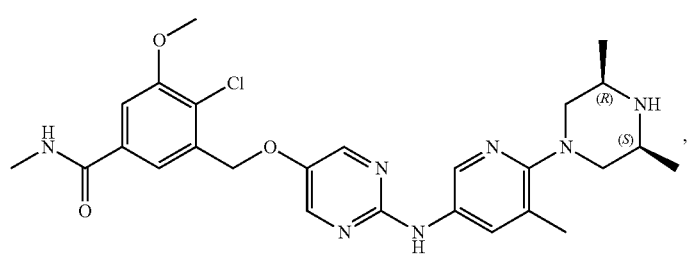
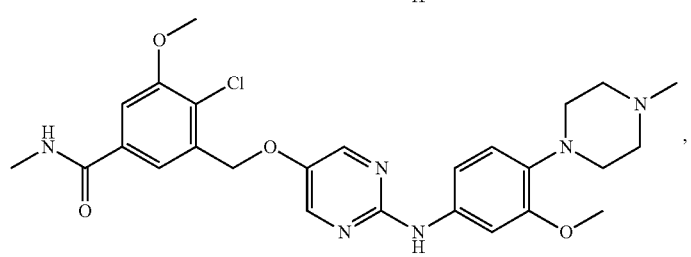
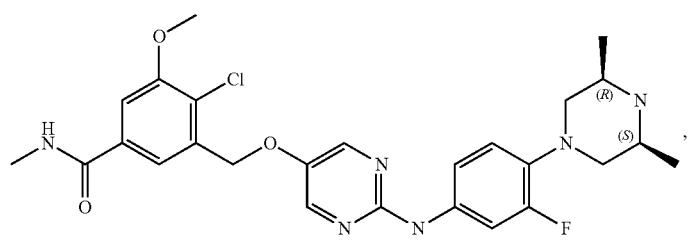

-continued
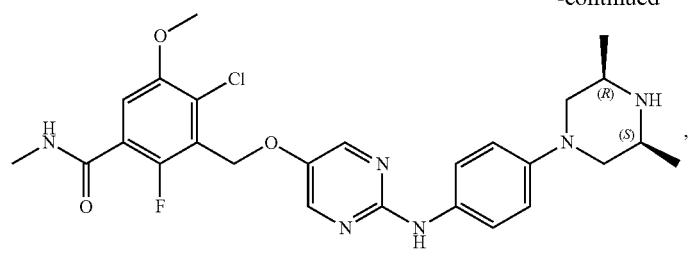
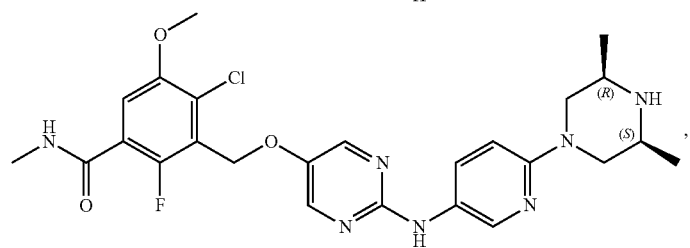
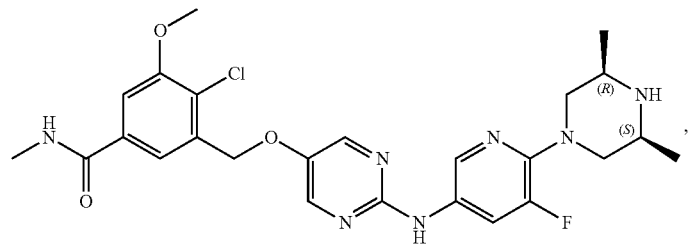
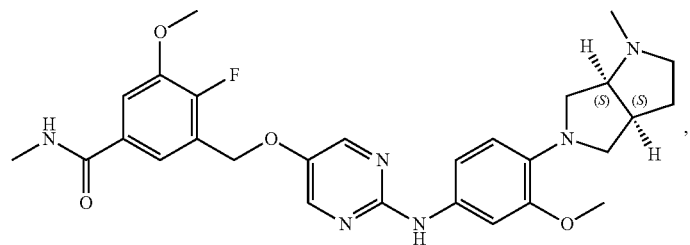
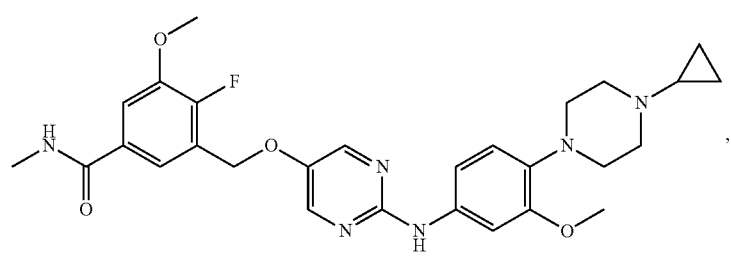
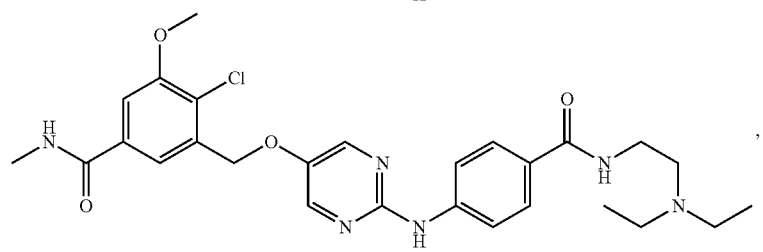
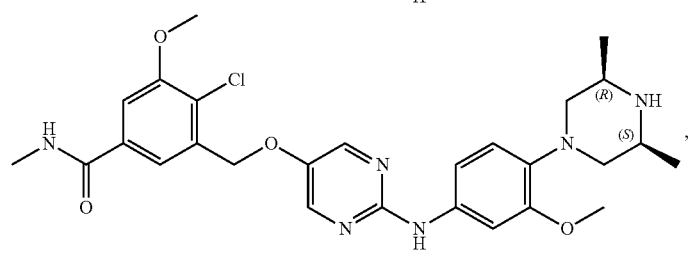

-continued
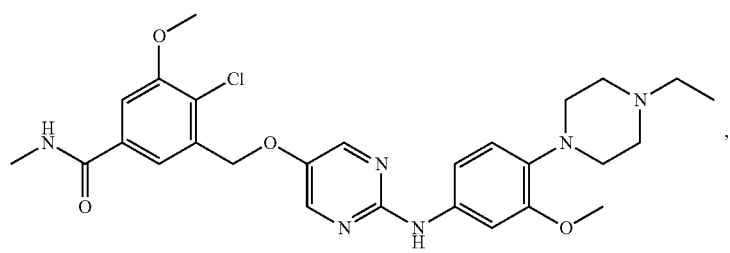
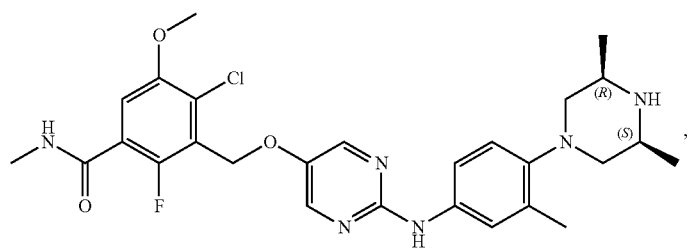
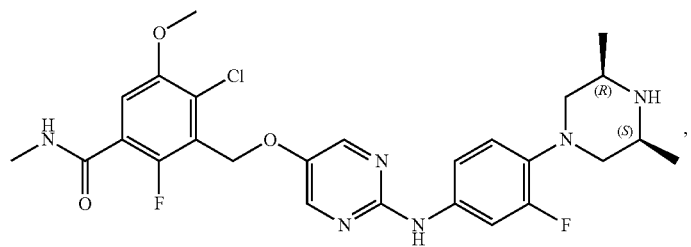
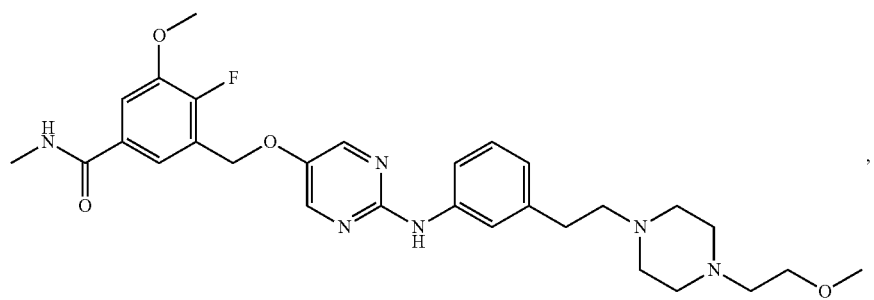
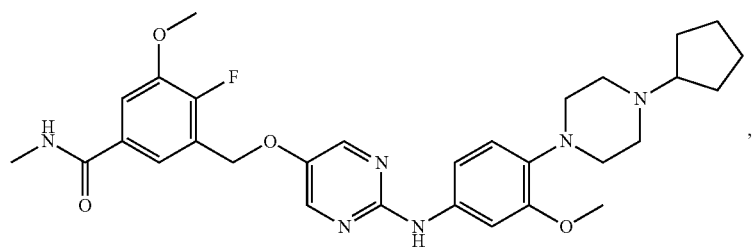
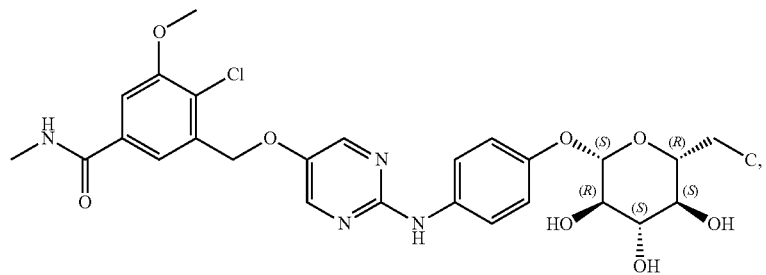

-continued
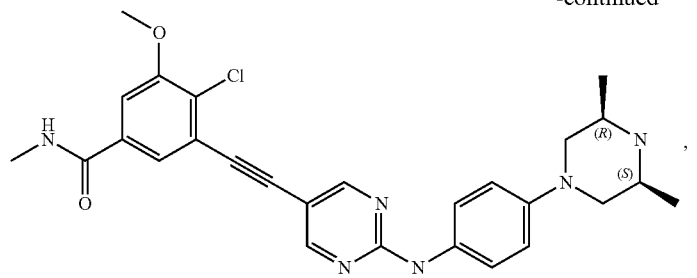
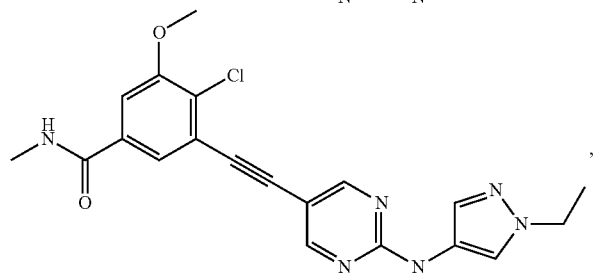
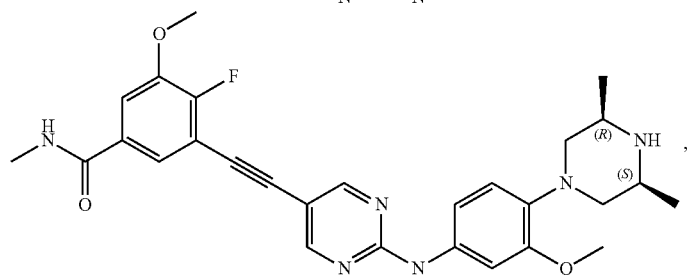
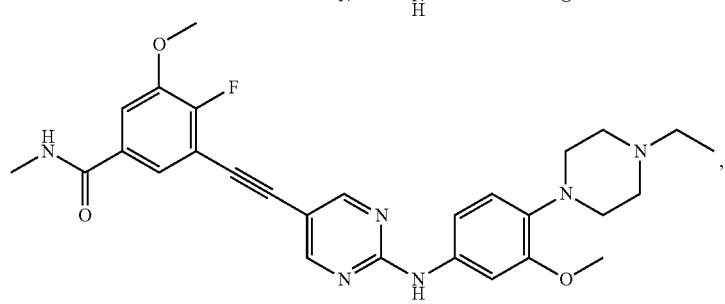
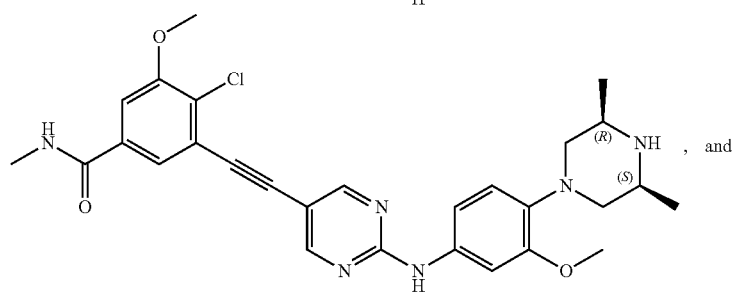, and
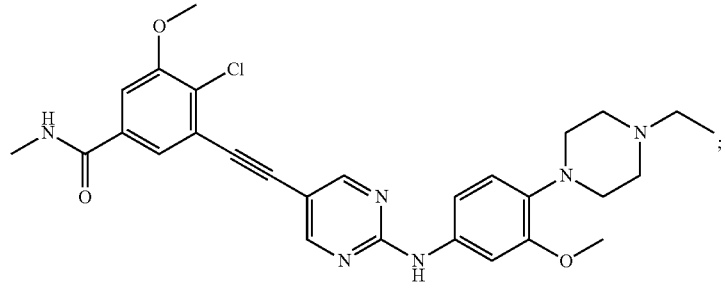;
and/or a pharmaceutically acceptable salt thereof.

19. The compound of formula (I) according to claim 1 and/or a pharmaceutical acceptable salt thereof as a medicament.

20. A pharmaceutical composition comprising a compound of formula (I) according to claim 1 or 18 and/or a pharmaceutically acceptable salt thereof and optionally a pharmaceutically acceptable carrier.

21. A method for in vivo or in vitro inhibiting the activity of FGFR comprising contacting FGFR with an effective amount of a compound of formula (I) according to claim 1 and/or a pharmaceutically acceptable salt thereof.

22. A method for treating a disease responsive to inhibition of FGFR comprising administering to a subject in need thereof an effective amount to treat said disease of a compound of formula (I) according to claim 1 and/or a pharmaceutically acceptable salt thereof.

23. The method according to claim 22, wherein the disease responsive to inhibition of FGFR is cancer selected from lung cancer, stomach cancer, liver cancer, breast cancer, ovarian cancer, endometrial carcinoma, and bladder carcinoma.

\* \* \* \* \*

UNITED STATES PATENT AND TRADEMARK OFFICE
CERTIFICATE OF CORRECTION

PATENT NO. : 9,701,680 B2
APPLICATION NO. : 14/775653
DATED : July 11, 2017
INVENTOR(S) : Wei-Guo Su et al.

It is certified that error appears in the above-identified patent and that said Letters Patent is hereby corrected as shown below:

In the Claims

Claim 1, Column 190, Line 55, "or C=C;" should read -- or C≡C; --.

Claim 1, Column 191, Line 31, "–$C_1$-$C_6$ alkyl-$NH_2$, $H_2$" should read -- –$C_1$-$C_6$ alkyl-$NH_2$, --.

Claim 2, Column 191, Line 51, "–$OC_1$–C alkyl," should read -- –$OC_1$–$C_6$ alkyl, --.

Claim 3, Column 192, Line 21, "–$S(O)_2$–$C_{1-6}$ alkyl," should read -- –$S(O)_2$–$C_1$-$C_6$ alkyl, --.

Claim 5, Column 193, Lines 21-22, "–$S(O)_2$–$C_{1-6}$ alkyl," should read -- –$S(O)_2$–$C_1$-$C_6$ alkyl, --.

Claim 5, Column 193, Line 31, "–$C(O)C_{1-6}$ alkyl," should read -- –$C(O)C_1$-$C_6$ alkyl, --.

Claim 18, Columns 197-198, formula at the bottom of the page,

" 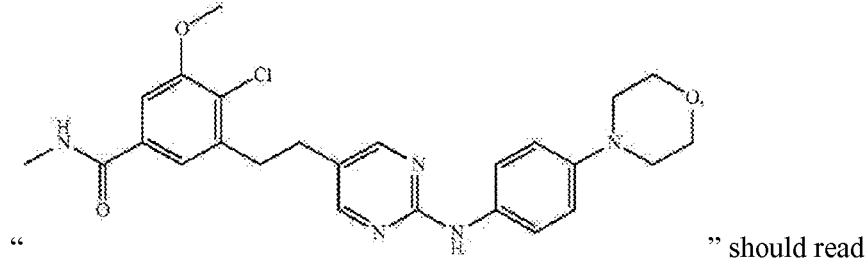 " should read

-- 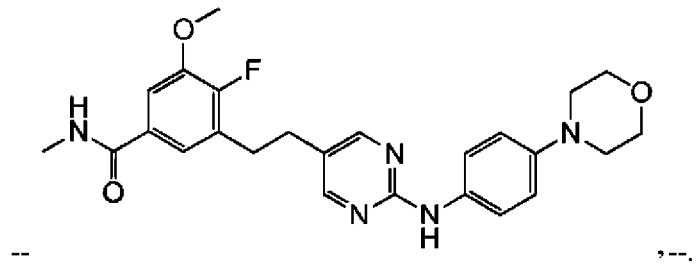 ,--.

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,701,680 B2

Claim 18, Columns 201-202, the left formula at the bottom of the page,

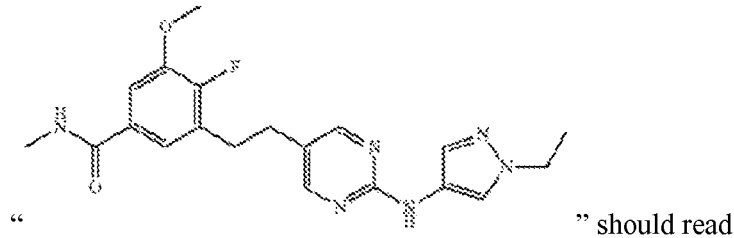

" should read

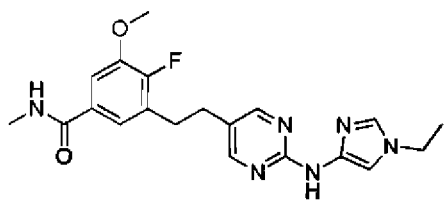

--.

Claim 18, Columns 209-210, formula at the top of the page,

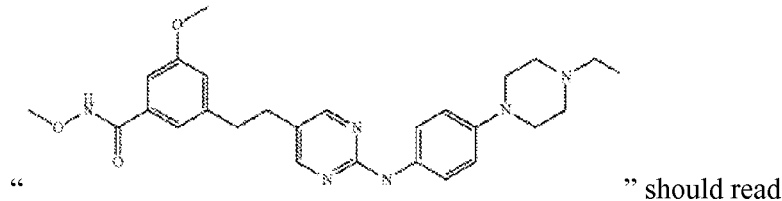

" should read

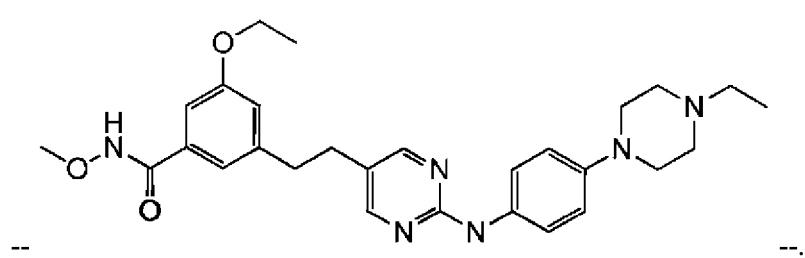

--.

Claim 18, Columns 245-246, formula at the bottom of the page,

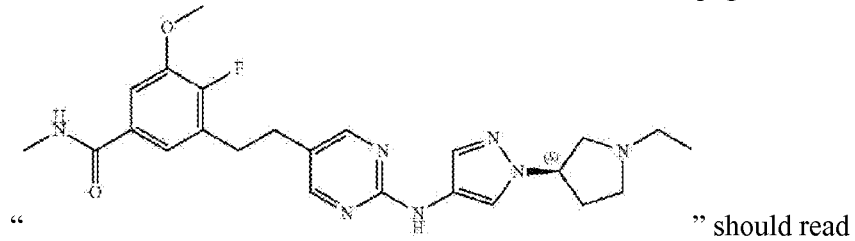

" should read

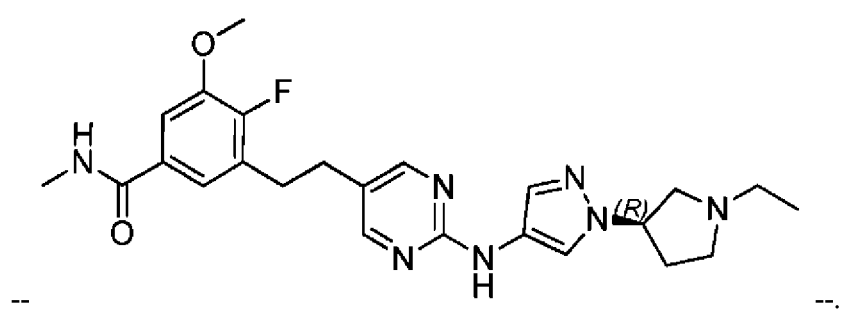

--.